(12) United States Patent
Lee et al.

(10) Patent No.: US 8,372,610 B2
(45) Date of Patent: Feb. 12, 2013

(54) PRODUCTION OF ODD CHAIN FATTY ACID DERIVATIVES IN RECOMBINANT MICROBIAL CELLS

(75) Inventors: Grace J. Lee, South San Francisco, CA (US); John R. Haliburton, South San Francisco, CA (US); Zhihao Hu, South San Francisco, CA (US); Andreas W. Schirmer, South San Francsico, CA (US)

(73) Assignee: LS9, Inc., South San Francisco, CA (US)

( * ) Notice: Subject to any disclaimer, the term of this patent is extended or adjusted under 35 U.S.C. 154(b) by 0 days.

(21) Appl. No.: 13/232,927

(22) Filed: Sep. 14, 2011

(65) Prior Publication Data

US 2012/0070868 A1 Mar. 22, 2012

Related U.S. Application Data

(60) Provisional application No. 61/383,086, filed on Sep. 15, 2010.

(51) Int. Cl.
*C12P 7/64* (2006.01)
*C12N 1/20* (2006.01)
*C12N 15/74* (2006.01)

(52) U.S. Cl. .................. 435/134; 435/252.33; 435/136; 435/471

(58) Field of Classification Search ........................ None
See application file for complete search history.

(56) References Cited

U.S. PATENT DOCUMENTS

| 2009/0081746 A1 | 3/2009 | Liao et al. |
| 2010/0209986 A1 | 8/2010 | Liao et al. |
| 2010/0251601 A1* | 10/2010 | Hu et al. .................. 44/313 |
| 2011/0166370 A1 | 7/2011 | Saunders et al. |
| 2011/0201068 A1 | 8/2011 | Pharkya et al. |

OTHER PUBLICATIONS

Choi et al. J. Bacteriol. (2000) 182 (2), 365-370.*
Singh et al. FEMS Microbiol. Lett. (Dec. 1, 2009) 301 (2), 188.*
Atsumi et al., "Directed Evolution of *Methanococcus jannaschii* Citramalate Synthase for Biosynthesis of 1-Propanol and 1-Butanol by *Escherichia coil*", *Appln.Environ.Microbiol.* 74(24) : 7802-7808 (2008).
Atsumi et al., "Non-fermentative pathways for synthesis of branched-chain higher alcohols as biofuels", *Nature*, 451: 86-89 (2008).
Cann et al., "Production of 2-methyl-1-butanol in engineered *Escherichia coli*", *Appl Microbiol Biotechnol.* 81: 89-98 (2008).
Han et al., "A Novel Alternate Anaplerotic Pathway to the Glyoxylate Cycle in Streptomycetes," *J. Bacteriol*, 179(16): 5157-5164 (1997).
Kaneda, T., "Iso-and Anteiso-Fatty Acids in Bacteria: Biosynthesis, Function and Taxonomic Significance", *Microbiological Reviews, American Society for Microbiology*, 55(2): 288-302 (1991).
Khandekar et al., "Identification, Substrate Specificity, and Inhibition of the Streptococcus Pneumoniae β-Ketoacyl-Acyl Carrier Protein Synthase III (FabH)", *J. Biol. Chem 276*: 30024-30030 (2001).
Knothe, G., "Dependence of Biodiesel Fuel Properties on the Structure of Fatty Acid Alkyl Esters," *Fuel Process. Technol*, 86: 1059-1070 (2005).

(Continued)

*Primary Examiner* — Nashaat Nashed
(74) *Attorney, Agent, or Firm* — Linda R. Judge; LS9, Inc.

(57) ABSTRACT

Recombinant microbial cells are provided which have been engineered to produce fatty acid derivatives having linear chains containing an odd number of carbon atoms by the fatty acid biosynthetic pathway. Also provided are methods of making odd chain fatty acid derivatives using the recombinant microbial cells, and compositions comprising odd chain fatty acid derivatives produced by such methods.

6 Claims, 3 Drawing Sheets

OTHER PUBLICATIONS

Lee et al., Systems metabolic engineering of *Escherichia coli* for L-threonine production. Mol. Syst. Biol 3:149 (2007).

Qiu et al., "Crystal structure and substrate specificity of the β-ketoacyl-acyl carrier protein synthase III (FabH) from *Staphylococcus aureus*", *Protein Science 14*: 2087-2094 (2005).

Ogawa-Miyata,Y., et al., "Mutation Analysis of the Feedback Inhibition Site of Aspartokinase III of *Escherichia coli* K-12 and its Use in L-threonine production", *Biosci. Biotechnol. Biochem. 65*: 1149-1154 (2001).

Xu, H., et al., "Isoleucine Biosynthesis in *Leptospira interrogans* Serotype lai Strain 56601 Proceeds via a Threonine-Independent Pathway" *J. Bacteriol. 186*: 5400-5409 (2004).

Zhang, et al., "Expanding metabolism for biosynthesis of nonnatural alcohols", *PNAS* 105(52): 20653-20658 (2008).

* cited by examiner

PRODUCTION OF ODD CHAIN FATTY ACID DERIVATIVES IN RECOMBINANT MICROBIAL CELLS

CROSS-REFERENCE TO RELATED APPLICATIONS

This application claims priority to and benefit of U.S. Provisional Patent Application No. 61/383,086 filed Sep. 15, 2010, the entire content of which is hereby incorporated by reference.

SEQUENCE LISTING

The instant application Sequence listing which has been submitted in ASCII format via EFS-Web and is hereby incorporated by reference in its entirety. Said ASCII copy, created on Oct. 19, 2011, is named LS0033US.txt and is 325,704 bytes in size.

BACKGROUND

Crude petroleum is a very complex mixture containing a wide range of hydrocarbons. It is converted into a diversity of fuels and chemicals through a variety of chemical processes in refineries. Crude petroleum is a source of transportation fuels as well as a source of raw materials for producing petrochemicals. Petrochemicals are used to make specialty chemicals such as plastics, resins, fibers, elastomers, pharmaceuticals, lubricants, and gels.

The most important transportation fuels—gasoline, diesel, and jet fuel—contain distinctively different mixtures of hydrocarbons which are tailored toward optimal engine performance. For example, gasoline comprises straight chain, branched chain, and aromatic hydrocarbons generally ranging from about 4 to 12 carbon atoms, while diesel predominantly comprises straight chain hydrocarbons ranging from about 9 to 23 carbon atoms. Diesel fuel quality is evaluated by parameters such as cetane number, kinematic viscosity, oxidative stability, and cloud point (Knothe G., *Fuel Process Technol.* 86:1059-1070 (2005)). These parameters, among others, are impacted by the hydrocarbon chain length as well as by the degree of branching or saturation of the hydrocarbon.

Microbially-produced fatty acid derivatives can be tailored by genetic manipulation. Metabolic engineering enables microbial strains to produce various mixtures of fatty acid derivatives, which can be optimized, for example, to meet or exceed fuel standards or other commercially relevant product specifications. Microbial strains can be engineered to produce chemicals or precursor molecules that are typically derived from petroleum. In some instances, it is desirable to mimic the product profile of an existing product, for example the product profile of an existing petroleum-derived fuel or chemical product, for efficient drop-in compatibility or substitution. Recombinant cells and methods described herein demonstrate microbial production of fatty acid derivatives with varied ratios of odd:even length chains as a means to precisely control the structure and function of, e.g., hydrocarbon-based fuels and chemicals.

There is a need for cost-effective alternatives to petroleum products that do not require exploration, extraction, transportation over long distances, or substantial refinement, and avoid the types of environmental damage associated with processing of petroleum. For similar reasons, there is a need for alternative sources of chemicals which are typically derived from petroleum. There is also a need for efficient and cost-effective methods for producing high-quality biofuels, fuel alternatives, and chemicals from renewable energy sources.

Recombinant microbial cells engineered to produce fatty acid precursor molecules having desired chain lengths (such as, chains having odd numbers of carbons), and fatty acid derivatives made therefrom, methods using these recombinant microbial cells to produce compositions comprising fatty acid derivatives having desired acyl chain lengths and desired ratios of odd:even length chains, and compositions produced by these methods, address these needs.

SUMMARY

The present invention provides novel recombinant microbial cells which produce odd chain length fatty acid derivatives and cell cultures comprising such novel recombinant microbial cells. The invention also provides methods of making compositions comprising odd chain length fatty acid derivatives comprising culturing recombinant microbial cells of the invention, compositions made by such methods, and other features apparent upon further review.

In a first aspect, the invention provides a recombinant microbial cell comprising a polynucleotide encoding a polypeptide having enzymatic activity effective to increase the production of propionyl-CoA in the cell relative to the production of propionyl-CoA in a parental microbial cell lacking or having a reduced amount of said enzymatic activity, wherein the recombinant microbial cell produces a fatty acid derivative composition comprising odd chain fatty acid derivatives when the cell is cultured in the presence of a carbon source under conditions effective to express the polynucleotide. In some embodiments, the recombinant microbial cell comprises: (a) a polynucleotide encoding a polypeptide having enzymatic activity effective to produce an increased amount of propionyl-CoA in the recombinant microbial cell, relative to the amount of propionyl-CoA produced in a parental microbial cell lacking or having a reduced amount of said enzymatic activity, wherein the polypeptide is exogenous to the recombinant microbial cell, or expression of the polynucleotide is modulated in the recombinant microbial cell as compared to the expression of the polynucleotide in the parental microbial cell; (b) a polynucleotide encoding a polypeptide having β-ketoacyl-ACP synthase activity that utilizes propionyl-CoA as a substrate, and (c) a polynucleotide encoding a polypeptide having fatty acid derivative enzyme activity, wherein the recombinant microbial cell produces a fatty acid derivative composition comprising odd chain fatty acid derivatives when the cell is cultured in the presence of a carbon source under conditions effective to express the polynucleotides according to (a), (b), and (c). In some embodiments, expression of at least one polynucleotide according to (a) is modulated by overexpression of the polynucleotide, such as by operatively linking the polynucleotide to an exogenous promoter.

In some embodiments, at least 5%, at least 10%, at least 20%, at least 30%, at least 40%, at least 50%, at least 60%, at least 70%, at least 80% or at least 90% of the fatty acid derivatives in the composition produced by the microbial cell of the first aspect are odd chain fatty acid derivatives. In some embodiments, the recombinant microbial cell of the first aspect produces at least 50 mg/L, at least 75 mg/L, at least 100 mg/L, at least 200 mg/L, at least 500 mg/L, at least 1000 mg/L, at least 2000 mg/L, at least 5000 mg/L, or at least 10000 mg/L odd chain fatty acid derivatives when cultured in a culture medium containing a carbon source under conditions effective to express the polynucleotides according to (a), (b), and (c).

In some embodiments, the polynucleotide encoding a polypeptide having enzymatic activity effective to produce an increased amount of propionyl-CoA in the recombinant microbial cell according to (a) is selected from: (i) one or more polynucleotide encoding a polypeptide having aspartokinase activity, homoserine dehydrogenase activity, homoserine kinase activity, threonine synthase activity, or threonine deaminase activity; (ii) one or more polynucleotide encoding a polypeptide having (R)-citramalate synthase activity, isopropylmalate isomerase activity, or beta-isopropylmalate dehydrogenase activity; and (iii) one or more polynucleotide encoding a polypeptide having methylmalonyl-CoA mutase activity, methylmalonyl-CoA decarboxylase activity, methylmalonyl-CoA carboxyltransferase activity, or methylmalonyl-CoA epimerase activity. In some embodiments, the microbial cell comprises one or more polynucleotide according to (i) and one or more polynucleotide according to (ii). In some embodiments, the microbial cell comprises one or more polynucleotide according to (i) and/or (ii), and one or more polynucleotide according to (iii).

In some embodiments, the polypeptide having β-ketoacyl-ACP synthase activity that utilizes propionyl-CoA as a substrate is exogenous to the recombinant microbial cell. In a more particular embodiment, expression of a polypeptide having β-ketoacyl-ACP synthase activity endogenous to the recombinant microbial cell is attenuated.

In some embodiments of the first aspect, the fatty acid derivative enzyme activity comprises thioesterase activity, and the fatty acid derivative composition produced by the recombinant microbial cell is a fatty acid composition comprising odd chain fatty acids and even chain fatty acids. In some embodiments, at least 5%, at least 10%, at least 20%, at least 30%, at least 40%, at least 50%, at least 60%, at least 70%, at least 80% or at least 90% of the fatty acids in the composition are odd chain fatty acids. In some embodiments, the recombinant microbial cell produces at least 50 mg/L, at least 75 mg/L, at least 100 mg/L, at least 200 mg/L, at least 500 mg/L, at least 1000 mg/L, at least 2000 mg/L, at least 5000 mg/L, or at least 10000 mg/L odd chain fatty acids when cultured in a culture medium containing a carbon source under conditions effective to express the polynucleotides.

In some embodiments of the first aspect, the fatty acid derivative enzyme activity comprises ester synthase activity, and the fatty acid derivative composition produced by the recombinant microbial cell is a fatty ester composition comprising odd chain fatty esters and even chain fatty esters. In some embodiments, at least 5%, at least 10%, at least 20%, at least 30%, at least 40%, at least 50%, at least 60%, at least 70%, at least 80% or at least 90% of the fatty esters in the composition are odd chain fatty esters. In some embodiments, the recombinant microbial cell produces at least 50 mg/L, at least 75 mg/L, at least 100 mg/L, at least 200 mg/L, at least 500 mg/L, at least 1000 mg/L, at least 2000 mg/L, at least 5000 mg/L, or at least 10000 ma odd chain fatty esters when cultured in a culture medium containing a carbon source under conditions effective to express the polynucleotides.

In some embodiments of the first aspect, the fatty acid derivative enzyme activity comprises fatty aldehyde biosynthesis activity, and the fatty acid derivative composition produced by the recombinant microbial cell is a fatty aldehyde composition comprising odd chain fatty aldehydes and even chain fatty aldehydes. In some embodiments, at least 5%, at least 10%, at least 20%, at least 30%, at least 40%, at least 50%, at least 60%, at least 70%, at least 80% or at least 90% of the fatty aldehydes in the composition are odd chain fatty aldehydes. In some embodiments, the recombinant microbial cell produces at least 50 mg/L, at least 75 mg/L, at least 100 mg/L, at least 200 mg/L, at least 500 mg/L, at least 1000 mg/L, at least 2000 mg/L, at least 5000 mg/L, or at least 10000 mg/L odd chain fatty aldehydes when cultured in a culture medium containing a carbon source under conditions effective to express the polynucleotides.

In some embodiments of the first aspect, the fatty acid derivative enzyme activity comprises fatty alcohol biosynthesis activity, and the fatty acid derivative composition produced by the recombinant microbial cell is a fatty alcohol composition comprising odd chain fatty alcohols and even chain fatty alcohols. In some embodiments, at least 5%, at least 10%, at least 20%, at least 30%, at least 40%, at least 50%, at least 60%, at least 70%, at least 80% or at least 90% of the fatty alcohols in the composition are odd chain fatty alcohols. In some embodiments, the recombinant microbial cell produces at least 50 mg/L, at least 75 mg/L, at least 100 mg/L, at least 200 mg/L, at least 500 mg/L, at least 1000 mg/L, at least 2000 mg/L, at least 5000 mg/L, or at least 10000 mg/L odd chain fatty alcohols when cultured in a culture medium containing a carbon source under conditions effective to express the polynucleotides.

In some embodiments of the first aspect, the fatty acid derivative enzyme activity comprises hydrocarbon biosynthesis activity, and the fatty acid derivative composition produced by the recombinant microbial cell is a hydrocarbon composition, such as an alkane composition, an alkene composition, a terminal olefin composition, an internal olefin composition, or a ketone composition, the hydrocarbon composition comprising odd chain hydrocarbons and even chain hydrocarbons. In some embodiments, at least 5%, at least 10%, at least 20%, at least 30%, at least 40%, at least 50%, at least 60%, at least 70%, at least 80% or at least 90% of the hydrocarbons in the composition are even chain hydrocarbons. In some embodiments, the recombinant microbial cell produces at least 50 mg/L, at least 75 mg/L, at least 100 mg/L, at least 200 mg/L, at least 500 mg/L, at least 1000 mg/L, at least 2000 mg/L, at least 5000 mg/L, or at least 10000 mg/L even chain hydrocarbons when cultured in a culture medium containing a carbon source under conditions effective to express the polynucleotides.

In various embodiments, the carbon source comprises a carbohydrate, such as a sugar, such as a monosaccharide, a disaccharide, an oligosaccharide, or a polysaccharide. In more preferred embodiments, the carbon source comprises a monosaccharide, preferably a hexose or a pentose, preferably a hexose such as glucose. In some embodiments, the carbon source is obtained from biomass, such as a cellulosic hydrolysate.

In various embodiments, the parental (e.g., host) microbial cell is a filamentous fungi, an algae, a yeast, or a prokaryote such as a bacterium. In various preferred embodiments, the host cell is a bacterial cell. In more preferred embodiments the host cell is an *E. coli* cell or a *Bacillus* cell.

Exemplary pathways for making even chain fatty acid derivatives and odd chain fatty acid derivatives are shown in FIGS. 1A and 1B, respectively. FIGS. 2 and 3 provide an overview of various approaches to direct metabolic flux through propionyl-CoA to increase odd chain fatty acid derivative production; FIG. 2 showing exemplary pathways through the intermediate α-ketobutyrate, and FIG. 3 showing an exemplary pathway through the intermediate methylmalonyl-CoA.

In one embodiment, the recombinant microbial cell according to the first aspect comprises a polynucleotide encoding a polypeptide having β-ketoacyl-ACP synthase activity that utilizes propionyl-CoA as a substrate, preferably a β-ketoacyl-ACP synthase III activity categorized as EC 2.3.1.180. In one embodiment, the polypeptide having β-ketoacyl-ACP synthase activity is encoded by a fabH gene. In one embodiment, the polypeptide having β-ketoacyl-ACP synthase activity is endogenous to the parental microbial cell. In another embodiment, the polypeptide having β-ketoacyl-ACP synthase activity is exogenous to the parental microbial cell. In another embodiment, expression of a polynucleotide encoding a polypeptide having β-ketoacyl-ACP synthase activity is modulated in the recombinant microbial cell. In some instances, expression of the polynucleotide is modulated by operatively linking the polynucleotide to an exogenous promoter, such that the polynucleotide is overexpressed in the recombinant microbial cell. In another embodiment, the polypeptide having β-ketoacyl-ACP synthase activity comprises a sequence selected from SEQ ID NOs: 1, 2, 3, 4, 5, 6, 7, 8, 9, 10, 11, 12, and 13, or a variant or a fragment thereof having β-ketoacyl-ACP synthase activity that utilizes propionyl-CoA as a substrate and catalyzes the condensation of propionyl-CoA with malonyl-ACP to form an odd chain acyl-ACP in vitro or in vivo, preferably in vivo. In another embodiment, the polypeptide having β-ketoacyl-ACP synthase activity that utilizes propionyl-CoA as a substrate comprises one or more sequence motif selected from SEQ ID NOs:14-19 and catalyzes the condensation of propionyl-CoA with malonyl-ACP to form an odd chain acyl-ACP in vitro or in vivo, preferably in vivo.

In one embodiment, the recombinant microbial cell according to the first aspect comprises an endogenous polynucleotide sequence (such as, an endogenous fabH gene) encoding a polypeptide having β-ketoacyl-ACP synthase activity, and expression of such endogenous polynucleotide sequence in the recombinant microbial cell is attenuated. In some embodiments, expression of the endogenous polynucleotide is attenuated by deletion of all or part of the sequence of the endogenous polynucleotide in the recombinant microbial cell. Such a recombinant microbial cell preferably further comprises a polynucleotide sequence encoding an exogenous polypeptide having β-ketoacyl-ACP synthase activity that utilizes propionyl-CoA as a substrate.

In one embodiment, the recombinant microbial cell according to the first aspect comprises a polynucleotide encoding a polypeptide having aspartokinase activity which is categorized as EC 2.7.2.4. In some embodiments, the polypeptide having aspartokinase activity is encoded by a thrA, a dapG or a hom3 gene. In one embodiment, the polypeptide having aspartokinase activity is endogenous to the parental microbial cell, or is exogenous to the parental microbial cell. In another embodiment, expression of the polynucleotide encoding the polypeptide having aspartokinase activity is modulated in the recombinant microbial cell. In some instances, expression of the polynucleotide is modulated by operatively linking the polynucleotide to an exogenous promoter, such that the polynucleotide is overexpressed in the recombinant microbial cell. In another embodiment, the polypeptide having aspartokinase activity comprises a sequence selected from SEQ ID NOs:20, 21, 22, 23, 24, or a variant or a fragment thereof having aspartokinase activity and which catalyzes the conversion of aspartate to aspartyl phosphate in vitro or in vivo, preferably in vivo.

In one embodiment, the recombinant microbial cell according to the first aspect comprises a polynucleotide encoding a polypeptide having homoserine dehydrogenase activity which is categorized as EC 1.1.1.3. In some embodiments, the polypeptide having homoserine dehydrogenase activity is encoded by a thrA, a hom or a hom6 gene. In one embodiment, the polypeptide having homoserine dehydrogenase activity is endogenous to the parental microbial cell, or is exogenous to the parental microbial cell. In another embodiment, expression of the polynucleotide encoding the polypeptide having homoserine dehydrogenase activity is modulated in the recombinant microbial cell. In some instances, expression of the polynucleotide is modulated by operatively linking the polynucleotide to an exogenous promoter, such that the polynucleotide is overexpressed in the recombinant microbial cell. In another embodiment, the polypeptide having homoserine dehydrogenase activity comprises a sequence selected from SEQ ID NOs:20, 21, 25, 26, 27, or a variant or a fragment thereof having homoserine dehydrogenase activity and which catalyzes the conversion of aspartate semialdehyde to homoserine in vitro or in vivo, preferably in vivo.

In a particular embodiment, the recombinant microbial cell according to the first aspect comprises a polynucleotide encoding a polypeptide having both aspartokinase and homoserine dehydrogenase activity. In one embodiment, the polypeptide having aspartokinase and homoserine dehydrogenase activity is endogenous to the parental microbial cell, or is exogenous to the parental microbial cell. In another embodiment, expression of the polynucleotide encoding the polypeptide having aspartokinase and homoserine dehydrogenase activity is modulated in the recombinant microbial cell. In some instances, expression of the polynucleotide is modulated by operatively linking the polynucleotide to an exogenous promoter, such that the polynucleotide is overexpressed in the recombinant microbial cell. In one embodiment the polypeptide having aspartokinase and homoserine dehydrogenase activity comprises the sequence SEQ ID NO:20 or a variant or a fragment thereof, such as SEQ ID NO:21, which catalyzes the conversion of aspartate to aspartyl phosphate and the conversion of aspartate semialdehyde to homoserine in vitro or in vivo, preferably in vivo.

In one embodiment, the recombinant microbial cell according to the first aspect comprises a polynucleotide encoding a polypeptide having homoserine kinase activity which is categorized as EC 2.7.1.39. In some embodiments, the polypeptide having homoserine kinase activity is encoded by a thrB gene or a thrl gene. In one embodiment, the polypeptide having homoserine kinase activity is endogenous to the parental microbial cell, or is exogenous to the parental microbial cell. In another embodiment, expression of the polynucleotide encoding the polypeptide having homoserine kinase activity is modulated in the recombinant microbial cell. In some instances, expression of the polynucleotide is modulated by operatively linking the polynucleotide to an exogenous promoter, such that the polynucleotide is overexpressed in the recombinant microbial cell. In another embodiment, the polypeptide having homoserine kinase activity comprises a sequence selected from SEQ ID NOs:28, 29, 30, 31, or a variant or a fragment thereof having homoserine kinase activity and which catalyzes the conversion of homoserine to O-phospho-L-homoserine in vitro or in vivo, preferably in vivo.

In one embodiment, the recombinant microbial cell according to the first aspect comprises a polynucleotide encoding a polypeptide having threonine synthase activity which is categorized as EC 4.2.3.1. In one embodiment, the polypeptide having threonine synthase activity is encoded by a thrC gene. In one embodiment, the polypeptide having threonine synthase activity is endogenous to the parental microbial cell, or is exogenous to the parental microbial cell. In another embodiment, expression of the polynucleotide encoding the polypeptide having threonine synthase activity is modulated in the recombinant microbial cell. In some instances, expression of the polynucleotide is modulated by operatively linking the polynucleotide to an exogenous promoter, such that the polynucleotide is overexpressed in the recombinant microbial cell. In another embodiment, the polypeptide having threonine synthase activity comprises a sequence selected from SEQ ID NOs:32, 33, 34, or a variant or a fragment thereof having threonine synthase activity and which catalyzes the conversion of O-phospho-L-homoserine to threonine in vitro or in vivo, preferably in vivo.

In one embodiment, the recombinant microbial cell according to the first aspect comprises a polynucleotide encoding a polypeptide having threonine deaminase activity which is categorized as EC 4.3.1.19. In some embodiments, the polypeptide having threonine deaminase activity is encoded by a tdcB gene or an ilvA gene. In one embodiment, the polypeptide having threonine deaminase activity is endogenous to the parental microbial cell, or is exogenous to the parental microbial cell. In another embodiment, expression of the polynucleotide encoding the polypeptide having threonine deaminase activity is modulated in the recombinant microbial cell. In some instances, expression of the polynucleotide is modulated by operatively linking the polynucleotide to an exogenous promoter, such that the polynucleotide is overexpressed in the recombinant microbial cell. In another embodiment, the polypeptide having threonine deaminase activity comprises a sequence selected from SEQ ID NOs:35, 36, 37, 38, 39, or a variant or a fragment thereof having threonine deaminase activity and which catalyzes the conversion of threonine to 2-ketobutyrate in vitro or in vivo, preferably in vivo.

In one embodiment, the recombinant microbial cell according to the first aspect comprises a polynucleotide encoding a polypeptide having (R)-citramalate synthase activity which is categorized as EC 2.3.1.182. In one embodiment, the polypeptide having (R)-citramalate synthase activity is encoded by a cimA gene. In one embodiment, the polypeptide having (R)-citramalate synthase activity is endogenous to the parental microbial cell, or is exogenous to the parental microbial cell. In another embodiment, expression of the polynucleotide encoding the polypeptide having (R)-citramalate synthase activity is modulated in the recombinant microbial cell. In some instances, expression of the polynucleotide is modulated by operatively linking the polynucleotide to an exogenous promoter, such that the polynucleotide is overexpressed in the recombinant microbial cell. In another embodiment, the polypeptide having (R)-citramalate synthase activity comprises a sequence selected from SEQ ID NOs:40, 41, 42, 43, or a variant or a fragment thereof having (R)-citramalate synthase activity and which catalyzes the reaction of acetyl-CoA and pyruvate to (R)-citramalate in vitro or in vivo, preferably in vivo.

In one embodiment, the recombinant microbial cell according to the first aspect comprises a polynucleotide encoding a polypeptide having isopropylmalate isomerase activity which is categorized as EC 4.2.1.33. In one embodiment, the polypeptide having isopropylmalate isomerase activity comprises a large subunit and a small subunit encoded by leuCD genes. In one embodiment, the polypeptide having isopropylmalate isomerase activity is endogenous to the parental microbial cell, or is exogenous to the parental microbial cell. In another embodiment, expression of the polynucleotide encoding the polypeptide having isopropylmalate isomerase activity is modulated in the recombinant microbial cell. In some instances, expression of the polynucleotide is modulated by operatively linking the polynucleotide to an exogenous promoter, such that the polynucleotide is overexpressed in the recombinant microbial cell. In another embodiment, the polypeptide having isopropylmalate isomerase activity comprises a large subunit and a small subunit. In other embodiments, the polypeptide having isopropylmalate isomerase activity comprises a large subunit sequence selected from SEQ ID NOs:44 and 46 and a small subunit sequence selected from SEQ ID NOs:45 and 47, or variants or fragments thereof having isopropylmalate isomerase activity and which catalyzes the conversion of (R)-citramalate to citraconate and citraconate to beta-methyl-D-malate in vitro or in vivo, preferably in vivo.

In one embodiment, the recombinant microbial cell according to the first aspect comprises a polynucleotide encoding a polypeptide having beta-isopropylmalate dehydrogenase activity which is categorized as EC 1.1.1.85. In some embodiments, the polypeptide having beta-isopropyl malate dehydrogenase activity is encoded by a leuB gene or a leu2 gene. In one embodiment, the polypeptide having beta-isopropylmalate dehydrogenase activity is endogenous to the parental microbial cell, or is exogenous to the parental microbial cell. In another embodiment, expression of the polynucleotide encoding the polypeptide having beta-isopropylmalate dehydrogenase activity is modulated in the recombinant microbial cell. In some instances, expression of the polynucleotide is modulated by operatively linking the polynucleotide to an exogenous promoter, such that the polynucleotide is overexpressed in the recombinant microbial cell. In another embodiment, the polypeptide having beta-isopropyl malate dehydrogenase activity comprises a sequence selected from SEQ ID NOs:48, 49, 50, or a variant or a fragment thereof having beta-isopropylmalate dehydrogenase activity and which catalyzes conversion of beta-methyl-D-malate to 2-ketobutyrate in vitro or in vivo, preferably in vivo.

In one embodiment, the recombinant microbial cell according to the first aspect comprises a polynucleotide encoding a polypeptide having methylmalonyl-CoA mutase activity which is categorized as EC 5.4.99.2. In some embodiments, the polypeptide having methylmalonyl-CoA mutase activity is encoded by an scpA (also known as sbm) gene. In one embodiment, the polypeptide having methylmalonyl-CoA mutase activity is endogenous to the parental microbial cell, or is exogenous to the parental microbial cell. In another embodiment, expression of the polynucleotide encoding the polypeptide having methylmalonyl-CoA mutase activity is modulated in the recombinant microbial cell. In some instances, expression of the polynucleotide is modulated by operatively linking the polynucleotide to an exogenous promoter, such that the polynucleotide is overexpressed in the recombinant microbial cell. In another embodiment, the polypeptide having methylmalonyl-CoA mutase activity comprises a sequence selected from SEQ ID NOs:51, 52, 53, 54, 55, 56, 57, 58, or a variant or a fragment thereof having methylmalonyl-CoA mutase activity and which catalyzes conversion of succinyl-CoA to methylmalonyl-CoA in vitro or in vivo, preferably in vivo.

In one embodiment, the recombinant microbial cell according to the first aspect comprises a polynucleotide encoding a polypeptide having methylmalonyl-CoA decarboxylase activity which is categorized as EC 4.1.1.41. In some embodiments, the polypeptide having methylmalonyl-CoA decarboxylase activity is encoded by an scpB (also known as ygfG) gene. In one embodiment, the polypeptide having methylmalonyl-CoA decarboxylase activity is endogenous to the parental microbial cell, or is exogenous to the parental microbial cell. In another embodiment, expression of the polynucleotide encoding the polypeptide having methylmalonyl-CoA decarboxylase activity is modulated in the recombinant microbial cell. In some instances, expression of the polynucleotide is modulated by operatively linking the polynucleotide to an exogenous promoter, such that the polynucleotide is overexpressed in the recombinant microbial cell. In another embodiment, the polypeptide having methylmalonyl-CoA decarboxylase activity comprises a sequence selected from SEQ ID NOs:59, 60, 61, or a variant or a fragment thereof having methylmalonyl-CoA decarboxylase activity and which catalyzes conversion of methylmalonyl-CoA to propionyl-CoA in vitro or in vivo, preferably in vivo.

In one embodiment, the recombinant microbial cell according to the first aspect comprises a polynucleotide encoding a polypeptide having methylmalonyl-CoA carboxyltransferase activity which is categorized as EC 2.1.3.1. In one embodiment, the polypeptide having methylmalonyl-CoA carboxyltransferase activity is endogenous to the parental microbial cell, or is exogenous to the parental microbial cell. In another embodiment, expression of the polynucleotide encoding the polypeptide having methylmalonyl-CoA carboxyltransferase activity is modulated in the recombinant microbial cell. In some instances, expression of the polynucleotide is modulated by operatively linking the polynucleotide to an exogenous promoter, such that the polynucleotide is overexpressed in the recombinant microbial cell. In another embodiment, the polypeptide having methylmalonyl-CoA carboxyltransferase activity comprises the sequence SEQ ID NO:62, or a variant or a fragment thereof having methylmalonyl-CoA carboxyltransferase activity and which catalyzes conversion of methylmalonyl-CoA to propionyl-CoA in vitro or in vivo, preferably in vivo.

In one embodiment, the recombinant microbial cell according to the first aspect comprises a polynucleotide encoding a polypeptide having methylmalonyl-CoA epimerase activity which is categorized as EC 5.1.99.1. In one embodiment, the polypeptide having methylmalonyl-CoA epimerase activity is endogenous to the parental microbial cell, or is exogenous to the parental microbial cell. In another embodiment, expression of the polynucleotide encoding the polypeptide having methylmalonyl-CoA epimerase activity is modulated in the recombinant microbial cell. In some instances, expression of the polynucleotide is modulated by operatively linking the polynucleotide to an exogenous promoter, such that the polynucleotide is overexpressed in the recombinant microbial cell. In another embodiment, the polypeptide having methylmalonyl-CoA epimerase activity comprises the sequence SEQ ID NO:63, or a variant or a fragment thereof having methylmalonyl-CoA epimerase activity and which catalyzes conversion of (R)-methylmalonyl-CoA to (S)-methylmalonyl-CoA in vitro or in vivo, preferably in vivo.

In one embodiment, the recombinant microbial cell according to the first aspect comprises an endogenous polynucleotide sequence (such as, an endogenous scpC gene (also known as ygfH)) encoding a polypeptide having propionyl-CoA::succinyl-CoA transferase activity, and expression of the endogenous polynucleotide in the recombinant microbial cell is attenuated. In some embodiments, expression of the endogenous polynucleotide is attenuated by deletion of all or part of the sequence of the endogenous polynucleotide in the recombinant microbial cell.

In one embodiment, the recombinant microbial cell according to the first aspect comprises an endogenous polynucleotide sequence (such as, an endogenous fadE gene) encoding a polypeptide having acyl-CoA dehydrogenase activity, and expression of the endogenous polynucleotide in the recombinant microbial cell is attenuated. In some embodiments, expression of the endogenous polynucleotide is attenuated by deletion of all or part of the sequence of the endogenous polynucleotide in the recombinant microbial cell.

In other embodiments, a recombinant microbial cell according to the first aspect comprises a polynucleotide encoding a polypeptide having a fatty acid derivative enzyme activity, wherein the recombinant microbial cell produces a fatty acid derivative composition comprising odd chain fatty acid derivatives when cultured in the presence of a carbon source.

In various embodiments, the fatty acid derivative enzyme activity comprises a thioesterase activity, an ester synthase activity, a fatty aldehyde biosynthesis activity, a fatty alcohol biosynthesis activity, a ketone biosynthesis activity, and/or a hydrocarbon biosynthesis activity. In some embodiments, the recombinant microbial cell comprises polynucleotides encoding two or more polypeptides, each polypeptide having a fatty acid derivative enzyme activity. In more particular embodiments, the recombinant microbial cell expresses or overexpresses one or more polypeptides having fatty acid derivative enzyme activity selected from: (1) a polypeptide having thioesterase activity; (2) a polypeptide having decarboxylase activity; (3) a polypeptide having carboxylic acid reductase activity; (4) a polypeptide having alcohol dehydrogenase activity (EC 1.1.1.1); (5) a polypeptide having aldehyde decarbonylase activity (EC 4.1.99.5); (6) a polypeptide having acyl-CoA reductase activity (EC 1.2.1.50); (7) a polypeptide having acyl-ACP reductase activity; (8) a polypeptide having ester synthase activity (EC 3.1.1.67); (9) a polypeptide having OleA activity; or (10) a polypeptide having OleCD or OleBCD activity; wherein the recombinant microbial cell produces a composition comprising odd chain fatty acids, odd chain fatty esters, odd chain wax esters, odd chain fatty aldehydes, odd chain fatty alcohols, even chain alkanes, even chain alkenes, even chain internal olefins, even chain terminal olefins, or even chain ketones.

In one embodiment, the fatty acid derivative enzyme activity comprises a thioesterase activity, wherein a culture comprising the recombinant microbial cell produces a fatty acid composition comprising odd chain fatty acids when cultured in the presence of a carbon source. In some embodiments, the polypeptide has a thioesterase activity which is categorized as EC 3.1.1.5, EC 3.1.2.-, or EC 3.1.2.14. In some embodiments, the polypeptide having a thioesterase activity is encoded by a tesA, a tesB, a fatA, or a fatB gene. In some embodiments, the polypeptide having thioesterase activity is endogenous to the parental microbial cell, or is exogenous to the parental microbial cell. In another embodiment, expression of the polynucleotide encoding the polypeptide having thioesterase activity is modulated in the recombinant microbial cell. In some instances, expression of the polynucleotide is modulated by operatively linking the polynucleotide to an exogenous promoter, such that the polynucleotide is overexpressed in the recombinant microbial cell. In another embodiment, the polypeptide having thioesterase activity comprises a sequence selected from SEQ ID NO: 64, 65, 66, 67, 68, 69, 70, 71 and 72, or a variant or a fragment thereof having thioesterase activity and which catalyzes the hydrolysis of an odd chain acyl-ACP to an odd chain fatty acid, or catalyzes the alcoholysis of an odd chain acyl-ACP to an odd chain fatty ester, in vitro or in vivo, preferably in vivo. In some embodiments, the recombinant microbial cell according to the first aspect, comprising a polynucleotide encoding a polypeptide having thioesterase activity, when cultured in the presence of a carbon source, produces at least 50 mg/L, at least 75 mg/L, at least 100 mg/L, at least 200 mg/L, at least 500 mg/L, at least 1000 mg/L, or at least 2000 mg/L odd chain fatty acids when cultured in a culture medium containing a carbon source under conditions effective to express the polynucleotides. In some embodiments, the recombinant microbial cell according to the first aspect, comprising a polynucleotide encoding a polypeptide having thioesterase activity, produces a fatty acid composition comprising odd chain fatty acids and even chain fatty acids. In some embodiments, at least 5%, at least 10%, at least 20%, at least 30%, at least 40%, at least 50%, at least 60%, at least 70%, at least 80% or at least 90% of the fatty acids in the composition are odd chain fatty acids.

The invention includes a cell culture comprising the recombinant microbial cell according to the first aspect.

In a second aspect, the invention includes a method of producing odd chain fatty acid derivatives (or a fatty acid derivative composition comprising odd chain fatty acid derivatives) in a recombinant microbial cell, the method comprising expressing in the cell a recombinant polypeptide having enzymatic activity effective to increase the production of propionyl-CoA in the cell, and culturing the cell in the presence of a carbon source under conditions effective to express the recombinant polypeptide and produce the odd chain fatty acid derivatives.

In one embodiment, the method of making a fatty acid derivative composition comprising odd chain fatty acid derivatives comprises obtaining a recombinant microbial cell according to the first aspect, culturing the cell in a culture medium containing a carbon source under conditions effective to express the polynucleotides according to (a), (b), and (c) and produce a fatty acid derivative composition comprising odd chain fatty acid derivatives, and optionally recovering the composition from the culture medium.

In some embodiments, the fatty acid derivative composition produced by the method according to the second aspect comprises odd chain fatty acid derivatives and even chain fatty acid derivatives, wherein at least 5%, at least 6%, at least 8%, at least 10%, at least 20%, at least 30%, at least 40%, at least 50%, at least 60%, at least 70%, at least 80% or at least 90% by weight of the fatty acid derivatives in the composition are odd chain fatty acid derivatives. In some embodiments, the fatty acid derivative composition comprises odd chain fatty acid derivatives in an amount (e.g., a titer) of at least 50 mg/L, at least 75 mg/L, at least 100 mg/L, at least 200 mg/L, at least 500 mg/L, at least 1000 mg/L, at least 2000 mg/L, at least 5000 mg/L, at least 10000 mg/L, or at least 20000 mg/L.

In various embodiments of the second aspect, the fatty acid derivative enzyme activity comprises a thioesterase activity, an ester synthase activity, a fatty aldehyde biosynthesis activity, a fatty alcohol biosynthesis activity, a ketone biosynthesis activity, and/or a hydrocarbon biosynthesis activity. In some embodiments, the recombinant microbial cell comprises polynucleotides encoding two or more polypeptides, each polypeptide having a fatty acid derivative enzyme activity. In more particular embodiments, the recombinant microbial cell expresses or overexpresses one or more polypeptides having fatty acid derivative enzyme activity selected from: (1) a polypeptide having thioesterase activity; (2) a polypeptide having decarboxylase activity; (3) a polypeptide having carboxylic acid reductase activity; (4) a polypeptide having alcohol dehydrogenase activity (EC 1.1.1.1); (5) a polypeptide having aldehyde decarbonylase activity (EC 4.1.99.5); (6) a polypeptide having acyl-CoA reductase activity (EC 1.2.1.50); (7) a polypeptide having acyl-ACP reductase activity; (8) a polypeptide having ester synthase activity (EC 3.1.1.67); (9) a polypeptide having OleA activity; or (10) a polypeptide having OleCD or OleBCD activity; wherein the recombinant microbial cell produces a composition comprising odd chain fatty acids, odd chain fatty esters, odd chain wax esters, odd chain fatty aldehydes, odd chain fatty alcohols, even chain alkanes, even chain alkenes, even chain internal olefins, even chain terminal olefins, and/or even chain ketones.

The invention includes a fatty acid derivative composition comprising odd chain fatty acid derivatives produced by the method according to the second aspect.

In a third aspect, the invention includes a method of making a recombinant microbial cell which produces a higher titer or higher proportion of odd chain fatty acid derivatives than a parental microbial cell, the method comprising obtaining a parental microbial cell comprising a polynucleotide encoding a polypeptide having fatty acid derivative enzyme activity, and engineering the parental microbial cell to obtain a recombinant microbial cell which produces or is capable of producing a greater amount of propionyl-CoA than the amount of propionyl-CoA produced by the parental microbial cell when cultured under the same conditions, wherein the recombinant microbial cell produces a higher titer or higher proportion of odd chain fatty acid derivatives when cultured in the presence of a carbon source under conditions effective to produce propionyl-CoA and fatty acid derivatives in the recombinant microbial cell, relative to the titer or proportion of odd chain fatty acid derivatives produced by the parental microbial cell cultured under the same conditions.

In a fourth aspect, the invention includes a method of increasing the titer or proportion of odd chain fatty acid derivatives produced by a microbial cell, the method comprising obtaining a parental microbial cell that is capable of producing a fatty acid derivative, and engineering the parental microbial cell to obtain a recombinant microbial cell which produces or is capable of producing a greater amount of propionyl-CoA than the amount of propionyl-CoA produced by the parental microbial cell when cultured under the same conditions, wherein the recombinant microbial cell produces a higher titer or higher proportion of odd chain fatty acid derivatives when cultured in the presence of a carbon source under conditions effective to produce propionyl-CoA and fatty acid derivatives in the recombinant microbial cell, relative to the titer or proportion of odd chain fatty acid derivatives produced by the parental microbial cell cultured under the same conditions.

In some embodiments according to the third or fourth aspect, the step of engineering the parental microbial cell comprises engineering the cell to express polynucleotides encoding polypeptides selected from (a) one or more polypeptides having aspartokinase activity, homoserine dehydrogenase activity, homoserine kinase activity, threonine synthase activity, and threonine deaminase activity; (b) one or more polypeptides having (R)-citramalate synthase activity, isopropylmalate isomerase activity, and beta-isopropylmalate dehydrogenase activity; and (c) one or more polypeptides having methylmalonyl-CoA mutase activity, methylmalonyl-CoA decarboxylase activity, methylmalonyl-CoA carboxyltransferase activity, and methylmalonyl-CoA epimerase activity; wherein at least one polypeptide according to (a), (b) or (c) is exogenous to the parental microbial cell, or wherein expression of at least one polynucleotide according to (a), (b) or (c) is modulated in the recombinant microbial cell as compared to the expression of the polynucleotide in the parental microbial cell. In some embodiments, expression of at least one polynucleotide is modulated by overexpression of the polynucleotide, such as by operatively linking the polynucleotide to an exogenous promoter. In some embodiments, the engineered cell expresses one or more polypeptide according to (a) and one or more polypeptide according to (b).

In some embodiments according to the third or fourth aspect, the parental microbial cell comprises a polynucleotide encoding a polypeptide having β-ketoacyl-ACP synthase activity that utilizes propionyl-CoA as a substrate. In some embodiments, the recombinant microbial cell is engineered to express an exogenous polynucleotide or to overexpress an endogenous polynucleotide encoding a polypeptide having β-ketoacyl-ACP synthase activity that utilizes propionyl-CoA as a substrate. In some embodiments, the recombinant microbial cell is engineered to express an exogenous polynucleotide encoding a polypeptide having β-ketoacyl-ACP synthase activity that utilizes propionyl-CoA as a substrate, and expression of an endogenous polynucleotide encoding a polypeptide having β-ketoacyl-ACP synthase activity is attenuated.

These and other objects and features of the invention will become more fully apparent when the following detailed description is read in conjunction with the accompanying figures.

BRIEF DESCRIPTION OF THE DRAWINGS

FIG. 1A shows a reaction pathway utilizing the two-carbon primer acetyl-CoA, which generates the even chain length β-ketoacyl-ACP intermediate acetoacetyl-ACP, leading to even chain (ec)-acyl-ACP intermediates and even chain fatty acid derivatives produced therefrom; and FIG. 1B shows a reaction pathway utilizing the three carbon primer propionyl-CoA, which generates the odd chain length β-ketoacyl-ACP intermediate 3-oxovaleryl-ACP, leading to odd chain (oc)-acyl-ACP intermediates and odd chain fatty acid derivatives produced therefrom.

DETAILED DESCRIPTION

Figures 1A, 1B:
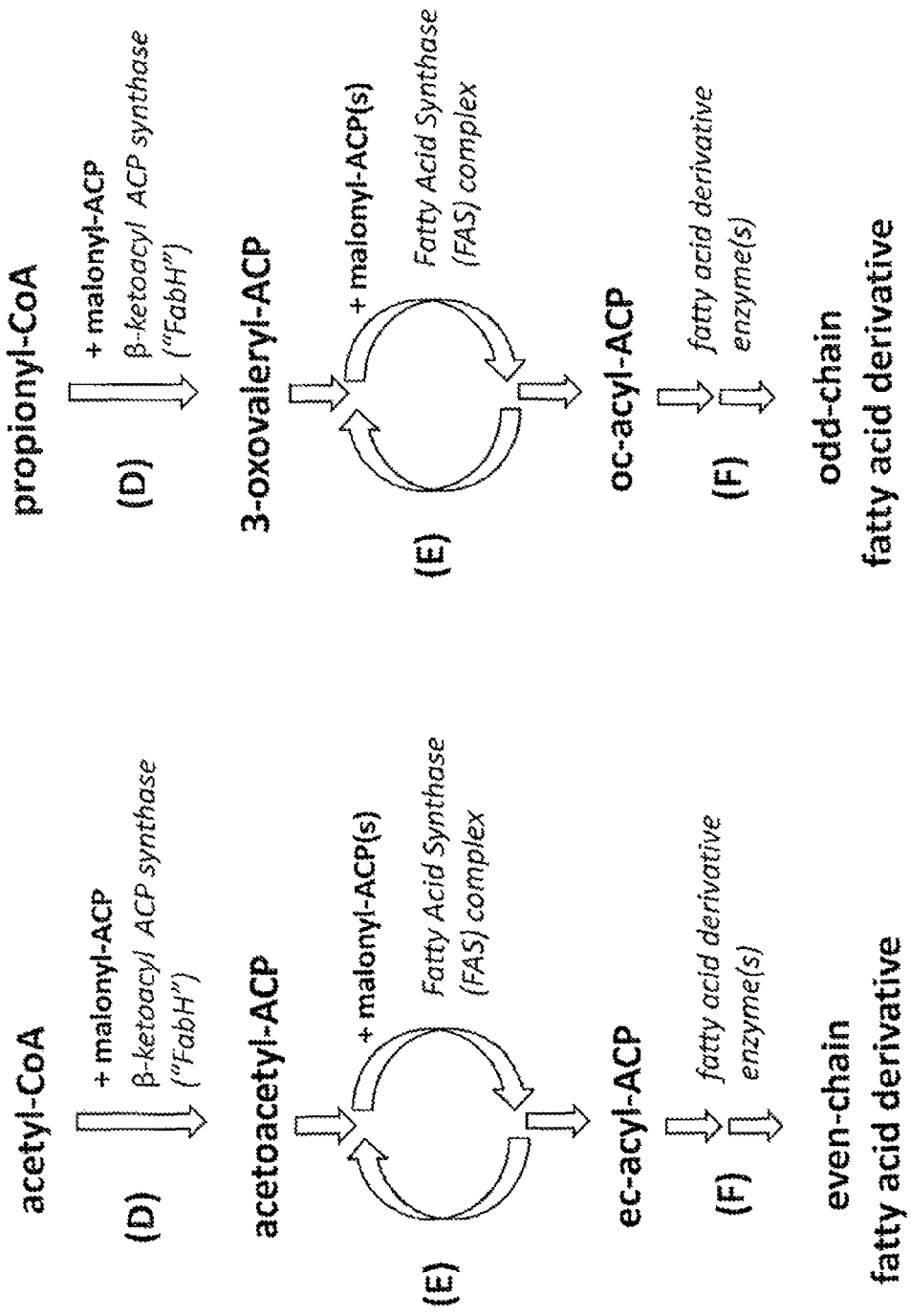
FIGS. 1A and 1B compare exemplary intermediates and products of fatty acid biosynthetic pathways when supplied with different acyl-CoA "primer" molecules.

The invention is not limited to the specific compositions and methodology described herein, as these may, of course, vary. It is also to be understood that the terminology used herein is for the purpose of describing particular embodiments only, and is not intended to limit the scope of the present invention.

Accession Numbers: Sequence Accession numbers throughout this description were obtained from databases provided by the NCBI (National Center for Biotechnology Information) maintained by the National Institutes of Health, U.S.A. (which are identified herein as "NCBI Accession Numbers" or alternatively as "GenBank Accession Numbers"), and from the UniProt Knowledgebase (UniProtKB) and Swiss-Prot databases provided by the Swiss Institute of Bioinformatics (which are identified herein as "UniProtKB Accession Numbers"). Unless otherwise expressly indicated, the sequence identified by an NCBI/GenBank Accession number is version number 1 (that is, the Version Number of the sequence is "AccessionNumber.1"). The NCBI and UniProtKB accession numbers provided herein were current as of Aug. 2, 2011.

Enzyme Classification (EC) Numbers: EC numbers are established by the Nomenclature Committee of the International Union of Biochemistry and Molecular Biology (IUBMB), description of which is available on the IUBMB Enzyme Nomenclature website on the World Wide Web. EC numbers classify enzymes according to the reaction catalyzed. EC numbers referenced herein are derived from the KEGG Ligand database, maintained by the Kyoto Encyclopedia of Genes and Genomics, sponsored in part by the University of Tokyo. Unless otherwise indicated, EC numbers are as provided in the KEGG database as of Aug. 2, 2011.

Unless defined otherwise, all technical and scientific terms used herein have the same meaning as commonly understood to one of ordinary skill in the art to which this invention belongs. Although any materials and methods similar or equivalent to those described herein can be used in the practice or testing of the invention, the preferred compositions and methods are now described.

DEFINITIONS

As used herein, the term "fatty acid" refers to a carboxylic acid having the formula R—(C=O)—OH, wherein R represents a carbon chain which can be between about 4 and about 36 carbon atoms in length, more generally between about 4 and about 22 carbon atoms in length. Fatty acids can be saturated or unsaturated. If unsaturated, R can have one or more points of unsaturation, that is, R can be monounsaturated or polyunsaturated. R can be a straight chain (also referred to herein as a "linear chain") or a branched chain. The term "fatty acid" may be used herein to refer to a "fatty acid derivative" which can include one or more different fatty acid derivative, or mixtures of fatty acids derivatives.

An "odd chain fatty acid" (abbreviated "oc-FA") as used herein refers to a fatty acid molecule having a linear carbon chain containing an odd number of carbon atoms, inclusive of the carbonyl carbon. Non-limiting examples of oc-FAs include tridecanoic acid (C13:0), pentadecanoic acid (C15:0), and heptadecanoic acid (C17:0), which are saturated oc-FAs, and heptadecenoic acid (C17:1), which is an unsaturated (i.e., a monounsaturated) oc-FA.

The term "β-ketoacyl-ACP" as used herein refers to the product of the condensation of an acyl-CoA primer molecule with malonyl-ACP catalyzed by an enzyme having beta ketoacyl-ACP synthase activity (e.g., EC 2.3.1.180) as represented by part (D) of the pathways shown in FIGS. 1A and 1B. The acyl-CoA primer molecule may have an acyl group containing an even number of carbon atoms, such as acetyl-CoA as represented in FIG. 1A, in which case the resulting β-ketoacyl-ACP intermediate is acetoacetyl-ACP, which is an even chain (ec-)β-ketoacyl-ACP. The acyl-CoA primer molecule may have an acyl group containing an odd number of carbon atoms, such as propionyl-CoA as represented in FIG. 1B, in which case the resulting β-ketoacyl-ACP intermediate is 3-oxovaleryl-ACP, which is an odd chain (oc-)β-ketoacyl-ACP. The β-ketoacyl-ACP intermediate enters the fatty acid synthase (FAS) cycle, represented by part (E) of FIGS. 1A and 1B, where it is subjected to a round of elongation (i.e., keto reduction, dehydration, and enoyl reduction), adding two carbon units to the acyl chain, followed by additional elongation cycles, which each involve condensation with another malonyl-ACP molecule, keto reduction, dehydration, and enoyl reduction, such that the acyl chain of the acyl-ACP is elongated by two carbon units per elongation cycle.

An "acyl-ACP" generally refers to the product of one or more rounds of FAS-catalyzed elongation of a β-ketoacyl-ACP intermediate. Acyl-ACP is an acyl thioester formed between the carbonyl carbon of an alkyl chain and the sulfhydryl group of the 4'-phosphopantethionyl moiety of an acyl carrier protein (ACP), and, in the case of a linear carbon chain, typically has the formula CH3-(CH2)n-C(=O)-s-ACP wherein n may be an even number (e.g., an "even chain acyl-ACP" or "ec-acyl-ACP", which is produced, for example, when acetyl-CoA is the primer molecule, see FIG. 1A) or an odd number (e.g., an "odd chain acyl-ACP" or "oc-acyl-ACP", which is produced, for example, when propionyl-CoA is the primer molecule, see FIG. 1B).

Unless otherwise specified, a "fatty acid derivative" (abbreviated "FA derivative") is intended to include any product made at least in part by the fatty acid biosynthetic pathway of the recombinant microbial cell. A fatty acid derivative also includes any product made at least in part by a fatty acid pathway intermediate, such as an acyl-ACP intermediate. The fatty acid biosynthetic pathways described herein can include fatty acid derivative enzymes which can be engineered to produce fatty acid derivatives, and in some instances additional enzymes can be expressed to produce fatty acid derivatives having desired carbon chain characteristics, such as, for example, compositions of fatty acid derivatives having carbon chains containing a desired number of carbon atoms, or compositions of fatty acid derivatives having a desired proportion of derivatives containing odd numbered carbon chains, and the like. Fatty acid derivatives include, but are not limited to, fatty acids, fatty aldehydes, fatty alcohols, fatty esters (such as waxes), hydrocarbons (such as alkanes and alkenes (including terminal olefins and internal olefins)) and ketones.

The term "odd chain fatty acid derivative" (abbreviated "oc-FA derivative") refers to a product of the reaction of an oc-acyl-ACP, as defined above, with one or more fatty acid derivative enzymes. The resulting fatty acid derivative product likewise has a linear carbon chain containing an odd number of carbon atoms, unless the fatty acid derivative is itself the product of decarbonylation or decarboxylation of an oc-FA derivative or an oc-acyl-ACP, in which case the resulting oc-FA derivative has an even number of carbon atoms; for example, when the fatty acid derivative is an ec-alkane or ec-alkene produced by decarbonylation of an oc-fatty aldehyde, an ec-terminal olefin produced by decarboxylation of an oc-fatty acid, an ec-ketone or an ec-internal olefin produced by decarboxylation of an oc-acyl-ACP, and so forth. It is to be understood that such even chain length products of oc-FA derivatives or oc-acyl-ACP precursor molecules, despite having linear chains containing an even number of carbon atoms, are nevertheless considered to fall under the definition of "oc-FA derivatives".

An "endogenous" polypeptide refers to a polypeptide encoded by the genome of the parental microbial cell (also termed "host cell") from which the recombinant cell is engineered (or "derived").

A "exogenous" polypeptide refers to a polypeptide which is not encoded by the genome of the parental microbial cell. A variant (i.e., mutant) polypeptide is an example of an exogenous polypeptide.

In embodiments of the invention wherein a polynucleotide sequence encodes an endogenous polypeptide, in some instances the endogenous polypeptide is overexpressed. As used herein, "overexpress" means to produce or cause to be produced a polynucleotide or a polypeptide in a cell at a greater concentration than is normally produced in the corresponding parental cell (such as, a wild-type cell) under the same conditions. A polynucleotide or a polypeptide can be "overexpressed" in a recombinant microbial cell when the polynucleotide or polypeptide is present in a greater concentration in the recombinant microbial cell as compared to its concentration in a non-recombinant microbial cell of the same species (such as, the parental microbial cell) under the same conditions. Overexpression can be achieved by any suitable means known in the art.

In some embodiments, overexpression of the endogenous polypeptide in the recombinant microbial cell can be achieved by the use of an exogenous regulatory element. The term "exogenous regulatory element" generally refers to a regulatory element (such as, an expression control sequence or a chemical compound) originating outside of the host cell. However, in certain embodiments, the term "exogenous regulatory element" (e.g., "exogenous promoter") can refer to a regulatory element derived from the host cell whose function is replicated or usurped for the purpose of controlling the expression of the endogenous polypeptide in the recombinant cell. For example, if the host cell is an *E. coli* cell, and the polypeptide is an endogenous polypeptide, then expression of the endogenous polypeptide the recombinant cell can be controlled by a promoter derived from another *E. coli* gene. In some embodiments, the exogenous regulatory element that causes an increase in the level of expression and/or activity of an endogenous polypeptide is a chemical compound, such as a small molecule.

In some embodiments, the exogenous regulatory element which controls the expression of a polynucleotide (e.g., an endogenous polynucleotide) encoding an endogenous polypeptide is an expression control sequence which is operably linked to the endogenous polynucleotide by recombinant integration into the genome of the host cell. In certain embodiments, the expression control sequence is integrated into a host cell chromosome by homologous recombination using methods known in the art (e.g., Datsenko et al., *Proc. Natl. Acad. Sci. U.S.A.*, 97(12): 6640-6645 (2000)).

Expression control sequences are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription (Maniatis et al., *Science*, 236: 1237-1245 (1987)). Exemplary expression control sequences are described in, for example, Goeddel, *Gene Expression Technology: Methods in Enzymology*, Vol. 185, Academic Press, San Diego, Calif. (1990).

In the methods of the invention, an expression control sequence is operably linked to a polynucleotide sequence. By "operably linked" is meant that a polynucleotide sequence and expression control sequence(s) are connected in such a way as to permit gene expression when the appropriate molecules (e.g., transcriptional activator proteins) are bound to the expression control sequence(s). Operably linked promoters are located upstream of the selected polynucleotide sequence in terms of the direction of transcription and translation. Operably linked enhancers can be located upstream, within, or downstream of the selected polynucleotide. Additional nucleic acid sequences, such as nucleic acid sequences encoding selection markers, purification moieties, targeting proteins, and the like, can be operatively linked to the polynucleotide sequence, such that the additional nucleic acid sequences are expressed together with the polynucleotide sequence.

In some embodiments, the polynucleotide sequence is provided to the recombinant cell by way of a recombinant vector, which comprises a promoter operably linked to the polynucleotide sequence. In certain embodiments, the promoter is a developmentally-regulated, an organelle-specific, a tissue-specific, an inducible, a constitutive, or a cell-specific promoter.

As used herein, the term "vector" refers to a nucleic acid molecule capable of transporting another nucleic acid, i.e., a polynucleotide sequence, to which it has been linked. One type of useful vector is an episome (i.e., a nucleic acid capable of extra-chromosomal replication). Useful vectors are those capable of autonomous replication and/or expression of nucleic acids to which they are linked. Vectors capable of directing the expression of genes to which they are operatively linked are referred to herein as "expression vectors." In general, expression vectors of utility in recombinant DNA techniques are often in the form of "plasmids," which refer generally to circular double stranded DNA loops that, in their vector form, are not bound to the chromosome. The terms "plasmid" and "vector" are used interchangeably herein, inasmuch as a plasmid is the most commonly used form of vector. However, also included are such other forms of expression vectors that serve equivalent functions and that become known in the art subsequently hereto.

In some embodiments, the recombinant vector comprises at least one sequence selected from the group consisting of (a) an expression control sequence operatively linked to the polynucleotide sequence; (b) a selection marker operatively linked to the polynucleotide sequence; (c) a marker sequence operatively linked to the polynucleotide sequence; (d) a purification moiety operatively linked to the polynucleotide sequence; (e) a secretion sequence operatively linked to the polynucleotide sequence; and (f) a targeting sequence operatively linked to the polynucleotide sequence.

The expression vectors described herein include a polynucleotide sequence described herein in a form suitable for expression of the polynucleotide sequence in a host cell. It will be appreciated by those skilled in the art that the design of the expression vector can depend on such factors as the choice of the host cell to be transformed, the level of expression of polypeptide desired, etc. The expression vectors described herein can be introduced into host cells to produce polypeptides, including fusion polypeptides, encoded by the polynucleotide sequences as described herein.

Expression of genes encoding polypeptides in prokaryotes, for example, *E. coli*, is often carried out with vectors containing constitutive or inducible promoters directing the expression of either fusion or non-fusion polypeptides. Fusion vectors add a number of amino acids to a polypeptide encoded therein, usually to the amino- or carboxy-terminus of the recombinant polypeptide. Such fusion vectors typically serve one or more of the following three purposes: (1) to increase expression of the recombinant polypeptide; (2) to increase the solubility of the recombinant polypeptide; and (3) to aid in the purification of the recombinant polypeptide by acting as a ligand in affinity purification. Often, in fusion expression vectors, a proteolytic cleavage site is introduced at the junction of the fusion moiety and the recombinant polypeptide. This enables separation of the recombinant polypeptide from the fusion moiety after purification of the fusion polypeptide. Examples of such enzymes, and their cognate recognition sequences, include Factor Xa, thrombin, and enterokinase. Exemplary fusion expression vectors include pGEX (Pharmacia Biotech, Inc., Piscataway, N.J.; Smith et al., *Gene*, 67: 31-40 (1988)), pMAL (New England Biolabs, Beverly, Mass.), and pRITS (Pharmacia Biotech, Inc., Piscataway, N.J.), which fuse glutathione S-transferase (GST), maltose E binding protein, or protein A, respectively, to the target recombinant polypeptide.

Vectors can be introduced into prokaryotic or eukaryotic cells via conventional transformation or transfection techniques. As used herein, the terms "transformation" and "transfection" refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in, for example, Sambrook et al. (supra).

For stable transformation of bacterial cells, it is known that, depending upon the expression vector and transformation technique used, only a small fraction of cells will take up and replicate the expression vector. In order to identify and select these transformants, a gene that encodes a selectable marker (e.g., resistance to an antibiotic) can be introduced into the host cells along with the gene of interest. Selectable markers include those that confer resistance to drugs such as, but not limited to, ampicillin, kanamycin, chloramphenicol, or tetracycline. Nucleic acids encoding a selectable marker can be introduced into a host cell on the same vector as that encoding a polypeptide described herein or can be introduced on a separate vector. Host cells which are stably transformed with the introduced nucleic acid, resulting in recombinant cells, can be identified by growth in the presence of an appropriate selection drug.

Similarly, for stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to an antibiotic) can be introduced into the host cells along with the gene of interest. Preferred selectable markers include those which confer resistance to drugs, such as G418, hygromycin, and methotrexate. Nucleic acids encoding a selectable marker can be introduced into a host cell on the same vector as that encoding a polypeptide described herein or can be introduced on a separate vector. Host cells stably transfected with the introduced nucleic acid, resulting in recombinant cells, can be identified by growth in the presence of an appropriate selection drug.

"Gene knockout", as used herein, refers to a procedure by which a gene encoding a target protein is modified or inactivated so to reduce or eliminate the function of the intact protein. Inactivation of the gene may be performed by general methods such as mutagenesis by UV irradiation or treatment with N-methyl-N'-nitro-N-nitrosoguanidine, site-directed mutagenesis, homologous recombination, insertion-deletion mutagenesis, or "Red-driven integration" (Datsenko et al., *Proc. Natl. Acad. Sci. USA*, 97:6640-45, 2000). For example, in one embodiment, a construct is introduced into a parental cell, such that it is possible to select for homologous recombination events in the resulting recombinant cell. One of skill in the art can readily design a knock-out construct including both positive and negative selection genes for efficiently selecting transfected (i.e., recombinant) cells that undergo a homologous recombination event with the construct. The alteration in the parental cell may be obtained, for example, by replacing through a single or double crossover recombination a wild type (i.e., endogenous) DNA sequence by a DNA sequence containing the alteration. For convenient selection of transformants (i.e., recombinant cells), the alteration may, for example, be a DNA sequence encoding an antibiotic resistance marker or a gene complementing a possible auxotrophy of the host cell. Mutations include, but are not limited to, deletion-insertion mutations. An example of such an alteration in a recombinant cell includes a gene disruption, i.e., a perturbation of a gene such that the product that is normally produced from this gene is not produced in a functional form. This could be due to a complete deletion, a deletion and insertion of a selective marker, an insertion of a selective marker, a frameshift mutation, an in-frame deletion, or a point mutation that leads to premature termination. In some instances, the entire mRNA for the gene is absent. In other situations, the amount of mRNA produced varies.

The phrase "increasing the level of expression of an endogenous polypeptide" means to cause the overexpression of a polynucleotide sequence encoding the endogenous polypeptide, or to cause the overexpression of an endogenous polypeptide sequence. The degree of overexpression can be about 1.5-fold or more, about 2-fold or more, about 3-fold or more, about 5-fold or more, about 10-fold or more, about 20-fold or more, about 50-fold or more, about 100-fold or more, or any range therein.

The phrase "increasing the level of activity of an endogenous polypeptide" means to enhance the biochemical or biological function (e.g., enzymatic activity) of an endogenous polypeptide. The degree of enhanced activity can be about 10% or more, about 20% or more, about 50% or more, about 75% or more, about 100% or more, about 200% or more, about 500% or more, about 1000% or more, or any range therein.

The phrase, "the expression of said polynucleotide sequence is modified relative to the wild type polynucleotide sequence", as used herein means an increase or decrease in the level of expression and/or activity of an endogenous polynucleotide sequence. In some embodiments, an exogenous regulatory element which controls the expression of an endogenous polynucleotide is an expression control sequence which is operably linked to the endogenous polynucleotide by recombinant integration into the genome of the host cell. In some embodiments, the expression control sequence is integrated into a host cell chromosome by homologous recombination using methods known in the art.

As used herein, the phrase "under conditions effective to express said polynucleotide sequence(s)" means any conditions that allow a recombinant cell to produce a desired fatty acid derivative. Suitable conditions include, for example, fermentation conditions. Fermentation conditions can comprise many parameters, such as temperature ranges, levels of aeration, and media composition. Each of these conditions, individually and in combination, allows the host cell to grow. Exemplary culture media include broths or gels. Generally, the medium includes a carbon source that can be metabolized by a recombinant cell directly. Fermentation denotes the use of a carbon source by a production host, such as a recombinant microbial cell of the invention. Fermentation can be aerobic, anaerobic, or variations thereof (such as micro-aerobic). As will be appreciated by those of skill in the art, the conditions under which a recombinant microbial cell can process a carbon source into an oc-acyl-ACP or a desired oc-FA derivative (e.g., an oc-fatty acid, an oc-fatty ester, an oc-fatty aldehyde, an oc-fatty alcohol, an ec-alkane, an ec-alkene or an ec-ketone) will vary in part, based upon the specific microorganism. In some embodiments, the process occurs in an aerobic environment. In some embodiments, the process occurs in an anaerobic environment. In some embodiments, the process occurs in a micro-aerobic environment.

As used herein, the term "carbon source" refers to a substrate or compound suitable to be used as a source of carbon for prokaryotic or simple eukaryotic cell growth. Carbon sources can be in various forms, including, but not limited to polymers, carbohydrates (e.g., sugars, such as monosaccharides, disaccharides, oligosaccharides, and polysaccharides), acids, alcohols, aldehydes, ketones, amino acids, peptides, and gases (e.g., CO and $CO_2$). Exemplary carbon sources include, but are not limited to: monosaccharides, such as glucose, fructose, mannose, galactose, xylose, and arabinose; disaccharides, such as sucrose, maltose, cellobiose, and turanose; oligosaccharides, such as fructo-oligosaccharide and galacto-oligosaccharide; polysaccharides, such as starch, cellulose, pectin, and xylan; cellulosic material and variants such as hemicelluloses, methyl cellulose and sodium carboxymethyl cellulose; saturated or unsaturated fatty acids, succinate, lactate, and acetate; alcohols, such as ethanol, methanol, and glycerol, or mixtures thereof. The carbon source can be a product of photosynthesis, such as glucose. In certain preferred embodiments, the carbon source is derived from biomass. In another preferred embodiment, the carbon source comprises sucrose. In another preferred embodiment, the carbon source comprises glucose.

As used herein, the term "biomass" refers to any biological material from which a carbon source is derived. In some embodiments, a biomass is processed into a carbon source, which is suitable for bioconversion. In other embodiments, the biomass does not require further processing into a carbon source. The carbon source can be converted into a biofuel. An exemplary source of biomass is plant matter or vegetation, such as corn, sugar cane, or switchgrass. Another exemplary source of biomass is metabolic waste products, such as animal matter (e.g., cow manure). Further exemplary sources of biomass include algae and other marine plants. Biomass also includes waste products from industry, agriculture, forestry, and households, including, but not limited to, fermentation waste, ensilage, straw, lumber, sewage, garbage, cellulosic urban waste, and food leftovers. The term "biomass" also can refer to sources of carbon, such as carbohydrates (e.g., monosaccharides, disaccharides, or polysaccharides).

To determine if conditions are sufficient to allow production of a product or expression of a polypeptide, a recombinant microbial cell can be cultured, for example, for about 4, 8, 12, 24, 36, 48, 72, or more hours. During and/or after culturing, samples can be obtained and analyzed to determine if the conditions allow production or expression. For example, the recombinant microbial cells in the sample or the medium in which the recombinant microbial cells were grown can be tested for the presence of a desired product. When testing for the presence of a desired product, such as an odd chain fatty acid derivative (e.g., an oc-fatty acid, an oc-fatty ester, an oc-fatty aldehyde, an oc-fatty alcohol, or an ec-hydrocarbon), assays such as, but not limited to, gas chromatography (GC), mass spectroscopy (MS), thin layer chromatography (TLC), high-performance liquid chromatography (HPLC), liquid chromatography (LC), GC coupled with a flame ionization detector (GC-FID), GC-MS, and LC-MS, can be used. When testing for the expression of a polypeptide, techniques such as, but not limited to, Western blotting and dot blotting, may be used.

As used herein, the term "microorganism" means prokaryotic and eukaryotic microbial species from the domains Archaea, Bacteria and Eucarya, the latter including yeast and filamentous fungi, protozoa, algae, and higher Protista. The terms "microbes" and "microbial cells" (i.e., cells from microbes) and are used interchangeably with "microorganisms" and refer to cells or small organisms that can only be seen with the aid of a microscope.

In some embodiments, the host cell (e.g., parental cell) is a microbial cell. In some embodiments, the host cell is a microbial cell selected from the genus *Escherichia, Bacillus, Lactobacillus, Pantoea, Zymomonas, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia, Streptomyces, Synechococcus, Chlorella,* or *Prototheca*.

In other embodiments, the host cell is a *Bacillus lentus* cell, a *Bacillus brevis* cell, a *Bacillus stearothermophilus* cell, a *Bacillus lichenoformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell.

In other embodiments, the host cell is a *Trichoderma koningii* cell, a *Trichoderma viride* cell, a *Trichoderma reesei* cell, a *Trichoderma longibrachiatum* cell, an *Aspergillus awamori* cell, an *Aspergillus fumigates* cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcus opacus* cell, a *Rhizomucor miehei* cell, or a *Mucor michei* cell.

In yet other embodiments, the host cell is a *Streptomyces lividans* cell or a *Streptomyces murinus* cell.

In yet other embodiments, the host cell is an Actinomycetes cell.

In some embodiments, the host cell is a *Saccharomyces cerevisiae* cell.

In still other embodiments, the host cell is a CHO cell, a COS cell, a VERO cell, a BHK cell, a HeLa cell, a Cvl cell, an MDCK cell, a 293 cell, a 3T3 cell, or a PC12 cell.

In some embodiments, the host cell is a cell from an eukaryotic plant, algae, cyanobacterium, green-sulfur bacterium, green non-sulfur bacterium, purple sulfur bacterium, purple non-sulfur bacterium, extremophile, yeast, fungus, an engineered organism thereof, or a synthetic organism. In some embodiments, the host cell is light-dependent or fixes carbon. In some embodiments, the host cell has autotrophic activity. In some embodiments, the host cell has photoautotrophic activity, such as in the presence of light. In some embodiments, the host cell is heterotrophic or mixotrophic in the absence of light.

In certain embodiments, the host cell is a cell from *Avabidopsis thaliana, Panicum virgatum, Miscanthus giganteus, Zea mays, Botryococcuse braunii, Chlamydomonas reinhardtii, Dunaliela salina, Synechococcus* Sp. PCC 7002, *Synechococcus* Sp. PCC 7942, *Synechocystis* Sp. PCC 6803, *Thermosynechococcus* elongates BP-1, *Chlorobium tepidum, Chlorojlexus auranticus, Chromatiumm vinosum, Rhodospirillum rubrum, Rhodobacter capsulatus, Rhodopseudomonas palusris, Clostridium ljungdahlii, Clostridiuthermocellum, Penicillium chrysogenum, Pichia pastoris, Saccharomyces cerevisiae, Schizosaccharomyces pombe, Pseudomonas jluorescens, Pantoea citrea* or *Zymomonas mobilis*. In certain embodiments, the host cell is a cell from *Chlorella fusca, Chlorella protothecoides, Chlorella pyrenoidosa, Chlorella kessleri, Chlorella vulgaris, Chlorella saccharophila, Chlorella sorokiniana, Chlorella ellipsoidea, Prototheca stagnora, Prototheca portoricensis, Prototheca moriformis, Prototheca wickerhamii,* or *Prototheca zopfii*.

In some embodiments, the host cell is a bacterial cell. In some embodiments, the host cell is a Gram-positive bacterial cell. In some embodiments, the host cell is a Gram-negative bacterial cell.

In certain embodiments, the host cell is an *E. coli* cell. In some embodiments, the *E. coli* cell is a strain B, a strain C, a strain K, or a strain W *E. coli* cell.

In certain embodiments of the invention, the host cell is engineered to express (or overexpress) a transport protein. Transport proteins can export polypeptides and organic compounds (e.g., fatty acids or derivatives thereof) out of a host cell.

As used herein, the term "metabolically engineered" or "metabolic engineering" involves rational pathway design and assembly of polynucleotides corresponding to biosynthetic genes, genes associated with operons, and control elements of such polynucleotides, for the production of a desired metabolite such as, for example, an oc-β-ketoacyl-ACP, an oc-acyl-ACP, or an oc-fatty acid derivative, in a recombinant cell, such as a recombinant microbial cell as described herein. "Metabolic engineering" can further include optimization of metabolic flux by regulation and optimization of transcription, translation, protein stability and protein functionality using genetic engineering and appropriate culture conditions including the reduction of, disruption, or knocking out of, a competing metabolic pathway that competes with an intermediate leading to a desired pathway. A "biosynthetic gene" can be endogenous (native) to the host cell (i.e., a gene which is not modified from the host cell), or, can be exogenous (heterologous) to the host cell either by virtue of being foreign to the host cell, or by being modified by mutagenesis, recombination, and/or association in the recombinant cell with a exogenous (heterologous) expression control sequence. A biosynthetic gene encodes a "biosynthetic polypeptide" or a "biosynthetic enzyme".

The term "biosynthetic pathway", also referred to as "metabolic pathway", refers to a set of biochemical reactions, catalyzed by biosynthetic enzymes, which convert one chemical species into another. As used herein, the term "fatty acid biosynthetic pathway" (or more simply, "fatty acid pathway") refers to a set of biochemical reactions that produces fatty acid derivatives (e.g., fatty acids, fatty esters, fatty aldehydes, fatty alcohols, alkanes, alkenes, ketones, and so forth). The fatty acid pathway includes fatty acid pathway biosynthetic enzymes (i.e., "fatty acid pathway enzymes") that can be engineered, as described herein, to produce fatty acid derivatives, and in some embodiments can be expressed with additional enzymes to produce fatty acid derivatives having desired carbon chain characteristics. For example, an "odd chain fatty acid biosynthetic pathway" (i.e., an "oc-FA pathway") as described herein includes enzymes sufficient to produce oc-fatty acid derivatives.

The term "recombinant microbial cell" refers to a microbial cell (i.e., a microorganism) that has been genetically modified (i.e., "engineered") by the introduction of genetic material into a "parental microbial cell" (i.e., host cell) of choice, thereby modifying or altering the cellular physiology and biochemistry of the parental microbial cell. Through the introduction of genetic material, the recombinant microbial cell acquires a new or improved property compared to that of the parental microbial cell, such as, for example, the ability to produce a new intracellular metabolite, or greater quantities of an existing intracellular metabolite. Recombinant microbial cells provided herein express a plurality of biosynthetic enzymes (e.g., fatty acid pathway enzymes, such as oc-FA pathway enzymes) involved in pathways for the production of, for example, an oc-acyl-ACP intermediate or an oc-fatty acid derivative, from a suitable carbon source. The genetic material introduced into the parental microbial cell may contain gene(s), or parts of genes, encoding one or more of the enzymes involved in a biosynthetic pathway (that is, biosynthetic enzymes) for the production of an oc-fatty acid derivative, and may alternatively or in addition include additional elements for the expression and/or regulation of expression of genes encoding such biosynthetic enzymes, such as promoter sequences. Accordingly, recombinant microbial cells described herein have been genetically engineered to express or overexpress biosynthetic enzymes involved in oc-fatty acid (oc-FA) biosynthetic pathways as described herein.

It is understood that the terms "recombinant microbial cell" and "recombinant microorganism" refer not only to the particular recombinant microbial cell/microorganism, but to the progeny or potential progeny of such a cell.

A recombinant microbial cell can, alternatively or in addition to comprising genetic material introduced into the parental microbial cell, include a reduction, disruption, deletion or a "knocking-out" of a gene or polynucleotide to alter the cellular physiology and biochemistry of the parental microbial cell. Through the reduction, disruption, deletion or knocking-out of a gene or polynucleotide (also known as "attenuation" of the gene or polynucleotide), the recombinant microbial cell acquires a new or improved property (such as, for example, the ability to produce a new or greater quantities of an intracellular metabolite, the ability to improve the flux of a metabolite through a desired pathway, and/or the ability to reduce the production of an undesirable by-product) compared to that of the parental microbial cell.

Engineering Recombinant Microbial Cells to Produce Odd Chain Fatty Acid Derivatives Many microbial cells normally produce straight chain fatty acids in which the linear aliphatic chains predominantly contain an even number of carbon atoms, and generally produce relatively low amounts of fatty acids having linear aliphatic chains containing an odd number of carbon atoms. The relatively low amounts of linear odd chain fatty acids (oc-FAs) and other linear odd chain fatty acid derivatives (oc-FA derivatives) produced by such microbial cells, such as E. coli, can in some instances be attributed to low levels of propionyl-CoA present in such cells. Such cells predominantly utilize acetyl-CoA as the primer molecule for fatty acid biosynthesis, leading to the majority of fatty acids and other fatty acid derivatives produced in such cells being linear even chain fatty acids (ec-FAs) and other linear even chain fatty acid derivatives (ec-FA derivatives).

The invention is based in part on the discovery that by engineering a microorganism to produce an increased amount of propionyl-CoA compared to that produced by a parental microorganism, the engineered microorganism produces a greater amount (titer) of oc-FA derivatives compared to the amount of oc-FA derivatives produced by the parental microorganism, and/or produces a fatty acid derivative composition having a higher proportion of oc-FA derivatives compared to the proportion of oc-FA derivatives in the fatty acid derivative composition produced by the parental microorganism.

As the ultimate goal is to provide environmentally responsible and cost-effective methods for the production of fatty acid derivatives, including oc-FA derivatives, on an industrial scale starting from a carbon source (such as, for example, carbohydrate or biomass), improvements in yield of microbially produced oc-FA derivative molecules and/or optimization of the composition of microbially produced fatty acid derivative molecules (such as by increasing the proportion of odd chain product relative to even chain product) is desirable. Accordingly, strategies for the overproduction of various pathway intermediates have been examined to increase metabolic flux through pathways leading to odd chain fatty acid production. Pathways that direct metabolic flux from a starting material, such as a sugar, to propionyl-CoA, through an odd chain acyl-ACP (oc-acyl-ACP) intermediate, to an oc-FA derivative product, can be engineered in an industrially useful microorganism.

In one aspect, the invention includes a recombinant microbial cell comprising one or more polynucleotides encoding polypeptides (e.g., enzymes) having enzymatic activities which participate in the biosynthesis of propionyl-CoA, and/or participate in the biosynthesis of an oc-acyl-ACP intermediate, when the recombinant microbial cell is cultured in the presence of a carbon source under conditions effective to expresses the polynucleotides. In some embodiments, the recombinant microbial cell further comprises one or more polynucleotides each encoding a polypeptide having fatty acid derivative enzyme activity, wherein the recombinant microbial cell produces an odd chain fatty acid derivative when cultured in the presence of a carbon source under conditions sufficient to expresses the polynucleotides. The invention also includes methods of making compositions comprising odd chain fatty acid derivatives, comprising culturing a recombinant microbial cell of the invention. The invention also includes methods of increasing the amount of propionyl-CoA produced by a microbial cell, and methods of increasing the amount or proportion of odd chain fatty acid derivatives produced by a microbial cell, and other features apparent upon further review.

The recombinant microbial cell can be a filamentous fungi, an algae, a yeast, or a prokaryote such as a bacterium (e.g., an E. coli or a Bacillus sp).

In general, odd chain fatty acid derivatives (such as, odd chain fatty acids, odd chain fatty esters (including odd chain fatty acid methyl esters (oc-FAMEs), odd chain fatty acid ethyl esters (oc-FAEEs), and odd chain wax esters), odd chain fatty aldehydes, odd chain fatty alcohols, and, due to decarbonylation or decarboxylation of an odd chain precursor, even chain hydrocarbons such as even chain alkanes, even chain alkenes, even chain terminal olefins, even chain internal olefins, and even chain ketones) can be produced in a recombinant microbial cell of the invention via the odd chain fatty acid biosynthetic pathway ("oc-FA pathway") depicted in FIG. 1B.

To produce an odd chain fatty acid derivative, the recombinant microbial cell utilizes propionyl-CoA as a "primer" for the initiation of the fatty acyl chain elongation process. As shown in FIG. 1B, the fatty acyl elongation process initially involves condensation of the odd chain length primer molecule propionyl-CoA with a malonyl-ACP molecule, catalyzed by an enzyme having β-ketoacyl ACP synthase activity (such as, a β-ketoacyl ACP synthase III enzyme), to form an initial odd chain β-ketoacyl-ACP intermediate (e.g., 3-oxovaleryl-ACP), as depicted in step (D) of FIG. 1B. The odd chain β-ketoacyl-ACP intermediate undergoes keto-reduction, dehydration and enoyl-reduction at the β-carbon via the fatty acid synthase (FAS) complex to form an initial odd chain acyl-ACP intermediate, which undergoes further cycles of condensation with malonyl-ACP, keto-reduction, dehydration, and enoyl-reduction, adding two carbon units per cycle to form acyl-ACP intermediates of increasing odd-numbered carbon chain lengths ("oc-acyl-ACP") as depicted in step (E) of FIG. 1B. The oc-acyl-ACP intermediate reacts with one or more fatty acid derivative enzymes, as depicted in step (F) of FIG. 1B, resulting in an odd chain fatty acid derivative (oc-FA derivative) product. This is in contrast to the process in a cell that produces relatively low levels of propionyl-CoA (such as, for example, a wild-type *E. coli* cell). Such a cell produces predominantly straight-chain fatty acids having an even number of carbon atoms, and low or trace amounts of straight-chain fatty acids having an odd number of carbon atoms. As depicted in FIG. 1A, the even chain length primer molecule acetyl-CoA initially condenses with a malonyl-ACP molecule to form an even chain β-keto acyl-ACP intermediate (e.g., acetoacetyl-ACP), as depicted in step (D) of FIG. 1A, which likewise undergoes FAS-catalyzed cycles of keto-reduction, dehydration, enoyl-reduction and condensation with additional malonyl-ACP molecules, likewise adding two carbon units per cycle, this time to form acyl-ACP intermediates of increasing even-numbered carbon chain lengths ("ec-acyl-ACP") as depicted in step (E) of FIG. 1A. The ec-acyl-ACP intermediate reacts with one or more fatty acid derivative enzymes, as depicted in step (F) of FIG. 1A, resulting in an even chain fatty acid derivative.

The propionyl-CoA "primer" molecule can be supplied to the oc-FA biosynthetic pathway of the recombinant microbial cell of the invention by a number of methods. Methods to increase the production of propionyl-CoA in a microbial cell include, but are not limited to, the following:

Propionyl-CoA can be generated by the native biosynthetic machinery of the parental microbial cell (e.g., by enzymes endogenous to the parental microbial cell). In such instances, to increase the amount of propionyl-CoA produced in the recombinant microbial cell, one or more enzymes endogenous to the parental microbial cell which contribute to the production of propionyl-CoA can be overexpressed in the recombinant microbial cell.

Figure 2:
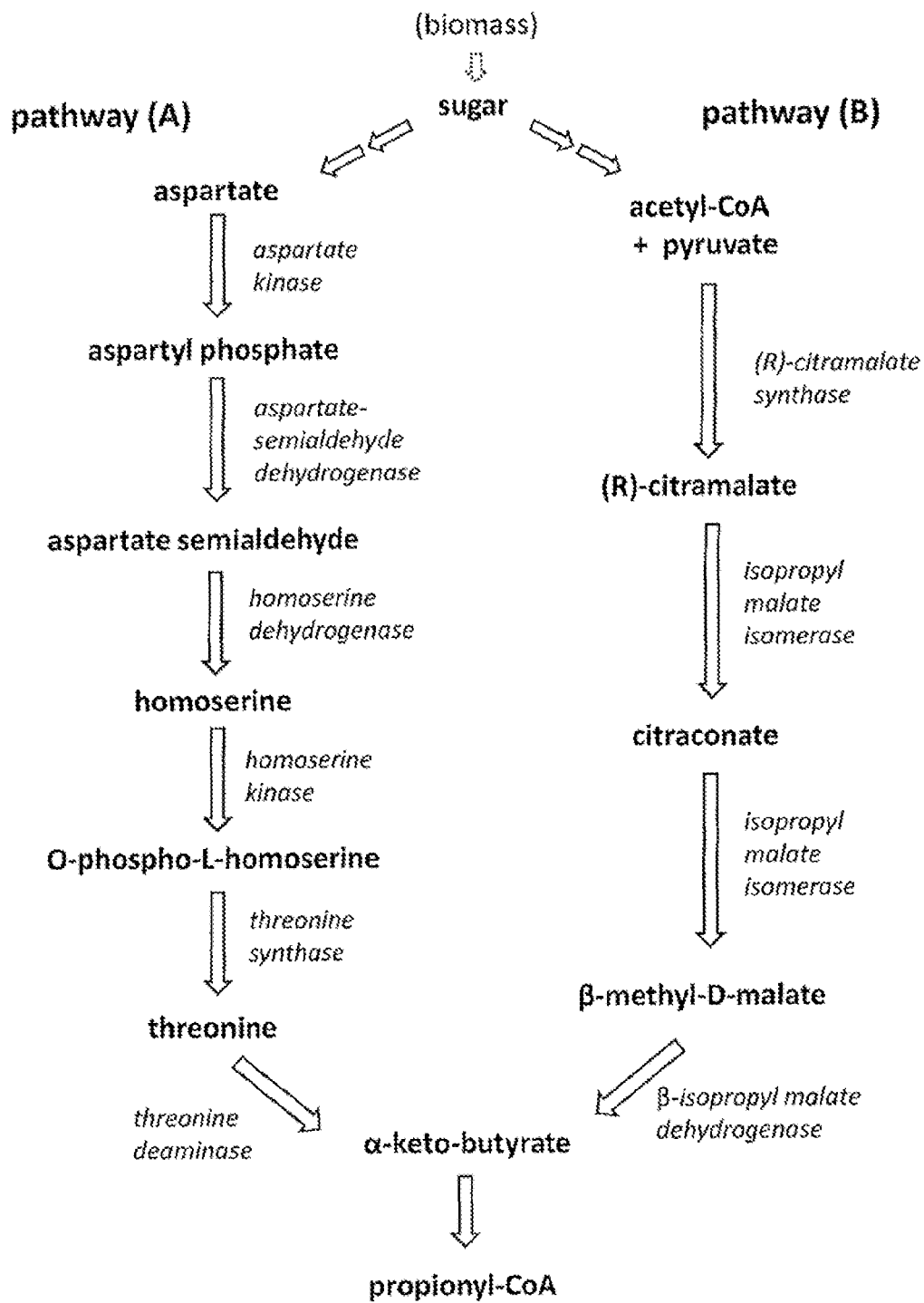
FIG. 2 depicts exemplary pathways for increased production of propionyl-CoA via the intermediate α-ketobutyrate, by a threonine biosynthetic pathway (pathway (A)) and by a citramalate biosynthetic pathway (pathway (B)) as described herein.

Propionyl-CoA can be generated by engineering the cell to overexpress endogenous enzymes and/or express exogenous enzymes which divert metabolic flux through the intermediate α-ketobutyrate, as shown in FIG. 2. Non-limiting examples of enzymes for use in engineering such pathways are provided in Tables 1 and 2, below.

Figure 3:
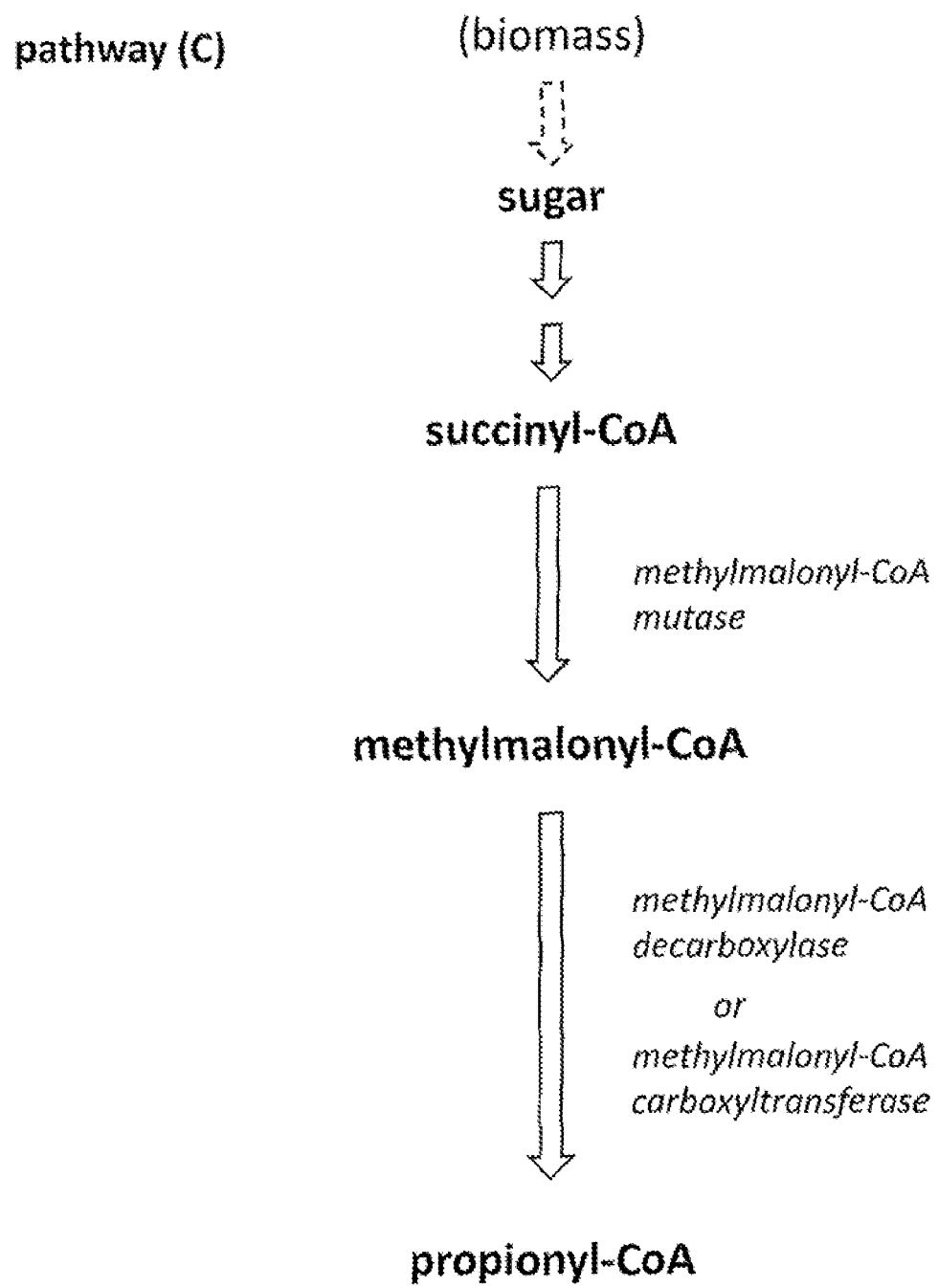
FIG. 3 depicts an exemplary pathway for increased production of propionyl-CoA via a methylmalonyl-CoA biosynthetic pathway (pathway (C)) as described herein.

Propionyl-CoA can be generated by engineering the cell to overexpress endogenous enzymes and/or express exogenous enzymes which divert metabolic flux from succinyl-CoA through the intermediate methylmalonyl-CoA, as shown FIG. 3. Non-limiting examples of enzymes for use in engineering such pathways are provided in Table 3, below.

In an exemplary approach, propionyl-CoA can be generated by engineering the cell to overexpress endogenous enzymes and/or express exogenous enzymes which divert metabolic flux from malonyl-CoA through the intermediates malonate semialdehyde and 3-hydroxypropionate. Non-limiting examples of enzymes for use in engineering such pathways are provided, for example, in United States Patent Application Publication Number US20110201068A1.

In another approach, propionyl-CoA can be generated by engineering the cell to overexpress endogenous enzymes and/ or express exogenous enzymes which divert metabolic flux from D-lactate through the intermediates lactoyl-CoA and acryloyl-CoA. Non-limiting examples of enzymes for use in engineering such pathways are provided, for example, in United States Patent Application Publication Number US20110201068A1.

As noted above, initiation of the odd chain elongation process involves condensation of propionyl-CoA with a malonyl-ACP molecule to form an oc-β-ketoacyl-ACP intermediate. This step, as represented by part (D) of FIG. 1B, is catalyzed in the recombinant microbial cell by an enzyme having β-ketoacyl-ACP synthase activity, preferably β-ketoacyl-ACP synthase III activity (e.g., EC 2.3.1.180) which utilizes propionyl-CoA as a substrate. The enzyme can be endogenous to the recombinant microbial cell, or can be exogenous to the recombinant microbial cell.

In one embodiment, a polynucleotide encoding a polypeptide endogenous to the parental microbial cell having β-ketoacyl-ACP synthase activity that utilizes propionyl-CoA as a substrate is expressed or is overexpressed in the recombinant microbial cell. In another embodiment, a polynucleotide encoding a polypeptide having β-ketoacyl-ACP synthase activity that utilizes propionyl-CoA as a substrate which is exogenous to the parental microbial cell is expressed in the recombinant microbial cell.

The oc-β-ketoacyl-ACP intermediate generated in step (D) of the oc-FA pathway (FIG. 1B) can undergo elongation by successive cycles of keto-reduction, dehydration and enoyl-reduction at the beta carbon and further condensation with malonyl-ACP molecules catalyzed by a fatty acid synthase (FAS) complex, such as for example a Type II FAS complex, adding 2-carbon units to the lengthening odd-carbon chain of the oc-acyl-ACP intermediate as represented by step (E) of FIG. 1B. In one embodiment, an endogenous FAS complex native to the recombinant microbial cell catalyzes cycles of condensation with malonyl-ACP/keto-reduction/dehydration/enoyl-reduction to produce the oc-acyl-ACP intermediate.

Odd chain fatty acid derivatives (such as oc-fatty acids, oc-fatty esters, oc-fatty aldehydes, oc-fatty alcohols, ec-ketones, and ec-hydrocarbons) can be produced from the oc-acyl-ACP intermediate, as will be described in more detail below. Accordingly, in some embodiments, the recombinant microbial cell further comprises one or more polynucleotide sequences each encoding a polypeptide having fatty acid derivative enzyme activity, such as thioesterase (e.g., TesA), decarboxylase, carboxylic acid reductase (CAR; e.g., CarA, CarB, or FadD9), alcohol dehydrogenase/aldehyde reductase; aldehyde decarbonylase (ADC), fatty alcohol forming acyl-CoA reductase (FAR), acyl ACP reductase (AAR), ester synthase, acyl-CoA reductase (ACR1), OleA, OleCD, or OleBCD, wherein the microbial cell produces a composition comprising an oc-fatty acid, an oc-fatty ester (such as an oc-fatty acid methyl ester, an oc-fatty acid ethyl ester, an oc-wax ester), an oc-fatty aldehyde, an oc-fatty alcohol, an ec-ketone, or an ec-hydrocarbon (such as an ec-alkane, an ec-alkene, an ec-terminal olefin, or an ec-internal olefin), when the recombinant microbial cell is cultured in the presence of a carbon source under conditions effective to expresses the polynucleotides. The invention also includes methods for the production of an oc-fatty acid derivative comprising culturing a recombinant microbial cell of the invention.

Engineering Microbial Cells to Produce Increased Amounts of Propionyl-CoA

In one aspect, the invention includes a method of increasing the amount of odd chain fatty acid derivatives produced by a microbial cell, which comprises engineering a parental microbial cell to produce an increased amount of propionyl-CoA. Engineering the parental microbial cell to produce an increased amount of propionyl-CoA can be accomplished, for example, by engineering the cell to express polynucleotides encoding: (a) polypeptides having aspartokinase activity, homoserine dehydrogenase activity, homoserine kinase activity, threonine synthase activity, and threonine deaminase activity; (b) polypeptides having (R)-citramalate synthase activity, isopropylmalate isomerase activity, and beta-isopropylmalate dehydrogenase activity; or (c) a polypeptide having methylmalonyl-CoA mutase activity and one or more polypeptides having methylmalonyl-CoA decarboxylase activity and methylmalonyl carboxyltransferase activity, and optionally a polypeptide having methylmalonyl epimerase activity; wherein at least one polypeptide is exogenous to the recombinant microbial cell, or expression of at least one polynucleotide is modulated in the recombinant microbial cell as compared to the expression of the polynucleotide in the parental microbial cell, and wherein the recombinant microbial cell produces a greater amount of propionyl-CoA when cultured in the presence of a carbon source under conditions effective to express the polynucleotides, relative to the amount of propionyl-CoA produced by the parental microbial cell cultured under the same conditions.

In some embodiments, at least one polypeptide encoded by a polynucleotide according to (a) is an exogenous polypeptide (for example, a polypeptide originating from an organism other than the parental microbial cell, or, a variant of a polypeptide native to the parental microbial cell). In some instances, at least one polypeptide encoded by a polynucleotide according to (a) is an endogenous polypeptide (that is, a polypeptide native to the parental microbial cell), and the endogenous polypeptide is overexpressed in the recombinant microbial cell.

In some embodiments, at least one polypeptide encoded by a polynucleotide according to (b) is an exogenous polypeptide. In some instances, at least one polypeptide encoded by a polynucleotide according to (b) is an endogenous polypeptide, and the endogenous polypeptide is overexpressed in the recombinant microbial cell.

In some embodiments, the recombinant microbial cell comprises one or more polynucleotide according to (a) and one or more polynucleotide according to (b). In some instances, at least one polypeptide encoded by a polynucleotide according to (a) or (b) is an exogenous polypeptide. In some instances, at least one polypeptide encoded by a polynucleotide according to (a) or (b) is an endogenous polypeptide, and the endogenous polypeptide is overexpressed in the recombinant microbial cell.

In some embodiments, at least one polypeptide encoded by a polynucleotide according to (c) is an exogenous polypeptide. In some instances, at least one polypeptide encoded by a polynucleotide according to (c) is an endogenous polypeptide, and the endogenous polypeptide is overexpressed in the recombinant microbial cell.

By engineering a parental microbial cell to obtain a recombinant microbial cell that has increased metabolic flux through propionyl-CoA compared to the parental (e.g., non-engineered) microbial cell, the engineered microbial cell produces a greater amount (titer) of oc-FA derivative compared to the amount of oc-FA derivative produced by the parental microbial cell, and/or produces a fatty acid derivative composition having a higher proportion of oc-FA derivative compared to the proportion of oc-FA derivative in the fatty acid derivative composition produced by the parental microbial cell.

Accordingly, in another aspect, the invention includes a method of increasing the amount or proportion of odd chain fatty acid derivatives produced by a microbial cell, the method comprising engineering a parental microbial cell to obtain a recombinant microbial cell which produces a greater amount, or is capable of producing a greater amount, of propionyl-CoA relative to the amount of propionyl-CoA produced by the parental microbial cell cultured under the same conditions, wherein, when the recombinant microbial cell and the parental microbial cell are each cultured in the presence of a carbon source under identical conditions effective to increase the level of propionyl-CoA in the recombinant microbial cell relative to the parental microbial cell, the culture of the recombinant microbial cell produces a greater amount or a greater proportion of odd chain fatty acid derivatives relative to the amount or proportion of odd chain fatty acid derivatives produced by the parental microbial cell. In some embodiments, the recombinant microbial cell comprises polynucleotides encoding polypeptides according to one or more of pathways (a), (b), and (c), as described in more detail below, wherein at least one encoded polypeptide is exogenous to the recombinant microbial cell, or wherein expression of at least one polynucleotide is modulated in the recombinant microbial cell as compared to the expression of the polynucleotide in the parental microbial cell. In some embodiments, the recombinant microbial cell comprises at least one polynucleotide encoding a polypeptide having fatty acid derivative enzyme activity. In some embodiments, the recombinant microbial cell comprises a polynucleotide encoding a polypeptide having β-ketoacyl-ACP synthase activity that utilizes propionyl-CoA as a substrate.

Exemplary metabolic pathways useful for increasing propionyl-CoA production in a recombinant microbial cell are described below. It is to be understood that these exemplary pathways for increasing propionyl-CoA production in a recombinant cell are not intended to limit the scope of the invention; any suitable metabolic pathway that increases propionyl-CoA production in the cell and/or increases metabolic flux in the cell through the propionyl-CoA intermediate is suitable for use in recombinant microbial cells, compositions, and methods of the invention. Metabolic pathways which increase propionyl-CoA production and/or increase metabolic flux through the propionyl-CoA intermediate are therefore suitable for use in recombinant microbial cells, compositions, and methods of the invention.

Production of Propionyl-CoA Via an α-Ketobutyrate Intermediate

Manipulation of various amino acid biosynthetic pathways has been shown to increase the production of those various amino acids in microbial cells (Guillouet S., et al., *Appl. Environ. Microbiol.* 65:3100-3107 (1999); Lee K. H., et al., *Mol. Syst. Biol.* 3:149 (2007)). Amino acid biosynthetic pathways have been used in the production of short chain branched alcohols in *E. coli* (Atsumi S, and Liao J. C., *Appl. Environ. Microbiol.* 74(24): 7802-7808 (2008); Cann A. F. and Liao J. C., *Appl Microbiol Biotechnol.* 81(1):89-98 (2008); Zhang K., et al., *Proc. Natl. Acad. Sci. U S A.* 105 (52):20653-20658 (2008)).

Directing the flux of certain amino acid biosynthetic metabolites to the production of the intermediate α-ketobutyrate (also known as alpha-ketobutyrate, 2-ketobutyrate, 2-ketobutanoate, 2-oxobutyrate and 2-oxobutanoate) results in increased propionyl-CoA production. Accordingly, in one embodiment, the invention includes a recombinant microbial cell comprising polynucleotides encoding one or more enzymes (i.e., "oc-FA pathway enzymes") which participate in the conversion of a carbon source (for example, a carbohydrate, such as a sugar) to α-ketobutyrate when the recombinant microbial cell is cultured in the presence of the carbon source under conditions sufficient to expresses the polynucleotides. The α-ketobutyrate molecule is an intermediate in the microbial production of propionyl-CoA which serves as a primer in the production of linear odd chain fatty acid derivatives according to the oc-FA pathway (FIG. 1B).

Pyruvate dehydrogenase complex (PDC) catalyzes the oxidative decarboxylation of α-ketobutyrate to produce propionyl-CoA in bacteria (Danchin, A. et al., *Mol. Gen. Genet.* 193: 473-478 (1984); Bisswanger, H., *J. Biol. Chem.* 256:815-822 (1981)). The pyruvate dehydrogenase complex is a multienzyme complex that contains three activities: a pyruvate decarboxylase (E1), a dihydrolipoyl transacetylase (E2), and a dihydrolipoyl dehydrogenase (E3). Other suitable ketoacid dehydrogenase complexes exist that use a similar catalytic scheme employing α-ketoacid substrates other than pyruvate. The TCA cycle α-ketoglutarate dehydrogenase complex is an example. In one embodiment, the pyruvate dehydrogenase complex endogenous to the host cell (i.e., the pyruvate dehydrogenase complex native to the parental cell) is utilized to catalyze the conversion of α-ketobutyrate to propionyl-CoA. In other embodiments, genes encoding one or more PDC complex polypeptides having pyruvate decarboxylase, dihydrolipoyl transacetylase, and/or dihydrolipoyl dehydrogenase activity are overexpressed in the recombinant microbial cell. Other enzymes or enzyme complexes which catalyze the conversion of α-ketobutyrate to propionyl-CoA can be expressed or overexpressed in the recombinant microbial cell to further increase metabolic flux from α-ketobutyrate to propionyl-CoA.

One or more enzymes endogenous to the parental microbial cell may compete for substrate with enzymes of the engineered oc-FA biosynthetic pathway in the recombinant microbial cell, or may break down or otherwise divert an intermediate (such as, α-ketobutyrate) away from the oc-FA biosynthetic pathway; genes encoding such undesired endogenous enzymes may be attenuated to increase the production of odd chain fatty acid derivatives by the recombinant microbial cell. For example, in $E.\ coli$, endogenous acetohydroxyacid synthase (AHAS) complexes, such as AHAS I (e.g., encoded by ilvBN genes), AHAS II (e.g., encoded by ilvGM genes) and AHAS III (e.g., encoded by ilvIH genes), catalyze the conversion of α-ketobutyrate to α-aceto-α-hydroxybutyrate and may thus divert metabolic flux away from propionyl-CoA and reduce oc-FA production. Deleting or otherwise reducing the expression of one or more endogenous AHAS genes may thus direct biosynthesis in the recombinant microbial cell more towards propionyl-CoA and ultimately more towards odd chain fatty acid production. Other endogenous enzymes which may compete with oc-FA biosynthetic pathway enzymes include enzymes with acetohydroxyacid isomeroreductase activity (e.g., encoded by an ilvC gene) which catalyzes the conversion of α-aceto-α-hydroxybutyrate to 2,3-dihydroxy-3-methylvalerate, and dihydroxy acid dehydratase activity (e.g., encoded by an ilvD gene), which catalyzes the conversion of 2,3-dihydroxy-3-methylvalerate to 2-keto-3-methylvalerate; deleting or otherwise reducing the expression of one or more of these genes may direct biosynthesis in the recombinant microbial cell more towards propionyl-CoA and ultimately more towards odd chain fatty acid production.

Either or both of the following exemplary pathways can be engineered in the recombinant microbial cell to increase metabolic flux through the common α-ketobutyrate intermediate resulting in increased propionyl-CoA production in the cell. These exemplary pathways are shown in FIG. 2 and are described in more detail below.

Pathway A (Threonine Intermediate)

The first pathway leading to the common α-ketobutyrate intermediate, as represented by pathway (A) of FIG. 2, involves production of the intermediate threonine by threonine biosynthetic enzymes, followed by the deamination of threonine to α-ketobutyrate catalyzed by an enzyme with threonine dehydratase activity.

In pathway (A), increasing metabolic flux to threonine can be accomplished by expressing polynucleotides encoding enzymes involved in threonine biosynthesis, including enzymes with aspartate kinase activity (e.g., EC 2.7.2.4; also termed aspartokinase activity), which catalyzes the conversion of aspartate to aspartyl phosphate; aspartate-semialdehyde dehydrogenase activity (e.g., EC 1.2.1.11), which catalyzes the conversion of aspartyl phosphate to aspartate semialdehyde; homoserine dehydrogenase activity (e.g., EC 1.1.1.3), which catalyzes the conversion of aspartate semialdehyde to homoserine; homoserine kinase activity (e.g., EC 2.7.1.39), which catalyzes the conversion of homoserine to O-phospho-L-homoserine; and threonine synthase activity (e.g., EC 4.2.3.1), which catalyzes the conversion of O-phospho-L-homoserine to threonine. Not all of the activities listed above need be engineered in the recombinant microbial cell to increase metabolic flux through the threonine intermediate; in some instances, an activity already present in the parental microbial cell (for example, a polypeptide having that activity which is produced by a native gene in the parental microbial cell) will be sufficient to catalyze a step listed above. In one embodiment, the recombinant microbial cell is engineered to recombinantly express one or more polynucleotides selected from: a polynucleotide encoding a polypeptide having aspartate kinase activity, wherein the polypeptide catalyzes the conversion of aspartate to aspartyl phosphate; a polynucleotide encoding a polypeptide having aspartate-semialdehyde dehydrogenase activity, wherein the polypeptide catalyzes the conversion of aspartyl phosphate to aspartate semialdehyde; a polynucleotide encoding a polypeptide having homoserine dehydrogenase activity, wherein the polypeptide catalyzes the conversion of aspartate semialdehyde to homoserine; a polynucleotide encoding a polypeptide having homoserine kinase activity, wherein the polypeptide catalyzes the conversion of homoserine to O-phospho-L-homoserine; a polynucleotide encoding a polypeptide having threonine synthase activity, wherein the polypeptide catalyzes the conversion of O-phospho-L-homoserine to threonine; wherein the recombinant microbial cell has increased metabolic flux through the pathway intermediate threonine compared to the parental microbial cell. In some instances, the polypeptide encoded by recombinantly expressed polynucleotide is present in the recombinant microbial cell at a greater concentration compared to its concentration in the parent microbial cell when cultured under the same conditions, i.e., the polypeptide is "overexpressed" in the recombinant cell. For example, the recombinantly expressed polynucleotide can be operatively linked to a promoter which expresses the polynucleotide in the recombinant microbial cell at a greater concentration than is normally expressed in the parental microbial cell when cultured under the same conditions. In one embodiment, an $E.\ coli$ thrA gene is used, which encodes a bifunctional ThrA with aspartate kinase and homoserine dehydrogenase activities. In another embodiment, a mutant $E.\ coli$ thrA gene is used, encoding a variant enzyme with aspartate kinase and homoserine dehydrogenase activities and with reduced feedback inhibition relative to the parent ThrA enzyme (designated ThrA*; Ogawa-Miyata, Y., et al., *Biosci. Biotechnol. Biochem.* 65:1149-1154 (2001); Lee J.-H., et al., *J. Bacteriol.* 185: 5442-5451 (2003)).

Threonine can be deaminated to α-ketobutyrate by an enzyme with threonine deaminase activity (e.g., EC 4.3.1.19; also known as threonine ammonia-lyase activity, and was previously classified as EC 4.2.1.16, threonine dehydratase). In one embodiment, threonine deaminase activity which is already present in (i.e., is endogenous to) the parental microbial cell is sufficient to catalyze the conversion of threonine to α-ketobutyrate. In another embodiment, the recombinant microbial cell is engineered to recombinantly express a polypeptide having threonine deaminase activity, wherein the polypeptide catalyzes the conversion of threonine to α-ketobutyrate. In some embodiments, the polypeptide having threonine deaminase activity is overexpressed in the recombinant microbial cell.

Non-limiting examples of enzymes and polynucleotides encoding such enzymes for use in engineering pathway (A) are provided in Table 1.

In some embodiments, a polynucleotide encoding a parent fatty acid pathway polypeptide (such as a polypeptide described in Table 1 or identified by EC number or by homology to an exemplary polypeptide) is modified using methods well known in the art to generate a variant polypeptide having an enzymatic activity noted above (e.g., aspartokinase activ-

TABLE 1

Non-limiting examples of enzymes and nucleic acid coding sequences for use in pathway A of the oc-FA biosynthetic pathway shown in FIG. 2.

| EC Number | Organism | Gene symbol | UniProtKB (SwissProt) Accession Number, or literature reference | NCBI Protein Accession Number | SEQ ID NO |
|---|---|---|---|---|---|
| EC 2.7.2.4 | aspartate kinase (aspartokinase) | | | | |
| | E. coli K-12 MG1655 | thrA | P00561 | NP_414543 | 20 |
| | E. coli (mutant) | thrA* | Ogawa-Miyata et al, 2001; Lee et al, 2003 | | 21 |
| | B. subtilis 168 | dapG | Q04795 | ZP_03591402 | 22 |
| | P. putida F1 | Pput1442 | A5W0E0 | YP_001266784 | 23 |
| | S. cerevisiae | hom3 | | NP_010972 | 24 |
| EC 1.1.1.3 | homoserine dehydrogenase | | | | |
| | E. coli K12 MG1655 | thrA | P00561 | NP_414543 | 20 |
| | E. coli (mutant) | thrA* | Ogawa-Miyata et al, 2001; Lee et al, 2003 | | 21 |
| | B. subtilis 168 | hom | P19582 | NP_391106 | 25 |
| | P. putida F1 | Pput_4251 | A5W8B5 | YP_001269559 | 26 |
| | S. cerevisiae | hom6 | P31116 | NP_012673 | 27 |
| EC 2.7.1.39 | homoserine kinase | | | | |
| | E. coli K12 MG1655 | thrB | P00547 | NP_414544 | 28 |
| | B. subtilis 168 | thrB | P04948 | NP_391104 | 29 |
| | P. putida F1 | Pput_0138 | A5VWQ3 | YP_001265497 | 30 |
| | S. cerevisiae | thr1 | P17423 | NP_011890 | 31 |
| EC 4.2.3.1 | threonine synthase | | | | |
| | E. coli K12 MG1655 | thrC | P00934 | NP_414545 | 32 |
| | B. subtilis 168 | thrC | P04990 | NP_391105 | 33 |
| | C. glutamicum ATCC 13032 | thrC | P23669 | YP_226461 | 34 |
| EC 4.3.1.19 | threonine deaminase (threonine ammonia-lyase; previously termed threonine dehydratase) | | | | |
| | E. coli K12 MG1655 | tdcB | P0AGF6 | NP_417587 | 35 |
| | E. coli K12 MG1655 | ilvA | P04968 | NP_418220 | 36 |
| | B. subtilis 168 | ilvA | P37946 | NP_390060 | 37 |
| | C. glutamicum ATCC 13032 | ilvA | Q04513 | YP_226365 | 38 |
| | C. glutamicum ATCC 13032 | tdcB | Q8NRR7 | YP_225271 | 39 |

Additional polypeptides can be identified, for example, by searching a relevant database (such as the KEGG database (University of Tokyo), the PROTEIN or the GENE databases (Entrez databases; NCBI), the UNIPROTKB or ENZYME databases (ExPASy; Swiss Institute of Bioinformatics), and the BRENDA database (The Comprehensive Enzyme Information System; Technical University of Braunschweig)), all which are available on the World Wide Web, for polypeptides categorized by the above noted EC numbers. For example, additional aspartokinase polypeptides can be identified by searching for polypeptides categorized under EC 2.7.2.4; additional homoserine dehydrogenase polypeptides can be identified by searching for polypeptides categorized under EC 1.1.1.3; additional homoserine kinase polypeptides can be identified by searching for polypeptides categorized under EC 2.7.1.39; additional threonine synthase polypeptides can be identified by searching for polypeptides categorized under EC 4.2.3.1; and additional threonine deaminase polypeptides can be identified by searching for polypeptides categorized under EC 4.3.1.19.

ity, homoserine dehydrogenase activity, homoserine kinase activity, threonine synthase activity, threonine deaminase activity) and an improved property, compared to that of the parent polypeptide, which is more suited to the microbial cell and/or to the pathway being engineered; such as, for example, increased catalytic activity or improved stability under conditions in which the recombinant microbial cell is cultured; reduced inhibition (e.g., reduced feedback inhibition) by a cellular metabolite or by a culture media component, and the like.

Pathway B (Citramalate Intermediate)

The second pathway leading to the common α-ketobutyrate intermediate, as represented by pathway (B) of FIG. 2, involves the production of the intermediate citramalate (which is also known as 2-methylmalate) via an enzyme with citramalate synthase activity, and the conversion of citramalate to α-ketobutyrate by the action of enzymes with isopropylmalate isomerase and alcohol dehydrogenase activities.

Citramalate synthase activity (e.g., EC 2.3.1.182), which catalyzes the reaction of acetyl-CoA and pyruvate to form (R)-citramalate, can be supplied by expression of a cimA gene from a bacterium such as *Methanococcus jannaschi* or *Leptospira interrogans* (Howell, D. M. et al., *J. Bacteriol.* 181(1):331-3 (1999); Xu, H., et al., *J. Bacteriol.* 186:5400-5409 (2004)) which encodes a CimA polypeptide such as CimA from *M. jannaschii* (SEQ ID NO: 40) or *L. interrogans* (SEQ ID NO:42). Alternatively, a modified cimA nucleic acid sequence encoding a CimA variant with improved catalytic activity or stability in the recombinant microbial cell and/or reduced feedback inhibition can be used, such as, for example, a CimA variant described by Atsumi S, and Liao J. C. (*Appl. Environ. Microbiol.* 74(24): 7802-7808 (2008)), preferably the cimA3.7 variant (SEQ ID NO:41) encoded by the cimA3.7 gene. Alternatively, a *Leptospira interrogans* CimA variant (SEQ ID NO:43) can be used. Isopropylmalate isomerase activity (EC 4.2.1.33; also termed isopropylmalate dehydratase), which catalyzes the conversion of (R)-citramalate first to citraconate and then to beta-methyl-D-malate, can be provided, for example, by expression of a heterodimeric protein encoded by *E. coli* or *B. subtilis* leuCD genes. Alcohol dehydrogenase activity (EC 1.1.1.85; beta-isopropyl malate dehydrogenase), which catalyzes the conversion of beta-methyl-D-malate to 2-ketobutyrate (i.e., α-ketobutyrate) can be provided, for example, by expression of an *E. coli* or *B. subtilis* leuB gene or a yeast leu2 gene. Non-limiting examples of fatty acid pathway enzymes and polynucleotides encoding such enzymes for use in engineering pathway (B) of the oc-FA pathway are provided in Table 2.

2.3.1.182; additional isopropyl malate isomerase polypeptides can be identified by searching for polypeptides categorized under EC 4.2.1.33; and additional beta-isopropyl malate dehydrogenase polypeptides can be identified by searching for polypeptides categorized under EC 1.1.1.85.

In some embodiments, a polynucleotide encoding a parent fatty acid pathway polypeptide (such as a polypeptide described in Table 2 or identified by EC number or by homology to an exemplary polypeptide) is modified using methods well known in the art to generate a variant polypeptide having an enzymatic activity noted above (e.g., (R)-citramalate synthase activity, isopropyl malate isomerase activity, beta-isopropyl malate dehydrogenase activity) and an improved property, compared to that of the parent polypeptide, which is more suited to the microbial cell and/or to the pathway being engineered; such as, for example, increased catalytic activity or improved stability under conditions in which the recombinant microbial cell is cultured; reduced inhibition (e.g., reduced feedback inhibition) by a cellular metabolite or by a culture media component, and the like.

Production of Propionyl-CoA via Methylmalonyl-CoA
Pathway C (Methylmalonyl-CoA Intermediate)

The following exemplary pathway can be engineered in the recombinant microbial cell to increase metabolic flux through a methylmalonyl-CoA intermediate resulting in increased propionyl-CoA production in the cell. This exemplary pathway is shown in FIG. 3 and is described in more detail below.

Directing metabolic flux through methylmalonyl-CoA can result in increased propionyl-CoA production. Accordingly, in one embodiment, the invention includes a recombinant microbial cell comprising polynucleotides encoding which

TABLE 2

Non-limiting examples of enzymes and nucleic acid coding sequences for use in pathway (B) of the oc-FA biosynthetic pathway shown in FIG. 2.

| EC number | Organism | Gene symbol | UniProtKB (Swiss-Prot) Protein Accession Number, or literature reference | NCBI Protein Accession Number | SEQ ID NO |
|---|---|---|---|---|---|
| EC 2.3.1.182 | (R)-citramalate synthase | | | | |
| | *M. jannaschii* | cimA | Q58787 | NP_248395 | 40 |
| | *M. jannaschii* (mutant) | cimA 3.7 | Atsumi and Liao (2008) | | 41 |
| | *Leptospira interrogans* | cimA | Q8F3Q1 | AAN49549 | 42 |
| | *Leptospira interrogans* (mutant) | cimA* | (this disclosure) | | 43 |
| EC 4.2.1.33 | isopropylmalate isomerase (3-isopropylmalate dehydratase) | | | | |
| | *E. coli* K12 MG1655 | leuCD | P0A6A6 (C, Lg subunit); P30126 (D, Sm subunit) | (C) NP_414614 (D) NP_414613 | 44 45 |
| | *B. subtilis* 168 | leuCD | P80858 (C, Lg subunit); P94568 (D, Sm subunit) | (C) NP_390704 (D) NP_390703 | 46 47 |
| EC 1.1.1.85 | beta-isopropylmalate dehydrogenase (3-isopropylmalate dehydrogenase) | | | | |
| | *E. coli* K12 MG1655 | leuB | P30125 | NP_414615 | 48 |
| | *B. subtilis* | leuB | P05645 | NP_390705.2 | 49 |
| | *S. cerevisiae* | leu2 | P04173 | NP_009911.2 | 50 |

Additional polypeptides can be identified, for example, by searching a relevant database (such as the KEGG database (University of Tokyo), the PROTEIN or the GENE databases (Entrez databases; NCBI), the UNIPROTKB or ENZYME databases (ExPASy; Swiss Institute of Bioinformatics), and the BRENDA database (The Comprehensive Enzyme Information System; Technical University of Braunschweig)), all which are available on the World Wide Web, for polypeptides categorized by the above noted EC numbers. For example, additional (R)-citramalate synthase polypeptides can be identified by searching for polypeptides categorized under EC participate in the conversion of a carbon source (for example, a carbohydrate, such as a sugar) to succinyl-CoA and to methylmalonyl-CoA when the recombinant microbial cell is cultured in the presence of the carbon source under conditions sufficient to expresses the polynucleotides. Succinyl-CoA and methylmalonyl-CoA are intermediates in the microbial production of propionyl-CoA, which serves as a primer in the production of linear odd chain fatty acid derivatives according to the oc-FA pathway (FIG. 1B).

The pathway leading to propionyl-CoA as shown in FIG. 3 (also referred to herein as "pathway (C)") involves the conversion of succinyl-CoA to methylmalonyl-CoA via an enzyme having methylmalonyl-CoA mutase activity, and the conversion of methylmalonyl-CoA to propionyl-CoA by the action of an enzyme having methylmalonyl-CoA decarboxylase activity, and/or by the action of an enzyme having methylmalonyl-CoA carboxyltransferase activity. In some instances, depending on the stereoisomer of methylmalonyl-CoA utilized by the particular methylmalonyl-CoA decarboxylase or methylmalonyl-CoA carboxyltransferase employed, an enzyme having methylmalonyl-CoA epimerase activity may be utilized to interconvert (R)- and (S)-methylmalonyl-CoA.

Succinyl-CoA can be provided to this pathway by the cellular TCA cycle. In some instances, flux from fumarate to succinate can be increased by, for example, overexpressing endogenous frd (fumurate reductase) or other gene(s) involved in production of succinate or succinyl-CoA. The conversion of succinyl-CoA to methylmalonyl-CoA can be catalyzed by an enzyme having methylmalonyl-CoA mutase activity (e.g., EC 5.4.99.2). Such activity can be supplied to the recombinant microbial cell by expression of an exogenous scpA (also known as sbm) gene or by overexpression of an endogenous scpA gene. An exemplary sbm gene includes that from E. coli (Haller, T. et al., Biochemistry 39:4622-4629 (2000)) which encodes an Sbm polypeptide (Accession NP_417392, SEQ ID NO: 51) having methylmalonyl-CoA mutase activity. Alternatively, a methylmalonyl-CoA mutase from, for example, Propionibacterium freundenreichii subsp. shermanii which comprises an α-subunit or "large subunit" (MutB, Accession YP_003687736) and a β-subunit or "small subunit" (MutA, Accession CAA33089) can be used. Non-limiting examples of polypeptides that catalyze the conversion of succinyl-CoA to methylmalonyl-CoA are provided in Table 3, below.

In one embodiment, conversion of methylmalonyl-CoA to propionyl-CoA can be catalyzed by a polypeptide having methylmalonyl-CoA decarboxylase activity (e.g., EC 4.1.1.41), which catalyzes the decarboxylation of methylmalonyl-CoA to propionyl-CoA. Such activity can be supplied to the recombinant microbial cell by expression of an exogenous scpB (also known as ygfG) gene or by overexpression of an endogenous scpB gene. Exemplary methylmalonyl-CoA decarboxylase polypeptides include, for example, a methylmalonyl-CoA decarboxylase polypeptide encoded by the E. coli scpB gene (Haller et al., supra), or a methylmalonyl-CoA decarboxylase polypeptide encoded by Salmonella enterica or Yersinia enterocolitica. In another embodiment, conversion of methylmalonyl-CoA to propionyl-CoA can be catalyzed by a polypeptide having methylmalonyl-CoA carboxyltransferase activity (e.g., EC 2.1.3.1), such as, for example, a methylmalonyl-CoA carboxyltransferase from P. freundenreichii subsp. shermanii (mmdA, NBCI Accession No. Q8 GBW6.3). Depending on the stereoisomer of methylmalonyl-CoA utilized by the methylmalonyl-CoA decarboxylase or by the methylmalonyl-CoA carboxyltransferase, conversion between (R)-methylmalonyl-CoA and (5)-methylmalonyl-CoA may be desired, which can be catalyzed by a polypeptide having methylmalonyl-CoA epimerase activity (e.g., EC 5.1.99.1), such as, for example, a methylmalonyl-CoA epimerase from Bacillus subtilis (yqjC; Haller et al., Biochemistry 39:4622-4629 (2000)) or Propionibacterium freundenreichii subsp. shermanii (NCBI Accession No. YP_003688018).

One or more enzymes endogenous to the parental microbial cell may compete for substrate with enzymes of the engineered oc-FA biosynthetic pathway in the recombinant microbial cell, or may break down or otherwise divert an intermediate away from the oc-FA biosynthetic pathway; genes encoding such undesired endogenous enzymes may be attenuated to increase the production of odd chain fatty acid derivatives by the recombinant microbial cell. For example, in E. coli, the endogenous propionyl-CoA:succinyl-CoA transferase (NCBI Accession Number NP_417395), encoded by the E. coli scpC (also known as ygfH) gene, catalyzes the conversion of propionyl-CoA to succinyl-CoA and may thus divert metabolic flux away from propionyl-CoA and reduce oc-FA production. Deleting or otherwise reducing the expression of the scpC (ygfH) gene may thus direct biosynthesis in the recombinant microbial cell more towards propionyl-CoA and ultimately more towards odd chain fatty acid production.

Non-limiting examples of fatty acid pathway enzymes and polynucleotides encoding such enzymes that catalyze the conversion of succinyl-CoA to methylmalonyl-CoA and the conversion of methylmalonyl-CoA to propionyl-CoA for use in engineering pathway (C) of the oc-FA pathway are provided in Table 3.

TABLE 3

Non-limiting examples of enzymes and nucleic acid coding sequences for use in pathway (C) of the oc-FA biosynthetic pathway shown in FIG. 3.

| EC number | Organism | Gene symbol | UniProtKB(Swiss-Prot) Protein Accession Number, or literature reference | NCBI Protein Accession Number | SEQ ID NO |
|---|---|---|---|---|---|
| EC 5.4.99.2 | Methylmalonyl-CoA mutase | | | | |
| | E. coli | scpA (sbm) | P27253 | NP_417392 | 51 |
| | Salmonella enterica | SARI_04585 | A9MRG0 | YP_001573500 | 52 |
| | P. freundenreichii subsp. shermanii | mutA | (sm) P11652 | (sm) CAA33089 | 53 |
| | | mutB | (lg) D7GCN5 | (lg) YP_003687736 | 54 |
| | Bacillus megaterium | mutA | (sm) D5DS48 | (sm) YP_003564880 | 55 |
| | | mutB | (lg) D5DS47 | (lg) YP_003564879 | 56 |
| | Corynebacterium glutamicum | mcmA | (sm) Q8NQA8 | (sm) YP_225814 | 57 |
| | | mcmB | (lg) Q8NQA9 | (lg) YP_225813 | 58 |
| EC 4.1.1.41 | Methylmalonyl-CoA decarboxylase | | | | |
| | E. coli | scpB (ygfG) | C6UT22 | YP_001731797 | 59 |
| | Salmonella enterica | SARI_04583 | A9MRF8 | YP_001573498 | 60 |
| | Yersinia enterocolitica | YE1894 | A1JMG8 | YP_001006155 | 61 |

TABLE 3-continued

Non-limiting examples of enzymes and nucleic acid coding sequences for use in pathway (C) of the oc-FA biosynthetic pathway shown in FIG. 3.

| EC number | Organism | Gene symbol | UniProtKB(Swiss-Prot) Protein Accession Number, or literature reference | NCBI Protein Accession Number | SEQ ID NO |
|---|---|---|---|---|---|
| EC 2.1.3.1 | Methylmalonyl-CoA carboxyltransferase | | | | |
| | P. freudenreichii subsp. shermanii | mmdA | Q8GBW6 | Q8GBW6.3 | 62 |
| EC 5.1.99.1 | Methylmalonyl-CoA epimerase | | | | |
| | P. freudenreichii subsp. shermanii | PFREUD_10590; mmcE | D7GDH1 | YP_003688018 | 63 |

Additional polypeptides can be identified, for example, by searching a relevant database (such as the KEGG database (University of Tokyo), the PROTEIN or the GENE databases (Entrez databases; NCBI), the UNIPROTKB or ENZYME databases (ExPASy; Swiss Institute of Bioinformatics), and the BRENDA database (The Comprehensive Enzyme Information System; Technical University of Braunschweig)), all which are available on the World Wide Web, for polypeptides categorized by the above noted EC numbers. For example, additional methylmalonyl-CoA mutase polypeptides can be identified by searching for polypeptides categorized under EC 5.4.99.2, additional methylmalonyl-CoA decarboxylase polypeptides can be identified by searching for polypeptides categorized under EC 4.1.1.41, additional methylmalonyl-CoA carboxyltransferase polypeptides can be identified by searching for polypeptides categorized under EC 2.1.3.1, and additional methylmalonyl-CoA epimerase polypeptides can be identified by searching for polypeptides categorized under EC 5.1.99.1.

In some embodiments, a polynucleotide encoding a parent fatty acid pathway polypeptide (such as a polypeptide described in Table 3 or identified by EC number or by homology to an exemplary polypeptide) is modified using methods well known in the art to generate a variant polypeptide having an enzymatic activity noted above (e.g., methylmalonyl-CoA mutase activity, methylmalonyl-CoA decarboxylase activity, methylmalonyl-CoA epimerase activity, methylmalonyl-CoA carboxyltransferase activity) and an improved property, compared to that of the parent polypeptide, which is more suited to the microbial cell and/or to the pathway being engineered; such as, for example, increased catalytic activity or improved stability under conditions in which the recombinant microbial cell is cultured; reduced inhibition (e.g., reduced feedback inhibition) by a cellular metabolite or by a culture media component, and the like.

Engineering Microbial Cells to Produce Increased Amounts of oc-FA Derivatives

Propionyl-CoA to oc-β-Ketoacyl-ACP

As discussed above, propionyl-CoA serves as a primer for subsequent FAS-catalyzed elongation steps in the production of oc-FA derivatives. The initiation of this process involves condensation of propionyl-CoA with a malonyl-ACP molecule to form the oc-β-ketoacyl-ACP intermediate 3-oxovaleryl-ACP (FIG. 1B). This initiation step, as represented by step (D) of FIG. 1B, is catalyzed in the recombinant microbial cell by an enzyme having β-ketoacyl-ACP synthase activity (such as, a Type III β-ketoacyl-ACP synthase (e.g., EC 2.3.1.180)) that utilizes propionyl-CoA as a substrate.

The substrate specificity of a β-ketoacyl-ACP synthase from a particular microorganism often reflects the fatty acid composition of that microorganism (Han, L., et al., *J. Bacteriol.* 180:4481-4486 (1998); Qui, X., et al., *Protein Sci.* 14:2087-2094 (2005)). For example, the *E. coli* FabH enzyme utilizes propionyl-CoA and acetyl-CoA with a very strong preference for acetyl-CoA (Choi, K. H., et al., *J. Bacteriology* 182:365-370 (2000); Qui, et al., supra) reflecting the high proportion of linear even chain fatty acids produced, while the enzyme from *Streptococcus pneumoniae* utilizes short straight chain acyl-CoA primers of between two and four carbons in length as well as various branched-chain acyl-CoA primers (Khandekar S. S., et al., *J. Biol. Chem.* 276:30024-30030 (2001)) reflecting the variety of linear chain and branched chain fatty acids produced. A polynucleotide sequence encoding a polypeptide having β-ketoacyl-ACP synthase activity that utilizes propionyl-CoA as a substrate can generally be obtained from a microbial cell containing a β-ketoacyl-ACP synthase with a broad acyl-CoA substrate specificity. Sources of broad-specificity β-ketoacyl-ACP synthases may include bacteria that produce a variety of fatty acid structures including branched chain fatty acids, such as, for example, *Bacillus* (e.g., *B. subtilis*), *Listeria* (e.g., *L. monocytogenes*), *Streptomyces* (e.g., *S. coelicolor*), and *Propionibacterium* (e.g., *P. freudenreichii* subsp. *shermanii*). Particularly preferred β-ketoacyl-ACP synthase enzymes include those with a greater preference for propionyl-CoA vs. acetyl-CoA than that exhibited by the endogenous FabH. For example, when an *E. coli* cell is engineered, preferred β-ketoacyl-ACP synthase enzymes may include, but are not limited to, *B. subtilis* FabH1 (Choi et al. 2000, supra), *Streptomyces glauscens* FabH (Han, L., et al., *J. Bacteriol.* 180:4481-4486 (1998)), *Streptococcus pneumoniae* FabH (Khandekar S. S., et al., *J. Biol. Chem.* 276:30024-30030 (2001), and *Staphylococcus aureus* FabH (Qui, X. et al., *Protein Sci.* 14:2087-2094 (2005)).

One or more endogenous enzymes may compete for substrate with enzymes of the engineered oc-FA biosynthetic pathway in the recombinant microbial cell, or may break down an oc-FA pathway intermediate or may otherwise divert metabolic flux away from oc-FA production; genes encoding such undesired endogenous enzymes may be attenuated to increase the production of oc-FA derivatives by the recombinant microbial cell. For example, while the endogenous fabH-encoded β-ketoacyl-ACP synthase of *E. coli* utilizes propionyl-CoA as a substrate, it has a much greater preference for the two-carbon acetyl-CoA molecule than for the three-carbon propionyl-CoA molecule (Choi et al. 2000, supra). Cells expressing the *E. coli* fabH gene thus preferentially utilize acetyl-CoA as a primer for fatty acid synthesis and predominantly produce even chain fatty acid molecules in vivo. Deleting or otherwise reducing the expression of an endogenous fabH gene and expressing an exogenous gene encoding a β-ketoacyl-ACP synthase with greater preference for propionyl-CoA than that exhibited by the endogenous FabH (for example, when engineering *E. coli*, replacing the endogenous *E. coli* FabH with *B. subtilis* FabH1 or an alternative exogenous FabH with a greater preference for propionyl-CoA than acetyl-CoA relative to that exhibited by *E. coli* FabH) may direct metabolic flux in the recombinant microbial cell more towards an oc-β-ketoacyl-ACP intermediate and ultimately more towards production of oc-FA derivatives.

Non-limiting examples of fatty acid pathway enzymes and polynucleotides encoding such enzymes for use in engineering step D of the oc-FA pathway are provided in Table 4.

TABLE 4

Non-limiting examples of enzymes and coding sequences for use
in step D of the oc-FA biosynthetic pathways shown in FIG. 1B.

| EC number | Organism | Gene symbol | UniProtKB (Swiss-Prot) Protein Accession Number, or literature reference | NCBI Protein Accession Number | SEQ ID NO |
|---|---|---|---|---|---|
| EC 2.3.1.180 | β-ketoacyl-ACP synthase III | | | | |
| | E. coli | fabH | P0A6R0 | AAC74175 | 1 |
| | B. subtilis 168 | fabH1 | O34746 | NP_389015 | 2 |
| | B. subtilis 168 | fabH2 | O07600 | NP_388898 | 3 |
| | Streptomyces coelicolor | fabH | Q9K3G9 | CAB99151 | 4 |
| | Streptomyces glaucescens | fabH | Q54206 | AAA99447 | 5 |
| | Streptomyces avermitilis MA-4680 | fabH3 | Q82KT2 | NP_823466 | 6 |
| | Listeria monocytogenes | fabH | B8DFA8 | YP_002349314 | 7 |
| | L. monocytogenes (mutant) | fabH2 | (this disclosure) | | 8 |
| | Staphylococcus aureus MW2 | fabH | Q8NXE2 | NP_645682 | 9 |
| | Streptococcus pneumoniae | fabH | P0A3C5 | AAK74580 | 10 |
| | Streptococcus mutans UA159 | fabH | Q8DSN2 | NP_722071 | 11 |
| | Lactococcus lactis subsp. lactis | fabH | Q9CHG0 | NP_266927 | 12 |
| | Propionibacterium freundenreichii subsp. shermanii | fabH | D7GD58 | YP_003687907 | 13 |

Additional β-ketoacyl-ACP synthase polypeptides can be identified, for example, by searching a relevant database (such as the KEGG database (University of Tokyo), the PROTEIN or the GENE databases (Entrez databases; NCBI), the UNIPROTKB or ENZYME databases (ExPASy; Swiss Institute of Bioinformatics), and the BRENDA database (The Comprehensive Enzyme Information System; Technical University of Braunschweig)), all which are available on the World Wide Web, for polypeptides categorized under EC 2.3.1.180.

Additional β-ketoacyl-ACP synthase polypeptides can also be identified by searching a sequence pattern database, such as the Prosite database (ExPASy Proteomics Server, Swiss Institute of Bioinformatics) for a polypeptide comprising one or more of the sequence motifs listed below. This is readily accomplished, for example, by using the ScanProsite tool which is available on the World Wide Web site of the ExPASy Proteomics Server.

In one embodiment, the β-ketoacyl-ACP synthase polypeptide comprises one or more sequence motif selected from:

(SEQ ID NO: 14)
D-T-[N,S]D-[A,E]-W-I-x(2)-[M,R]-T-G-I-x-[N,E]-R-[R,H]

(SEQ ID NO: 15)
[S,A]-x-D-x(2)-A-[A,V]-C-[A,S]-G-F-x(3)-[M,L]-x(2)-A (SEQ ID NO: 16)
D-R-x-T-[A,I]-[I,V]-x-F-[A,G]-D-G-A-[A,G]-[G,A]-[A,V]

(SEQ ID NO: 17)
H-Q-A-N-x-R-I-[M,L]

(SEQ ID NO: 18)
G-N-T-[G,S]-A-A-S-[V,I]-P-x(2)-[I,L]-x(6)-G (SEQ ID NO: 19)
[I,V]-x-L-x(2)-F-G-G-G-[L,F]-[T,S]-W-G wherein the amino acid residues in each of the brackets indicate alternative amino acid residues at the particular position, each x indicates any amino acid residue, and each n in "x(n)" indicates the number of x residues in a contiguous stretch of amino acid residues.

In some embodiments, a polynucleotide encoding a parent fatty acid pathway polypeptide (such as a polypeptide described in Table 4 or identified by EC number or by motif or by homology to an exemplary polypeptide) is modified using methods well known in the art to generate a variant polypeptide having β-ketoacyl-ACP synthase activity, and an improved property, compared to that of the parent polypeptide, which is more suited to the microorganism and/or to the pathway being engineered; such as, for example, increased catalytic activity and/or increased specificity for propionyl-CoA (relative to, e.g., acetyl-CoA); improved catalytic activity or improved stability under conditions in which the recombinant microbial cell is cultured; reduced inhibition (e.g., reduced feedback inhibition) by a cellular metabolite or by a culture media component, and the like.

The invention includes an isolated polypeptide comprising a sequence having at least 80% identity to one of SEQ ID NOs:1, 2, 3, 4, 5, 6, 7, 8, 9, 10, 11, 12, and 13, wherein the polypeptide has β-ketoacyl-ACP synthase activity that utilizes propionyl-CoA as a substrate. In some instances, the polypeptide sequence further comprises one or more sequence motif selected from SEQ ID NOs:14-19. The invention also includes an isolated polynucleotide encoding any one of said polypeptides. In one embodiment, the polypeptide comprises a substitution at position W310 or at an equivalent position thereto. In one embodiment, the polypeptide comprises a W310G substitution. In one embodiment, the polypeptide comprises a sequence having at least 80% identity to SEQ ID NO: 7 and comprises the substitution W310G. In some embodiments, the polypeptide exhibits greater specificity for propionyl-CoA than for acetyl-CoA.

As used herein, "a polypeptide having β-ketoacyl-ACP synthase activity that utilizes propionyl-CoA as a substrate" includes any polypeptide having a detectable level of β-ketoacyl-ACP synthase activity when supplied with the substrate propionyl-CoA.

Enzymatic activity and specificity of β-ketoacyl-ACP synthases for substrates, such as propionyl-CoA, can be determined using known methods. For example, Choi et al. (*J. Bacteriology* 182(2):365-370 (2000)) described in detail a filtered disc assay suitable for determining β-ketoacyl-ACP synthase ("FabH") activity against acetyl-CoA substrate, which can be modified to assay propionyl-CoA as a substrate. The assay contains 25 μM ACP, 1 mM β-mercaptoethanol, 65 μM malonyl-CoA, 45 μM [1-$^{14}$C]acetyl-CoA (specificity activity about 45.8 Ci/mol), *E. coli* FadD (0.2 μg), and 0.1 M sodium phosphate buffer (pH 7.0) in a final volume of 40 μL. To assay β-ketoacyl-ACP synthase activity, [1-$^{14}$C]acetyl-CoA can be substituted with $^{14}$C labeled propionyl-CoA. The reaction is initiated by the addition of FabH, and the mixture is incubated at 37° C. for 12 minutes. A 35 mL aliquot is then removed and deposited on a Whatman 3 MM filter disc. The discs are then washed with three changes (20 mL/disc for 20 minutes each) of ice-cold trichloroacetic acid. The concentration of the trichloroacetic acid is then reduced from 10 to 5 to 1% in each successive wash. The filters are dried an counted in 3 mL of scintillation cocktail.

Alternatively, FabH activity can be determined using a radioactively labeled malonyl-CoA substrate and gel electrophoresis to separate and quantitate the products (Choi et al. 2000, supra). The assay mixture contains 25 μM ACP, 1 mM β-mercaptoethanol, 70 μM [2-$^{14}$C] malonyl-CoA (specific activity, ~9 Ci/mol), 45 μM of a CoA-substrate (such as acetyl-CoA or propionyl-CoA), FadD (0.2 μg), 100 μM NADPH, FabG (0.2 μg) and 0.1 M sodium phosphate buffer (pH 7.0) in a final volume of 40 μL. The reaction can be initiated by the addition of FabH. The mixture is incubated at 37° C. for 12 minutes and then placed in an ice slurry, gel loading buffer is then added, and the mixture is loaded onto a conformationally sensitive 13% polyacrylamide gel containing 0.5 to 2.0 M urea. Electrophoresis can be performed at 25° C. at 32 mA/gel. The gels are then dried, and the bands quantitated by exposure of the gel to a Phospholmager screen. Specific activity can be calculated from the slopes of the plot of product formation vs. FabH protein concentration in the assay.

oc-β-Ketoacyl-ACP to oc-Acyl-ACP

The oc-β-ketoacyl-ACP intermediate 3-oxovaleryl-ACP generated in step (D) can undergo elongation by successive cycles of condensation with malonyl-ACP/keto-eduction/dehydration/enoyl-reduction, catalyzed by a fatty acid synthase (FAS) complex, such as, for example, a type II fatty acid synthase complex, thereby adding 2-carbon units to the lengthening fatty acid chain of the resulting oc-acyl-ACP, as represented by step (E) of FIG. 1B. In one embodiment, a FAS enzyme complex (such as, for example, a Type II FAS complex) endogenous to the microbial cell is used to catalyze cycles of condensation with malonyl-CP/keto-reduction/dehydration/enoyl-reduction to produce the oc-acyl-ACP intermediate.

oc-AcvI-ACP to oc-FA Derivative

Odd chain fatty acid derivatives can be produced by a recombinant microbial cell of the invention. The oc-acyl-ACP intermediate is converted to an oc-FA derivative in a reaction catalyzed by one or more enzymes each having fatty acid derivative activity (i.e., fatty acid derivative enzymes), as represented by step (F) of FIG. 1B. A fatty acid derivative enzyme can, for example, convert an oc-acyl-ACP to an initial oc-FA derivative, or, can convert the initial oc-FA derivative to a second oc-FA derivative. In some instances, the initial oc-FA derivative is converted to a second oc-FA derivative by an enzyme having a different fatty acid derivative activity. In some instances, the second oc-FA derivative is further converted to a third oc-FA derivative by another fatty acid derivative enzyme, and so on.

Accordingly, in some embodiments, the recombinant microbial cell further comprises one or more polynucleotides, each polynucleotide encoding a polypeptide having a fatty acid derivative enzyme activity, wherein the recombinant microbial cell produces an oc-FA derivative when cultured in the presence of a carbon source under conditions effective to express the polynucleotides.

In various embodiments, the fatty acid derivative activity comprises thioesterase activity, wherein the recombinant microbial cell produces oc-fatty acids; ester synthase activity, wherein the recombinant microbial cell produces oc-fatty esters; fatty aldehyde biosynthesis activity, wherein the recombinant microbial cell produces oc-fatty aldehydes; fatty alcohol biosynthesis activity, wherein the recombinant microbial cell produces oc-fatty alcohols; ketone biosynthesis activity, wherein the recombinant microbial cell produces ec-ketones; or hydrocarbon biosynthesis activity, wherein the recombinant microbial cell produces ec-hydrocarbons. In some embodiments, the recombinant microbial cell comprises polynucleotides encoding two or more polypeptides, each polypeptide having fatty acid derivative enzyme activity.

In more particular embodiments, the recombinant microbial cell expresses or overexpresses one or more polypeptides having fatty acid derivative enzyme activity as described hereinabove, wherein the recombinant microbial cell produces an oc-FA composition comprising oc-fatty acids, oc-fatty esters, oc-wax esters, oc-fatty aldehydes, oc-fatty alcohols, ec-ketones, ec-alkanes, ec-alkanes, ec-internal olefins, or ec-terminal olefins.

The following are further examples of fatty acid derivative enzymes, and oc-FA derivatives produced by reactions catalyzed by such enzymes, in accordance with various embodiments of the invention.

oc-Fatty Acid

In one embodiment, the recombinant microbial cell comprises a polynucleotide encoding a thioesterase, and the oc-acyl-ACP intermediate produced by the recombinant microbial cell is hydrolyzed by the thioesterase (e.g., 3.1.1.5, EC 3.1.2.-; such as, for example, EC 3.1.2.14) resulting in production of an oc-fatty acid. In some embodiments, a composition comprising fatty acids (also referred to herein as a "fatty acid composition") comprising oc-fatty acids is produced by culturing the recombinant cell in the presence of a carbon source under conditions effective to express the polynucleotide. In some embodiments, the fatty acid composition comprises oc-fatty acids and ec-fatty acids. In some embodiments, the composition is recovered from the cell culture.

In some embodiments, the recombinant microbial cell comprises a polynucleotide encoding a polypeptide having thioesterase activity, and one or more additional polynucleotides encoding polypeptides having other fatty acid derivative enzyme activities. In some such instances, the oc-fatty acid produced by the action of the thioesterase is converted by one or more enzymes having different fatty acid derivative enzyme activities to another oc-fatty acid derivative, such as, for example, an oc-fatty ester, oc-fatty aldehyde, oc-fatty alcohol, or ec-hydrocarbon.

In one embodiment, an oc-acyl-ACP intermediate reacts with a thioesterase to form an oc-fatty acid. The oc-fatty acid can be recovered from the cell culture, or can be further converted to another oc-FA derivative, such as an oc-fatty ester, an oc-fatty aldehyde, an oc-fatty alcohol, or an ec-terminal olefin.

The chain length of a fatty acid, or a fatty acid derivative made therefrom, can be selected for by modifying the expression of certain thioesterases. Thioesterase influences the chain length of fatty acids produced as well as that of the derivatives made therefrom. Hence, the recombinant microbial cell can be engineered to express, overexpress, have attenuated expression, or not to express one or more selected thioesterases to increase the production of a preferred fatty acid or fatty acid derivative substrate. For example, $C_{10}$ fatty acids can be produced by expressing a thioesterase that has a preference for producing $C_{10}$ fatty acids and attenuating thioesterases that have a preference for producing fatty acids other than $C_{10}$ fatty acids (e.g., a thioesterase which prefers to produce $C_{14}$ fatty acids). This would result in a relatively homogeneous population of fatty acids that have a carbon chain length of 10. In other instances, $C_{14}$ fatty acids can be produced by attenuating endogenous thioesterases that produce non-$C_{14}$ fatty acids and expressing thioesterases that use $C_{14}$-ACP. In some situations, $C_{12}$ fatty acids can be produced by expressing thioesterases that use $C_{12}$-ACP and attenuating thioesterases that produce non-$C_{12}$ fatty acids. Fatty acid overproduction can be verified using methods known in the art, for example, by use of radioactive precursors, HPLC, or GC-MS subsequent to cell lysis.

Additional non-limiting examples of thioesterases and polynucleotides encoding them for use in the oc-fatty acid pathway are provided in Table 5 and in PCT Publication No. WO 2010/075483 incorporated by reference herein.

oc-Fatty Ester

In one embodiment, the recombinant microbial cell produces an oc-fatty ester, such as, for example, an oc-fatty acid methyl ester or an oc-fatty acid ethyl ester or an oc-wax ester. In some embodiments, an oc-fatty acid produced by the recombinant microbial cell is converted into the oc-fatty ester.

In some embodiments, the recombinant microbial cell comprises a polynucleotide encoding a polypeptide (i.e., an enzyme) having ester synthase activity (also referred to herein as an "ester synthase polypeptide" or an "ester synthase enzyme"), and the oc-fatty ester is produced by a reaction catalyzed by the ester synthase polypeptide expressed or overexpressed in the recombinant microbial cell. In some embodiments, a composition comprising fatty esters (also referred to herein as a "fatty ester composition") comprising oc-fatty esters is produced by culturing the recombinant cell in the presence of a carbon source under conditions effective to express the polynucleotide. In some embodiments, the fatty ester composition comprises oc-fatty esters and ec-fatty esters. In some embodiments, the composition is recovered from the cell culture.

Ester synthase polypeptides include, for example, an ester synthase polypeptide classified as EC 2.3.1.75, or any other polypeptide which catalyzes the conversion of an acyl-thioester to a fatty ester, including, without limitation, a wax-ester synthase, an acyl-CoA:alcohol transacylase, an acyl-transferase, or a fatty acyl-CoA:fatty alcohol acyltransferase. For example, the polynucleotide may encode wax/dgat, a bifunctonal ester synthase/acyl-CoA:diacylglycerol acyl-transferase from *Simmondsia chinensis*, *Acinetobacter* sp. Strain ADP1, *Alcanivorax borkumensis*, *Pseudomonas aeruginosa*, *Fundibacterjadensis*, *Arabidopsis thaliana*, or *Alkaligenes eutrophus*. In a particular embodiment, the ester synthase polypeptide is an *Acinetobacter* sp. diacylglycerol O-acyltransferase (wax-dgaT; UniProtKB Q8GGG1, GenBank AAO17391) or *Simmondsia chinensis* wax synthase (UniProtKB Q9XGY6, GenBank AAD38041). In a particular embodiment, the polynucleotide encoding the ester syn-

TABLE 5

Non-limiting examples of thioesterases and coding sequences thereof for use in the oc-FA pathway shown in FIG. 1B.

| EC number | Organism | Gene symbol | UniProtKB (Swiss-Prot) Protein Accession Number, or literature reference | NCBI Protein Accession Number | SEQ ID NO |
|---|---|---|---|---|---|
| EC 3.1.1.5, EC 3.1.2.- | Thioesterase | | | | |
| | *E. coli* K-12 MG1655 | tesA | P0ADA1 | AAC73596 | 64 |
| | *E. coli* (without leader sequence) | 'tesA | Cho et al, *J. Biol. Chem.*, 270: 4216-4219 (1995) | | 65 |
| | *E. coli* K-12 MG1655 | tesB | P0AGG2 | AAC73555 | 66 |
| | *Arabidopsis thaliana* | fatA | Q42561 | NP_189147 | 67 |
| | *Arabidopsis thaliana* | fatB | Q9SJE2 | NP_172327 | 68 |
| | *Umbellularia california* | fatB | Q41635 | AAA34215 | 69 |
| | *Cuphea hookeriana* | fatA1 | Q9ZTF7 | AAC72883 | 70 |
| | *Cuphea hookeriana* | fatB2 | Q39514 | AAC49269 | 71 |
| | *Cuphea hookeriana* | fatB3 | Q9ZTF9 | AAC72881 | 72 | thase polypeptide is overexpressed in the recombinant microbial cell. In some embodiments the recombinant microbial cell further comprises a polynucleotide encoding a thioesterase.

In another embodiment, the recombinant microbial cell produces an oc-fatty ester, such as, for example, an oc-fatty acid methyl ester or an oc-fatty acid ethyl ester, wherein the recombinant microbial cell expresses a polynucleotide encoding an ester synthase/acyltransferase polypeptide classified as 2.3.1.20, such as AtfA1 (an acyltransferase derived from *Alcanivorax borkumensis* SK2, UniProtKB Q0VKV8, GenBank YP_694462) or AtfA2 (another acyltransferase derived from *Alcanivorax borkumensis* SK2, UniProtKB Q0VNJ6, GenBank YP_693524). In a particular embodiment, the polynucleotide encoding the ester synthase polypeptide is overexpressed in the recombinant microbial cell. In some embodiments the recombinant microbial cell further comprises a polynucleotide encoding a thioesterase.

In another embodiment, the recombinant microbial cell produces an oc-fatty ester, such as, for example, an oc-fatty acid methyl ester or an oc-fatty acid ethyl ester, wherein the recombinant microbial cell expresses a polynucleotide encoding a ester synthase polypeptide, such as ES9 (a wax ester synthase from *Marinobacter hydrocarbonoclasticus* DSM 8798, UniProtKB A3RE51, GenBank ABO21021, encoded by the ws2 gene), or ES376 (another wax ester synthase derived from *Marinobacter hydrocarbonoclasticus* DSM 8798, UniProtKB A3RE50, GenBank ABO21020, encoded by the ws1 gene). In a particular embodiment, the polynucleotide encoding the ester synthase polypeptide is overexpressed in the recombinant microbial cell. In some embodiments the recombinant microbial cell further comprises a polynucleotide encoding a thioesterase.

Additional non-limiting examples of ester synthase polypeptides and polynucleotides encoding them suitable for use in these embodiments include those described in PCT Publication Nos. WO 2007/136762 and WO2008/119082 which are incorporated by reference herein.

oc-Fatty Aldehyde

In one embodiment, the recombinant microbial cell produces an oc-fatty aldehyde. In some embodiments, an oc-fatty acid produced by the recombinant microbial cell is converted into the an oc-fatty aldehyde. In some embodiments, the oc-fatty aldehyde produced by the recombinant microbial cell is then converted into an oc-fatty alcohol or an ec-hydrocarbon.

In some embodiments, the recombinant microbial cell comprises a polynucleotide encoding a polypeptide (i.e., an enzyme) having fatty aldehyde biosynthesis activity (also referred to herein as a "fatty aldehyde biosynthesis polypeptide" or a "fatty aldehyde biosynthesis enzyme"), and the oc-fatty aldehyde is produced by a reaction catalyzed by the fatty aldehyde biosynthesis polypeptide expressed or overexpressed in the recombinant microbial cell. In some embodiments, a composition comprising fatty aldehydes (also referred to herein as a "fatty aldehyde composition") comprising oc-fatty aldehydes is produced by culturing the recombinant cell in the presence of a carbon source under conditions effective to express the polynucleotide. In some embodiments, the fatty aldehyde composition comprises oc-fatty aldehydes and ec-fatty aldehydes. In some embodiments, the composition is recovered from the cell culture.

In some embodiments, the oc-fatty aldehyde is produced by expressing or overexpressing in the recombinant microbial cell a polynucleotide encoding a polypeptide having a fatty aldehyde biosynthesis activity such as carboxylic acid reductase (CAR) activity (encoded, for example, by a car gene). Examples of carboxylic acid reductase (CAR) polypeptides and polynucleotides encoding them useful in accordance with this embodiment include, but are not limited to, FadD9 (EC 6.2.1.-, UniProtKB Q50631, GenBank NP_217106), CarA (GenBank ABK75684), CarB (GenBank YP889972) and related polypeptides described in PCT Publication No. WO 2010/042664 which is incorporated by reference herein. In some embodiments the recombinant microbial cell further comprises a polynucleotide encoding a thioesterase.

In some embodiments, the oc-fatty aldehyde is produced by expressing or overexpressing in the recombinant microbial cell a polynucleotide encoding a fatty aldehyde biosynthesis polypeptide, such as a polypeptide having acyl-ACP reductase (AAR) activity, encoded by, for example, an aar gene. Examples of acyl-ACP reductase polypeptides useful in accordance with this embodiment include, but are not limited to, acyl-ACP reductase from *Synechococcus elongatus* PCC 7942 (GenBank YP_400611) and related polypeptides described in PCT Publication No. WO 2010/042664 which is incorporated by reference herein.

In some embodiments, the oc-fatty aldehyde is produced by expressing or overexpressing in the recombinant microbial cell a polynucleotide encoding a fatty aldehyde biosynthesis polypeptide, such as a polypeptide having acyl-CoA reductase activity (e.g., EC 1.2.1.x), encoded by, for example, an acrl gene. Examples of acyl-CoA reductase polypeptides useful in accordance with this embodiment include, but are not limited to, ACR1 from *Acinetobacter* sp. strain ADP1 (GenBank YP_047869) and related polypeptides described in PCT Publication No. WO 2010/042664 which is incorporated by reference herein. In some embodiments the recombinant microbial cell further comprises polynucleotides encoding a thioesterase and an acyl-CoA synthase.

oc-Fatty Alcohol

In one embodiment, the recombinant microbial cell produces an oc-fatty alcohol. In some embodiments, an oc-fatty aldehyde produced by the recombinant microbial cell is converted to the oc-fatty alcohol. In other embodiments, an oc-fatty acid produced by the recombinant microbial cell is converted to the oc-fatty alcohol In some embodiments, the recombinant microbial cell comprises a polynucleotide encoding a polypeptide (i.e., an enzyme) having fatty alcohol biosynthesis activity (also referred to herein as a "fatty alcohol biosynthesis polypeptide" or a "fatty alcohol biosynthesis enzyme"), and the oc-fatty alcohol is produced by a reaction catalyzed by the fatty alcohol biosynthesis enzyme expressed or overexpressed in the recombinant microbial cell. In some embodiments, a composition comprising fatty alcohols (also referred to herein as a "fatty alcohol composition") comprising oc-fatty alcohols is produced by culturing the recombinant cell in the presence of a carbon source under conditions effective to express the polynucleotide. In some embodiments, the fatty alcohol composition comprises oc-fatty alcohols and ec-fatty alcohols. In some embodiments, the composition is recovered from the cell culture.

In some embodiments, the oc-fatty alcohol is produced by expressing or overexpressing in the recombinant microbial cell a polynucleotide encoding a polypeptide having fatty alcohol biosynthesis activity such as alcohol dehydrogenase (aldehyde reductase) activity, e.g., EC 1.1.1.1. Examples of alcohol dehydrogenase polypeptides useful in accordance with this embodiment include, but are not limited to, *E. coli* alcohol dehydrogenase YqhD (GenBank AP_003562) and related polypeptides described in PCT Publication Nos. WO 2007/136762 and WO2008/119082 which are incorporated by reference herein. In some embodiments the recombinant microbial cell further comprises a polynucleotide encoding a fatty aldehyde biosynthesis polypeptide. In some embodiments the recombinant microbial cell further comprises a polynucleotide encoding a thioesterase.

In some embodiments, the oc-fatty alcohol is produced by expressing or overexpressing in the recombinant microbial cell a polynucleotide encoding a fatty alcohol biosynthesis polypeptide, such as a polypeptide having fatty alcohol forming acyl-CoA reductase (FAR) activity, e.g., EC 1.1.1.x. Examples of FAR polypeptides useful in accordance with this embodiment include, but are not limited to, those described in PCT Publication No. WO 2010/062480 which is incorporated by reference herein. In some embodiments the recombinant microbial cell further comprises polynucleotides encoding a thioesterase and an acyl-CoA synthase.

ec-Hydrocarbon

In one embodiment, the recombinant microbial cell produces an ec-hydrocarbon, such as an ec-alkane or an ec-alkene (e.g., an ec-terminal olefin or an ec-internal olefin) or an ec-ketone. In some embodiments, an oc-acyl-ACP intermediate is converted by decarboxylation, removing a carbon atom to form an ec-internal olefin or an ec-ketone. In some embodiments, an oc-fatty aldehyde produced by the recombinant microbial cell is converted by decarbonylation, removing a carbon atom to form an ec-hydrocarbon. In some embodiments, an oc-fatty acid produced by the recombinant microbial cell is converted by decarboxylation, removing a carbon atom to form an ec-terminal olefin.

In some embodiments, the recombinant microbial cell comprises a polynucleotide encoding a polypeptide (i.e., an enzyme) having hydrocarbon biosynthesis activity (also referred to herein as a "hydrocarbon biosynthesis polypeptide" or a "hydrocarbon biosynthesis enzyme"), and the ec-hydrocarbon is produced by a reaction catalyzed by the hydrocarbon biosynthesis enzyme expressed or overexpressed in the recombinant microbial cell. In some embodiments, a composition comprising hydrocarbons (also referred to herein as a "hydrocarbon composition") comprising ec-hydrocarbons is produced by culturing the recombinant cell in the presence of a carbon source under conditions effective to express the polynucleotide. In some embodiments, the hydrocarbon composition comprises ec-hydrocarbons and oc-hydrocarbons. In some embodiments, the hydrocarbon composition is recovered from the cell culture.

In some embodiments, the ec-hydrocarbon is produced by expressing or overexpressing in the recombinant microbial cell a polynucleotide encoding a polypeptide having hydrocarbon biosynthesis activity such as an aldehyde decarbonylase (ADC) activity (e.g., EC 4.1.99.5), for example, a polynucleotide encoding an aldehyde decarbonylase from *Prochlorococcus marinus* MIT9313 (GenBank NP_895059) or *Nostoc punctiforme* (GenBank Accession No. YP_001865325). Additional examples of aldehyde decarbonylase and related polypeptides useful in accordance with this embodiment include, but are not limited to, those described in PCT Publication Nos. WO 2008/119082 and WO 2009/140695 which are incorporated by reference herein. In some embodiments the recombinant microbial cell further comprises a polynucleotide encoding a fatty aldehyde biosynthesis polypeptide. In some embodiments the recombinant microbial cell further comprises a polynucleotide encoding an acyl-ACP reductase.

In some embodiments, an ec-terminal olefin is produced by expressing or overexpressing in the recombinant microbial cell a polynucleotide encoding a hydrocarbon biosynthesis polypeptide, such as a polypeptide having decarboxylase activity as described, for example, in PCT Publication No. WO 2009/085278 which is incorporated by reference herein. In some embodiments the recombinant microbial cell further comprises a polynucleotide encoding a thioesterase.

In some embodiments, an ec-internal olefin is produced by expressing or overexpressing in the recombinant microbial cell a polynucleotide encoding a hydrocarbon biosynthesis polypeptide, such as a polypeptide having OIeCD or OIeBCD activity as described, for example, in PCT Publication No. WO 2008/147781 which is incorporated by reference herein.

In some embodiments, an ec-ketone is produced by expressing or overexpressing in the recombinant microbial cell a polynucleotide encoding a hydrocarbon biosynthesis polypeptide, such as a polypeptide having OleA activity as described, for example, in PCT Publication No. WO 2008/147781 which is incorporated by reference herein.

Saturation Levels of oc-FA Derivatives

The degree of saturation of oc-acyl-ACPs (which can then be converted into various oc-FA derivatives as described hereinabove) can be controlled by regulating the degree of saturation of fatty acid intermediates. For example, the sfa, gns, and fab families of genes can be expressed, overexpressed, or expressed at reduced levels (e.g., attenuated), to control the amount of saturation of an oc-acyl-ACP.

oc-FA Pathway Polypeptides and Polynucleotides

The disclosure identifies polynucleotides useful in the recombinant microbial cells, methods, and compositions of the invention; however it will be recognized that absolute sequence identity to such polynucleotides is not necessary. For example, changes in a particular polynucleotide sequence can be made and the encoded polypeptide screened for activity. Such changes typically comprise conservative mutations and silent mutations (such as, for example, codon optimization). Modified or mutated (i.e., mutant) polynucleotides and encoded variant polypeptides can be screened for a desired function, such as, an improved function compared to the parent polypeptide, including but not limited to increased catalytic activity, increased stability, or decreased inhibition (e.g., decreased feedback inhibition), using methods known in the art.

The disclosure identifies enzymatic activities involved in various steps (i.e., reactions) of the oc-FA biosynthetic pathways described herein according to Enzyme Classification (EC) number, and provides exemplary polypeptides (i.e., enzymes) categorized by such EC numbers, and exemplary polynucleotides encoding such polypeptides. Such exemplary polypeptides and polynucleotides, which are identified herein by Accession Numbers and/or Sequence Identifier Numbers (SEQ ID NOs), are useful for engineering oc-FA pathways in parental microbial cells to obtain the recombinant microbial cells described herein. It is to be understood, however, that polypeptides and polynucleotides described herein are exemplary and non-limiting. The sequences of homologues of exemplary polypeptides described herein are available to those of skill in the art using databases such as, for example, the Entrez databases provided by the National Center for Biotechnology Information (NCBI), the ExPasy databases provided by the Swiss Institute of Bioinformatics, the BRENDA database provided by the Technical University of Braunschweig, and the KEGG database provided by the Bioinformatics Center of Kyoto University and University of Tokyo, all which are available on the World Wide Web.

It is to be further understood that a variety of microbial cells can be modified to contain an oc-FA pathway described herein, resulting in recombinant microbial cells suitable for the production of odd chain fatty acid derivatives. It is also understood that a variety of cells can provide sources of genetic material, including sequences of polynucleotides encoding polypeptides suitable for use in a recombinant microbial cell provided herein.

The disclosure provides numerous examples of polypeptides (i.e., enzymes) having activities suitable for use in the oc-FA biosynthetic pathways described herein. Such polypeptides are collectively referred to herein as "oc-FA pathway polypeptides" (alternatively, "oc-FA pathway enzymes"). Non-limiting examples of oc-FA pathway polypeptides suitable for use in recombinant microbial cells of the invention are provided in the Tables and Description and in the Examples herein.

In some embodiments, the invention includes a recombinant microbial cell comprising a polynucleotide sequence (also referred to herein as an "oc-FA pathway polynucleotide" sequence) which encodes an oc-FA pathway polypeptide.

Additional oc-FA pathway polypeptides and polynucleotides encoding them suitable for use in engineering an oc-FA pathway in a recombinant microbial cell of the invention can be obtained by a number of methods. For example, EC numbers classify enzymes according to the reaction catalyzed. Enzymes that catalyze a reaction in a biosynthetic pathway described herein can be identified by searching the EC number corresponding to that reaction in a database such as, for example: the KEGG database (Kyoto Encyclopedia of Genes and Genomes; Kyoto University and University of Tokyo); the UNIPROTKB database or the ENZYME database (ExPASy Proteomics Server; Swiss Institute of Bioinformatics); the PROTEIN database or the GENE database (Entrez databases; National Center for Biotechnology Information (NCBI)); or the BRENDA database (The Comprehensive Enzyme Information System; Technical University of Braunschweig); all of which are available on the World Wide Web. In one embodiment, an oc-FA pathway polynucleotide encoding an oc-FA pathway polypeptide having an enzymatic activity categorized by an EC number (such as, an EC number listed in the Description or in one of Tables herein), or a fragment or a variant thereof having that activity, is used in engineering the corresponding step of an oc-FA pathway in a recombinant microbial cell.

In some embodiments, an oc-FA pathway polynucleotide sequence encodes a polypeptide which is endogenous to the parental cell of the recombinant cell being engineered. Some such endogenous polypeptides are overexpressed in the recombinant microbial cell. An "endogenous polypeptide", as used herein, refers to a polypeptide which is encoded by the genome of the parental (e.g, wild-type) cell that is being engineered to produce the recombinant microbial cell.

An oc-FA pathway polypeptide, such as for example an endogenous oc-FA pathway polypeptide, can be overexpressed by any suitable means. As used herein, "overexpress" means to express or cause to be expressed a polynucleotide or polypeptide in a cell at a greater concentration than is normally expressed in a corresponding parental (for example, wild-type) cell under the same conditions. For example, a polypeptide is "overexpressed" in a recombinant microbial cell when it is present in a greater concentration in the recombinant cell as compared to its concentration in a non-recombinant host cell of the same species (e.g., the parental cell) when cultured under the same conditions.

In some embodiments, the oc-FA pathway polynucleotide sequence encodes an exogenous or heterologous polypeptide. In other words, the polypeptide encoded by the polynucleotide is exogenous to the parental microbial cell. An "exogenous" (or "heterologous") polypeptide, as used herein, refers to a polypeptide not encoded by the genome of the parental (e.g, wild-type) microbial cell that is being engineered to produce the recombinant microbial cell. Such a polypeptide can also be referred to as a "non-native" polypeptide. A variant (that is, a mutant) polypeptide is an example of an exogenous polypeptide.

In certain embodiments, an oc-FA pathway polypeptide comprises an amino acid sequence other than that of one of the exemplary polypeptides provided herein; for example, an oc-FA pathway polypeptide can comprise a sequence which is a homologue, a fragment, or a variant of the sequence of the exemplary polypeptide.

The terms "homolog," "homologue," and "homologous" as used herein refer to a polynucleotide or a polypeptide comprising a sequence that is at least 50%, preferably at least 60%, more preferably at least 70% (e.g., at least 75%, at least 80%, at least 85%, at least 90%, at least 91%, at least 92%, at least 93%, at least 94%, at least 95%, at least 96%, at least 97%, at least 98%, or at least 99%) homologous to the corresponding polynucleotide or polypeptide sequence. One of ordinary skill in the art is well aware of methods to determine homology between two or more sequences. Briefly, calculations of "homology" between two sequences can be performed as follows. The sequences are aligned for optimal comparison purposes (e.g., gaps can be introduced in one or both of a first and a second amino acid or polynucleotide sequence for optimal alignment and non-homologous sequences can be disregarded for comparison purposes). In a preferred embodiment, the length of a first sequence that is aligned for comparison purposes is at least about 30%, preferably at least about 40%, more preferably at least about 50%, even more preferably at least about 60%, and even more preferably at least about 70%, at least about 80%, at least about 90%, or about 100% of the length of a second sequence. The amino acid residues or nucleotides at corresponding amino acid positions or nucleotide positions of the first and second sequences are then compared. When a position in the first sequence is occupied by the same amino acid residue or nucleotide as the corresponding position in the second sequence, then the molecules are identical at that position (as used herein, amino acid or nucleic acid "identity" is equivalent to amino acid or nucleic acid "homology"). The percent identity between the two sequences is a function of the number of identical positions shared by the sequences, taking into account the number of gaps and the length of each gap, which need to be introduced for optimal alignment of the two sequences.

The comparison of sequences and determination of percent homology (i.e., percent identity) between two sequences can be accomplished using a mathematical algorithm, such as BLAST (Altschul et al., *J. Mol. Biol.*, 215(3): 403-410 (1990)). The percent homology between two amino acid sequences also can be determined using the Needleman and Wunsch algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6 (Needleman and Wunsch, *J. Mol. Biol.*, 48: 444-453 (1970)). The percent homology between two nucleotide sequences also can be determined using the GAP program in the GCG software package, using a NWSgapdna.CMP matrix and a gap weight of 40, 50, 60, 70, or 80 and a length weight of 1, 2, 3, 4, 5, or 6. One of ordinary skill in the art can perform initial homology calculations and adjust the algorithm parameters accordingly. A preferred set of parameters (and the one that should be used if a practitioner is uncertain about which parameters should be applied to determine if a molecule is within a homology limitation of the claims) are a Blossum 62 scoring matrix with a gap penalty of 12, a gap extend penalty of 4, and a frameshift gap penalty of 5. Additional methods of sequence alignment are known in the biotechnology arts (see, e.g., Rosenberg, BMC Bioinformatics, 6: 278 (2005); Altschul et al., *FEBS J.*, 272(20): 5101-5109 (2005)).

An "equivalent position" (for example, an "equivalent amino acid position" or "equivalent nucleic acid position") is defined herein as a position (such as, an amino acid position or nucleic acid position) of a test polypeptide (or test polynucleotide) sequence which aligns with a corresponding position of a reference polypeptide (or reference polynucleotide) sequence, when optimally aligned using an alignment algorithm as described herein. The equivalent amino acid position of the test polypeptide need not have the same numerical position number as the corresponding position of the reference polypeptide; likewise, the equivalent nucleic acid position of the test polynucleotide need not have the same numerical position number as the corresponding position of the reference polynucleotide.

In some embodiments, the oc-FA pathway polypeptide is a variant of a reference (e.g., a parent) polypeptide, such as a variant of an exemplary oc-FA pathway polypeptide described herein. A "variant" (alternatively, "mutant") polypeptide as used herein refers to a polypeptide having an amino acid sequence that differs from that of a parent (e.g., wild-type) polypeptide by at least one amino acid. The variant can comprise one or more conservative amino acid substitutions, and/or can comprise one or more non-conservative substitutions, compared to the parent polypeptide sequence. In some embodiments, the variant polypeptide has 1, 2, 3, 4, 5, 6, 7, 8, 9, 10, 15, 20, 30, 40, 50, or more amino acid substitutions, additions, insertions, or deletions compared to the parent polypeptide sequence. In some embodiments, the sequence of the variant polypeptide is at least 80%, at least 85%, at least 90%, at least 91%, at least 92%, at least 93%, at least 94%, at least 95%, at least 96%, at least 97%, at least 98%, or at least 99% identical to the sequence of the parent polypeptide.

In some embodiments, the oc-FA pathway polypeptide is a fragment of a reference (e.g., a parent) polypeptide, such as a fragment of an exemplary oc-FA pathway polypeptide described herein. The term "fragment" refers to a shorter portion of a full-length polypeptide or protein ranging in size from four amino acid residues to the entire amino acid sequence minus one amino acid residue. In certain embodiments of the invention, a fragment refers to the entire amino acid sequence of a domain of a polypeptide or protein (e.g., a substrate binding domain or a catalytic domain).

In some embodiments, a homologue, a variant, or a fragment comprises one or more sequence motif as defined herein. In one embodiment, a homologue, a variant, or a fragment of a β-ketoacyl-ACP synthase polypeptide comprises one or more sequence motif selected from SEQ ID NOs:14-19. Determination that a sequence contains a particular sequence motif can be readily accomplished, for example, using the ScanProsite tool available on the World Wide Web site of the ExPASy Proteomics Server.

It is understood that an oc-FA polypeptide may have conservative or non-essential amino acid substitutions, relative to a parent polypeptide, which does not have a substantial effect on a biological function or property of the oc-FA polypeptide. Whether or not a particular substitution will be tolerated (i.e., will not adversely affect a desired biological function, such as enzymatic activity) can be determined, for example, as described in Bowie et al. (*Science,* 247: 1306-1310 (1990)).

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

Variants can be naturally occurring or created in vitro. In particular, variants can be created using genetic engineering techniques, such as site directed mutagenesis, random chemical mutagenesis, exonuclease III deletion procedures, or standard cloning techniques. Alternatively, such variants, fragments, analogs, or derivatives can be created using chemical synthesis or modification procedures.

Methods of making variants are well known in the art. These include procedures in which nucleic acid sequences obtained from natural isolates are modified to generate nucleic acids that encode polypeptides having characteristics that enhance their value in industrial or laboratory applications (including, but not limited to, increased catalytic activity (turnover number), improved stability, and reduced feedback inhibition). In such procedures, a large number of modified nucleic acid sequences having one or more nucleotide differences with respect to the sequence obtained from the natural isolate are generated and characterized. Typically, these nucleotide differences result in amino acid changes with respect to the polypeptides encoded by the nucleic acids from the natural isolates. For example, variants can be prepared by using random or site-directed mutagenesis.

Variants can also be created by in vivo mutagenesis. In some embodiments, random mutations in a nucleic acid sequence are generated by propagating the sequence in a bacterial strain, such as an *E. coli* strain, which carries mutations in one or more of the DNA repair pathways. Such "mutator" strains have a higher random mutation rate than that of a wild-type strain. Propagating a DNA sequence in one of these strains will eventually generate random mutations within the DNA. Mutator strains suitable for use for in vivo mutagenesis are described in, for example, International Patent Application Publication No. WO 1991/016427.

Variants can also be generated using cassette mutagenesis. In cassette mutagenesis, a small region of a double-stranded DNA molecule is replaced with a synthetic oligonucleotide "cassette" that differs from the native sequence. The oligonucleotide often contains a completely and/or partially randomized native sequence.

Recursive ensemble mutagenesis can also be used to generate variants. Recursive ensemble mutagenesis is an algorithm for protein engineering (i.e., protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described in, for example, Arkin et al., *Proc. Natl. Acad. Sci.*, U.S.A., 89: 7811-7815 (1992).

In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in, for example, Delegrave et al., *Biotech. Res,* 11: 1548-1552 (1993).

Preferred fragments or variants of a parent polypeptide (e.g., fragments or variants of a parent oc-FA pathway polypeptide) retain some or all of a biological function or property (such as, enzymatic activity, thermal stability) of the parent polypeptide. In some embodiments, the fragment or variant retains at least 75% (e.g., at least 80%, at least 90%, or at least 95%) of a biological function or property of the parent polypeptide. In other embodiments, the fragment or variant retains about 100% of a biological function or property of the parent polypeptide.

In some embodiments, the fragment or variant of the parent polypeptide exhibits an increased catalytic activity (as reflected by, for example, a higher turnover number, an altered pH optimum, a decreased $K_m$ for a desired substrate, or an increased $k_{cat}/K_m$ for a desired substrate), relative to that of the parent polypeptide, under conditions in which the recombinant microbial cell is cultured. For example, if the parent polypeptide is endogenous to (that is, is derived from) a thermophilic cell, and if the recombinant microbial cell is generally cultured at a lower temperature than the thermophilic cell, the parent polypeptide may exhibit significantly reduced activity at the lower temperature; in which case, the variant polypeptide preferably exhibits an increased catalytic activity (such as, a higher turnover number), relative to that of the parent polypeptide, at that lower temperature.

In other embodiments, the fragment or variant of the parent polypeptide exhibits improved stability, relative to that of the parent polypeptide, under conditions in which the recombinant microbial cell is cultured. Such stability can include stability towards changes in temperature, ionic strength, pH, or any other differences in growth or media conditions between the recombinant microbial cell and the cell from which the parent polypeptide was derived. For example, if the parent polypeptide is derived from a psychrotrophic cell, and if the recombinant microbial cell is generally cultured at a higher temperature than the psychrotrophic cell, the parent polypeptide may be relatively unstable at the higher temperature; in which case, the variant polypeptide preferably exhibits improved stability relative to that of the parent polypeptide at that higher temperature.

In other embodiments, the fragment or variant of the parent polypeptide exhibits reduced inhibition of catalytic activity (such as, reduced feedback inhibition) by a cellular metabolite or by a culture media component, relative to such inhibition exhibited by the parent polypeptide, under conditions in which the recombinant microbial cell is cultured.

In certain embodiments, an oc-FA pathway polypeptide is a homologue, a fragment, or a variant of a parent polypeptide, wherein the oc-FA pathway polypeptide is effective in carrying out an oc-FA pathway reaction in a recombinant microbial cell. Such an oc-FA pathway polypeptide is suitable for use in a recombinant microbial cell of the invention.

The effectiveness of a test polypeptide (such as, for example, an oc-FA pathway polypeptide described herein, or a homologue, a fragment, or a variant thereof) in carrying out a reaction of an oc-FA pathway can be determined by a number of methods. For example, to determine the effectiveness of a test polypeptide in catalyzing a specific reaction of a biochemical pathway, first a cell is engineered (if necessary) to obtain a parental cell that comprises all the activities needed to catalyze the reactions of the biochemical pathway in question, except for the specific pathway reaction being tested (although, in some instances, the parental cell may express endogenous polypeptide(s) that catalyze the specific pathway reaction being tested; in such instances the endogenous activity will preferably be low enough to readily detect an increase in product owing to the activity of the test polypeptide). A polynucleotide encoding the test polypeptide, operatively linked to a suitable promoter (e.g., in an expression vector), is then introduced into the parental cell, generating a test cell. The test cell and the parental cell are cultured separately under identical conditions which are sufficient for expression of the pathway polypeptides in the parental and test cell cultures and expression of the test polypeptide in the test cell culture. At various times during and/or after culturing, samples are obtained from the test cell culture and the parental cell culture. The samples are analyzed for the presence of a particular pathway intermediate or product. Presence of the pathway intermediate or product can be determined by methods including, but not limited to, gas chromatography (GC), mass spectroscopy (MS), thin layer chromatography (TLC), high-performance liquid chromatography (HPLC), liquid chromatography (LC), GC coupled with a flame ionization detector (GC-FID), GC-MS, and LC-MS. The presence of an oc-FA pathway intermediate or product in the test cell culture sample(s), and the absence (or a reduced amount) of the oc-FA pathway intermediate or product in the parent cell culture sample(s), indicates that the test polypeptide is effective in carrying out an oc-FA pathway reaction and is suitable for use in a recombinant microbial cell of the invention.

Production of Odd Chain Fatty Acid Derivatives in Recombinant Microbial Cells

In one aspect, the invention includes a method of making an odd chain fatty acid derivative composition, the method comprising culturing a recombinant microbial cell of the invention in a culture medium containing a carbon source under conditions effective to express the recombinant polynucleotide sequences, and optionally isolating the produced odd chain fatty acid derivative composition.

An "odd chain fatty acid derivative composition" (abbreviated "oc-FA derivative composition") is a composition comprising an odd chain fatty acid derivative as defined herein, such as, for example, an odd chain fatty acid, an odd chain fatty ester (e.g., an odd chain fatty methyl ester, an odd chain fatty ethyl ester, an odd chain wax ester), an odd chain fatty aldehyde, an odd chain fatty alcohol, an even chain hydrocarbon (such as an even chain alkane, an even chain alkene, an even chain terminal olefin, an even chain internal olefin), or an even chain ketone. Similarly, an "odd chain fatty acid composition" is a composition comprising odd chain fatty acids, an "odd chain fatty alcohol composition" is a composition comprising odd chain fatty alcohols, an "even chain alkane composition" is a composition comprising even chain alkanes, and so on. It is to be understood that a composition comprising odd chain fatty acid derivatives may also comprise even chain fatty acid derivatives.

In one aspect, the invention includes a method of making a composition comprising an odd chain fatty acid derivative, the method comprising: obtaining a recombinant microbial cell (such as, a culture comprising a recombinant microbial cell) comprising: (a) polynucleotides encoding polypeptides having enzymatic activities effective to produce an increased amount of propionyl-CoA in the recombinant microbial cell, relative to the amount of propionyl-CoA produced in a parental microbial cell lacking or having a reduced amount of said enzymatic activity, wherein at least one polypeptide is exogenous to the recombinant microbial cell or wherein expression of at least one polynucleotide is modulated in the recombinant microbial cell as compared to the expression of the polynucleotide in the parental microbial cell; (b) a polynucleotide encoding a polypeptide having β-ketoacyl-ACP synthase activity that utilizes propionyl-CoA as a substrate; and (c) one or more polynucleotides encoding a polypeptide having fatty acid derivative enzyme activity, wherein the recombinant microbial cell produces a fatty acid derivative composition comprising odd chain fatty acid derivatives and even chain fatty acid derivatives when cultured in the presence of a carbon source under conditions effective to express the polynucleotides according to (a), (b), and (c); culturing the recombinant microbial cell in a culture medium containing a carbon source under conditions effective to express the polynucleotides according to (a), (b), and (c) and produce a fatty acid derivative composition comprising odd chain fatty acid derivatives and even chain fatty acid derivatives, and optionally recovering the composition from the culture medium.

In some embodiments, at least 5%, at least 10%, at least 20%, at least 30%, at least 40%, at least 50%, at least 60%, at least 70%, at least 80% or at least 90% by weight of the fatty acid derivatives in the composition are odd chain fatty acid derivatives. In some embodiments, the fatty acid derivative composition comprises odd chain fatty acid derivatives in an amount (e.g., a titer) of at least 10 mg/L, at least 15 mg/L, at least 20 mg/L, at least 25 mg/L, at least 50 mg/L, at least 75 mg/L, at least 100 mg/L, at least 125 mg/L, at least 150 mg/L, at least 175 mg/L, at least 200 mg/L, at least 225 mg/L, at least 250 mg/L, at least 275 mg/L, at least 300 mg/L, at least 325 mg/L, at least 350 mg/L, at least 375 mg/L, at least 400 mg/L, at least 425 mg/L, at least 450 mg/L, at least 475 mg/L, at least 500 mg/L, at least 525 mg/L, at least 550 mg/L, at least 575 mg/L, at least 600 mg/L, at least 625 mg/L, at least 650 mg/L, at least 675 mg/L, at least 700 mg/L, at least 725 mg/L, at least 750 mg/L, at least 775 mg/L, at least 800 mg/L, at least 825 mg/L, at least 850 mg/L, at least 875 mg/L, at least 900 mg/L, at least 925 mg/L, at least 950 mg/L, at least 975 mg/L, at least 1000 mg/L, at least 1050 mg/L, at least 1075 mg/L, at least 1100 mg/L, at least 1125 mg/L, at least 1150 mg/L, at least 1175 mg/L, at least 1200 mg/L, at least 1225 mg/L, at least 1250 mg/L, at least 1275 mg/L, at least 1300 mg/L, at least 1325 mg/L, at least 1350 mg/L, at least 1375 mg/L, at least 1400 mg/L, at least 1425 mg/L, at least 1450 mg/L, at least 1475 mg/L, at least 1500 mg/L, at least 1525 mg/L, at least 1550 mg/L, at least 1575 mg/L, at least 1600 mg/L, at least 1625 mg/L, at least 1650 mg/L, at least 1675 mg/L, at least 1700 mg/L, at least 1725 mg/L, at least 1750 mg/L, at least 1775 mg/L, at least 1800 mg/L, at least 1825 mg/L, at least 1850 mg/L, at least 1875 mg/L, at least 1900 mg/L, at least 1925 mg/L, at least 1950 mg/L, at least 1975 mg/L, at least 2000 mg/L, at least 3000 mg/L, at least 4000 mg/L, at least 5000 mg/L, at least 6000 mg/L, at least 7000 mg/L, at least 8000 mg/L, at least 9000 mg/L, at least 10000 mg/L, at least 20000 mg/L, or a range bounded by any two of the foregoing values.

In various embodiments, the fatty acid derivative enzyme activity comprises a thioesterase activity, an ester synthase activity, a fatty aldehyde biosynthesis activity, a fatty alcohol biosynthesis activity, a ketone biosynthesis activity, and/or a hydrocarbon biosynthesis activity. In some embodiments, the recombinant microbial cell comprises polynucleotides encoding two or more polypeptides, each polypeptide having a fatty acid derivative enzyme activity.

In various embodiments, the recombinant microbial cell produces a composition comprising odd chain fatty acids, odd chain fatty esters, odd chain wax esters, odd chain fatty aldehydes, odd chain fatty alcohols, odd chain alkanes, even chain alkenes, even chain internal olefins, even chain terminal olefins, or even chain ketones.

In various embodiments, the recombinant microbial cell comprises polynucleotides encoding polypeptides having enzymatic activities effective to produce an increased amount of propionyl-CoA in the recombinant microbial cell, selected from: (i) polynucleotides encoding polypeptides having aspartokinase activity, homoserine dehydrogenase activity, homoserine kinase activity, threonine synthase activity, and threonine deaminase activity, or (ii) polynucleotides encoding polypeptides having (R)-citramalate synthase activity, isopropylmalate isomerase activity, and beta-isopropyl malate dehydrogenase activity, or (iii) polypeptides having methylmalonyl-CoA mutase activity, methylmalonyl-CoA decarboxylase activity and/or methylmalonyl-CoA carboxyltransferase activity, or (i) and (ii), or (i) and (iii), or (ii) and (iii), or (i), (ii), and (iii), wherein at least one polypeptide is exogenous to the recombinant microbial cell, or wherein expression of at least one polynucleotide is modulated in the recombinant microbial cell as compared to the expression of the polynucleotide in the parental microbial cell.

The fatty acid derivative compositions comprising odd chain fatty acid derivatives produced by the methods of invention may be recovered or isolated from the recombinant microbial cell culture. The term "isolated" as used herein with respect to products, such as fatty acid derivatives, refers to products that are separated from cellular components, cell culture media, or chemical or synthetic precursors. The fatty acid derivatives produced by the methods described herein can be relatively immiscible in the fermentation broth, as well as in the cytoplasm. Therefore, the fatty acid derivatives can collect in an organic phase either intracellularly or extracellularly. The collection of the products in the organic phase can lessen the impact of the fatty acid derivative on cellular function and can allow the recombinant microbial cell to produce more product.

In some embodiments, the fatty acid derivative composition (which comprises odd chain fatty acid derivatives) produced by the methods of invention are purified. As used herein, the term "purify," "purified," or "purification" means the removal or isolation of a molecule from its environment by, for example, isolation or separation. "Substantially purified" molecules are at least about 60% free (e.g., at least about 70% free, at least about 75% free, at least about 85% free, at least about 90% free, at least about 95% free, at least about 97% free, at least about 99% free) from other components with which they are associated. As used herein, these terms also refer to the removal of contaminants from a sample. For example, the removal of contaminants can result in an increase in the percentage of a fatty acid derivative (such as, a fatty acid or a fatty alcohol or a fatty ester or a hydrocarbon) relative to other components in a sample. For example, when a fatty ester or a fatty alcohol is produced in a recombinant microbial cell, the fatty ester or fatty alcohol can be purified by the removal of recombinant microbial cell proteins. After purification, the percentage of the fatty ester or fatty alcohol in the sample relative to other components is increased.

As used herein, the terms "purify," "purified," and "purification" are relative terms which do not require absolute purity. Thus, for example, when a fatty acid derivative composition is produced in recombinant microbial cells, a purified fatty acid derivative composition is a fatty acid derivative composition that is substantially separated from other cellular components (e.g., nucleic acids, polypeptides, lipids, carbohydrates, or other hydrocarbons).

The fatty acid derivative composition (which comprises odd chain fatty acid derivatives) may be present in the extracellular environment, or it may be isolated from the extracellular environment of the recombinant microbial cell. In certain embodiments, the fatty derivative is secreted from the recombinant microbial cell. In other embodiments, the fatty acid derivative is transported into the extracellular environment. In yet other embodiments, the fatty acid derivative is passively transported into the extracellular environment. The fatty acid derivative can be isolated from a recombinant microbial cell using methods known in the art.

Fatty acid derivatives (including odd chain fatty acid derivatives produced according to the methods of the present invention) can be distinguished from organic compounds derived from petrochemical carbon on the basis of dual carbon-isotopic fingerprinting or $^{14}C$ dating. Additionally, the specific source of biosourced carbon (e.g., glucose vs. glycerol) can be determined by dual carbon-isotopic fingerprinting (see, e.g., U.S. Pat. No. 7,169,588).

The ability to distinguish fatty acid derivatives produced by recombinant microbial cells from petroleum-based organic compounds is beneficial in tracking these materials in commerce. For example, organic compounds or chemicals comprising both biologically-based and petroleum-based carbon isotope profiles may be distinguished from organic compounds and chemicals made only of petroleum-based materials. Hence, the materials prepared in accordance with the inventive methods may be followed in commerce on the basis of their unique carbon isotope profile.

Fatty acid derivatives produced by recombinant microbial cells can be distinguished from petroleum-based organic compounds by comparing the stable carbon isotope ratio ($^{13}C/^{12}C$) in each fuel. The $^{13}C/^{12}C$ ratio in a given fatty acid derivative thereof produced according to the methods of the invention is a consequence of the $^{13}C/^{12}C$ ratio in atmospheric carbon dioxide at the time the carbon dioxide is fixed. It also reflects the precise metabolic pathway. Regional variations also occur. Petroleum, $C_3$ plants (the broadleaf), $C_4$ plants (the grasses), and marine carbonates all show significant differences in $^{13}C/^{12}C$ and the corresponding $\delta^{13}C$ values. Furthermore, lipid matter of $C_3$ and $C_4$ plants analyze differently than materials derived from the carbohydrate components of the same plants as a consequence of the metabolic pathway.

The $^{13}C$ measurement scale was originally defined by a zero set by Pee Dee Belemnite (PDB) limestone, where values are given in parts per thousand deviations from this material. The "$\delta^{13}C$" values are expressed in parts per thousand (per mil), abbreviated, ‰, and are calculated as follows:

$$\delta^{13}C(\text{‰}) = [(^{13}C/^{12}C)_{sample} - (^{13}C/^{12}C)_{standard}]/(^{13}C/^{12}C)_{standard} \times 1000$$

In some embodiments, a fatty acid derivative produced according to the methods of the invention has a $\delta^{13}C$ of about −30 or greater, about −28 or greater, about −27 or greater, about −20 or greater, about −18 or greater, about −15 or greater, about −13 or greater, or about −10 or greater. Alternatively, or in addition, a fatty acid derivative has a $\delta^{13}C$ of about −4 or less, about −5 or less, about −8 or less, about −10 or less, about −13 or less, about −15 or less, about −18 or less, or about −20 or less. Thus, the fatty acid derivative can have a $\delta^{13}C$ bounded by any two of the above endpoints. For example, a fatty acid derivative can have a $\delta^{13}C$ of about −30 to about −15, about −27 to about −19, about −25 to about −21, about −15 to about −5, about −13 to about −7, or about −13 to about −10. In some embodiments, a fatty acid derivative can have a $\delta^{13}C$ of about −10, −11, −12, or −12.3. In other embodiments, a fatty acid derivative has a $\delta^{13}C$ of about −15.4 or greater. In yet other embodiments, a fatty acid derivative has a $\delta^{13}C$ of about −15.4 to about −10.9, or a $\delta^{13}C$ of about −13.92 to about −13.84.

A fatty acid derivative produced by a recombinant microbial cell can also be distinguished from petroleum-based organic compounds by comparing the amount of $^{14}C$ in each compound. Because $^{14}C$ has a nuclear half life of 5730 years, petroleum based fuels containing "older" carbon can be distinguished from fatty acids or derivatives thereof which contain "newer" carbon (see, e.g., Currie, "Source Apportionment of Atmospheric Particles", *Characterization of Environmental Particles*, J. Buffle and H. P. van Leeuwen, Eds., Vol. I of the IUPAC Environmental Analytical Chemistry Series, Lewis Publishers, Inc., pp. 3-74 (1992)).

As used herein, "fraction of modern carbon" or $f_M$ has the same meaning as defined by National Institute of Standards and Technology (NIST) Standard Reference Materials (SRMs) 4990B and 4990C, known as oxalic acids standards HOxI and HOxII, respectively. The 14-12 fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), $f_M$ is approximately 1.1.

In some embodiments, a fatty acid derivative produced according to the methods of the invention has a $f_M^{14}C$ of at least about 1, e.g., at least about 1.003, at least about 1.01, at least about 1.04, at least about 1.111, at least about 1.18, or at least about 1.124. Alternatively, or in addition, the fatty acid derivative has an $f_M^{14}C$ of about 1.130 or less, e.g., about 1.124 or less, about 1.18 or less, about 1.111 or less, or about 1.04 or less. Thus, the fatty acid derivative can have a $f_M^{14}C$ bounded by any two of the above endpoints. For example, the fatty acid derivative can have a $f_M^{14}C$ of about 1.003 to about 1.124, a $f_M^{14}C$ of about 1.04 to about 1.18, or a $f_M^{14}C$ of about 1.111 to about 1.124.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language ("e.g.", "such as", "for example") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Media Compositions

Che-9 media: M9 supplemented with extra $NH_4Cl$ (an additional 1 g/L), Bis-Tris buffer (0.2 M), Triton X-100 (0.1% v/v), and trace minerals (27 mg/L $FeCl_3.6\ H_2O$, 2 mg/L $ZnCl.4H_2O$, 2 mg/L $CaCl_2.6H_2O$, 2 mg/L $Na_2MoO_4.2H_2O$, 1.9 mg/L $CuSO_4.5H_2O$, 0.5 mg/L $H_3BO_3$, 100 mL/L concentrated HCl).

2NBT: Che-9 supplemented with 20 g/L (2% w/v) glucose.
4NBT: Che-9 supplemented with 40 g/L (4% w/v) glucose.

Example 1

Bacterial Strains and Plasmids

*E. coli* MG1655 ΔfadE (Strain "D1")

This example describes the construction of a recombinant microbial cell in which the expression of a fatty acid degradation enzyme is attenuated. The fadE gene of *E. coli* (also known as yafH), which encodes an acyl coenzyme A dehydrogenase (GenBank Accession No. AAC73325) involved in fatty acid degradation, was deleted from *E. coli* strain MG1655 using the Red system described by Datsenko, K. A. et al. (*Proc. Natl. Acad. Sci. USA* 97: 6640-6645 (2000)), with the following modifications.

The following two primers were used to create the deletion of fadE:

```
Del-fadE-F
                                   (SEQ ID NO: 82)
5' AAAAACAGCA ACAATGTGAG CTTTGTTGTAATTAT ATTGTAA ACATATT GATTCCGGGGATCCGTCGACC;
and Del-fadE-R
                                   (SEQ ID NO: 83)
5' AAACGGAGCCT TTCGGCTCCGTTATT CATTTACGCGGCTTCAAC

TTTCCTG TAGGCTGGAGCTGCTTC
```

The Del-fadE-F and Del-fadE-R primers were used to amplify the kanamycin resistance ($Km^R$) cassette from plasmid pKD13 (Datsenko et al., supra) by PCR. The PCR product was then used to transform electrocompetent *E. coli* MG1655 cells containing plasmid pKD46, which expresses Red recombinase (Datsenko et al., supra), which had been previously induced with arabinose for 3-4 hours. Following a 3-hour outgrowth in SOC medium at 37° C., the cells were plated on Luria agar plates containing 50 µg/mL of kanamycin. Resistant colonies were identified and isolated after an overnight incubation at 37° C. Disruption of the fadE gene was confirmed in some of the colonies by PCR amplification using primers fadE-L2 and fadE-R1, which were designed to flank the *E. coli* fadE gene.

```
fadE-L2  '-CGGGCAGGTGCTATGACCAGGAC; (SEQ ID NO: 84)
and fadE-R1  5'-CGCGGCGTTGACCGGCAGCCTGG (SEQ ID NO: 85)
```

After the fadE deletion was confirmed, a single colony was used to remove the $Km^R$ marker using the pCP20 plasmid (Datsenko et al., supra). The resulting MG1655 *E. coli* strain with the fadE gene deleted and the $Km^R$ marker removed was designated *E. coli* MG1655 ΔfadE, or strain "D1".

*E. coli* MG1655 ΔfadE ΔtonA (Strain "DV2")

This example describes the construction of a recombinant microbial cell in which the expression of a fatty acid degradation enzyme and the expression of an outer membrane protein receptor are attenuated. The tonA (also known as fhuA) gene of *E. coli* MG1655, which encodes a ferrichrome outer membrane transporter which also acts as a bacteriophage receptor (GenBank Accession No. NP_414692) was deleted from strain D1 (described above) using the Red system according to Datsenko et al., supra, with the following modifications:

The primers used to create the tonA deletion were:

```
Del-tonA-F
                                   (SEQ ID NO: 86)
5'-ATCATTCTCGTTTACGTTATCATTCACTTTACATCAGAGATATAC CAATGATTCCGGGGATCCGTCGACC;
and Del-tonA-R
                                   (SEQ ID NO: 87)
5'-GCACGGAAATCCGTGCCCCAAAAGAGAAATTAGAAACGGAAG

GTTGCGG TTGTAGGCTGGAGCTGCTTC
```

The Del-tonA-F and Del-tonA-R primers were used to amplify the kanamycin resistance ($Km^R$) cassette from plasmid pKD13 by PCR. The PCR product obtained in this way was used to transform electrocompetent *E. coli* MG1655 D1 cells containing pKD46 (Datsenko et al., supra), which cells had been previously induced with arabinose for 3-4 hours. Following a 3-hour outgrowth in SOC medium at 37° C., cells were plated on Luria agar plates containing 50 µg/mL of kanamycin. Resistant colonies were identified and isolated after an overnight incubation at 37° C. Disruption of the tonA gene was confirmed in some of the colonies by PCR amplification using primers flanking the *E. coli* tonA gene: tonA-verF and tonA-verR:.

```
tonA-verF
                                   (SEQ ID NO: 88)
5'-CAACAGCAACCTGCTCAGCAA;
and tonA-verR
                                   (SEQ ID NO: 89)
5'-AAGCTGGAGCAGCAAAGCGTT
```

After the tonA deletion was confirmed, a single colony was used to remove the $Km^R$ marker using the pCP20 plasmid (Datsenko et al., supra). The resulting MG1655 *E. coli* strain having fadE and tonA gene deletions was designated *E. coli* MG1655 ΔfadE ΔtonA, or strain "DV2".

*E. coli* MG1655 ΔfadE ΔtonA lacI::tesA (Strain "DV2 'tesA")

This example describes the construction of a recombinant microbial cell comprising a polynucleotide encoding a polypeptide having a fatty acid derivative enzyme activity. The tesA polynucleotide sequence encoding *E. coli* acyl-CoA thioesterase I (EC 3.1.1.5, 3.1.2.-; e.g., GenBank Accession AAC73596; SEQ ID NO:64) was modified to remove the leader sequence, such that the resulting 'tesA gene product was truncated by 25 amino acids and the amino acid at the original position 26, alanine, was replaced with methionine, which then became the first amino acid of the 'TesA polypeptide sequence (SEQ ID NO:65; Cho et al., *J. Biol. Chem.*, 270:4216-4219 (1995)).

An integration cassette containing the 'tesA coding sequence operatively linked to the $P_{Trc}$ promoter plus a kanamycin resistance gene was PCR— amplified from plasmid pACYC-$P_{Trc}$-tesA (Example 1, below) using the primers lacI-forward: GGCTGGCTGGCATAAATATCTC (SEQ ID NO:90) and lacZ-reverse: GCGTTAAAGTTGTTCTGCT-TCATCAGCAGGATATCCTGCAC-CATCGTCTGGATTTTGAACTTTTGCTTTGC CACG-GAAC (SEQ ID NO:91), electroporated into strain DV2 and integrated into the chromosome using Red recombinase expressed from the pKD46 plasmid (Datsenko et al., supra). The transformants were selected on LB plates supplemented with kanamycin. Correct integration was assessed using diagnostic PCR.

pDG2 Expression Vector

The pDG2 expression vector was the base plasmid for many of the constructs described below. The pCDFDuet-1 vector (Novagen/EMD Biosciences) carries the CloDF13 replicon, lacI gene and streptomycin/spectinomycin resistance gene (aadA). To construct the pDG2 plasmid, the C-terminal portion of the plsX gene, which contains an internal promoter for the downstream fabH gene (Podkovyrov and Larson, *Nucl. Acids Res.* (1996) 24 (9): 1747-1752 (1996)) was amplified from *E. coli* MG1655 genomic DNA using primers

```
                                        (SEQ ID NO: 92)
5'-TGAATTCCATGGCGCAACTCACTCTTCTTTTAGTCG-3'
and
                                        (SEQ ID NO: 93)
5'-CAGTACCTCGAGTCTTCGTATACATATGCGCT CAGTCAC-3'
```

These primers introduced NcoI and XhoI restriction sites near the ends, as well as an internal NdeI site.

Both the plsX insert (containing the EcfabH promoter), and the pCDFDuet-1 vector, were digested with restriction enzymes NcoI and XhoI. The cut vector was treated with Antarctic phosphatase. The insert was ligated into the vector and transformed into transformation-competent *E. coli* cells. Clones were screened by DNA sequencing. The pDG2 plasmid sequence is provided herein as SEQ ID NO:73.

FabH Expression Plasmids

The pDG6 plasmid, expressing *B. subtilis* FabH1, was constructed using the pDG2 plasmid. The fabH1 coding sequence was amplified from *Bacillus subtilis* strain 168 using primers 5'-CCTTGGGGCATATGAAAGCTG-3' (SEQ ID NO:94) and 5'-TTTAGTCATCTCGAGTGCACCTCACCTTT-3' (SEQ ID NO:95). These primers introduced NdeI and XhoI restriction sites at the ends of the amplification product.

Both the fabH1 insert and the pDG2 vector were digested with restriction enzymes NdeI and XhoI. The cut vector was treated with Antarctic phosphatase. The insert was ligated into the vector and transformed into transformation-competent *E. coli* cells. Clones were screened by DNA sequencing. The pDG6 plasmid sequence is provided herein as SEQ ID NO:74, and expresses the *B. subtilis* FabH1 polypeptide (SEQ ID NO:2) under the control of the EcfabH promoter.

Other plasmids based on pDG2 were prepared using a similar strategy as employed for the pDG6 plasmid. Plasmid pDG7 comprises a *Bacillus subtilis* fabH2 coding sequence which expresses the *B. subtilis* FabH2 polypeptide (SEQ ID NO:3). Plasmid pDG8 comprises a *Streptomyces coelicolor* fabH coding sequence which expresses the *S. coelicolor* FabH polypeptide (SEQ ID NO:4).

pACYC-$P_{Trc}$-tesA and pACYC-$P_{Trc2}$-tesA plasmids

Plasmid pACYC-$P_{Trc}$ was constructed by PCR-amplifying the lacI$^q$, $P_{Trc}$ promoter and terminator region from pTrcHis2A (Invitrogen, Carlsbad, Calif.) using primers

```
pTrc_F
                                        (SEQ ID NO: 96)
TTTCGCGAGGCCGGCCCCGCCAACACCCGCTGACG
and pTrc_R
                                        (SEQ ID NO: 97)
AAGGACGTCTTAATTAATCAGGAGAGCGTTCACCGACAA
```

The PCR product was then digested with AatII and NruI and insterted into plasmid pACYC177 (Rose, R. E., *Nucleic Acids Res.*, 16:356 (1988)) digested with AatII and ScaI. The nucleotide sequence of the pACYC-$P_{Trc}$ vector is provided herein as SEQ ID NO: 75.

To generate the pACYC-$P_{Trc2}$ plasmid, a single point mutation was introduced in the $P_{Trc}$ promoter of the pACYC-$P_{Trc}$ plasmid to generate the variant promoter P Trc2 and the pACYC-$P_{Trc2}$ plasmid. The wild-type $P_{Trc}$ promoter sequence is provided herein as SEQ ID NO:76, and the $P_{Trc2}$ variant promoter is provided herein as SEQ ID NO:77.

The nucleotide sequence encoding *E. coli* acyl-CoA thioesterase I (TesA, EC 3.1.1.5, 3.1.2.-; e.g., GenBank Accession AAC73596; SEQ ID NO:64) was modified to remove the leader sequence, such that the resulting 'tesA gene product was truncated by 25 amino acids and the amino acid at the original position 26, alanine, was replaced with methionine, which then became the first amino acid of the 'TesA polypeptide (SEQ ID NO:65; Cho et al., *J. Biol. Chem.*, 270:4216-4219 (1995)). DNA encoding the 'TesA polypeptide was inserted into the NcoI and EcoRI sites of the pACYC-$P_{Trc}$ vector and the pACYC-$P_{Trc2}$ vector, producing the pACYC-$P_{Trc}$-'esA and pACYC-$P_{Trc2}$-'tesA plasmids, respectively. Correct insertion of 'tesA sequence into the plasmids was confirmed by restriction digestion.

pOP80 plasmid

The pOP80 plasmid was constructed by digesting the cloning vector pCL1920 (GenBank AB236930; Lerner C. G. and Inouye M., *Nucleic Acids Res.* 18:4631 (1990)) with the restriction enzymes AflIII and SfoI. Three DNA fragments were produced by this digestion. The 3737 by fragment was gel-purified using a gel-purification kit (Qiagen, Inc., Valencia, Calif.). In parallel, a DNA sequence fragment containing the $P_{Trc}$ promoter and lacI region from the commercial plasmid pTrcHis2 (Invitrogen, Carlsbad, Calif.) was amplified by PCR using primers LF302 (5'-atatgacgtcGGCATCCGCT-TACAGACA-3', SEQ ID NO:98) and LF303 (5'-aattcttaagT-CAGGAGAGCGTTCACCGACAA-3', SEQ ID NO:99) introducing the recognition sites for the ZraI and AflII enzymes, respectively. After amplification, the PCR products were purified using a PCR-purification kit (Qiagen, Inc. Valencia, Calif.) and digested with ZraI and AflII following the recommendations of the supplier (New England BioLabs Inc., Ipswich, Mass.). After digestion, the PCR product was gel-purified and ligated with the 3737 by DNA sequence fragment derived from pCL1920 to generate the expression vector pOP80 containing the $P_{Trc}$ promoter.

*L. monocytogenes* fabH1 and fabH2 Plasmids (pTB.079 and pTB.081)

The genomic DNA of *Listeria monocytogenes* L123 (ATCC 19114D-5) was used as template to amplify the fabH gene using the following primers:

```
TREE044 (fabH_forward)
                                    (SEQ ID NO: 100)
GAGGAATAAACCATGAACGCAGGAATTTTAGGAGTAG;

primer 61 (fabH_reverse)
                                    (SEQ ID NO: 101)
CCCAAGCTTCGAATTCTTACTTACCCCAACGAATGATTAGG
```

The PCR product was then cloned into the NcoI/EcoRI sites of pDS80 (a pCL1920-based vector carrying the phage lambda $P_L$ promoter; SEQ ID NO:78) and transformed into transformation-competent *E. coli* cells. Individual colonies were picked for sequence verification of cloned inserts. The nucleic acid sequence of wild type *L. monocytogenes* fabH encodes the wild type LmFabH1 protein (SEQ ID NO:7), and the plasmid expressing this sequence was designated pTB.079.

A mutant *L. monocytogenes* fabH gene was discovered containing a T to G change at position 928, resulting in a change in the expressed protein at amino acid position 310 from Tryptophan (W) to Glycine (G), i.e., a W310G variant. The mutant *L. monocytogenes* fabH gene encoding the FabH W310G variant (SEQ ID NO:8) was designated LmFabH2, and the plasmid expressing this sequence pTB.081.

Example 2

Engineering *E. coli* for Production of Odd Chain Fatty Acids by Pathway (A)

The following example describes the construction of recombinant *E. coli* strains which express exogenous genes and/or overexpress endogenous genes encoding enzymes which serve to increase metabolic flux through the intermediates threonine and α-ketobutyrate to propionyl-CoA by pathway (A) of FIG. 2, leading to the increased production of odd chain acyl-ACPs and odd chain fatty acid derivatives in these recombinant cells.

This example also demonstrates the effect on oc-FA production of attenuating the expression of an endogenous gene and replacing it with an exogenous gene; in this example, expression of the endogenous *E. coli* fabH gene encoding β-ketoacyl-ACP synthase was attenuated by deletion of the gene, and β-ketoacyl-ACP synthase activity was supplied by expression of the exogenous *B. subtilis* fabH1 gene.

DV2 $P_L$ thrA*BC

A recombinant *E. coli* strain was constructed in which chromosomal genes involved in threonine biosynthesis were placed under control of a strong chromosomally-integrated lambda $P_L$ promoter, and one of the genes was mutated.

To introduce a single mutation in the native aspartokinase I (thrA) gene, the gene was amplified from *E. coli* MG1655 DNA in two parts. The first part was amplified using primers TREE026 and TREE028 while the second part was amplified using TREE029 and TREE030 (Table 6). The primers used to amplify the two components contained overlapping sequences which were then used to "stitch" the individual pieces together. The two PCR products were combined in a single PCR reaction and primers TREE026 and TREE030 to amplify the entire thrA gene. Primers TREE028 and TREE029 were designed to create a mutation in the native thrA at codon 345, which resulted in an S345F variant of aspartokinase I (SEQ ID NO: 21). This mutation has been shown to eliminate feedback inhibition of the enzyme by threonine in the host strain (Ogawa-Miyata, Y., et al., *Biosci. Biotechnol. Biochem.* 65:1149-1154 (2001); Lee J.-H., et al., *J. Bacteriol.* 185: 5442-5451 (2003)). The modified version of this gene was designated "thrA*".

The $P_L$ promoter was amplified using primers Km_trc_overF and TREE027 (Table 6) using plasmid pDS80 (a pCL1920-based vector carrying the phage lambda $P_L$ promoter; SEQ ID NO:78) as a template. This fragment was then stitched to a kanamycin resistance cassette flanked by FRT sites, which was amplified from plasmid pKD13 using primers TREE025 and Km_trc_overR (Table 6). The resulting PCR product containing the KmFRT cassette and $P_L$ promoter was stitched to the thrA* PCR product. Primers TREE025 and TREE030 were used to amplify the entire KmFRT-$P_L$-thrA* mutagenic cassette. These primers also contain approximately 50 by of homology to the integration site at the 5' end and the entire thrA gene as homology on the 3' end, targeting the cassette to the native thrA site in *E. coli*, which is part of an operon comprising the thrA, thrB and thrC genes. This mutagenic cassette was electroporated into the parental strain, *E. coli* DV2 (Example 1) containing the helper plasmid pKD46 expressing Red recombinase (Datsenko et al., supra). Clones containing the chromosomal integration were selected in the presence of kanamycin, and verified by diagnostic PCR. The kanamycin marker was then removed by expression of the pCP20 plasmid (Datsenko et al., supra). Proper integration and marker removal were verified by PCR and sequencing. The resulting strain, in which the mutant thrA* gene and the endogenous thrB and thrC genes were overexpressed by the chromosomally-integrated lambda $P_L$ promoter, was designated DV2 $P_L$ thrA*BC.

TABLE 6

Primers

| Primer | Sequence (5' → 3') | SEQ ID NO |
|---|---|---|
| TREE025 | CCTGACAGTGCGGGCTTTTTTTTTCGACCAAAGGTAACGAGGTAACAACCGTGTAGGCTGGAGCTGCTTCG | 102 |
| TREE026 | GTATATATTAATGTATCGATTAAATAAGGAGGAATAAACCATGCGAGTGTTGAAGTTCGGCG | 103 |
| TREE027 | CTGATGTACCGCCGAACTTCAACACTCGCATGGTTTATTCCTCCTTATTTAATCGATAC | 104 |
| TREE028 | GCGCCCGTATTTTCGTGGTGCTGATTAC | 105 |

TABLE 6-continued

Primers

| Primer | Sequence (5' → 3') | SEQ ID NO |
|---|---|---|
| TREE029 | GTAATCAGCACCACGTAAATACGGGCGC | 106 |
| TREE030 | TCAGACTCCTAACTTCCATGAGAGG | 107 |
| Km_trc_overR | AATATTTGCCAGAACCGTTATGATGTCGGCATTCCGGGGATCCGTCGACC | 108 |
| Km_trc_overF | CTTCGAACTGCAGGTCGACGGATCCCCGGAATGCCGACATCATAACGGTTCTGGC | 109 |
| EG238 | GCTGATCATTAACTATCCGCTGGATGACC | 110 |
| TREE017 | ACTGGAAAGCGGGCAGTGAGCGCAACGCAATTAATGTAAG | 111 |
| TREE018 | TCACTGCCCGCTTTCC | 112 |
| TREE019 | ACCGGCAGATCGTATGTAATATGCATGGTTTATTCCTCCTTATTTAATCGATACA | 113 |
| TREE020 | ATGCATATTACATACGATCTGCC | 114 |
| TREE021 | GGTCGACGGATCCCCGGAATTAAGCGTCAACGAAACCG | 115 |
| TREE022 | GAAGCAGCTCCAGCCTACACCAGACGATGGTGCAGGAT | 116 |
| TREE023 | GCAAAGACCAGACCGTTCATA | 117 |
| Kan/Chlor 1 | ATTCCGGGGATCCGTCGACC | 118 |
| Kan/Chlor 4 | TGTAGGCTGGAGCTGCTTCG | 119 |

DV2 $P_L$ thrA*BC $P_L$ tdcB

The native E. coli catabolic threonine deaminase (tdcB) gene (also known as threonine ammonia-lyase) was overexpressed by integrating an extra copy of the gene into the lacZ locus and placing it under the control of a strong chromosomally-integrated lambda $P_L$ promoter.

Catabolic threonine deaminase catalyzes the degradation of threonine to α-keto-butyrate, the first reaction of the threonine degradation/isoleucine production pathway. The reaction catalyzed likely involves initial elimination of water (hence the earlier classification of this enzyme as a threonine dehydratase), followed by isomerization and hydrolysis of the product with C—N bond breakage. Increased expression of this gene has been shown to dramatically increase levels of isoleucine in heterologous organisms (Guillouet S. et al., Appl. Environ. Microbiol. 65:3100-3107 (1999)). Furthermore, threonine deaminase is relatively resistant to isoleucine feedback mechanisms (Guillouet et al., supra).

E. coli MG1655 genomic DNA was amplified using primers TREE020 and TREE021 (Table 6) to obtain the native tdcB gene. At the same time, primers Kan/Chlor 1 and Kan/Chlor 4 (Table 6) were used to amplify an FRT-Kanamycin resistance cassette to be used for integration selection/screening as previously described. Using E. coli MG1655 genomic DNA as template, primers EG238 and TREE018 (Table 6) were used to amplify a region of homology 3' to the lacZ integration site, while primers TREE022 and TREE023 (Table 6) were used to amplify a region of homology 5' to the lacZ site. The plasmid pDS80 (a pCL1920-based vector carrying the phage lambda $P_L$ promoter; SEQ ID NO:78) was used as a template to amplify a fragment containing the $P_L$ promoter by using primers TREE017 and TREE018 (Table 6). Each of these fragments were designed with overlaps for corresponding adjacent piece and were stitched together using SOEing PCR techniques. The resulting $P_L$ tdcB mutagenic cassette (approx. 4.3 kb) contained approximately 700 bp of homology to the integration site at the 5' end and 750 bp of homology to the integration site at the 3' end. The $P_L$ tdcB mutagenic cassette was electroporated into the host strain, E. coli DV2 $P_L$ thrA*BC (above) containing the helper plasmid, pKD46 (Datsenko et al., supra). Clones containing the chromosomal integration were selected for in the presence of kanamycin, and verified by PCR and sequencing analysis. The kanamycin marker was then removed using the pCP22 plasmid (Datsenko et al., supra). The resulting strain was designated DV2 $P_L$ thrA*BC $P_L$ tdcB. The strain was transformed with the plasmid pACYC-$p_{trc2}$-'tesA (Example 1), which expressed a truncated form of E. coli tesA.

The strain was also transformed with plasmid pDG6 (Example 1) expressing the B. subtilis FabH1 enzyme. Fermentation experiments were conducted, and the titers of free fatty acids (FFA), odd chain fatty acids (oc-FA), and the fraction of FFA produced as oc-FA were determined, as shown in Example 5 and Table 9. Alternatively, the strain can be transformed with a plasmid expressing a different FabH polypeptide, such as pDG7 expressing B. subtilis FabH2, pDG8 expressing Streptomyces coelicolor FabH, pTB.079 expressing Listeria monocytogenes FabH, or pTB.081 expressing a Listeria monocytogenes FabH W310G variant. Fermentation experiments are conducted, and the titers of free fatty acids (FFA), odd chain fatty acids (oc-FA), and the fraction of FFA produced as oc-FA are determined.

DV2 $P_L$-thrA*BC $P_{T5}$-BsfabH1

A recombinant E. coli strain was constructed in which the B. subtilis fabH1 gene was integrated into the chromosome and placed under transcriptional control of the strong constitutive T5 promoter.

First, a PCR product was generated for the chromosomal integration of a loxPcat integration cassette comprising a chloramphenicol resistance gene, a T5 promoter ($P_{T5}$), and BsfabH1 coding sequence, at the site of the fadE deletion scar of DV2 $P_L$ thrA*BC. The individual components of the integration cassette were first PCR-amplified. The loxP-cat-loxP $P_{T5}$ component was amplified from plasmid p100.38 (SEQ ID NO:79) using primers TREE133 and TREE135 (Table 7). The BsfabH1 gene was amplified from a plasmid carrying the BsfabH1 gene using primers TREE134 and TREE136. Primers TREE133 and TREE136 contain the 5' and 3' 50 by of homology sequence for integration. The primers used to amplify the components contain overlapping sequence which were then used to "stitch" the individual pieces together. The loxP-cat-$P_{T5}$ and BsfabH1 PCR products were stitched together by combining both pieces in a single PCR reaction and using primers TREE133 and TREE136 to amplify the final loxPcat-$P_{T5}$-BsfabH1 integration cassette.

DV2 $P_L$-thrA*BC $P_{T5}$-BsfabH1 ΔEcfabH

A recombinant *E. coli* strain was constructed in which the expression of an endogenous gene (in this instance, the fabH gene of *E. coli*) was attenuated by deletion of that gene.

The fabH gene of *E. coli* was deleted from DV2 $P_L$-thrA*BC $P_{T5}$-BsfabH1 using the Red recombinase system (Datsenko et al., supra). Primers TREE137 and TREE138 (Table 7), were used to amplify the kanamycin resistance cassette from plasmid pKD13 by PCR. The PCR product was then used to transform electrocompetent DV2 $P_L$-thrA*BC $P_{T5}$-BsfabH1 cells containing plasmid pKD46. Deletion of EcfabH and removal of the kanamycin marker were carried out according to the method described by Wanner and Datsenko, supra. Primers TREE139 and TREE140 were used to confirm the deletion of EcfabH. The final markerless strain was designated DV2 $P_L$-thrA*BC $P_{T5}$-BsfabH1 ΔEcfabH.

TABLE 7

Primers

| Primer Name | Sequence | SEQ ID NO |
|---|---|---|
| TREE133 | AAAAACAGCAACAATGTGAGCTTTGTTGTAATTATATTGTAAACATATTG TCCGCTGTTTCTGCATTCTTACgt | 120 |
| TREE134 | GATGACGACGAACACGCATTaagGAGGTGAATAAGGAGGAATAAcatAT GAAAGCTGGCATTCTTGGTGTTG | 121 |
| TREE135 | GTAACGTCCAACACCAAGAATGCCAGCTTTCATatgTTATTCCTCCTTATT CACCTCcttAATGCGTGTTCG | 122 |
| TREE136 | AAACGGAGCCTTTCGGCTCCGTTATTCATTTACGCGGCTTCAACTTTCCG TTATCGGCCCCAGCGGATTG | 123 |
| TREE137 | CGCAGTTTGCAAGTGACGGTATATAACCGAAAAGTGACTGAGCGTACat gATTCCGGGGATCCGTCGACC | 124 |
| TREE138 | GCAAATTGCGTCATGTTTTAATCCTTATCCTAGAAACGAACCAGCGCGG ATGTAGGCTGGAGCTGCTTCG | 125 |
| TREE139 | GCAGCGACAAGTTCCTCAGC | 126 |
| TREE140 | CCGCAGAAGCTTCAGCAAACG | 127 |
| fadE-L2 | CGGGCAGGTGCTATGACCAGGAC | 128 |
| fadE-R2 | GGGCAGGATAAGCTCGGGAGG | 129 |

The loxP-cat-$P_{T5}$-BsfabH1 cassette was integrated using the Red recombinase system (Datsenko, et al., supra). The loxP-cat-$P_{T5}$-BsfabH1 PCR product was used to transform electrocompetent DV2 $P_L$-thrA*BC cells containing plasmid pKD46, which had been previously induced with arabinose for 3-4 hours at 30° C. Following a 3 hour 37° C. outgrowth in SOC medium, cells were plated on Luria agar plates containing 17 μg/mL chloramphenicol and incubated overnight at 37° C. Chloramphenicol-resistant colonies were screened by PCR for proper integration of loxP-cat-$P_{T5}$-BsfabH1. Primers fadE-L2 and fadE-R2 (Table 7) which flank the chromosomal integration site, were used to confirm the integration. Upon verification of integration, the chloramphenicol marker gene was removed by expressing a Cre recombinase which promotes recombination between the two loxP sites that flank the chloramphenicol resistance gene. The plasmid pJW168, which harbors the cre recombinase gene, was transformed into strain DV2 $P_L$-thrA*BC loxP-cat-$P_{T5}$-BsfabH1 and the marker was removed according to the method described by Palmeros et al. (*Gene* 247:255-264 (2000)). The resulting strain DV2 $P_L$-thrA*BC $P_{T5}$-BsfabH1 was verified by sequencing.

DV2 $P_L$-thrA*BC $P_L$-tdcB $P_{T5}$-BsfabH1 ΔEcfabH

A recombinant *E. coli* strain was constructed containing chromosomally-integrated genes overexpressing enzymes of pathway (A) and step (D) of the oc-FA biosynthetic pathway shown in FIG. 2 and FIG. 1B, respectively. The $P_L$-tdcB mutagenic cassette (prepared as described above) was integrated into strain DV2 $P_L$-thrA*BC $P_{T5}$-BsfabH1 ΔEcfabH to generate the strain DV2 $P_L$-thrA*BC $P_L$-tdcB $P_{T5}$-BsfabH1 ΔEcfabH. In this strain, the integrated *E. coli* thrA*BC genes and the integrated *E. coli* tdcB gene were both under the control of strong lambda $P_L$ promoters, the integrated *B. subtilis* fabH1 gene was under the control of the strong T5 promoter, and the endogenous *E. coli* fabH gene was deleted. Fermentation experiments were conducted, and the results are provided in Table 9.

Example 3

Engineering *E. coli* for Production of Odd Chain Fatty Acids by Pathway (B)

The following example describes the construction of recombinant *E. coli* strains which express exogenous genes and/or overexpress endogenous genes encoding enzymes which serve to increase metabolic flux through the intermediates citramalate and α-ketobutyrate to propionyl-CoA by pathway (B) of FIG. 2, leading to the increased production of odd chain acyl-ACPs and odd chain fatty acid derivatives in these recombinant cells.

DV2 $P_{Trc}$-cimA3.7 leuBCD

To prepare an *E. coli* strain overexpressing endogenous leuBCD genes and an exogenous cimA3.7 gene, a PCR product was generated for the chromosomal integration of a KmFRT cassette, a $P_{Trc}$ promoter, and cimA3.7 between the endogenous chromosomal *E. coli* leuA and leuB genes. This integration disrupted the native leuABCD operon, placing cimA3.7 and leuBCD in an operon under control of the strong IPTG-inducible promoter, $P_{Trc}$.

DNA encoding cimA3.7 was synthesized by Geneart AG (Regensburg, Germany). The DNA was cloned into the SfiI site of plasmid pMK-RQ (kanR) (Geneart AG, Regensburg, Germany). Flanking the coding sequence, a 5' KpnI restriction site and a 3' SacI restriction site were introduced directly upstream of the ATG start codon and immediately downstream of the TAA stop codon respectively. The cimA 3.7 cloning vector was verified by sequencing.

The individual components of the integration cassette were PCR-amplified as follows. The KmFRT component was amplified from plasmid pKD13 using primers TREE146 and Km_trc_overR (Table 8). The $P_{Trc}$ promoter was amplified from pOP80 (Example 1) using primers Km_trc_overF and TREE033.

The cimA3.7 coding sequence was amplified from the cimA 3.7 cloning vector described above using primers TREE032 and TREE035. To provide the 3' homology sequence for integration, *E. coli* native leuBC genes were amplified using *E. coli* genomic DNA and primers TREE034 and TREE104. The forward primer TREE146, which was used to amplify the KmFRT cassette, included the 5' 50 bp of homology sequence for integration. Each of the primers used to amplify the components contained overlapping sequence which were used to "stitch" the individual pieces together. First, KmFRT and $P_{Trc}$ were stitched together by combining both pieces in a single PCR reaction and using primers TREE146 and TREE033 to amplify the KmFRT-$P_{Trc}$ product. KmFRT-$P_{Trc}$ was then stitched with cimA3.7 using primers TREE146 and TREE035 to generate KmFRT-$P_{Trc}$-cimA3.7. The final piece, leuBC was stitched to KmFRT-$P_{Trc}$-cimA3.7 using primers TREE146 and TREE104 to generate the final integration cassette: KmFRT-$P_{Trc}$-cimA3.7 leuBC.

TABLE 8

Primers

| Primer Name | Primer Sequence (5' → 3') | SEQ ID NO |
|---|---|---|
| Km_trc_overF | CTTCGAACTGCAGGTCGACGGATCCCCGGAATGCCGACATCATAACGGTTCTGGC | 130 |
| Km_trc_overR | AATATTTGCCAGAACCGTTATGATGTCGGCATTCCGGGGATCCGTCGACC | 131 |
| TREE032 | GTATATATTAATGTATCGATTAAATAAGGAGGAATAAACCatgatggtaaggatatttgatacaacac | 132 |
| TREE033 | ctaagtgttgtatcaaatatccttaccatcatGGTTTATTCCTCCTTATTTAATCGATAC | 133 |
| TREE034 | gatttgttggctatagttagagaagttactggaaaattgTAACAAGGAAACCGTGTGATGTCGAAG | 134 |
| TREE035 | GTAATTCTTCGACATCACACGGTTTCCTTGTTAcaattttccagtaacttctctaactatag | 135 |
| TREE104 | GGTAGCGAAGGTTTTGCCCGGC | 136 |
| TREE106 | GATTGGTGCCCCAGGTGACCTG | 137 |
| TREE146 | GAGTTGCAACGCAAAGCTCAACACAACGAAAACAACAAGGAAACCGTGTGaGTGTAGGCTGGAGCTGCTTCG | 138 |
| TREE151 | CTTCCACGGCGTCGGCCTG | 139 |

The KmFRT-$P_{Trc}$-cimA3.7 leuBC cassette was integrated into the *E. coli* genome using the Red recombinase system (Datsenko et al., supra). The KmFRT-$P_{Trc}$-cimA3.7 leuBC PCR product was used to transform electrocompetent *E. coli* MG1655 DV2 cells containing plasmid pKD46, which had been previously induced with arabinose for 3-4 hours at 30° C. Following a 3-hour 37° C. outgrowth in SOC medium, cells were plated on Luria agar plates containing 50 µg/mL kanamycin and incubated overnight at 37° C. Kanamycin-resistant colonies were screened by PCR for proper integration of KmFRT-$P_{Trc}$-cimA3.7. Primers TREE151 and TREE106, which flank the chromosomal integration site, were used to confirm the integration. Upon verification of integration, the kanamycin marker gene was removed in accordance with the method described by Datsenko et al., supra. Successful integration of P imA3.7 and removal of the kanamycin marker gene in the final strain, DV2 P imA3.7/e BCD was verified by sequencing.

The strain was transformed with the plasmid pACYC-$p_{trc2}$-tesA, which expressed a truncated form of *E. coli* tesA, and, in some instances, pDG6, which expressed *B. subtilis* fabH1. Fermentation experiments were conducted, and the titers of free fatty acids (FFA), odd chain fatty acids (oc-FA), and the fraction of FFA produced as oc-FA, are provided in Table 9.

Example 4

Engineering E. coli for Production of Odd Chain Fatty Acids by Pathways (A) and (B) Combined The following example describes the construction of recombinant E. coli strains which express exogenous genes and/or overexpress endogenous genes encoding enzymes which serve to increase metabolic flux through the common intermediate α-ketobutyrate to propionyl-CoA by the combined (A) and (B) pathways of FIG. 2, leading to even greater production of oc-acyl-ACPs and odd chain fatty acids in these recombinant cells.

DV2 $P_L$-thrA*BC $P_{Trc}$-cimA3.7 leuBCD $P_{T5}$-BsfabH1 ΔEcfabH (strain "G1")

To begin combining pathways (A) and (B) of FIG. 2, the $P_{Trc}$-cimA3.7_leuBCD cassette (Example 5) was integrated into strain DV2 $P_L$-thrA*BC $P_{T5}$-BsfabH1 ΔEcfabH (Example 4) to generate the strain DV2 $P_L$-thrA*BC $P_{Trc}$-cimA3.7_leuBCD $P_{T5}$-BsfabH1 ΔEcfabH, which was also called strain G1. This strain overexpressed polypeptides having (R)-citramalate synthase activity, isopropylmalate isomerase activity, and beta-isopropyl malate dehydrogenase activity according to pathway (B) of the oc-FA pathway, and overexpressed polypeptides having aspartokinase activity, homoserine dehydrogenase activity, homoserine kinase activity, and threonine synthase activity according to pathway (A) of the oc-FA pathway (FIG. 2).

DV2 $P_L$-thrA*BCP-tdcB $P_{Trc}$-cimA3.7 leuBCD $P_{T5}$-BsfabH1 ΔEcfabH (strain "G2")

To create a strain engineered to overexpress polypeptides having activities corresponding to the combined pathways (A) and (B) of the of the oc-FA pathway, the $P_L$-tdcB cassette (Example 4) was integrated into strain G1, to generate strain DV2 $P_L$-thrA*BC $P_L$-tdcB $P_{Trc}$-cimA3.7 leuBCD $P_{T5}$-BsfabH1 ΔEcfabH, which was also called strain G2. In this strain, the integrated E. coli thrA*BC genes and the integrated E. coli tdcB gene (encoding polypeptides having aspartokinase activity, homoserine dehydrogenase activity, homoserine kinase activity, threonine synthase activity, and threonine deaminase activity, corresponding to pathway (A)) were placed under the control of strong lambda $P_L$ promoters, and were overexpressed. The exogenous cimA3.7 gene and the native E. coli leuBCD genes (encoding polypeptides having (R)-citramalate synthase activity, isopropylmalate isomerase activity, and beta-isopropyl malate dehydrogenase activity corresponding pathway (B)), were also integrated into the E. coli chromosome under control of the strong IPTG-inducible promoter P Trc and therefore were also overexpressed. The integrated B. subtilis fabH1 gene, encoding a branched chain beta ketoacyl-ACP synthase corresponding to part (D) of the oc-FA pathway (FIG. 1B), was under the control of the strong T5 promoter. The endogenous E. coli fabH gene was deleted from this strain.

Example 5

Evaluation of Odd Chain Fatty Acid Production

All strains were evaluated for free fatty acid (FFA) production by performing a 96 deep-well plate fermentation using the 4N-BT protocol. Single colonies or a scraping from a glycerol stock were used to inoculate 300 μL of LB+ antibiotic(s). LB seed cultures were grown for 6-8 hours at 37° C. with shaking at 250 rpm until turbid. 20 μL of the LB cultures were used to inoculate 400 μL of 2N-BT. These were allowed to grow overnight at 32° C. with shaking at 250 rpm. The following morning, 20 μL of 2N-BT culture was transferred to 400 μL of 4N-BT. The 4N-BT cultures were allowed to grow for 6 hours at 32° C. with shaking at 250 rpm at which point, cells were induced with 1 mM IPTG. Upon induction, cultures were allowed to grow for an additional 16-18 hours before being extracted and analyzed for FFA production. 40 μL of 1M HCl was added to each well, followed by 4004 of butyl acetate spiked with 500 mg/L C24 alkane internal standard. Cells were extracted by vortexing for 15 minutes at 2000 rpm. Extracts were derivatized with an equal volume of N,O-bis(trimethylsilyl)trifluoroacetamide (BSTFA) before being analyzed by GC/MS.

TABLE 9

Production of Odd Chain Fatty Acids in Recombinant E. coli Strains

| | Strain | fabH | tesA | Total FFA titer | oc-FA titer | oc-FA/Total FFA |
|---|---|---|---|---|---|---|
| 1 | DV2 | Ec | p | 2054 | 6 | <0.01 |
| 2 | DV2 thrA*BC tdcB | Ec | p | 1364 | 246 | 0.18 |
| 3 | DV2 thrA*BC tdcB | Ec pBsH1 | p | 1460 | 545 | 0.37 |
| 4 | DV2 thrA*BC tdcB | ΔEc IntBsH1 | p | 1148 | 832 | 0.72 |
| 5 | DV2 cimA3.7 leuBCD | Ec | p | 1617 | 73 | 0.04 |
| 6 | DV2 cimA3.7 leuBCD | Ec pBsH1 | p | 1650 | 214 | 0.13 |
| 7 | "G1": DV2 thrA*BC cimA3.7 leuBCD | ΔEc IntBsH1 | p | 1104 | 286 | 0.26 |
| 8 | G1/Tn7-tesA | ΔEc IntBsH1 | int | 885 | 267 | 0.30 |
| 9 | "G2": DV2 thrA*BC tdcB cimA3.7 leuBCD | ΔEc IntBsH1 | p | 617 | 551 | 0.89 |
| 10 | G2/Tn7-tesA | ΔEc IntBsH1 | int | 923 | 840 | 0.91 | all titers are in milligrams per liter (mg/L)
FFA = free fatty acid (oc-FA + ec-FA)
oc-FA = odd chain fatty acid; ec-FA = even chain fatty acid
Ec = chromosomal (native) E. coli fabH gene
ΔEc = deleted chromosomal E. coli fabH gene
pBsH1 = plasmid-expressed BsfabH1 (pDG6)
IntBsH1 = chromosomally integrated BsfabH1
p = plasmid-expressed 'tesA gene (pACYC-$p_{Trc2}$-tesA)
int = chromosomally integrated 'tesA gene The odd chain fatty acids produced in these experiments generally included C13:0, C15:0, C17:0 and C17:1 fatty acids, with C15:0 being the predominant oc-FA produced.

Comparison of strains 1 and 2 demonstrates that microbial cells overexpressing genes involved in the biosynthesis and degradation of threonine, which increased metabolic flux through the pathway intermediate α-ketobutyrate, significantly increased the proportion of odd chain length fatty acids produced by the cells. While the parental DV2 strain produced straight chain fatty acids with only a negligible amount of odd chain length fatty acids, the DV2 strain overexpressing the thrA*BC and tdcB genes (encoding polypeptides having aspartokinase activity, homoserine dehydrogenase activity, homoserine kinase activity, threonine synthase activity and threonine deaminase activity) produced a significantly greater amount and significantly greater proportion of odd chain length fatty acids; about 18% (by weight) of the straight chain fatty acids produced were odd chain length fatty acids.

Strains 2 and 3 demonstrate the effect on oc-FA production by including an exogenous β-ketoacyl ACP synthase with high specificity towards propionyl-CoA. Strain 2 contained the native (endogenous) E. coli fabH gene. By introducing a plasmid expressing the B. subtilis fabH1 gene, oc-FA production was markedly increased from about 18% (in Strain 2) to about 37% of the straight chain fatty acids produced (in Strain 3).

A striking effect on oc-FA production was observed when the endogenous E. coli fabH gene was deleted and the B. subtilis fabH1 gene was chromosomally integrated. In Strain 4, the proportion of oc-FA increased to 72% of the straight chain fatty acids produced.

Strains 5 and 6 demonstrate that increasing metabolic flux through α-ketobutyrate by another approach, this time by a pathway involving citramalate biosynthesis and degradation, also increased the proportion of odd chain length fatty acids produced. Engineering the DV2 strain to overexpress the cimA3.7 and leuBCD genes (encoding polypeptides having (R)-citramalate synthase activity, isopropylmalate isomerase activity, and β-isopropylmalate dehydrogenase activity) resulted in about 4% of the straight chain fatty acids produced having odd chain lengths, which increased to about 13% when plasmid-expressed B. subtilis fabH1 was included.

Strains 7 and 9 show the effect of combining the threonine and citramalate pathways on oc-FA production. In strain G1, in which the thrA*BC, cimA3.7 and leuBCD genes were overexpressed, the endogenous E. coli fabH gene was deleted and the B. subtilis fabH1 gene was chromosomally integrated, about 26% of the straight chain fatty acids produced were odd chain fatty acids. In strain G2, in which the thrA*BC, tdcB, cimA3.7 and leuBCD genes were overexpressed, the endogenous E. coli fabH gene was deleted and the B. subtilis fabH1 gene was chromosomally integrated, nearly 90% of the straight chain fatty acids produced were odd chain fatty acids. Strains G1/Tn7-tesA and G/Tn7-tesA (strains 8 and 10, respectively), in which the 'tesA gene was chromosomally integrated at the Tn7 attachment site, showed amounts and proportions of oc-FA similar to those in strains G1 and G2 (strains 7 and 9, respectively) in which the 'tesA gene was plasmid-expressed.

Example 6

Engineering E. coli for Production of Odd Chain Fatty Acids by Pathway (C)

The following example describes the construction of recombinant E. coli strains which express exogenous genes and/or overexpress endogenous genes encoding enzymes which serve to increase metabolic flux through the intermediate methylmalonyl-CoA to produce propionyl-CoA by pathway (C) of FIG. 3, leading to the increased production of odd chain acyl-ACPs and odd chain fatty acid derivatives in these recombinant cells. In particular, this example describes production of odd chain fatty acids in an E. coli strain which overexpresses endogenous methylmalonyl-CoA mutase (scpA/sbm) and methylmalonyl-CoA decarboxylase (scpW-ygfG) genes on a plasmid and the chromosomal propionyl-CoA:succinyl-CoA transferase (scpC/ygfH) and scpWygfG genes are deleted. E. coli strain DV2, plasmid pDG6 (expressing B. subtilis FabH1), and plasmid pACYC-$p_{Trc2}$-tesA (expressing the truncated 'TesA polypeptide) were prepared as described in Example 1.

Plasmid pACYC-$P_{Trc}$-sbm-ygfG

Plasmid pACYC-$P_{Trc}$-sbm-ygfG is the pACYC-$P_{Trc}$ plasmid (Example 1), which overexpresses E. coli sbm encoding methylmalonyl-CoA mutase and E. coli ygfG encoding methylmalonyl-CoA decarboxylase. The sequence of pACYC-$P_{Trc}$-sbm-ygfG is provided herein as SEQ ID NO:80

Strain sDF4

Strain sDF4 is E. coli strain DV2 from which the chromosomal scpB and scpC genes were deleted, the native frd promoter replaced with the trc promoter, and the 'tesA gene was chromosomally integrated at the Tn7 attachment site.

To integrate the 'tesA gene, a $P_{Trc}$-'tesA integration cassette was first prepared by amplifying the pACYC-$P_{Trc}$-'tesA plasmid (Example 1) using the following primers:

```
                                        (SEQ ID NO: 140)
IFF: 5'-GGGTCAATAGCGGCCGCCAATTCGCGCGCGAAGGCG (SEQ ID NO: 141)
IFR: 5'-TGGCGCGCCTCCTAGGGCATTACGCTGACTTGACGGG
```

The integration cassette was inserted into the NotI and AvrII restriction sites of pGRG25 (GenBank Accession No. DQ460223) creating the Tn7tes plasmid (SEQ ID NO: 81), in which the lacIq, $P_{Trc}$-'tesA cassette is flanked by the left and right Tn7 ends.

To prepare strain sDF4, plasmid Tn7tes was first electroporated into E. coli strain DV2 (Example 1) using a protocol described by McKenzie et al., BMC Microbiology 6:39 (2006). After electroporation, ampicillin-resistant cells were selected by growth in an LB medium containing 0.1% glucose and 100 µg/mL carbenicilin at 32° C. overnight. This was followed by selection of plasmids comprising the Tn7-transposition fractions, using the growth of cells on an LB plus 0.1% arabinose plates overnight at 32° C. Single colonies were selected and streaked onto new LB medium plates with and without ampicillin, and they were grown overnight at 42° C. to cure of Tn7tes plasmid. Thus, the lacIq, $P_{Trc}$-'tesA was integrated into the attTn7 site on the E. coli chromosome located between the pstS and glmS genes. Integration of these genes was confirmed by PCR and sequencing. The resulting strain was designated DV2 Tn7-tesA.

To delete the scpBC genes from DV2 Tn7-tesA, the following two primers were used:

```
ScpBC-KOfwd
                                        (SEQ ID NO: 142)
5'-GCTCAGTGAATTTATCCAGACGCAATATTTTGATTAAAGGA ATTTT TATGATTCCG GGGATCCGTCGACC;
and ScpBC-KOrc
                                        (SEQ ID NO: 143)
5'-ATTGCTGAAGATCGTGACGGGACGAGTCATTAACCCAGCATCGA

GCCGGTTGTAGGCTG GAGCTGCTTC
```

The ScpBC-KOfwd and ScpBC-KOrc primers were used to amplify the kanamycin resistance ($Km^R$) cassette from plasmid pKD13 (Datsenko et al., supra) by PCR. The PCR product was then used to transform electrocompetent E. coli DV2 Tn7-tesA cells containing plasmid pKD46, which expresses Red recombinase (Datsenko et al., supra) which had been previously induced with arabinose for 3-4 hours. Following a 3-hour outgrowth in SOC medium at 37° C., the cells were plated on Luria agar plates containing 50 µg/mL of kanamycin. Resistant colonies were identified and isolated after an overnight incubation at 37° C. Disruption of the scpBC genes was confirmed by PCR amplification using the following primers designed to flank the chromosomal scpBC genes:

```
ScpBC check -60 fwd
                              (SEQ ID NO: 144)
5'-CGGGTTCTGACTTGTAGCG ScpBC check +60 rc
                              (SEQ ID NO: 145)
5'-CCAACTTCGAAGCAATGATTGATG
```

After the scpBC deletion was confirmed, a single colony was picked and used to remove the $Km^R$ marker using the pCP20 plasmid (Datsenko et al., supra). The native fumarate reductase (frd) promoter was replaced with the PTrc promoter using a modification of the procedure of Datsenko et al. (supra). The resulting E. coli DV2 ΔscpBC::FRT, ΔPfrd::FRT-PTrc, attTn7::PTrc-'tesA strain was designated "sDF4".

Strains were transformed with plasmids as indicated below and evaluated for fatty acid production using the 96 deep-well plate fermentation procedure described in Example 5; since ScpA is a B-12 dependent enzyme, the 4N-BT culture media was supplemented with cobalamin.

TABLE 10

Production of Odd Chain Fatty Acids
in Recombinant E. coli Strains

| Strain | fabH | tesA | Total FFA | oc-FA | oc-FA/ total FFA |
|---|---|---|---|---|---|
| 11 DV2 pACYC-PTrc2-'tesA | Ec | p | 2054 | 6 | <0.01 |
| 12 sDF4 pACYC-PTrc-sbm-ygfG | Ec | int | 973 | 39 | 0.04 |
| 13 sDF4 pACYC-PTrc-sbm-ygfG pDG6 | Ec pBsH1 | int | 863 | 140 | 0.16 | all titers are in milligrams per liter (mg/L)
FFA = free fatty acid (oc-FA + ec-FA)
oc-FA = odd chain fatty acid; ec-FA = even chain fatty acid
Ec = chromosomal E. coli fabH gene; pBsH1 = plasmid-expressed BsfabH1 (pDG6)
p = plasmid-expressed 'tesA gene (pACYC-$p_{Trc2}$-tesA);
int = chromosomally integrated 'tesA gene Microbial cells overexpressing genes involved in the production of propionyl-CoA via the intermediates succinyl-CoA and methylmalonyl-CoA increased the proportion of odd chain length fatty acids produced by the cells. While the DV2 strain produced only a negligible amount of odd chain length fatty acids, the sDF4 strain overexpressing the endogenous E. coli sbm and ygfG genes (encoding polypeptides having methylmalonyl-CoA mutase activity and methylmalonyl-CoA decarboxylase activity) produced an increased amount of odd chain length fatty acids.

Strains 12 and 13 demonstrate the effect on oc-FA production by including an exogenous β-ketoacyl ACP synthase with high specificity towards propionyl-CoA. Strain 12 contained the native E. coli fabH gene. By introducing a plasmid expressing the B. subtilis fabH1 gene, oc-FA production further increased from about 4% of the fatty acids produced in Strain 12 to about 16% of the fatty acids produced in Strain 13.

Example 7

Production of Odd Chain Fatty Alcohols in E. coli

The following demonstrates the production of odd chain fatty alcohols by previously-described strains, which, in this example, also expressed a polypeptide having acyl-ACP reductase (AAR) activity. The AAR activity converted the oc-acyl-ACP intermediate to oc-fatty aldehyde, which reacted with endogenous aldehyde reductase to form oc-fatty alcohol.

Strains DV2, DV2 $P_L$-thrA*BC $P_L$-tdcB $P_{T5}$-BsfabH1 ΔEcfabH, and G1 (prepared as described in Examples 1, 2, and 4, respectively) were transformed either with plasmid pLS9185 or pDS171s. Plasmid pLS9185 expressed a Synechococcus elongatus fatty acyl-ACP reductase (AAR; GenBank Accession No. YP_400611). Plasmid pDS171s expressed S. elongatus AAR, an acyl carrier protein (ACP) from the cyanobacterium Nostoc punctiforme (cACP; GenBank Accession No. YP_001867863) and a phosphopantetheinyl transferase from Bacillus subtilis (Sfp; GenBank Accession No. YP_004206313). These strains were evaluated for fatty alcohol production using the 96 deep-well plate fermentation procedure described in Example 5.

TABLE 11

Production of Odd Chain Fatty Alcohols
in Recombinant E. coli Strains

| | Strain | pLS9185 | pDS171s | Total FAlc titer | oc-FAlc titer | oc-FAlc/ Total FAlc |
|---|---|---|---|---|---|---|
| 1 | DV2 | x | | 432 | 23 | 0.05 |
| 4 | DV2 thrA*BC tdcB ΔEcfabH IntBsFabH1 | x | | 398 | 325 | 0.82 |
| 7 | "G1": DV2 thrA*BC cimA3.7 leuBCD ΔEcfabH IntBsFabH1 | x | | 420 | 157 | 0.37 |
| 1 | DV2 | | x | 847 | 37 | 0.04 |
| 4 | DV2 thrA*BC tdcB ΔEcfabH IntBsFabH1 | | x | 906 | 735 | 0.81 |
| 7 | "G1": DV2 thrA*BC cimA3.7 leuBCD ΔEcfabH IntBsFabH1 | | x | 775 | 344 | 0.44 | all titers are in milligrams per liter (mg/L)
FAlc = fatty alcohol (oc-FAlc + ec-FAlc)
oc-FAlc = odd chain fatty alcohol; ec-FAlc = even chain fatty alcohol
ΔEcFabH = deleted chromosomal E. coli fabH gene
IntBsH1 = chromosomally integrated BsfabH1
pLS9185 = plasmid-expressed AAR
pDS171s = plasmid-expressed AAR, cACP, and Sfp Compared to the control strain DV2, both strains DV2 thrA*BC tdcB BsfabH1 ΔEcfabH and G1 produced significantly higher titers and proportions of odd chain fatty alcohols when transformed with a plasmid expressing AAR, or a plasmid expressing AAR, cACP, and Sfp. The proportion of fatty alcohols produced as odd chain fatty alcohols roughly reflects the proportions observed when these strains were evaluated for fatty acid production (Table 9), suggesting that AAR does not show a preference for odd or even chain fatty acyl-ACPs of similar overall chain length.

Example 8

Production of Even Chain Alkanes in E. coli

The following example demonstrates the production of even chain alkanes by a strain which expressed a polypeptide having acyl-ACP reductase (AAR) activity and a polypeptide having aldehyde decarbonylase (ADC) activity. The AAR activity converted the oc-acyl-ACP intermediate to oc-fatty aldehyde, and the ADC activity decarbonylated the oc-fatty aldehyde to form even chain (ec-)alkane.

Strains DV2, DV2 thrA*BC tdcB BsfabH1 ΔEcfabH, and G1 (prepared as described in Examples 1, 2, and 4, respectively) were transformed with plasmids pLS9185 and pLS9181. Plasmid pLS9185 expressed a *Synechococcus elongatus* fatty acyl-ACP reductase (AAR; GenBank Accession No. YP_400611). Plasmid pLS9181 expressed a *Nostoc punctiforme* aldehyde decarbonylase (ADC; GenBank Accession No. YP_001865325). Strains transformed with both plasmids were analyzed for alkane production using the 96 deep-well plate fermentation procedure described in Example 5 above, but with the added supplementation of 25 μM MnSO$_4$ (final concentration) at induction.

TABLE 12

Production of Even Chain Alkanes in Recombinant *E. coli* Strains

|   | Strain | AAR | ADC | Total Alk titer | ec-Alk titer | ec-Alk/ Total Alk |
|---|---|---|---|---|---|---|
| 1 | DV2 | x | x | 432 | 23 | 0.05 |
| 4 | DV2 thrA*BC tdcB ΔEcFabH IntBsFabH1 | x | x | 398 | 325 | 0.82 |
| 7 | "G1": DV2 thrA*BC cimA3.7 leuBCD ΔEcFabH IntBsFabH1 | x | x | 420 | 157 | 0.37 | all titers are in milligrams per liter (mg/L)
Alk = alkane (oc-Alk + ec-Alk); oc-Alk = odd chain alkane; ec-Alk = even chain alkane
ΔEcFabH = deleted chromosomal *E. coli* fabH gene
IntBsFabH1 = chromosomally integrated BsfabH1
AAR = plasmid-expressed aar gene (pLS9185)
ADC = plasmid-expressed adc gene (pLS9181)

Compared to the control strain DV2, both DV2 thrA*BC tdcB BsfabH1 ΔEcfabH and G1 produced significantly higher titers and proportions of even chain alkanes when transformed with plasmids expressing AAR and ADC. The proportion of alkanes produced as even chain alkanes roughly reflects the proportions of odd chain products produced when these strains were evaluated for fatty acid production (Table 9) and for fatty alcohol production (Table 11), suggesting that ADC, like AAR, does not show a preference between odd or even chain substrates of comparable overall chain length.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE TABLE

| SEQ ID NO | Organism | Other Information | Sequence |
|---|---|---|---|
| 1 | *Escherichia coli* | beta ketoacyl-ACP synthase III | MYTKIIGTGSYLPEQVRTNADLEKMVDTSDEWIVTRTGIRERHIAA PNETVSTMGFEAATRAIEMAGIEKDQIGLIVVATTSATHAFPSAAC QIQSMLGIKGCPAFDVAAACAGFTYALSVADQYVKSGAVKYALVV GSDVLARTCDPTDRGTIIIFGDGAGAAVLAASEEPGIISTHLHADGS YGELLTLPNADRVNPENSIHLTMAGNEVFKVAVTELAHIVDETLAA NNLDRSQLDWLVPHQANLRIISATAKKLGMSMDNVVVTLDRHGN TSAASVPCALDEAVRDGRIKPGQLVLLEAFGGGFTWGSALVRF |
| 2 | *Bacillus subtilis* | beta ketoacyl-ACP synthase III (FabH1) | MKAGILGVGRYIPEKVLTNHDLEKMVETSDEWIRTRTGIEERRIAA DDVFSSHMAVAAAKNALEQAEVAAEDLDMILVATVTPDQSFPTVS CMIQEQLGAKKACAMDISAACAGFMYGVVTGKQFIESGTYKHVLV VGVEKLSSITDWEDRNTAVLFGDGAGAAVVGPVSDDRGILSFELG ADGTGGQHLYLNEKRHTIMNGREVFKFAVRQMGESCVNVIEKAG LSKEDVDFLIPHQANIRIMEAARERLELPVEKMSKTVHKYGNTSAAS IPISLVEELEAGKIKDGDVVVMVGFGGGLTWGAIAIRWGR |
| 3 | *Bacillus subtilis* | beta ketoacyl-ACP synthase III (FabH2) | MSKAKITAIGTYAPSRRLTNADLEKIVDTSDEWIVQRTGMRERRIA DEHQFTSDLCIEAVKNLKSRYKGTLDDVDMILVATTTSDYAFPSTAC RVQEYFGWESTGALDINATCAGLTYGLHLANGLITSGLHQKILVIAG ETLSKVTDYTDRTTCVLFGDAAGALLVERDEETPGFLASVQGTSGN GGDILYRAGLRNEINGVQLVGSGKMVQNGREVYKWAARTVPGEF ERLLHKAGLSSDDLDWFVPHSANLRMIESICEKTPFPIEKTLTSVEHY GNTSSVSIVLALDLAVKAGKLKKDQIVLLFGFGGGLTYTGLLIKWGM |
| 4 | *Streptomyces coelicolor* | beta ketoacyl-ACP synthase III | MARGAGRLTGIGVYRPGGLLTSAELDTRFGHEDGYIEQITGIRTRLK ADPDDTFVEMAAQAADKALAHAGVLAEDLDCVLFSSASSVGQAS CRAASLTHRIGAGRAGGFDLNGGCAGFGYGLTLASGLIAAQQARQ ILVVAAERLSDITDPDDCGTVMVFGDAAGAAVVSAAEHPGIGPAV WGTHGPGEPWMTSAPPKPGAARPYMHMDGTRVVRWFGSQM PQVARDALEAAGLTWDDIGAFVPHQCNGRLIDAMVRRLRPPEHV AIARSIVTDGNTSSASIPLALESLLASATVRPGDKALLLGFGAGLTWC AQVVELP |

SEQUENCE TABLE

| SEQ ID NO | Organism | Other Information | Sequence |
|---|---|---|---|
| 5 | Streptomyces glaucescens | beta ketoacyl-ACP synthase III | MSKIKPAKGAPYARILGVGGYRPTRVVPNEVILETIDSSDEWIRSRS GIQTRHWANDEETVAAMSIEASGKAIADAGITAAQVGAVIVSTVT HFKQTPAVATEIADKLGTNKAAAFDISAGCAGFGYGLTLAKGMIVE GSAEYVLVIGVERLSDLTDLEDRATAFLFGDGAGAVVVGPSNEPAI GPTIWGSEGDKAETIKQTVPWTDYREGGVERFPAITQEGQAVFR WAVFEMAKVAQQALDAAGVAAADLDVFIPHQANERIIDSMVKTL KLPESVTVARDVRTTGNTSAASIPLAMERLLATGEAKSGDTALVIGF GAGLVYAASVVTLP |
| 6 | Streptomyces avermitilis | beta ketoacyl-ACP synthase III | MSGGRAAVITGIGGYVPPDLVTNDDLAQRLDTSDAWIRSRTGIAE RHVIAPGTATSDLAVEAGLRALKSAGDEHVDAVVLATTTPDQPCPA TAPQVAARLGLGQVPAFDVAAVCSGFLFGLATASGLIAAGVADKV LLVAADAFTTIINPEDRTTAVIFADGAGAVVLRAGAADEPGAVGPL VLGGSDGELSHLIEVPAGGSRQRSSGPTTDPDDQYFRMLGRDTYRH AVERMTDASQRAAELADWRIDDVDRFAAHQANARILDSVAERLG VPAERQLTNIARVGNTGAASIPLLLSQAAAAGRLGAGHRVLLTAFG GGLSWGAGTLVWPEVQPV |
| 7 | Listeria monocytogenes | beta ketoacyl-ACP synthase III | MNAGILGVGKYVPEKIVTNFDLEKIMDTSDEWIRTRTGIEERRIARD DEYTHDLAYEAAKVAIENAGLTPDDIDLFIVATVTQEATFPSVANIIQ DRLGATNAAGMDVEAACAGFTFGVVTAAQFIKTGAYKNIVVVGA DKLSKITNWDDRATAVLFGDGAGAVVMGPVSDDHGLLSFDLGSD GSGGKYLNLDENKKIYMNGREVFRFAVRQMGEASLRVLERAGLEK EELDLLIPHQANIRIMEASRERLNLPEEKLMKTVHKYGNTSSSSIALA LVDAVEEGRIKDNDNVLLVGFGGGLTWGALIIRWGK |
| 8 | Artificial sequence | L. monocytogenes beta ketoacyl-ACP synthase III variant | MNAGILGVGKYVPEKIVTNFDLEKIMDTSDEWIRTRTGIEERRIARD DEYTHDLAYEAAKVAIENAGLTPDDIDLFIVATVTQEATFPSVANIIQ DRLGATNAAGMDVEAACAGFTFGVVTAAQFIKTGAYKNIVVVGA DKLSKITNWDDRATAVLFGDGAGAVVMGPVSDDHGLLSFDLGSD GSGGKYLNLDENKKIYMNGREVFRFAVRQMGEASLRVLERAGLEK EELDLLIPHQANIRIMEASRERLNLPEEKLMKTVHKYGNTSSSSIALA LVDAVEEGRIKDNDNVLLVGFGGGLTWGALIIRGGK |
| 9 | Staphylococcus aureus | beta ketoacyl-ACP synthase III | MNVGIKGFGAYAPEKIIDNAYFEQFLDTSDEWISKMTGIKERHWA DDDQDTSDLAYEASLKAIADAGIQPEDIDMIIVATATGDMPFPTVA NMLQERLGTGKVASMDQLAACSGFMYSMITAKQYVQSGDYHNIL VVGADKLSKITDLTDRSTAVLFGDGAGAVIIGEVSDGRGIISYEMGS DGTGGKHLYLDKDTGKLKMNGREVFKFAVRIMGDASTRVVEKAN LTSDDIDLFIPHQANIRIMESARERLGISKDKMSVSVNKYGNTSAASI PLSIDQELKNGKIKDDDTIVLVGFGGGLTWGAMTIKWGK |
| 10 | Streptococcus pneumoniae | beta ketoacyl-ACP synthase III | MAFAKISQVAHYVPEQVVTNHDLAQIMDTNDEWISSRTGIRQRHI SRTESTSDLATEVAKKLMAKAGITGEELDFIILATITPDSMMPSTAAR VQANIGANKAFADLTAACSGFVFALSTAEKFIASGRFQKGLVIGSE TLSKAVDWSDRSTAVLFGDGAGGVLLEASEQEHFLAESLNSDGSRS ECLTYGHSGLHSPPFSDQESADSFLKMDGRTVFDFAIRDVAKSIKQTI DESPIEVTDLDYLLLHQANDRILDKMARKIGVDRAKLPANMMEYG NTSAASIPILLSECVEQGLIPLDGSQTVLLSGFGGGLTWGTLILTI |
| 11 | Streptococcus mutans | beta ketoacyl-ACP synthase III | MTFAKISQAAYYVPSQVVTNDDLSKIMDTSDEWITSRTGIRERRIS QSEDTSDLASQVAKELLKKASLKAKEIDFIIVATITPDAMMPSTAAC VQAKIGAVNAFADLTAACSGFIFALSAAEKMIKSGQYQKGLVIGA EVLSKIIDWSDRTTAVLFGDGAGGVLLEADSSEHFLFESIHSDGSRG ESLTSGEHAVSSPPSQVDKKDNCFLKMDGRAIFDFAIRDVSKSISML IRKSDMPVEAIDYFLLHQANIRILDKMAKKIGADREKFPANMMKY GNTSAASIPILLAECVENGTIELNGSHTVLLSGFGGGLTWGSLIVKI |
| 12 | Lactococcus lactis | beta ketoacyl-ACP synthase III | MTFAKITQVAHYVPENVVSNDDLSKIMDTNDEWIYSRTGIKNRHIS TGENTSDLAAKVAKQLISDSNLSPETIDFIIVATVTPDSLMPSTAARV QAQVGAVNAFAYDLTAACSGFVFALSTAEKLISSGAYQRGLVIGAE VFSKVIDWSDRSTAVLFGDGAAGVLIEAGASQPLIIAEKMQTDGSR GNSLLSSYADIQTPFASVSYESSNLSMEGRAIFDFAVRDVPKNIQAT LEKANLSAEEVDYYLLHQANSRILDKMAKKLGVTRQKFLQNMQEY GNTSAASIPILLSESVKNGIFSLDGQTKVVLTGFGGGLTWGTAIINL |
| 13 | Propionibacterium freudenreichii subsp. shermanii | beta ketoacyl-ACP synthase III | MIDSTPEWIEQRTGIRERRWATKDETVLSMATDAGRKALDMAGV KPEQVGAIIVSTVSHHIPSPGLSDYLAEELGCPAPATFDISAACAGFC YALTLAESIVRAGHAGKDGFVLIVGVERLSDMTMDDRGTDFLFG DGAGAVVGPSDPAIGPAVWGSKPANVKTIEIQSWTEADKNPT GFPLIQMDGHTVFKWALSEVADHAAEAIDAAGITPEQLDIFLPHQA NDRITDAIIRHLHLPDSVSVCRDIAEMGNTSAASIPIAMDAMIREGR AKSGQTALIIGFGAGLVYAGRVVVLP |

-continued

SEQUENCE TABLE

| SEQ ID NO | Organism | Other Information | Sequence |
|---|---|---|---|
| 14 | Artificial sequence | FabH motif | D-T-(N,S)D-(A,E)-W-I-(x)2-(M,R)-T-G-I-x-(N,E)-R-(R,H) |
| 15 | Artificial sequence | FabH motif | (S,A)-x-D-(x)2-A-(A,V)-C-(A,S)-G-F-(x)3-(M,L)-(x)2-A |
| 16 | Artificial sequence | FabH motif | D-R-x-T-(A,I)-(I,V)-x-F-(A,G)-D-G-A-(A,G)-(G,A)-(A,V) |
| 17 | Artificial sequence | FabH motif | H-Q-A-N-x-R-I-(M,L) |
| 18 | Artificial sequence | FabH motif | G-N-T-(G,S)-A-A-S-(V,I)-P-(x)2-(I,L)-(x)6-G |
| 19 | Artificial sequence | FabH motif | (I,V)-x-L-(x)2-F-G-G-G-(L,F)-(T,S)-W-G |
| 20 | Escherichia coli | Aspartate kinase/ Homoserine dehydrogenase (ThrA) | MRVLKFGGTSVANAERFLRVADILESNARQGQVATVLSAPAKITN HLVAMIEKTISGQDALPNISDAERIFAELLTGLAAAQPGFPLAQLKTF VDQEFAQIKHVLHGISLLGQCPDSINAALICRGEKMSIAIMAGVLEA RGHNVTVIDPVEKLLAVGHYLESTVDIAESTRRIAASRIPADHMVL MAGFTAGNEKGELVVLGRNGSDYSAAVLAACLRADCCEIWTDVD GVYTCDPRQVPDARLLKSMSYQEAMELSYFGAKVLHPRTITPIAQF QIPCLIKNTGNPQAPGTLIGASRDEDELPVKGISNLNNMAMFSVSG PGMKGMVGMAARVFAAMSRARISVVLITQSSSEYSISFCVPQSDC VRAERAMQEEFYLELKEGLLEPLAVTERLAIISVVGDGMRTLRGISA KFFAALARANINIVAIAQGSSERSISVVVNNDDATTGVRVTHQMLF NTDQVIEVFVIGVGGVGGALLEQLKRQQSWLKNKHIDLRVCGVAN SKALLTNVHGLNLENWQEELAQAKEPFNLGRLIRLVKEYHLLNPVIV DCTSSQAVADQYADFLREGFHVVTPNKKANTSSMDYYHQLRYAA EKSRRKFLYDTNVGAGLPVIENLQNLLNAGDELMKFSGILSGSLSYIF GKLDEGMSFSEATTLAREMGYTEPDPRDDLSGMDVARKLLILARET GRELELADIEIEPVLPAEFNAEGDVAAFMANLSQLDDLFAARVAKA RDEGKVLRYVGNIDEDGVCRVKIAEVDGNDPLFKVKNGENALAFYS HYYQPLPLVLRGYGAGNDTAAGVFADLLRTLSWKLGV |
| 21 | Artificial sequence | Escherichia coli ThrA S345F variant | MRVLKFGGTSVANAERFLRVADILESNARQGQVATVLSAPAKITN HLVAMIEKTISGQDALPNISDAERIFAELLTGLAAAQPGFPLAQLKTF VDQEFAQIKHVLHGISLLGQCPDSINAALICRGEKMSIAIMAGVLEA RGHNVTVIDPVEKLLAVGHYLESTVDIAESTRRIAASRIPADHMVL MAGFTAGNEKGELVVLGRNGSDYSAAVLAACLRADCCEIWTDVD GVYTCDPRQVPDARLLKSMSYQEAMELSYFGAKVLHPRTITPIAQF QIPCLIKNTGNPQAPGTLIGASRDEDELPVKGISNLNNMAMFSVSG PGMKGMVGMAARVFAAMSRARIFVVLITQSSSEYSISFCVPQSDC VRAERAMQEEFYLELKEGLLEPLAVTERLAIISVVGDGMRTLRGISA KFFAALARANINIVAIAQGSSERSISVVVNNDDATTGVRVTHQMLF NTDQVIEVFVIGVGGVGGALLEQLKRQQSWLKNKHIDLRVCGVAN SKALLTNVHGLNLENWQEELAQAKEPFNLGRLIRLVKEYHLLNPVIV DCTSSQAVADQYADFLREGFHVVTPNKKANTSSMDYYHQLRYAA EKSRRKFLYDTNVGAGLPVIENLQNLLNAGDELMKFSGILSGSLSYIF GKLDEGMSFSEATTLAREMGYTEPDPRDDLSGMDVARKLLILARET GRELELADIEIEPVLPAEFNAEGDVAAFMANLSQLDDLFAARVAKA RDEGKVLRYVGNIDEDGVCRVKIAEVDGNDPLFKVKNGENALAFYS HYYQPLPLVLRGYGAGNDVTAAGVFADLLRTLSWKLGV |
| 22 | Bacillus subtilis | Aspartate kinase | MKIIVQKFGGTSVKDDKGRKLALGHIKEAISEGYKVVVVVSAMGRK GDPYATDSLLGLLYGDQSAISPREQDLLLSCGETISSVVFTSMLLDN GVKAAALTGAQAGFLTNDQHTNAKIIEMKPERLFSVLANHDAVVV AGFQGATEKGDTTTIGRGGSDTSAAALGAAVDAEYIDIFTDVEGV MTADPRVVENAKPLPVVTYTEICNLAYQGAKVISPRAVEIAMQAK VPIRVRSTYSNDKGTLVTSHHSSKVGSDVFERLITGIAHVKDVTQFK VPAKIGQYNVQTEVFKAMANAGISVDFFNITPSEIVYTVAGNKTET AQRILMDGYDPMVTRNCAKVSAVGAGIMGVPGVTSKIVSALSE KEIPILQSADSHTTIWVLVHEADMVPAVNALHEVFELSK |
| 23 | Pseudomonas putida | Aspartate kinase | MALIVQKFGGTSVGSIERIEQVAEKVKKHREAGDDLVVVLSAMSGE TNRLIDLAKQITDQPVRELDVIVSTGEQVTIALLTMALIKRGVPAVS YTGNQVRILTDSSHNKARILQIDDQKIRADLKEGRVVVVAGFQGVD EHGSITTLGRGGSDTTGVALAAALKADECQIYTDVDGVYTTDPRVV PQARRLEKITFEEMLEMASLGSKVLQIRSVEFAGKYNVPLRVLHSFK EGPGTLITIDEEESMEQPIISGIAFNRDEAKLTIRGVPDTPGVAFKILG PISASNIEVDMIVQNVAHDNTTDFTFTVHRNEYEKAQSVLENTARE |

| SEQ ID NO | Organism | Other Information | Sequence |
|---|---|---|---|
| | | | IGAREVIGDTKIAKVSIVGVGMRSHAGVASCMFEALAKESINIQMIS<br>TSEIKVSVVLEEKYLELAVRALHTAFDLDAPARQGE |
| 24 | Saccharomyces cerevisiae | Aspartate kinase | MPMDFQPTSSHSNWVVQKFGGTSVGKFPVQIVDDIVKHYSKPDG<br>PNNNVAVVCSARSSYTKAEGTTSRLLKCCDLASQESEFQDIIEVIRQ<br>DHIDNADRFILNPALQAKLVDDTNKELELVKKYLNASKVLGEVSSRT<br>VDLVMSCGEKLSCLFMTALCNDRGCKAKYVDLSHIVPSDFSASALD<br>NSFYTFLVQALKEKLAPFVSAKERIVPVFTGFFGLVPTGLLNGVGRG<br>YTDLCAALIAVAVNADELQVWKEVDGIFTADPRKVPEARLLDSVTP<br>EEASELTYYGSEVIHPFTMEQVIRAKIPIRIKNVQNPLGNGTIIYPDN<br>VAKKGESTPPHPPENLSSSFYEKRKRGATAITTKNDIFVINIHSNKKT<br>LSHGFLAQIFTILDKYKLVVDLISTSEVHVSMALPIPDADSLKSLRQAE<br>EKLRILGSVDITKKLSIVSLVGKHMKQYIGIAGTMFTTLAEEGINIEMI<br>SQGANEINISCVINESDSIKALQCIHAKLLSERTNTSNQFEHAIDERLE<br>QLKRLGI |
| 25 | Bacillus subtilis | Homoserine dehydrogenase | MKAIRVGLLGLGTVGSGVVKIIQDHQDKLMHQVGCPVTIKKVLVK<br>DLEKKREVDLPKEVLTTEVYDVIDDPDVDVVIEVIGGVEQTKQYLVD<br>ALRSKKHVVTANKDLMAVYGSELLAEAKENGCDIYFEASVAGGIPIL<br>RTLEEGLSSDRITKMMGIVNGTTNFILTKMIKEKSPYEEVLKEAQDL<br>GFAEADPTSDVEGLDAARKMAILARLGFSMNVDLEDVKVKGISQIT<br>DEDISFSKRLGYTMKLIGIAQRDGSKIEVSVQPTLLPDHHPLSAVHN<br>EFNAVYVYGEAVGETMFYGPGAGSMPTATSVVSDLVAVMKNMR<br>LGVTGNSFVGPQYEKNMKSPSDIYAQQFLRIHVKDEVGSFSKITSVF<br>SERGVSFEKILQLPIKGHDELAEIVIVTHHTSEADFSDILQNLNDLEVV<br>QEVKSTYRVEGNGWS |
| 26 | Pseudomonas putida | Homoserine dehydrogenase | MKPVKVGICLGLGTVGGGTFNVLQRNAEEIARRAGRGIEVAQIAMR<br>SQNPNCQITGTPITADVFEVASNPEIDIVIELIGGYTIARDLVLKAIEN<br>GKHVVTANKALIAVHGNEIFAKAREKGVIVAFEAAVAGGIPVIKAIR<br>EGLSANRINWLAGIINGTGNFILTEMREKGRAFPDVLAEAQALGYA<br>EADPTFDVEGIDAAHKLTILASIAFGIPLQFDKAYTEGITQLTTADVN<br>YAEALGYRIKHLGVARRTAEGIELRVHPTLIPADRLIANVNGVMNA<br>VMVNGDAAGSTLYYGAGAGMEPTASSVVGDLVDVVRAMTSDPE<br>NRVPHLAFQPDSLSAHPILPIEACESAYYLRIQAKDHPGVLAQVASIL<br>SERGINIESIMQKEAEEQDGLVPMILVTHGVVEQRINDAIVALEALQ<br>DVVGKVVRIRVEQLN |
| 27 | Saccharomyces cerevisiae | Homoserine dehydrogenase | MSTKVVNVAVIGAGVVGSAFLDQLLAMKSTITYNLVLLAEAERSLIS<br>KDFSPLNVGSDWKAALAASTTKTLPLDDLIAHLKTSPKPVILVDNTS<br>SAYIAGFYTKFVENGISIATPNKKAFSSDLATWKALFSNKPTNGFVY<br>HEATVGAGLPIISFLREIIQTGDEVEKIEGIFSGTLSYIFNEFSTSQAND<br>VKFSDVVKVAKKLGYTEPDPRDDLNGLDVARKVTIVGRISGVEVES<br>PTSFPVQSLIPKPLESVKSADEFLEKLSDYDKDLTQLKKEAATENKVL<br>RFIGKVDVATKSVSVGIEKYDYSHPFASLKGSDNVISIKTKRYTNPVVI<br>QGAGAGAAVTAAGVLGDVIKIAQRL |
| 28 | Escherichia coli | Homoserine kinase | MVKVYAPASSANMSVGFDVLGAAVTPVDGALLGDVVTVEAAETF<br>SLNNLGRFADKLPSEPRENIVYQCWERFCQELGKQIPVAMTLEKN<br>MPIGSGLGSSACSVVAALMAMNEHCGKPLNDTRLLALMGELEGRI<br>SGSIHYDNVAPCFLGGMQLMIEENDIISQQVPGFDEWLWVLAYPG<br>IKVSTAEARAILPAQYRRQDCIAHGRHLAGFIHACYSRQPELAAKLM<br>KDVIAEPYRERLLPGFRQARQAVAEIGAVASGISGSGPTLFALCDKP<br>ETAQRVADWLGKNYLQNQEGFVHICRLDTAGARVLEN |
| 29 | Bacillus subtilis | Homoserine kinase | MNEADMLFSVTVPGSTANLGPGFDSVGMALSRYLKLTVFESDKW<br>SFEAETETVAGIPAGTDNLIYQVAKRTADLYGKEMPPVHVKVWSDI<br>PLARGLGSSAAAIVAAIELADELCGLKLSEADKLHLASLEEGHPDNA<br>GASLVGGLVIGLHEDDETQMIRVPNADIDVVVVIPFYEVLTRDARD<br>VLPKEFPYADAVKASAVSNILIAAIMSKDWPLVGKIMKKDMFHQP<br>YRAMLVPELSKVEHVAEMKGAYGTALSGAGPTILVMTEKGKGEEL<br>KEQLALHFPHCEVDALTVPKEGSIIERNPLYQVKSV |
| 30 | Pseudomonas putida | Homoserine kinase | MSVFTPVTRPELETFLAPYELGRLLDFQGIAAGTENSNFFVSLEQGE<br>FVLTLIERGPSEDMPFFIELLDTLHGADMPVPYAIRDRDGNGLRELC<br>GKPALLQPRLSGKHIKAPNNQHCAQVGELLAHIHLATREHIIERRTD<br>RGLDWMLASGVELLPRLTAEQAALLQPALDEISAHKAQILALPRAN<br>LHADLFRDNVMFEGTHLTGVIDFYNACSGPMLYDIAITVNDWCLD<br>EQGAVDVPRAQALLAAYAALRPFTAAEAELWPEMLRVGCVRFWL<br>SRLIAAESFAGMDVMIHDPSEFEVRLAQRQQVALHLPFAL |
| 31 | Saccharomyces cerevisiae | Homoserine kinase | MVRAFKIKVPASSANIGPGYDVLGVGLSLFLELDVTIDSSQAQETND<br>DPNNCKLSYTKESEGYSTVPLRSDANLITRTALYVLRCNNIRNFPSGT<br>KVHVSNPIPLGRGLGSSGAAVVAGVILGNEVAQLGFSKQRMLDYC |

SEQUENCE TABLE

| SEQ ID NO | Organism | Other Information | Sequence |
|---|---|---|---|
| | | | LMIERHPDNITAAMMGGFCGSFLRDLTPQEVERREIPLAEVLPEPS GGEDTGLVPPLPPTDIGRHVKYQWNPAIKCIAIIPQFELSTADSRGV LPKAYPTQDLVFNLQRLAVLTTALTMDPPNADLIYPAMQDRVHQP YRKTLIPGLTEILSCVTPSTYPGLLGICLSGAGPTILALATENFEEISQE11 NRFAKNGIKCSWKLLEPAYDGASVEQQ |
| 32 | Escherichia coli | Threonine synthase | MKLYNLKDHNEQVSFAQAVTQGLGKNQGLFFPHDLPEFSLTEIDE MLKLDFVTRSAKILSAFIGDEIPQEILEERVRAAFAFPAPVANVESDV GCLELFHGPTLAFKDFGGRFMAQMLTHIAGDKPVTILTATSGDTG AAVAHAFYGLPNVKVVILYPRGKISPLQEKLFCTLGGNIETVAIDGDF DACQALVKQAFDDEELKVALGLNSANSININISRLLAQICYYFEAVAQL PQETRNQLVVSVPSGNFGDLTAGLLAKSLGLPVKRFIAATNVNDTV PRFLHDGQWSPKATQATLSNAMDVSQPNNWPRVEELFRRKIWQ LKELGYAAVDDETTQQTMRELKELGYTSEPHAAVAYRALRDQLNP GEYGLFLGTAHPAKFKESVEAILGETLDLPKELAERADLPLLSHNLPA DFAALRKLMMNHQ |
| 33 | Bacillus subtilis | Threonine synthase | MWKGLIHQYKEFLPVTDQTPALTLHEGNTPLIHLPKLSEQLGIELHV KTEGVNPTGSFKDRGMVMAVAKAKEEGNDTIMCASTGNTSAAA AAYAARANMKCIVIIPNGKIAFGKLAQAVMYGAEIIAIDGNFDDAL KIVRSICEKSPIALVNSVNPYRIEGQKTAAFEVCEQLGEAPDVLAIPV GNAGNITAYWKGFKEYHEKNGTGLPKMRGFEAEGAAAIVRNEVIE NPETIATATAIRIGNPASWDKAVKAAEESNGKIDEVTDDEILHAYQLIA RVEGVFAEPGSCASIAGVLKQVKSGEIPKGSKVVAVLTGNGLKDPN TAVDISEIKPVTLPTDEDSILEYVKGAARV |
| 34 | Corynebacterium glutamicum | Threonine synthase | MDYISTRDASRTPARFSDILLGGLAPDGGLYLPATYPQLDDAQLSK WREVLANEGYAALAAEVISLFVDDIPVEDIKAITARAYTYPKFNSEDI VPVTELEDNIYLGHLSEGPTAAFKDMAMQLLGELFEYELRRRNETI NILGATSGDTGSSAEYAMRGREGIRVFMLTPAGRMTPFQQAQMF GLDDPNIFNIALDGVFDDCQDVVKAVSADAEFKKDNRIGAVNSIN WARLMAQVVYYVSSWIRTTTSNDQKVSFSVPTGNFGDICAGHIAR QMGLPIDRLIVATNENDVLDEFFRTGDYRVRSSADTHETSSPSMDI SRASNFERFIFDLLGRDATRVNDLFGTQVRQGGFSLADDANFEKAA AEYGFASGRSTHADRVATIADVHSRLDVLIDPHTADGVHVARQWR DEVNTPIIVLETALPVKFADTIVEAIGEAPQTPERFAAIMDAPFKVSD LPNDTDAVKQYIVDAIANTSVK |
| 35 | Escherichia coli | Threonine deaminase (TdcB) | MHITYDLPVAIDDIIEAKQRLAGRIYKTGMPRSNYFSERCKGEIFLKF ENMQRTGSFKIRGAFNKLSSLTDAEKRKGVVACSAGNHAQGVSLS CAMLGIDGKVVMPKGAPKSKVAATCDYSAEVVLHGDNFNDTIAK VSEIVEMEGRIFIPPYDDPKVIAGQGTIGLEIMEDLYDVDNVIVPIGG GGLIAGIAVAIKSINPTIRVIGVQSENVHGMAASFHSGEITTHRTTGT LADGCDVSRPGNLTYEIVRELVDDIVLVSEDEIRNSMIALIQRNKVV TEGAGALACAALLSGKLDQYIQNRKTVSIISGGNIDLSRVSQITGFVDA |
| 36 | Escherichia coli | Threonine deaminase (IlvA) | MADSQPLSGAPEGAEYLRAVLRAPVYEAAQVTPLQKMEKLSSRLD NVILVKREDRQPVHSFKLRGAYAMMAGLTEEQKAHGVITASAGN HAQGVAFSSARLGVKALIVMPTATADIKVDAVRGFGGEVLLHGAN FDEAKAKAIELSQQQGFTWVPPFDHPMVIAGQGTLALELLQQDA HLDRVFVPVGGGGLAAGVAVLIKQLMPQIKVIAVEAEDSACLKAAL DAGHPVDLPRVGLFAEGVAVKRIGDETFRLCQEYLDDIITVDSDAIC AAMKDLFEDVRAVAEPSGALALAGMKKYIALHNIRGERLAHILSGA NVNFHGLRYVSERCELGEQREALLAVTIPEEKGSFLKFCQLLGGRSV TEFNYRFADAKNACIFVGVRLSRGLEERKEILQMLNDGGYSVVDLS DDEMAKLHVRYMVGGRPSHPLQERLYSFEFPESPGALLRFLNTLGT YWNISLFHYRSHGTDYGRVLAAFELGDHEPDFETRLNELGYDCHDE TNNPAFRFFLAG |
| 37 | Bacillus subtilis | Threonine deaminase (IlvA) | MKPLLKENSLIQVKDILKAHQNVKDVVIHTPLQRNDRLSERYECNIY LKREDLQVVRSFKLRGAYHKMKQLSSEQTENGVVCASAGNHAQG VAFSCKHLGIHGKIFMPSTTPRQKVSQVELFGKGFIDIILTGDTFDDA YKSAAECCEAESRTFIHPFDDPDVMAGQGTLAVEILNDIDTEPHFLF ASVGGGGLLSGVGTYLKNVSPDTKVIAVEPAGAASYFESNKAGHV VTLDKIDKFVDGAAVKKIGEETFRTLETVVDDILLVPEGKVCTSILELY NECAVVAEPAGALSVAALDLYKDQIKGKNVVCVVSGGNNDIGRM QEMKERSLIFEGLQHYFIVNFPQRAGALREFLDEVLGPNDDITRFEY TKKNNKSNGPALVGIELQNKADYGPLIERMNKKPFHYVEVNKDED LFHLLI |
| 38 | Corynebacterium glutamicum | Threonine deaminase (IlvA) | MSETYVSEKSPGVMASGAELIRAADIQTAQARISSVIAPTPLQYCPR LSEETGAEIYLKREDLQDVRSYKIRGALNSGAQLTQEQRDAGIVAAS AGNHAQGVAYVCKSLGVQGRIYVPVQTPKQKRDRIMVHGGEFVS LVVTGNNFDEASAAAHEDAERTGATLIEPFDARNTVIGQGTVAAEI |

SEQUENCE TABLE

| SEQ ID NO | Organism | Other Information | Sequence |
|---|---|---|---|
| | | | LSQLTSMGKSADHVMVPVGGGGLLAGVVSYMADMAPRTAIVGIE PAGAASMQAALHNGGPITLETVDPFVDGAAVKRVGDLNYTIVEKN QGRVHMMSATEGAVCTEMLDLYQNEGIIAEPAGALSIAGLKEMSF APGSVVVCIISGGNNDVLRYAEIAERSLVHRGLKHYFLVNFPQKPG QLRHFLEDILGPDDDITLFEYLKRNNRETGTALVGIHLSEASGLDSLL ERMEESAIDSRRLEPGTPEYEYLT |
| 39 | Corynebacterium glutamicum | Threonine deaminase (TdcB) | MLTLNDVITAQQRTAPHVRRTPLFEADPIDGTQIWIKAEFLQKCGV FKTRGAFNRQLAASENGLLDPTVGIVAASGGNAGLANAFAAASLS VPATVLVPETAPQVKVDRLKQYGATVQQIGSEYAEAFEAAQTFESE TGALFCHAYDQPDIAAGAGVIGLEIVEDLPDVDTIVVAVGGGGLYA GIAAVVAAHDIKVVAVEPSKIPTLHNSLIAGQPVDVNVSGIAADSLG ARQIGREAFDIATAHPPIGVLVDDEAIIAARRHLWDNYRIPAEHGA AAALASLTSGAYKPAADEKVAVIVCGANTDLTTL |
| 40 | Methanocaldococcus jannaschii | Citramalate synthase | MMVRIFDTTLRDGEQTPGVSLTPNDKLEIAKKLDELGVDVIEAGSAI TSKGEREGIKLITKEGLNAEICSFVRALPVDIDAALECDVDSVHLVVP TSPIHMKYKLRKTEDEVLETALKAVEYAKEHGLIVELSAEDATRSDV NFLIKLFNEGEKVGADRVCVCDTVGVLTPQKSQELFKKITENVNLPV SVHCHNDFGMATANTCSAVLGGAVQCHVTVNGIGERAGNASLEE VVAALKILYGYDTKIKMEKLYEVSRIVSRLMKLPVPPNKAIVGDNAF AHEAGIHVDGLIKNTETYEPIKPEMVGNRRRIILGKHSGRKALKYKL DLMGINVSDEQLNKIYERVKEFGDLGKYISDADLLAIVREVTGKLVE EKIKLDELTVVSGNKITPIASVKLHYKGEDITLIETAYGVGPVDAAINA VRKAISGVADIKLVEYRVEAIGGGTDALIEVVVKLRKGTEIVEVRKSD ADIIRASVDAVMEGINMLLN |
| 41 | Artificial sequence | M. jannaschii Citramalate synthase variant | MMVRIFDTTLRDGEQTPGVSLTPNDKLEIAKKLDELGVDVIEAGSA VTSKGEREGIKLITKEGLNAEICSFVRALPVDIDAALECDVDSVHLVV PTSPIHMKYKLRKTEDEVLVTALKAVEYAKEQGLIVELSAEDATRSD VNFLIKLFNEGEKVGADRVCVCDTVGVLTPQKSQELFKKITENVNLP VSVHCHNDFGMATANACSAVLGGAVQCHVTVNGIGERAGNASL EEVVAASKILYGYDTKIKMEKLYEVSRIVSRLMKLPVPPNKAIVGDN AFAHEAGIHVDGLIKNTETYEPIKPEMVGNRRRIILGKHSGRKALKY KLDLMGINVSDEQLNKIYERVKEFGDLGKYISDADLLAIVREVTGKL |
| 42 | Leptospira interrogans | Citramalate synthase | MTKVETRLEILDVTLRDGEQTRGVSFSTSEKLNIAKFLLQKLNVDRV EIASARVSKGELETVQKIMEWAATEQLTERIEILGFVDGNKTVDWIK DSGAKVLNLLTKGSLHHLEKQLGKTPKEFFTDVSFVIEYAIKSGLKIN VYLEDWSNGFRNSPDYVKSLVEHLSKEHIERIFLPDTLGVLSPEETFQ GVDSLIQKYPDIHFEFHGHNDYDLSVANSLQAIRAGVKGLHASING LGERAGNTPLEALVTTIHDKSNSKTNINEIAITEASRLVEVFSGKRISA NRPIVGEDVFTQTAGVHADGDKKGNLYANPILPERFGRKRSYALGK LAGKASISENVKQLGMVLSEVVLQKVLERVIELGDQNKLVTPEDLPF IIADVSGRTGEKVLTIKSCNIHSGIGIRPHAQIELEYQGKIHKEISEGD GGYDAFMNALTKITNRLGISIPKLIDYEVRIPPGGKTDALVETRITWN KSLDLEEDQTFKTMGVHPDQTVAAVHATEKMLNQILQPWQI |
| 43 | Artificial sequence | Leptospira interrogans Citramalate synthase variant | MTKVETRLEILDVTLRDGEQTRGVSFSTSEKLNIAKFLLQKLNVDRV EIASARVSKGELETVQKIMEWAATEQLTERIEILGFVDGNKTVDWIK DSGAKVLNLLTKGSLHHLEKQLGKTPKEFFTDVSFVIEYAIKSGLKIN VYLEDWSNGFRNSPDYVKSLVEHLSKEHIERIFLPDTLGVLSPEETFQ GVDSLIQKYPDIHFEFHGHNDYDLSVANSLQAIRAGVKGLHASING LGERAGNTPLEALVTTIHDKSNSKTNINEIAITEASRLVEVFSGKRISA NRPIVGEDVFTQTAGVHADGDKKGNLYANPILPERFGRKRSYALGK LAGKASISENVKQLGMVLSEVVLQKVLERVIELGDQNKLVTPEDLPF IIADVSGR |
| 44 | Escherichia coli | Isopropylmalate isomerase large subunit | MAKTLYEKLFDAHVVYEAENETPLLYIDRHLVHEVTSPQAFDGLRA HGRPVRQPGKTFATMDHNVSTQTKDINACGEMARIQMQELIKNC KEFGVELYDLNHPYQGIVHVMGPEQGVTLPGMTIVCGDSHTATH GAFGALAFGIGTSEVEHVLATQTLKQGRAKTMKIEVQGKAAPGITA KDIVLAIIGKTGSAGGTGHVVEFCGEAIRDLSMEGRMTLCNMAIE MGAKAGLVAPDETTFNYVKGRLHAPKGKDFDDAVAYWKTLQTDE GATFDTVVTLQAEEISPQVTWGTNPGQVISVNDNIPDPASFADPV ERASAEKALAYMGLKPGIPLTEVAIDKVFIGSCTNSRIEDLRAAAEIA KGRKVAPGVQALVVPGSGPVKAQAEAEGLDKIFIEAGFEWRLPGC SMCLAMNNDRLNPGERCASTSNRNFEGRQGRGGRTHLVSPAMA AAAAVTGHFADIRNIK |

SEQUENCE TABLE

| SEQ ID NO | Organism | Other Information | Sequence |
|---|---|---|---|
| 45 | Escherichia coli | Isopropylmalate isomerase small subunit | MAEKFIKHTGLVVPLDAANVDTDAIIPKQFLQKVTRTGFGAHLFND WRFLDEKGQQPNPDFVLNFPQYQGASILLARENFGCGSSREHAP WALTDYGFKVVIAPSFADIFYGNSFNNQLLPVKLSDAEVDELFALVK ANPGIHFDVDLEAQEVKAGEKTYRFTIDAFRRHCMMNGLDSIGLTL QHDDAIAAYEAKQPAFMN |
| 46 | Bacillus subtilis | Isopropylmalate isomerase large subunit | MMPRTIIEKIWDQHIVKHGEGKPDLLYIDLHLIHEVTSPQAFEGLRQ KGRKVRRPQNTFATMDHNIPTVNRFEIKDEVAKRQVTALERNCEE FGVRLADLHSVDQGIVHVVGPELGLTLPGKTIVCGDSHTSTHGAFG ALAFGIGTSEVEHVLSTQTLWQQRPKTLEVRVDGTLQKGVTAKDVI LAVIGKYGVKFGTGYVIEYTGEVFRNMTMDERMTVCNMSIEAGA RAGLIAPDEVTFEYCKNRKYTPKGEEFDKAVEEWKALRTDPGAVYD KSIVLDGNKISPMVTWGINPGMVLPVDSEVPAPESFSAEDDKKEAI RAYEYMGLTPHQKIEDIKVEHVFIGSCTNSRMTDLRQAADMIKGK KVADSVRAIVVPGSQSVKLQAEKEGLDQIFLEAGFEWRESGCSMCL SMNNDVVPEGERCASTSNRNFEGRQKGARTHLVSPAMAAMAA IHGHFVDVRKFYQEKTVV |
| 47 | Bacillus subtilis | Isopropylmalate isomerase small subunit | MEPLKSHTGKAAVLNRINVDTDQIIPKQFLKRIERTGYGRFAFFDW RYDANGEPNPEFELNQPVYQGASILIAGENFGCGSSREHAPWALD DYGFKIIIAPSFADIFHQNCFKNGMLPIRMPYDNWKQLVGQYENQ SLQMTVDLENCILIHDSEGNQISFEVDPHWKEMLINGYDEISLTLLLE DEIKQFESQRSSWLQA |
| 48 | Escherichia coli | Beta-isopropylmalate dehydrogenase | MSKNYHIAVLPGDGIGPEVMTQALKVLDAVRNRFAMRITTSHYDV GGAAIDNHGQPLPPATVEGCEQADAVLFGSVGGPKWEHLPPDQ QPERGALLPLRKHFKLFSNLRPAKLYQGLEAFCPLRADIAANGFDILC QPERGALLPLRKHFKLFSNLRPAKLYQGLEAFCPLRADIAANGFDILC VRELTGGIYFGQPKGREGSGQYEKAFDTEVYHRFEIERIARIAFESAR KRRHKVTSIDKANVLQSSILWREIVNEIATEYPDVELAHMYIDNAT MQLIKDPSQFDVLLCSNLFGDILSDECAMITGSMGMLPSASLNEQ GFGLYEPAGGSAPDIAGKNIANPIAQILSLALLLRYSLDADDAACAIE RAINRALEEGIRTGDLARGAAAVSTDEMGDIIARYVAEGV |
| 49 | Bacillus subtilis | Beta-isopropylmalate dehydrogenase | MKKRIALLPGDGIGPEVLESATDVLKSVAERFNHEFEFEYGLIGGAAI DEHHNPLPEETVAACKNADAILLGAVGGPKWDQNPSELRPEKGLL SIRKQLDLFANLRPVKVFESLSDASPLKKEYIDNVDFVIVRELTGGLYF GQPSKRYVNTEGEQEAVDTLFYKRTEIERVIREGFKMAAARKGKVT SVDKANVLESSRLWREVAEDVAQEFPDVKLEHMLVDNAAMQLIY APNQFDVVVTENMFGDILSDEASMLTGSLGMLPSASLSSSGLHLFE PVHGSAPDIAGKGMANPFAAILSAAMLLRTSFGLEEEAKAVEDAV NKVLASGKRTRDLARSEEFSSTQAITEEVKAAIMSENTISNV |
| 50 | Saccharomyces cerevisiae | Beta-isopropylmalate dehydrogenase | MSAPKKIVVLPGDHVGQEITAEAIKVLKAISDVRSNVKFDFENHLIG GAAIDATGVPLPDEALEASKKADAVLLGAVGGPKWGTGSVRPEQ GLLKIRKELQLYANLRPCNFASDSLLDLSPIKPQFAKGTDFVVVRELV GGIYFGKRKEDDGDGVAWDSEQYTVPEVQRITRMAAFMALQHEP PLPIWSLDKANVLASSRLWRKTVEETIKNEFPTLKVQHQLIDSAAMI LVKNPTHLNGIIITSNMFGDIISDEASVIPGSLGLLPSASLASLPDKNT AFGLYEPCHGSAPDLPKNKVNPIATILSAAMMLKLSLNLPEEGKAIE DAVKKVLDAGIRTGDLGGSNSTTEVGDAVAEEVKKILA |
| 51 | Escherichia coli | Methylmalonyl-CoA mutase | MSNVQEWQQLANKELSRREKTVDSLVHQTAEGIAIKPLYTEADLD NLEVTGTLPGLPPYVRGPRATMYTAQPWTIRQYAGFSTAKESNAF YRRNLAAGQKGLSVAFDLATHRGYDSDNPRVAGDVGKAGVAIDT VEDMKVLFDQIPLDKMSVSMTMNGAVLPVLAFYIVAAEEQGVTP DKLTGTIQNDILKEYLCRNTYIYPPKPSMRIIADIIAWCSGNMPRFNT ISISGYHMGEAGANCVQQVAFTLADGIEYIKAAISAGLKIDDFAPRL SFFFGIGMDLFMNVAMLRAARYLWSEAVSGFGAQDPKSLALRTH CQTSGWSLTEQDPYNNVIRTTIEALAATLGGTQSLHTNAFDEALGL PTDPFSARIARNTQIIIQEESELCRTVDPLAGSYYIESLTDQIVKQARAII QQIDEAGGMAKAIEAGLPKRMIEEASAREQSLIDQGKRVIVGVNKY KLDHEDETDVLEIDNVMVRNEQIASLERIRATRDDAAVTAALNALT HAAQHNENLLAAAVNAARVRATLGEISDALEVAFDRYLVPSQCVT GVIAQSYHQSEKSASEFDAIVAQTEQFLADNGRRPRILIAKMGQDG HDRGAKVIASAYSDLGFDVDLSPMFSTPEEIARLAVENDVHVVGAS SLAAGHKTLIPELVEALKKWGREDICVVAGGVIPPQDYAFLQERGV AAIYGPGTPMLDSVRDVLNLISQHHD |
| 52 | Salmonella enterica | Methylmalonyl-CoA mutase | MANLQAWQTLANNELSRREKTVESLIRQTAEGIAVKPLYTEADLN NLEVTGTLPGLPPYVRGPRATMYTAQPWTIRQYAGFSTAKESNAF YRRNLAAGQKGLSVAFDLATHRGYDSDNPRVAGDVGKAGVAIDT VEDMKVLFDQIPLDKMSVSMTMNGAVLPVMAFYIVAAEEQGVSP EQLTGTIQNDILKEYLCRNTYIYPPKPSMRIIADIIAWCSGNMPRFNT |

SEQUENCE TABLE

| SEQ ID NO | Organism | Other Information | Sequence |
|---|---|---|---|
| | | | ISISGYHMGEAGANCVQQVAFTLADGIEYIKAALSAGLKIDDFAPRL SFFFGIGMDLFMNVAMLRAARYLWSEAVSGFGATNPKSLALRTHC QTSGWSLTEQDPYNNIIRTTIEALGATLGGTQSLHTNAFDEALGLPT DFSARIARNTQIIIQEESSICRTVDPLAGSYYVESLTDQIVKQARAIIK QIDAAGGMAKAIEAGLPKRMIEEASAREQSLIDQGERVIVGVNKYK LEKEDETAVLEIDNVKVRNEQIAALERIRATRDNRAVNAALQALTH AAQHHENLLAAAVEAARVRATLGEISDALEAAFDRYLVPSQCVTGV IAQSYHQSDKSAGEFDAIVAQTQQFLADTGRRPRILIAKMGQDGH DRGAKVIASAYSDLGFDVDLSPMFSTPDEIARLAVENDVHVIGASSL AAGHKTLIPELVAALKKWGREDICVVAGGVIPPQDYAFLKAHGVAA IYGPGTPMLESVRDVLARISQHHD |
| 53 | Propionibacterium freudenreichii | Methylmalonyl-CoA mutase beta (small) subunit | MSSTDQGTNPADTDDLTPTTLSLAGDFPKATEEQWEREVEKVLNR GRPPEKQLTFAECLKRLTVHTVDGIDIVPMYRPKDAPKKLGYPGVA PFTRGTTVRNGDMDAWDVRALHEDPDEKFTRKAILEGLERGVTSL LLRVDPDAIAPEHLDEVLSDVLLEMTKVEVFSRYDQGAAAEALVSV YERSDKPAKDLALNLGLDPIAFAALQGTEPDLTVLGDWVRRLAKFS PDSRAVTIDANIYHNAGAGDVAELAWALATGAEYVRALVEQGFTA TEAFDTINFRVTATHDQFLTIARLRALREAWARIGEVFGVDEDKRG ARQNAITSWRDVTREDPYVNILRGSIATFSASVGGAESITTLPFTQA LGLPEDDFPLRIARNTGIVLAEEVNIGRVNDPAGGSYYVESLTRSLA DAAWKEFQEVEKLGGMSKAVMTEHVTKVLDACNAERAKRLANR KQPITAVSEFPMIGARSIETKPFPAAPARKGLAWHRDSEVFEQLMD RSTSVSERPKVFLACLGTRRDFGGREGFSSPVWHIAGIDTPQVEGG TTAEIVEAFKKSGAQVADLCSSAKVYAQQGLEVAKALKAAGAKALY LSGAFKEFGDDAAEAEKLIDGRLFMGMDVVDTLSSTLDILGVAK |
| 54 | Propionibacterium freudenreichii | Methylmalonyl-CoA mutase alpha (large) subunit | MSTLPRFDSVDLGNAPVPADAAQRFEELAAKAGTEEAWETAEQIP VGTLFNEDVYKDMDWLDTYAGIPPFVHGPYATMYAFRPWTIRQY AGFSTAKESNAFYRRNLAAGQKGLSVAFDLPTHRGYDSDNPRVAG DVGMAGVAIDSIYDMRELFAGIPLDQMSVSMTMNGAVLPILALYV VTAEEQGVKPEQLAGTIQNDILKEFMVRNTYIYPPQPSMRIISEIFAY TSANMPKWNSISISGYHMQEAGATADIEMAYTLADGVDYIRAGES VGLNVDQFAPRLSFFWGIGMNFFMEVAKLRAARMLWAKLVHQF GPKNPKSMSLRTHSQTSGWSLTAQDVYNNVVRTCIEAMAATQG HTQSLHTNSLDEAIALPTDFSARIARNTQLFLQQESGTTRVIDPWSG SAYVEELTWDLARKAWGHIQEVEKVGGMAKAIEKGIPKMRIEEAA ARTQARIDSGRQPLIGVNKYRLEHEPPLDVLKVDNSTVLAEQKAKL VKLRAERDPEKVKAALDKITWAAANPDDKDPDRNLLKLCIDAGRA MATVGEMSDALEKVFGRYTAQIRTISGVYSKEVKNTPEVEEARELV EEFEQAEGRRPRILLAKMGQDGHDRGQKVIATAYADLGFDVDVG PLFQTPEETARQAVEADVHVVGVSSLAGGHLTLVPALRKELDKLGR PDILITVGGVIPEQDFDELRKDGAVEIYTPGTVIPESAISLVKKLRASL DA |
| 55 | Bacillus megaterium | Methylmalonyl-CoA mutase beta (small) subunit | MKTNTLSFHEFTRTPKEDWAQEVSKNTAISSKETLENIFLKPLYFESD TAHLDYLQQSPAGIDYLRGAGKESYILGEWEITQKIDLPSIKESNKLLL HSLRNGQNTAAFTCSEAMRQGKDIDEATEAEVASGATISTLEDVA HLFQHVALEAVPLFLNTGCTSVPLLSFLKAYCVDHNFNMRQLKGTV GMDPLGTLAEYGRVPLSTRDLYDHLAYATRLAHSNVPELKTIIVSSIP YHNSGANAVQELAYMLATGVQYIDECIKRGLSLHQVLPHMTFSFS VSSHLFMEISKLRAFRMLWANVVRAFDDTAVSVPFIHTETSHLTQS KEDMYTNALRSTVQAFASIVGGADSLHIEPYDSVTSSSSQFAHRLA RNTHLILQHETHISKVMDPAGGSWYVEAYTHELMTKAWELFGNIE DHGGMEEALKQGRIQDEVEQMKVKRQEDIECRIERLIGVTHYAPK QQDASQEIKSTPFKKEEIKMDKYSDQNASEFSSNLSLEDYTKLASKG VTAGWMLKQMAKQTQPDSVVPLTKWRAAEKFEKIRVYTKGMSI GIMELTDPSSRKKAEIARSLFESAGFACETIKNIDSYVEIADWMNEQ KHEAYVICGSDELVEKLLTKAMTYFEEDSVYVYVVGEEHVSRKTQW QQKGVMSVIHPKTNVIQCVKKLLCALEVEVHV |
| 56 | Bacillus megaterium | Methylmalonyl-CoA mutase alpha (large) subunit | MYKKPSFSNIPLSFSKQQREDDVTQSSYTAFQTNEQIELKSVYTKKD RDNLDFIHFAPGVPPFVRGPYATMYVNRPWTIRQYAGYSTAEESN AFYRRNLAAGQKGLSVAFDLATHRGYDSDHPRVVGDVGKAGVAI DSMMDMKQLFEGIPLDQMSVSMTMNGAVLPILAFYIVTAEEGQV KKEKLAGTIQNDILKEYMVRNTYIYPPEMSMRIIADIFKYTAEYMPK FNSISISGYHMQEAGAPADLELAYTLADGLEYVRTGLKAGITIDAFA PRLSFFWAIGMNYFMEVAKMRAGRLLWAKLMKQFEPDNPKSLAL RTHSQTGWSLTEQDPFNNVIRTCVEALAAVSGHTQSLHTNALDE AIALPTDFSARIARNTQLYLQNETEICSVIDPWGGSYYVESLTNELMI KAWKHLEEIEQLGGMTKAIEAGVPKMKIEEAAARRQARIDSQAEII VGVNQFQPEQEEPLDILDIDNTAVRMKQLEKLKKIRSERNEQAVIE ALNRLTNCAKTGENLLAFAVEAARARATLGEISEAIEKVAGRHQA TSKSVSGVYSAEFVHRDQIEEVRKLTAEFLEGEGRRPRILVAKMGQ |

SEQUENCE TABLE

| SEQ ID NO | Organism | Other Information | Sequence |
|---|---|---|---|
|  |  |  | DGHDRGSKVISTAFADLGFDVDIGPLFQTPQETARQAVENDVHVI GISSLAAGHKTLLPQLVDELKKLERDDIVVIVGGVIPKQDYSFLLEHG ASAIFGPGTVIPKAAVSVLHEIKKRLEE |
| 57 | Corynebacterium glutamicum | Methylmalonyl-CoA mutase beta (small) subunit | MTDLTKTAVPEELSENLETWYKAVAGVFARTQKKDIGDIAVDVWK KLIVTTPDGVDINPLYTRADESQRKFTEVPGEFPFTRGTTVDGERVG WGVTETFGHDSPKNINAAVLNALNSGTTTLGFEFSEEFTAADLKVA LEGVYLNMAPLLIHAGGSTSEVAAALYTLAEEAGTFFAALTLGSRPL TAQVDGSHSDTIEEAVQLAVNASKRANVRAILVDGSSFSNQGASD AQEIGLSIAAGVDYVRRLVDAGLSTEAALKQVAFRFAVTDEQFAQIS KLRVARRLWARVCEVLGFPELAVAPQHAVTARAMFSQRDPWVN MLRSTVAAFAAGVGGATDVEVRTFDDAIPDGVPGVSRNFAHRIAR NTNLLLLEESHLGHVVDPAGGSYFVESFTDDLAEKAWAVFSGIEAE GGYSAACASGTVTAMLDQTWEQTRADVASRKKKLTGINEFPNLAE SPLPADRRVEPAGVRRWAADFEALRNRSDAFLEKNGARPQITMIP LGPLSKHNIRTGFTSNLLASGGIEAINPGQLVPGTDAFAEAAQAAGI VVVCGTDQEYAETGEGAVEKLREAGVERILLAGAPKSFEGSAHAPD GYLNMTIDAAATLADLLDALGA |
| 58 | Corynebacterium glutamicum | Methylmalonyl-CoA mutase alpha (large) subunit | MTSIPNFSDIPLTAETRASESHNVDAGKVWNTPEGIDVKRVFTQA DRDEAQAAGHPVDSLPGQKPFMRGPYPTMYTNQPWTIRQYAGF STAAESNAFYRRNLAAGQKGLSVAFDLATHRGYDSDNERVVGDV GMAGVAIDSILDMRQLFDGIDLSSVSVSMTMNGAVLPILAFYIVAA EEQGVGPEQLAGTIQNDILKEFMVRNTYIYPPKPSMRIISNIFEYTSL KMPRFNSISISGYHIQEAGATADLELAYTLADGIEYIRAGKEVGLDV DKFAPRLSFFWGISMYTFMEIAKLRAGRLLWSELVAKFDPKNAKSQ SLRTHSQTSGWSLTAQDVYNNVARTAIEAMAATQGHTQSLHTNA LDEALALPTDFSARIARNTQLLLQQESGTVRPVDPWAGSYYVEWLT NELANRARKHIDEVEEAGGMAQATAQGIPKLRIEESAARTQARIDS GRQALIGVNRYVAEEDEEIEVLKVDNTKVRAEQLAKLAQLKAERND AEVKAALDALTAAARNEHKEPGDLDQNLLKLAVDAARAKATIGEIS DALEVVFGRHEAEIRTLSGVYKDEVGKEGTVSNVERAIALADAFEAE EGRRPRIFIAKMGQDGHDRGQKVVASAYADLGMDVDVGPLFQTP AEAARAAVDADVHVVGMSSLAAGHLTLLPELKKELAALGRDDILVT VGGVIPPGDFQDLYDMGAAAIYPPGTVIAESAIDLITRLAAHLGFDL DVDVNE |
| 59 | Escherichia coli | Methylmalonyl-CoA decarboxylase | MSYQYVNVVTINKVAVIEFNYGRKLNALSKVFIDDLMQALSDLNRP EIRCIILRAPSGSKVFSAGHDIHELPSGGRDPLSYDDPLRQITRMIQK FPKPIISMVEGSVWGGAFEMIMSSDLIIAASTSTFSMTPVNLGVPY NLVGIHNLTRDAGFHIVKELIFTASPITAQRALAVGILNHVVEVEELE DFTLQMAHHISEKAPLAIAVIKEELRVLGEAHTMNSDEFERIQGMR RAVYDSEDYQEGMNAFLEKRKPNFVGH |
| 60 | Salmonella enterica | Methylmalonyl-CoA decarboxylase | MSYQYVNVIIIQKVAVIEFNYARKLNALSKVFIDDLMQALSDLSRPEI RCIILRAPSGAKVFSAGHDIHELPSGRRDPLSYDDPLRQITRLIQKYPK PVISMVEGSVWGGAFEMIMSSDLIIAASTSTFSMTPVNLGVPYNLV GIHNLTRDAGFHIVKELIFTASPITAQRALAVGILNHVVEADELEDFT LQMAHHISEKAPLAIAVIKEELRVLGEAHTMNSDEFERIQGMRRAV YDSEDYQEGMNAFLEKRKPHFVGH |
| 61 | Yersinia enterocolitica | Methylmalonyl-CoA decarboxylase | MSYQYVKVLIANRVGIIEFNHARKLNALSKVFMDDLMLALHDLNN TDIRCIILRAAEGSKVFSAGHDIHELPTGRRDPLSYDDPLRQITRAIQK YPKPIISMVEGSVWGGAFEMIMSSDIIIACRNSTFSMTPVNLGVPY NLVGIHNLIRDAGFHIVKELIFTAAPITAERALSVGILNHVVEPSELED FTLKLAHVISEKAPLAIAVIKEELRVLGEAHTMNSDEFERIQGMRRA VYDSNDYQEGMSAFMEKRKPNFLGR |
| 62 | Propionibacterium freudenreichii | Methylmalonyl-CoA carboxyl transferase | MAENNNLKLASTMEGRVEQLAEQRQVIEAGGGERRVEKQHSQG KQTARERLNNLLDPHSFDEVGAFRKHRTTLFGMDKAVVPADGVVT GRGTILGRPVHAASQDFTVMGGSAGETQSTKVVETMEQALLTGT PFLFFYDSGGARIQEGIDSLSGYGKMFFANVKLSGVVPQIAIIAGPC AGGASYSPALTDFIIMTKKAHMFITGPQVIKSVTGEDVTADELGGA EAHMAISGNIHFVAEDDDAAELIAKKLLSFLPQNNTEEASFVNPNN DVSPNTELRDIVPIDGKKGYDVRDVIAKIVDWGDYLEVKAGYATNL VTAFARVNGRSVGIVANQPSVMSGCLDINASDKAAEFVNFCDSFN IPLVQLVDVPGFLPGVQQEYGGIIRHGAKMLYAYSEATVPKITVVLR KAYGGSYLAMCNRDLGADAVYAWPSAEIAVMGAEGAANVIFRKE IKAADDPPDAMRAEKIEEYQNAFNTPYVAAARGQVDDVIDPADTRR KIASALEMYATKRQTRPAKKPWKLPLLSEEEIMADEEEKDLMIATL NKRVASLESELGSLQSDTQGVTEDVLTAISAVAAYLGNDGSAEVVH FAPSPNWVREGRRALQNHSIR |

| SEQ ID NO | Organism | Other Information | Sequence |
|---|---|---|---|
| 63 | Propionibacterium freundenreichii | Methylmalonyl-CoA epimerase | MSNEDLFICIDHVAYACPDADEASKYYQETFGWHELHREENPEQG VVEIMMAPAAKLTEHMTQVQVMAPLNDESTVAKWLAKHNGRA GLHHMAWRVDDIDAVSATLRERGVQLLYDEPKLGTGGNRINFMH PKSGKGVLIELTQYPKN |
| 64 | Escherichia coli | Thioesterase (TesA) | MMNFNNVFRWHLPFLFLVLLTFRAAAADTLLILGDSLSAGYRMSA SAAWPALLNDKWQSKTSVVNASISGDTSQQGLARLPALLKQHQP RWVLVELGGNDGLRGFQPQQTEQTLRQILQDVKAANAEPLLMQI RLPANYGRRYNEAFSAIYPKLAKEFDVPLLPFFMEEVYLKPQWMQ DDGIHPNRDAQPFIADWMAKQLQPLVNHDS |
| 65 | Artificial sequence | Escherichia coli Thioesterase (TesA) mutant | MADTLLILGDSLSAGYRMSASAAWPALLNDKWQSKTSVVNASISG DTSQQGLARLPALLKQHQPRWVLVELGGNDGLRGFQPQQTEQTL RQILQDVKAANAEPLLMQIRLPANYGRRYNEAFSAIYPKLAKEFDV PLLPFFMEEVYLKPQWMQDDGIHPNRDAQPFIADWMAKQLQPL VNHDS |
| 66 | Escherichia coli | Thioesterase (TesB) | MSQALKNLLTLLNLEKIEEGLFRGQSEDLGLRQVFGGQVVGQALYA AKETVPEERLVHSFHSYFLRPGDSKKPIIYDVETLRDGNSFSARRVAA IQNGKPIFYMTASFQAPEAGFEHQKTMPSAPAPDGLPSETQIAQSL AHLLPPVLKDKFICDRPLEVRPVEFHNPLKGHVAEPHRQVWIRANG SVPDDLRVHQYLLGYASDLNFLPVALQPHGIGFLEPGIQIATIDHSM WFHRPFNLNEWLLYSVESTSASSARGFVRGEFYTQDGVLVASTVQ EGVMRNHN |
| 67 | Arabidopsis thaliana | Thioesterase (FatA) | MLKLSCNVTDSKLQRSLLFFSHSYRSDPVNFIRRRIVSCSQTKKTGLV PLRAVVSADQGSVVQGLATLADQLRLGSLTEDGLSYKEKFVVRSYE VGSNKTATVETIANLLQEVGCNHAQSVGFSTDGFATTTTMRKLHLI WVTARMHIEIYKYPAWGDVVEIETWCQSEGRIGTRRDWILKDSVT GEVTGRATSKWVMMNQDTRRLQKVSDDVRDEYLVFCPQEPRLA FPEENNRSLKKIPKLEDPAQYSMIGLKPRRADLDMNQHVNNVTYI GWVLESIPQEIVDTHELQVITLDYRRECQQDDVVDSLTTTTSEIGGT NGSATSGTQGHNDSQFLHLLRLSGDGQEINRGTTLWRKKPSS |
| 68 | Arabidopsis thaliana | Thioesterase (FatB) | MVATSATSSFFPVPSSSLDPNGKGNKIGSTNLAGLNSAPNSGRMK VKPNAQAPPKINGKKVGLPGSVDIVRTDTETSSHPAPRTFINQLPD WSMLLAAITTIFLAAEKQWMMLDWKPRRSDMLVDPFGIGRIVQD GLVFRQNFSIRSYEIGADRSASIETVMNHLQETALNHVKTAGLLGD GFGSTPEMFKKNLIWVVTRMQVVVDKYPTWGDVVEVDTWVSQS GKNGMRRDWLVRDCNTGETLTRASSVWVMMNKLTRRLSKIPEE VRGEIEPYFVNSDPVLAEDSRKLTKIDDKTADYVRSGLTPRWSDLDV NQHVNNVKYIGWILESAPVGIMERQKLKSMTLEYRRECGRDSVLQ SLTAVTGCDIGNLATAGDVECQHLLRLQDGAEVVRGRTEWSSKTP TTTWGTAP |
| 69 | Umbellularia californica | Thioesterase (FatB) | MATTSLSASAFCSMKAVMLARDGRGMKPRSSDLQLRAGNAPTSLK MINGTKFSYTESLKRLPDWSMLFAVITTIFSAAEKQWTNLEWKPKP KLPQLLDDHFGLHGLVFRRTFAIRSYEVGPDRSTSILAVMNHMQEA TLNHAKSVGILGDGFGTTLEMSKRDLMWVVRRTHVAVERYPTWG DTVEVECWIGASGNNGMRRDFLVRDCKTGEILTRCTSLSVLMNTR TRRLSTIPDEVRGEIGPAFIDNVAVKDDEIKKLQKLNDSTADYIQGGL TPRWNDLDVNQHVNNLKYVAWVFETVPDSIFESHHISSFTLEYRRE CTRDSVLRSLTTVSGGSSEAGLVCDHLLQLEGGSEVLRARTEWRPK LTDSFRGISVIPAEPRV |
| 70 | Cuphea hookeriana | Thioesterase (FatA1) | MLKLSCNAATDQILSSAVAQTALWGQPRNRSFSMSARRRGAVCC APPAAGKPPAMTAVIPKDGVASSGSGSLADQLRLGSRTQNGLSYT EKFIVRCYEVGINKTATVETMANLLQEVGCNHAQSVGFSTDGFATT PTMRKLNLIWVTARMHIEIYKYPAWSDVVEIETWCQSEGRIGTRR DWILKDYGNGEVIGRATSKWVMMNQNTRRLQKVDDSVREEYM VFCPREPRLSFPEENNRSLRKISKLEDPAEYSRLGLTPRRADLDMNQ HVNNVAYIGWALESVPQEIIDSYELETITLDYRRECQQDDVVDSLTS VLSDEESGTLPELKGTNGSASTPLKRDHDGSRQFLHLLRLSPDGLEI NRGRTEWRKKSTK |
| 71 | Cuphea hookeriana | Thioesterase (FatB2) | MVAAAASSAFFPVPAPGASPKPGKFGNWPSSLSPSFKPKSIPNGGF QVKANDSAHPKANGSAVSLKSGSLNTQEDTSSSPPPRTFLHQLPD WSRLLTAITTVFVKSKRPDMHDRKSKRPDMLVDSFGLESTVQDGL VFRQSFSIRSYEIGTDRTASIETLMNHLQETSLNHCKSTGILLDGFGR TLEMCKRDLIWVVIKMQIKVNRYPAWGDTVEINTRFSRLGKIGMG RDWLISDCNTGEILVRATSAYAMMNQKTRRLSKLPYEVHQEIVPLF VDSPVIEDSDLKVHKFKVKTGDSIQKGLTPGWNDLDVNQHVSNVK YIGWILESMPTEVLETQELCSLALEYRRECGRDSVLESVTAMDPSKV |

SEQUENCE TABLE

| SEQ ID NO | Organism | Other Information | Sequence |
|---|---|---|---|
| | | | GVRSQYQHLLRLEDGTAIVNGATEWRPKNAGANGAISTGKTSNG NSVS |
| 72 | Cuphea hookeriana | Thioesterase (FatB3) | MVAAAASSAFFSVPTPGISPKPGKFGNGGFQVKANANAHPSLKSG SLETEDDTSSSSPPPRTFINQLPDWSMLLSAITTIFGAAEKQWMML DRKSKRPDMLMEPFGVDSIVQDGVFFRQSFSIRSYEIGADRTTSIET LMNMFQETSLNHCKSNGLLNDGFGRTPEMCKKGLIWVVTKMQV EVNRYPIWGDSIEVNTWVSESGKNGMGRDWLISDCSTGEILVRAT SVWAMMNQKTRRLSKFPFEVRQEIAPNFVDSVPVIEDDRKLHKLD VKTGDSIHNGLTPRWNDLDVNQHVNNVKYIGWILKSVPTDVFEA QELCGVTLEYRRECGRDSVMESVTAMDPSKEGDRSVYQHLLRLED GADIAIGRTEWRPKNAGANGAISTGKTSNRNSVS |
| 73 | Artificial sequence | pDG2 plasmid | GGGGAATTGTGAGCGGATAACAATTCCCCTGTAGAAATAATTTT GTTTAACTTTAATAAGGAGATATACCATGGCGCAACTCACTCTTC TTTTAGTCGGCAATTCCGACGCCATCACGCCATTACTTGCTAAAG CTGACTTTGAACAACGTTCGCGTCTGCAGATTATTCCTGCGCAGT CAGTTATCGCCAGTGATGCCCGGCCTTCGCAAGCTATCCGCGCC AGTCGTGGGAGTTCAATGCGCGTGGCCCTGGAGCTGGTGAAAG AAGGTCGAGCGCAAGCCTGTGTCAGTGCCGGTAATACCGGGGC GCTGATGGGGCTGGCAAAATTATTACTCAAGCCCCTGGAGGGG ATTGAGCGTCCGGCGCTGGTGACGGTATTACCACATCAGCAAAA GGGCAAAACGGTGGTCCTTGACTTAGGGGCCAACGTCGATTGT GACAGCACAATGCTGGTGCAATTTGCCATTATGGGCTCAGTTCT GGCTGAAGAGGTGGTGGAAATTCCCAATCCTCGCGTGGCGTTG CTCAATATTGGTGAAGAAGAAGTAAAGGGTCTCGACAGTATTC GGGATGCCTCAGCGGTGCTTAAAACAATCCCTTCTATCAATTATA TCGGCTATCTTGAAGCCAATGAGTTGTTAACTGGCAAGACAGAT GTGCTGGTTTGTGACGGCTTTACAGGAAATGTCACATTAAAGAC GATGGAAGGTGTTGTCAGGATGTTCCTTTCTCTGCTGAAATCTC AGGGTGAAGGGAAAAAACGGTCGTGGTGGCTACTGTTATTAAA GCGTTGGCTACAAAAGAGCCTGACGAGGCGATTCAGTCACCTC AACCCCGACCAGTATAACGGCGCCTGTCTGTTAGGATTGCGCGG CACGGTGATAAAAAGTCATGGTGCAGCCAATCAGCGAGCTTTTG CGGTCGCGATTGAACAGGCAGTGCAGGCGGTGCAGCGACAAGT TCCTCAGCGAATTGCCGCTCGCCTGGAATCTGTATACCCAGCTG GTTTTGAGCTGCTGGACGGTGGCAAAAGCGGAACTCTGCGGTA GCAGGACGCTGCCAGCGAACTCGCAGTTTGCAAGTGACGGTAT ATAACCGAAAGTGACTGAGCGCATATGTATACGAAGACTCGA GTCTGGTAAAGAAACCGCTGCTGCGAAATTTGAACGCCAGCAC ATGGACTCGTCTACTAGCGCAGCTTAATTAACCTAGGCTGCTGC CACCGCTGAGCAATAACTAGCATAACCCCTTGGGGCCTCTAAAC GGGTCTTGAGGGGTTTTTTGCTGAAACCTCAGGCATTTGAGAAG CACACGGTCACACTGCTTCCGGTAGTCAATAAACCGGTAAACCA GCAATAGACATAAGCGGCTATTTAACGACCCTGCCCTGAACCGA CGACCGGGTCATCGTGGCCGGATCTTGCGGCCCCTCGGCTTGAA CGAATTGTTAGACATTATTTGCCGACTACCTTGGTGATCTCGCCT TTCACGTAGTGGACAAATTCTTCCAACTGATCTGCGCGCGAGGC CAAGCGATCTTCTTCTTGTCCAAGATAAGCCTGTCTAGCTTCAAG TATGACGGGCTGATACTGGGCCGGCAGGCGCTCCATTGCCCAG TCGGCAGCGACATCCTTCGGCGCGATTTTGCCGGTTACTGCGCT GTACCAAATGCGGGACAACGTAAGCACTACATTTCGCTCATCGC CAGCCCAGTCGGGCGGCGAGTTCCATAGCGTTAAGGTTTCATTT AGCGCCTCAAATAGATCCTGTTCAGGAACCGGATCAAAGAGTTC CTCCGCCGCTGGACCTACCAAGGCAACGCTATGTTCTCTTGCTTT TGTCAGCAAGATAGCCAGATCAATGTCGATCGTGGCTGGCTCGA AGATACCTGCAAGAATGTCATTGCGCTGCCATTCTCCAAATTGC AGTTCGCGCTTAGCTGGATAACGCCACGGAATGATGTCGTCGTG CACAACAATGGTGACTTCTACAGCGCGGAGAATCTCGCTCTCTC CAGGGGAAGCCGAAGTTTCCAAAAGGTCGTTGATCAAAGCTCG CCGCGTTGTTTCATCAAGCCTTACGGTCACCGTAACCAGCAAATC AATATCACTGTGTGGCTTCAGGCCGCCATCCACTGCGGAGCCGT ACAAATGTACGGCCAGCAACGTCGGTTCGAGATGGCGCTCGAT GACGCCAACTACCTCTGATAGTTGAGTCGATACTTCGGCGATCA CCGCTTCCCTCATACTCTTCCTTTTTCAATATTATTGAAGCATTTA TCAGGGTTATTGTCTCATGAGCGGATACATATTTGAATGTATTTA GAAAAATAAACAAATAGCTAGCTCACTCGGTCGCTACGCTCCGG GCGTGAGACTGCGGCGGGCGCTGCGGACACATACAAAGTTACC CACAGATTCCGTGGATAAGCAGGGGACTAACATGTGAGGCAAA ACAGCAGGGCCGCGCCGGTGGCGTTTTCCATAGGCTCCGCCCT CCTGCCAGAGTTCACATAAACAGACGCTTTTCGGTGCATCTGT GGGAGCCGTGAGGCTCAACCATGAATCTGACAGTACGGGCGAA ACCCGACAGGACTTAAAGATCCCCACCGTTTCCGGCGGGTCGCT CCCTCTTGCGCTCTCCTGTTCCGACCCTGCCGTTTACCGGATACC |

SEQUENCE TABLE

| SEQ ID NO | Organism | Other Information | Sequence |
|---|---|---|---|
| | | | TGTTCCGCCTTTCTCCCTTACGGGAAGTGTGGCGCTTTCTCATAG<br>CTCACACACTGGTATCTCGGCTCGGTGTAGGTCGTTCGCTCCAA<br>GCTGGGCTGTAAGCAAGAACTCCCCGTTCAGCCCGACTGCTGCG<br>CCTTATCCGGTAACTGTTCACTTGAGTCCAACCCGGAAAAGCAC<br>GGTAAAACGCCACTGGCAGCAGCCATTGGTAACTGGGAGTTCG<br>CAGAGGATTTGTTTAGCTAAACACGCGGTTGCTCTTGAAGTGTG<br>CGCCAAAGTCCGGCTACACTGGAAGGACAGATTTGGTTGCTGT<br>GCTCTGCGAAAGCCAGTTACCACGGTTAAGCAGTTCCCCAACTG<br>ACTTAACCTTCGATCAAACCACCTCCCCAGGTGGTTTTTTCGTTT<br>ACAGGGCAAAAGATTACGCGCAGAAAAAAAGGATCTCAAGAAG<br>ATCCTTTGATCTTTTCTACTGAACCGCTCTAGATTTCAGTGCAATT<br>TATCTCTTCAAATGTAGCACCTGAAGTCAGCCCCATACGATATAA<br>GTTGTAATTCTCATGTTAGTCATGCCCCGCGCCCACCGGAAGGA<br>GCTGACTGGGTTGAAGGCTCTCAAGGGCATCGGTCGAGATCCC<br>GGTGCCTAATGAGTGAGCTAACTTACATTAATTGCGTTGCGCTC<br>ACTGCCCGCTTTCCAGTCGGGAAACCTGTCGTGCCAGCTGCATT<br>AATGAATCGGCCAACGCGCGGGGAGAGGCGGTTTGCGTATTGG<br>GCGCCAGGGTGGTTTTTCTTTTCACCAGTGAGACGGGCAACAGC<br>TGATTGCCCTTCACCGCCTGGCCCTGAGAGAGTTGCAGCAAGCG<br>GTCCACGCTGGTTTGCCCCAGCAGGCGAAAATCCTGTTTGATGG<br>TGGTTAACGGCGGGATATAACATGAGCTGTCTTCGGTATCGTCG<br>TATCCCACTACCGAGATGTCCGCACCAACGCGCAGCCCGGACTC<br>GGTAATGGCGCGCATTGCGCCCAGCGCCATCTGATCGTTGGCAA<br>CCAGCATCGCAGTGGGAACGATGCCCTCATTCAGCATTTGCATG<br>GTTTGTTGAAAACCGGACATGGCACTCCAGTCGCCTTCCCGTTCC<br>GCTATCGGCTGAATTTGATTGCGAGTGAGATATTTATGCCAGCC<br>AGCCAGACGCAGACGCGCCGAGACAGAACTTAATGGGCCCGCT<br>AACAGCGCGATTTGCTGGTGACCCAATGCGACCAGATGCTCCAC<br>GCCCAGTCGCGTACCGTCTTCATGGAGAAAATAATACTGTTGA<br>TGGGTGTCTGGTCAGAGACATCAAGAAATAACGCCGGAACATT<br>AGTGCAGGCAGCTTCCACAGCAATGGCATCCTGGTCATCCAGCG<br>GATAGTTAATGATCAGCCCACTGACGCGTTGCGCGAGAAGATT<br>GTGCACCGCCGCTTTACAGGCTTCGACGCCGCTTCGTTCTACCAT<br>CGACACCACCACGCTGGCACCCAGTTGATCGGCGCGAGATTTAA<br>TCGCCGCGACAATTTGCGACGGCGCGTGCAGGGCCAGACTGGA<br>GGTGGCAACGCCAATCAGCAACGACTGTTTGCCCGCCAGTTGTT<br>GTGCCACGCGGTTGGGAATGTAATTCAGCTCCGCCATCGCCGCT<br>TCCACTTTTTCCCGCGTTTTCGCAGAAACGTGGCTGGCCTGGTTC<br>ACCACGCGGGAAACGGTCTGATAAGAGACACCGGCATACTCTG<br>CGACATCGTATAACGTTACTGGTTTCACATTCACCACCCTGAATT<br>GACTCTCTTCCGGGCGCTATATGCCATACCGCGAAAGGTTTTG<br>CGCCATTCGATGGTGTCCGGGATCTCGACGCTCTCCCTTATGCG<br>ACTCCTGCATTAGGAAATTAATACGACTCACTATA |
| 74 | Artificial sequence | pDG6 plasmid | ggggaattgtgagcggataacaattcccctgtagaaataattttgtttaactttaata<br>aggagatataccatggCGCAACTCACTCTTCTTTTAGTCGGCAATTCC<br>GACGCCATCACGCCATTACTTGCTAAAGCTGACTTTGAACAACG<br>TTCGCGTCTGCAGATTATTCCTGCGCAGTCAGTTATCGCCAGTGA<br>TGCCCGGCCTTCGCAAGCTATCCGCGCCAGTCGTGGGAGTTCAA<br>TGCGCGTGGCCCTGGAGCTGGTGAAAGAAGGTCGAGCGCAAG<br>CCTGTGTCAGTGCCGGTAATACCGGGGCGCTGATGGGGCTGGC<br>AAAATTATTACTCAAGCCCCTGGAGGGGATTGAGCGTCCGGCG<br>CTGGTGACGGTATTACCACATCAGCAAAAGGGCAAAACGGTGG<br>TCCTTGACTTAGGGGCCAACGTCGATTGTGACAGCACAATGCTG<br>GTGCAATTTGCCATTATGGGCTCAGTTCTGGCTGAAGAGGTGGT<br>GGAAATTCCCAATCCTCGCGTGGCGTTGCTCAATATTGGTGAAG<br>AAGAAGTAAAGGGTCTCGACAGTATTCGGGATGCCTCAGCGGT<br>GCTTAAAACAATCCCTTCTATCAATTATATCGGCTATCTTGAAGC<br>CAATGAGTTGTTAACTGGCAAGACAGATGTGCTGGTTTGTGACG<br>GCTTTACAGGAAATGTCACATTAAAGACGATGGAAGGTGTTGTC<br>AGGATGTTCCTTTCTCTGCTGAAATCTCAGGGTGAAGGGAAAAA<br>ACGGTCGTGGTGGCTACTGTTATTAAAGCGTTGGCTACAAAAGA<br>GCCTGACGAGGCGATTCAGTCACCTCAACCCCGACCAGTATAAC<br>GGCGCCTGTCTGTTAGGATTGCGCGGCACGGTGATAAAAAGTC<br>ATGGTGCAGCCAATCAGCGAGCTTTTGCGGTCGCGATTGAACA<br>GGCAGTGCAGGCGGTGCAGCGACAAGTTCCTCAGCGAATTGCC<br>GCTCGCCTGGAATCTGTATACCCAGCTGGTTTTGAGCTGCTGGA<br>CGGTGGCAAAAGCGGAACTCTGCGGTAGCAGGACGCTGCCAGC<br>GAACTCGCAGTTTGCAAGTGACGGTATATAACCGAAAAGTGACT<br>GAGCGcatATGAAAGCTGGCATTCTTGGTGTTGGACGTTACATTC<br>CTGAGAAGGTTTTAACAAATCATGATCTTGAAAAAATGGTTGAA<br>ACTTCTGACGAGTGGATTCGTACAAGAACAGGAATAGAAGAA<br>GAAGAATCGCAGCAGATGATGTGTTTTCATCACACATGGCTGTT<br>GCAGCAGCGAAAAATGCGCTGGAACAAGCTGAAGTGGCTGCTG |

SEQUENCE TABLE

| SEQ ID NO | Organism | Other Information | Sequence |
|---|---|---|---|
| | | | AGGATCTGGATATGATCTTGGTTGCAACTGTTACACCTGATCAG |
| | | | TCATTCCCTACGGTGTCTTGTATGATTCAAGAACAACTCGGCGC |
| | | | GAAGAAAGCGTGTGCTATGGATATCAGCGCGGCTTGTGCGGGC |
| | | | TTCATGTACGGGGTTGTAACCGGTAAACAATTTATTGAATCCGG |
| | | | AACCTACAAGCATGTTCTAGTTGTTGGTGTAGAGAAGCTCTCAA |
| | | | GCATTACCGACTGGGAAGACCGCAATACAGCCGTTCTGTTTGGA |
| | | | GACGGAGCAGGCGCTGCGGTAGTCGGGCCAGTCAGTGATGAC |
| | | | AGAGGAATCCTTTCATTTGAACTAGGAGCCGACGGCACAGGCG |
| | | | GTCAGCACTTGTATCTGAATGAAAAACGACATACAATCATGAAT |
| | | | GGACGAGAAGTTTTCAAATTTGCAGTCCGCCAAATGGGAGAAT |
| | | | CATGCGTAAATGTCATTGAAAAAGCCGGACTTTCAAAAGAGGAT |
| | | | GTGGACTTTTTGATTCCGCATCAGGCGAACATCCGTATCATGGA |
| | | | AGCTGCTCGCGAGCGTTTAGAGCTTCCTGTCGAAAAGATGTCTA |
| | | | AAACTGTTCATAAATATGGAAATACTTCTGCCGCATCCATTCCGA |
| | | | TCTCTCTTGTAGAAGAATTGGAAGCCGGTAAAATCAAAGACGGC |
| | | | GATGTGGTCGTTATGGTAGGGTTCGGCGGAGGACTAACATGGG |
| | | | GCGCCATTGCAATCCGCTGGGGCCGATAAAAAAAAGGTGAGGT |
| | | | GCActcgagtctggtaaagaaaccgctgctgcgaaatttgaacgccagcacatgg |
| | | | actcgtctactagcgcagcttaattaacctaggctgctgccaccgctgagcaataact |
| | | | agcataaccccttggggcctctaaacgggtcttgaggggttttttgctgaaacctcag |
| | | | gcatttgagaagcacacggtcacactgcttccggtagtcaataaaccggtaaaccag |
| | | | caatagacataagcggctatttaacgaccctgccctgaaccgacgaccgggtcatcg |
| | | | tggccggatcttgcggccctcggcttgaacgaattgttagacattatttgccgactac |
| | | | cttggtgatctcgccttttcacgtagtggacaaattcttccaactgatctgcgcgcgagg |
| | | | ccaagcgatcttcttcttgtccaagataagcctgtctagcttcaagtatgacgggctg |
| | | | atactgggccggcaggcgctccattgcccagtcggcagcgacatccttcggcgcgat |
| | | | tttgccggttactgcgctgtaccaaatgcgggacaacgtaagcactacatttcgctca |
| | | | tcgccagcccagtcgggcgcgagttccatagcgttaaggtttcatttagcgcctcaa |
| | | | atagatcctgttcaggaaccggatcaaagagttcctccgccgctggacctaccaagg |
| | | | caacgctatgttctcttgcttttgtcagcaagatagcagatcaatgtcgatcgtggct |
| | | | ggctcgaagatacctgcaagaatgtcattgcgctgccattctccaaattgcagttcgc |
| | | | gcttagctggataaccacggaatgatgtcgtcgtgcacaacaatggtgacttcta |
| | | | cagcgcggagaatctcgctctctccaggggaagccgaagtttccaaaaggtcgttga |
| | | | tcaaagctcgccgcgttgtttcatcaagccttacggtcaccgtaaccagcaaatcaat |
| | | | atcactgtgtggcttcaggccgccatccactgcggagccgtacaaatgtacggccag |
| | | | caacgtcggttcgagatggcgctcgatgacgccaactacctctgatagttgagtcgat |
| | | | acttcggcgatcaccgcttccctcatactcttccttttttcaatattattgaagcatttatc |
| | | | agggttattgtctcatgagcggatacatatttgaatgtatttagaaaaataaacaaat |
| | | | agctagctcactcggtcgctacgctccgggcgtgagactgcggcgggcgctgcggac |
| | | | acatacaaagttacccacagattccgtggataagcaggggactaacatgtgaggca |
| | | | aaacagcagggccgcgccggtggcgttttttccataggctccgccctcctgccagagtt |
| | | | cacataaacagacgcttttccggtgcatctgtgggagccgtgaggctcaaccatgaa |
| | | | tctgacagtacgggcgaaacccgacaggacttaaagatccccaccgtttccggcgg |
| | | | gtcgctccctcttgcgctctcctgttccgaccctgccgtttaccggatacctgttccgcc |
| | | | tttctcccttacgggaagtgtggcgctttctcatagctcacacactggtatctcggctc |
| | | | ggtgtaggtcgttcgctccaagctgggctgtaagcaagaactcccgttcagcccga |
| | | | ctgctgcgccttatccggtaactgttcacttgagtccaacccggaaaagcacggtaa |
| | | | aacgccactggcagcagccattggtaactggagttcgcagaggattgtttagcta |
| | | | aacacgcggttgctcttgaagtgtgcgccaaagtccggctacactggaaggacaga |
| | | | tttggttgctgtgctctgcgaaagccagttaccacggttaagcagttcccaactgac |
| | | | ttaaccttcgatcaaaccacctccccaggtggttttttcgtttacagggcaaaagatta |
| | | | cgcgcagaaaaaaaggatctcaagaagatcctttgatcttttctactgaaccgctcta |
| | | | gatttcagtgcaatttatctcttcaaatgtagcacctgaagtcagcccccatacgtat |
| | | | aagttgtaattctcatgttagtcatgccccgcgcccaccggaaggagctgactgggtt |
| | | | gaaggctctcaagggcatcggtcgagatcccggtgcctaatgagtgagctaacttac |
| | | | attaattgcgttgcgctcactgcccgctttccagtcgggaaacctgtcgtgccagctgc |
| | | | attaatgaatcggccaacgcgcggggagaggcggtttgcgtattggggcgcagggt |
| | | | ggttttttcttttcaccagtgagacgggcaacagctgattgcccttcaccgcctggccct |
| | | | gagagagttgcagcaagcggtccacgctggtttgcccccagcaggcgaaaatcctgtt |
| | | | tgatggtggttaacggcgggatataacatgagctgtcttcggtatcgtcgtatcccac |
| | | | taccgagatgtccgcaccaacgcgcagcccgactcggtaatggcgcgcattgcgc |
| | | | ccagcgccatctgatcgttggcaaccagcatcgcagtgggaacgatgccctcattca |
| | | | gcatttgcatggtttgttgaaaaccggacatggcactccagtcgccttcccgttccgct |
| | | | atcggctgaatttgattgcgagtgagatatttatgccagccagccagacgcagacgc |
| | | | gccgagacagaacttaatgggcccgctaacagcgcgatttgctggtgacccaatgc |
| | | | gaccagatgctccacgcccagtcgcgtaccgtcttcatgggagaaaataatactgtt |
| | | | gatgggtgtctggtcagagacatcaagaaataacgccggaacattagtgcaggcag |
| | | | cttccacagcaatggcatcctggtcatccagcggatagttaatgatcagcccactga |
| | | | cgcgttgcgcgagaagattgtgcaccgccgctttacaggcttgcgtgcgcttcgttc |
| | | | taccatcgacaccaccacgctggcacccagttgatcggcgcgagatttaatcgcgc |
| | | | gacaatttgcgacggcgcgtgcagggccagactggaggtggcaacgccaatcagc |
| | | | aacgactgtttgcccgccagttgttgtgccacgcggttgggaatgtaattcagctccg |
| | | | ccatcgccgcttccacttttttcccgcgttttcgcagaaacgtggctggcctggttcacc |
| | | | acgcgggaaacggtctgataagagacaccggcatactctgcgacatcgtataacgt |

| SEQ ID NO | Organism | Other Information | Sequence |
|---|---|---|---|
| | | | tactggtttcacattcaccaccctgaattgactctcttccgggcgctatcatgccatac cgcgaaaggttttgcgccattcgatggtgtccgggatctcgacgctctcccttatgcg actcctgcattaggaaattaatacgactcactata |
| 75 | Artificial sequence | pACYC-PTrc vector | ACTCACCAGTCACAGAAAAGCATCTTACGGATGGCATGACAGTA AGAGAATTATGCAGTGCTGCCATAACCATGAGTGATAACACTGC GGCCAACTTACTTCTGACAACGATCGGAGGACCGAAGGAGCTA ACCGCTTTTTTGCACAACATGGGGGATCATGTAACTCGCCTTGAT CGTTGGGAACCGGAGCTGAATGAAGCCATACCAAACGACGAGC GTGACACCACGATGCCTGCAGCAATGGCAACAACGTTGCGCAA ACTATTAACTGGCGAACTACTTACTCTAGCTTCCCGGCAACATT AATAGACTGGATGGAGGCGGATAAAGTTGCAGGACCACTTCTG CGCTCGGCCCTTCCGGCTGGCTGGTTTATTGCTGATAAATCTGG AGCCGGTGAGCGTGGGTCTCGCGGTATCATTGCAGCACTGGGG CCAGATGGTAAGCCCTCCCGTATCGTAGTTATCTACACGACGGG GAGTCAGGCAACTATGGATGAACGAAATAGACAGATCGCTGAG ATAGGTGCCTCACTGATTAAGCATTGGTAACTGTCAGACCAAGT TTACTCATATATACTTTAGATTGATTTAAAACTTCATTTTTAATTT AAAAGGATCTAGGTGAAGATCCTTTTTGATAATCTCATGACCAA AATCCCTTAACGTGAGTTTTCGTTCCACTGAGCGTCAGACCCCTT AATAAGATGATCTTCTTGAGATCGTTTTGGTCTGCGCGTAATCTC TTGCTCTGAAAACGAAAAACCGCCTTGCAGGGCGGTTTTTCGA AGGTTCTCTGAGCTACCAACTCTTTGAACCGAGGTAACTGGCTT GGAGGAGCGCAGTCACCAAAACTTGTCCTTTCAGTTTAGCCTTA ACCGGCGCATGACTTCAAGACTAACTCCTCTAAATCAATTACCA GTGGCTGCTGCCAGTGGTGCTTTTGCATGTCTTTCCGGGTTGGA CTCAAGACGATAGTTACCGGATAAGGCGCAGCGGTCGGACTGA ACGGGGGGTTCGTGCATACAGTCCAGCTTGGAGCGAACTGCCT ACCCGGAACTGAGTGTCAGGCGTGGAATGAGACAAACGCGGCC ATAACAGCGGAATGACACCGGTAAACCGAAAGGCAGGAACAG GAGAGCGCACGAGGGAGCCGCCAGGGGGAAACGCCTGGTATC TTTATAGTCCTGTCGGGTTTCGCCACCACTGATTTGAGCGTCAGA TTTCGTGATGCTTGTCAGGGGGGCGGAGCCTATGGAAAAACGG CTTTGCCGCGGCCCTCTCACTTCCCTGTTAAGTATCTTCCTGGCA TCTTCCAGGAAATCTCCGCCCCGTTCGTAAGCCATTTCCGCTCGC CGCAGTCGAACGACCGAGCGTAGCGAGTCAGTGAGCGAGGAA GCGGAATATATCCTGTATCACATATTCTGCTGACGCACCGGTGC AGCCTTTTTTCTCCTGCCACATGAAGCACTTCACTGACACCCTCA TCAGTGCCAACATAGTAAGCCAGTATACACTCCGCTAGCGCTGA GGTCTGCCTCGTGAAGAAGGTGTTGCTGACTCATACCAGGCCTG AATCGCCCCATCATCCAGCCAGAAAGTGAGGGAGCCACGGTTG ATGAGAGCTTTGTTGTAGGTGGACCAGTTGGTGATTTTGAACTT TTGCTTTGCCACGGAACGGTCTGCGTTGTCGGGAAGATGCGTGA TCTGATCCTTCAACTCAGCAAAAGTTCGATTTATTCAACAAAGCC ACGTTGTGTCTCAAAATCTCTGATGTTACATTGCACAAGATAAAA ATATATCATCATGAACAATAAAACTGTCTGCTTACATAAACAGTA ATACAAGGGGTGTTATGAGCCATATTCAACGGGAAACGTCTTGC TCGAGGCCGCGATTAAATTCCAACATGGATGCTGATTTATATGG GTATAAATGGGCTCGCGATAATGTCGGGCAATCAGGTGCGACA ATCTATCGATTGTATGGGAAGCCCGATGCGCCAGAGTTGTTTCT GAAACATGGCAAAGGTAGCGTTGCCAATGATGTTACAGATGAG ATGGTCAGACTAAACTGGCTGACGGAATTTATGCCTCTTCCGAC CATCAAGCATTTTATCCGTACTCCTGATGATGCATGGTTACTCAC CACTGCGATCCCCGGGAAAACAGCATTCCAGGTATTAGAAGAAT ATCCTGATTCAGGTGAAAATATTGTTGATGCGCTGGCAGTGTTC CTGCGCCGGTTGCATTCGATTCCTGTTTGTAATTGTCCTTTTAAC AGCGATCGCGTATTTCGTCTCGCTCAGGCGCAATCACGAATGAA TAACGGTTTGGTTGATGCGAGTGATTTTGATGACGAGCGTAATG GCTGGCCTGTTGAACAAGTCTGGAAAGAAATGCATAAGCTTTTG CCATTCTCACCGGATTCAGTCGTCACTCATGGTGATTTCTCACTT GATAACCTTATTTTTGACGAGGGGAAATTAATAGGTTGTATTGA TGTTGGACGAGTCGGAATCGCAGACCGATACCAGGATCTTGCC ATCCTATGGAACTGCCTCGGTGAGTTTTCTCCTTCATTACAGAAA CGGCTTTTTCAAAAATATGGTATTGATAATCCTGATATGAATAAA TTGCAGTTTCATTTGATGCTCGATGAGTTTTTCTAATCAGAATTG GTTAATTGGTTGTAACACTGGCAGAGCATTACGCTGACTTGACG GGACGGCGGCTTTGTTGAATAAATCGAACTTTTGCTGAGTTGAA GGATCAGATCACGCATCTTCCCGACAACGCAGACCGTTCCGTGG CAAAGCAAAAGTTCAAAATCACCAACTGGTCCACCTACAACAA GCTCTCATCAACCGTGGCTCCCTCACTTTCTGGCTGGATGATGG GGCGATTCAGGCCTGGTATGAGTCAGCAACACCTTCTTCACGAG GCAGACCTCAGCGCTCAAAGATGCAGGGGTAAAAGCTAACCGC ATCTTTACCGACAAGGCATCCGGCAGTTCAACAGATCGGGAAG GGCTGGATTTGCTGAGGATGAAGGTGGAGGAAGGTGATGTCAT |

| SEQ ID NO | Organism | Other Information | Sequence |
|---|---|---|---|
| | | | TCTGGTGAAGAAGCTCGACCGTCTTGGCCGCGACACCGCCGAC<br>ATGATCCAACTGATAAAAGAGTTTGATGCTCAGGGTGTAGCGGT<br>TCGGTTTATTGACGACGGGATCAGTACCGACGGTGATATGGGG<br>CAAATGGTGGTCACCATCCTGTCGGCTGTGGCACAGGCTGAAC<br>GCCGGAGGATCCTAGAGCGCACGAATGAGGGCCGACAGGAAG<br>CAAAGCTGAAAGGAATCAAATTTGGCCGCAGGCGTACCGTGGA<br>CAGGAACGTCGTGCTGACGCTTCATCAGAAGGGCACTGGTGCA<br>ACGGAAATTGCTCATCAGCTCAGTATTGCCCGCTCCACGGTTTAT<br>AAAATTCTTGAAGACGAAAGGGCCTCGTGATACGCCTATTTTTA<br>TAGGTTAATGTCATGATAATAATGGTTTCTTAGACGTCTTAATTA<br>ATCAGGAGAGCGTTCACCGACAAACAACAGATAAAACGAAAGG<br>CCCAGTCTTTCGACTGAGCCTTTCGTTTTATTTGATGCCTGGCAG<br>TTCCCTACTCTCGCATGGGGAGACCCCACACTACCATCGGCGCT<br>ACGGCGTTTCACTTCTGAGTTCGGCATGGGGTCAGGTGGGACC<br>ACCGCGCTACTGCCGCCAGGCAAATTCTGTTTTATCAGACCGCTT<br>CTGCGTTCTGATTTAATCTGTATCAGGCTGAAAATCTTCTCTCAT<br>CCGCCAAAACAGCCAAGCTGGAGACCGTTTAAACTCAATGATGA<br>TGATGATGATGGTCGACGGCGCTATTCAGATCCTCTTCTGAGAT<br>GAGTTTTTGTTCGGGCCCAAGCTTCGAATTCCCATATGGTACCA<br>GCTGCAGATCTCGAGCTCGGATCCATGGTTTATTCCTCCTTATTT<br>AATCGATACATTAATATATACCTCTTTAATTTTTAATAATAAAGTT<br>AATCGATAATTCCGGTCGAGTGCCCACACAGATTGTCTGATAAA<br>TTGTTAAAGAGCAGTGCCGCTTCGCTTTTTCTCAGCGGCGCTGTT<br>TCCTGTGTGAAATTGTTATCCGCTCACAATTCCACACATTATACG<br>AGCCGGATGATTAATTGTCAACAGCTCATTTCAGAATATTTGCCA<br>GAACCGTTATGATGTCGGCGCAAAAAACATTATCCAGAACGGG<br>AGTGCGCCTTGAGCGACACGAATTATGCAGTGATTTACGACCTG<br>CACAGCCATACCACAGCTTCCGATGGCTGCCTGACGCCAGAAGC<br>ATTGGTGCACCGTGCAGTCGATGATAAGCTGTCAAACCAGATCA<br>ATTCGCGCTAACTCACATTAATTGCGTTGCGCTCACTGCCCGCTT<br>TCCAGTCGGGAAACCTGTCGTGCCAGCTGCATTAATGAATCGGC<br>CAACGCGCGGGGAGAGGCGGTTTGCGTATTGGGCGCCAGGGT<br>GGTTTTTCTTTTCACCAGTGAGACGGGCAACAGCTGATTGCCCTT<br>CACCGCCTGGCCCTGAGAGAGTTGCAGCAAGCGGTCCACGCTG<br>GTTTGCCCCAGCAGGCGAAAATCCTGTTTGATGGTGGTTGACGG<br>CGGGATATAACATGAGCTGTCTTCGGTATCGTCGTATCCCACTA<br>CCGAGATATCCGCACCAACGCGCAGCCCGGACTCGGTAATGGC<br>GCGCATTGCGCCCAGCGCCATCTGATCGTTGGCAACCAGCATCG<br>CAGTGGGAACGATGCCCTCATTCAGCATTTGCATGGTTTGTTGA<br>AAACCGGACATGGCACTCCAGTCGCCTTCCCGTTCCGCTATCGG<br>CTGAATTTGATTGCGAGTGAGATATTTATGCCAGCCAGCCAGAC<br>GCAGACGCGCCGAGACAGAACTTAATGGGCCCGCTAACAGCGC<br>GATTTGCTGGTGACCCAATGCGACCAGATGCTCCACGCCCAGTC<br>GCGTACCGTCTTCATGGGAGAAAATAATACTGTTGATGGGTGTC<br>TGGTCAGAGACATCAAGAAATAACGCCGGAACATTAGTGCAGG<br>CAGCTTCCACAGCAATGGCATCCTGGTCATCCAGCGGATAGTTA<br>ATGATCAGCCCACTGACGCGTTGCGCGAGAAGATTGTGCACCG<br>CCGCTTTACAGGCTTCGACGCCGCTTCGTTCTACCATCGACACCA<br>CCACGCTGGCACCCAGTTGATCGGCGCGAGATTTAATCGCCGCG<br>ACAATTTGCGACGGCGCGTGCAGGGCCAGACTGGAGGTGGCAA<br>CGCCAATCAGCAACGACTGTTTGCCCGCCAGTTGTTGTGCCACG<br>CGGTTGGGAATGTAATTCAGCTCCGCCATCGCCGCTTCCACTTTT<br>TCCCGCGTTTTCGCAGAAACGTGGCTGGCCTGGTTCACCACGCG<br>GGAAACGGTCTGATAAGAGACACCGGCATACTCTGCGACATCG<br>TATAACGTTACTGGTTTCACATTCACCACCCTGAATTGACTCTCTT<br>CCGGGCGCTATCATGCCATACCGCGAAAGGTTTTGCACCATTCG<br>ATGGTGTCAACGTAAATGCATGCCGCTTCGCCTTCGCGCGCGAA<br>TTGATCTGCTGCCTCGCGCGTTTCGGTGATGACGGTGAAAACCT<br>CTGACACATGCAGCTCCCGGAGACGGTCACAGCTTGTCTGTAAG<br>CGGATGCCGGGAGCAGACAAGCCCGTCAGGGCGCGTCAGCGG<br>GTGTTGGCGGGCCGGCCTCG |
| 76 | Artificial sequence | PTrc promoter | CTGTTGACAATTAATCATCCGGCTCGTATAATGTGTGGAATTGT<br>GAGCGGATAACAATTTCACACAGGAAACAGCGCCGCTGAGAAA<br>AGCGAAGCGGCACTGCTCTTTAACAATTTATCAGACAATCTGT<br>GTGGGCACTCGACCGGAATTATCGATTAACTTTATTATTAAAAAT<br>TAAAGAGGTATATATTA |
| 77 | Artificial sequence | PTrc2 promoter | CTGTTGACAATTAATCATCCGGCTCGTGTAATGTGTGGAATTGT<br>GAGCGGATAACAATTTCACACAGGAAACAGCGCCGCTGAGAAA<br>AGCGAAGCGGCACTGCTCTTTAACAATTTATCAGACAATCTGT<br>GTGGGCACTCGACCGGAATTATCGATTAACTTTATTATTAAAAAT<br>TAAAGAGGTATATATTA |

SEQUENCE TABLE

| SEQ ID NO | Organism | Other Information | Sequence |
|---|---|---|---|
| 78 | Artificial sequence | pDS80 plasmid | CACTATACCAATTGAGATGGGCTAGTCAATGATAATTACTAGTC<br>CTTTTCCTTTGAGTTGTGGGTATCTGTAAATTCTGCTAGACCTTT<br>GCTGGAAAACTTGTAAATTCTGCTAGACCCTCTGTAAATTCCGCT<br>AGACCTTTGTGTGTTTTTTTGTTTATATTCAAGTGGTTATAATTT<br>ATAGAATAAAGAAAGAATAAAAAAAGATAAAAAGAATAGATCC<br>CAGCCCTGTGTATAACTCACTACTTTAGTCAGTTCCGCAGTATTA<br>CAAAAGGATGTCGCAAACGCTGTTTGCTCCTCTACAAAACAGAC<br>CTTAAAACCCTAAAGGCgtcGGCATCCGCTTACAGACAAGCTGTG<br>ACCGTCTCCGGGAGCTGCATGTGTCAGAGGTTTTCACCGTCATC<br>ACCGAAACGCGCGAGGCAGCAGATCAATTCGCGCGCGAAGGC<br>GAAGCGGCATGCATTTACGTTGACACCATCGAATGGTGCAAAAC<br>CTTTCGCGGTATGGCATGATAGCGCCCGGAAGAGAGTCAATTCA<br>GGGTGGTGAATGTGAAACCAGTAACGTTATACGATGTCGCAGA<br>GTATGCCGGTGTCTCTTATCAGACCGTTTCCCGCGTGGTGAACC<br>AGGCCAGCCACGTTTCTGCGAAAACGCGGGAAAAAGTGGAAGC<br>GGCGATGGCGGAGCTGAATTACATTCCCAACCGCGTGGCACAA<br>CAACTGGCGGGCAAACAGTCGTTGCTGATTGGCGTTGCCACCTC<br>CAGTCTGGCCCTGCACGCGCCGTCGCAAATTGTCGCGGCGATTA<br>AATCTCGCCGATCAACTGGGTGCCAGCGTGGTGGTGTCGAT<br>GGTAGAACGAAGCGGCGTCGAAGCCTGTAAAGCGGCGGTGCA<br>CAATCTTCTCGCGCAACGCGTCAGTGGGCTGATCATTAACTATCC<br>GCTGGATGACCAGGATGCCATTGCTGTGGAAGCTGCCTGCACTA<br>ATGTTCCGGCGTTATTTCTTGATGTCTCTGACCAGACACCCATCA<br>ACAGTATTATTTTCTCCCATGAAGACGGTACGCGACTGGGCGTG<br>GAGCATCTGGTCGCATTGGGTCACCAGCAAATCGCGCTGTTAGC<br>GGGCCCATTAAGTTCTGTCTCGGCGCGTCTGCGTCTGGCTGGCT<br>GGCATAAATATCTCACTCGCAATCAAATTCAGCCGATAGCGGAA<br>CGGGAAGGCGACTGGAGTGCCATGTCCGGTTTTCAACAAACCA<br>TGCAAATGCTGAATGAGGGCATCGTTCCCACTGCGATGCTGGTT<br>GCCAACGATCAGATGGCGCTGGGCGCAATGCGCGCCATTACCG<br>AGTCCGGGCTGCGCGTTGGTGCGGATATCTCGGTAGTGGGATA<br>CGACGATACCGAAGACAGCTCATGTTATATCCCGCCGTtAACCA<br>CCATCAAACAGGATTTTCGCCTGCTGGGGCAAACCAGCGTGGAC<br>CGCTTGCTGCAACTCTCTCAGGGCCAGGCGGTGAAGGGCAATC<br>AGCTGTTGCCCGTCTCACTGGTGAAAAGAAAAACCACCCTGGCG<br>CCCAATACGCAAACCGCCTCTCCCCGCGCGTTGGCCGATTCATTA<br>ATGCAGCTGGCACGACAGGTTTCCCGACTGGAAAGCGGGCAGT<br>GAGCGCAACGCAATTAATGTaAGTTAGCGCGAATTGATCTGGTT<br>TGACAGCTTATCATCGACTGCACGGTGCACCAATGCTTCTGGCG<br>TCAGGCAGCCATCGGAAGCTGTGGTATGGCTGTGCAGGTCGTA<br>AATCACTGCATAATTCGTGTCGCTCAAGGCGCACTCCCGTTCTG<br>GATAATGTTTTTTGCGCCGACATCATAACGGTTCTGGCAAATATT<br>ttcagatctctcacctaccaaacaatgcccccctgcaaaaaataaattcatataaaa<br>aacatacagataaccatctgcggtgataaattatctctggcggtgttgacataaatac<br>cactggcggtgatactgagcacagAATaTTCACACAGGAAACAGCGCCG<br>CTGAGAAAAAGCGAAGCGGCACTGCTCTTTAACAATTTATCAGA<br>CAATCTGTGTGGGCACTCGACCGGAATTATCGATTAACTTTATTA<br>TTAAAAATTAAAGAGGTATATATTAATGTATCGATTAAATAAGG<br>AGGAATAAACCATGGATCCGAGCTCGAGATCTGCAGCTGGTAC<br>CATATGGGAATTCGAAGCTTGGGCCCGAACAAAAACTCATCTCA<br>GAAGAGGATCTGAATAGCGCCGTCGACCATCATCATCATCATCA<br>TTGAGTTTAAACGGTCTCCAGCTTGGCTGTTTTGGCGGATGAGA<br>GAAGATTTTCAGCCTGATACAGATTAAATCAGAACGCAGAAGC<br>GGTCTGATAAAACAGAATTTGCCTGGCGGCAGTAGCGCGGTGG<br>TCCCACCTGACCCCATGCCGAACTCAGAAGTGAAACGCCGTAGC<br>GCCGATGGTAGTGTGGGGTCTCCCCATGCGAGAGTAGGGAACT<br>GCCAGGCATCAAATAAAACGAAAGGCTCAGTCGAAAGACTGGG<br>CCTTTCGTTTTATCTGTTGTTTGTCGGTGAACGCTCTCCTgacGCC<br>TGATGCGGTATTTTCTCCTTACGCATCTGTGCGGTATTTCACACC<br>GCATATGGTGCACTCTCAGTACAATCTGCTCTGATGCCGCATAG<br>TTAAGCCAGCCCCGACACCCGCCAACACCCGCTGACGAGCTTAG<br>TAAAGCCCTCGCTAGATTTTAATGCGGATGTTGCGATTACTTCGC<br>CAACTATTGCGATAACAAGAAAAAGCCAGCCTTTCATGATATAT<br>CTCCCAATTTGTGTAGGGCTTATTATGCACGCTTAAAAATAATAA<br>AAGCAGACTTGACCTGATAGTTTGGCTGTGAGCAATTATGTGCT<br>TAGTGCATCTAACGCTTGAGTTAAGCCGCGCCGCGAAGCGGCG<br>TCGGCTTGAACGAATTGTTAGACATTATTTGCCGACTACCTTGGT<br>GATCTCGCCTTTCACGTAGTGGACAAATTCTTCCAACTGATCTGC<br>GCGCGAGGCCAAGCGATCTTCTTCTTGTCCAAGATAAGCCTGTC<br>TAGCTTCAAGTATGACGGGCTGATACTGGGCCGGCAGGCGCTC<br>CATTGCCCAGTCGGCAGCGACATCCTTCGGCGCGATTTTGCCGG<br>TTACTGCGCTGTACCAAATGCGGGACAACGTAAGCACTACATTT<br>CGCTCATCGCCAGCCCAGTCGGGCGGCGAGTTCCATAGCGTTAA<br>GGTTTCATTTAGCGCCTCAAATAGATCCTGTTCAGGAACCGGAT |

SEQUENCE TABLE

| SEQ ID NO | Organism | Other Information | Sequence |
|---|---|---|---|
| | | | CAAAGAGTTCCTCCGCCGCTGGACCTACCAAGGCAACGCTATGT<br>TCTCTTGCTTTTGTCAGCAAGATAGCCAGATCAATGTCGATCGTG<br>GCTGGCTCGAAGATACCTGCAAGAATGTCATTGCGCTGCCATTC<br>TCCAAATTGCAGTTCGCGCTTAGCTGGATAACGCCACGGAATGA<br>TGTCGTCGTGCACAACAATGGTGACTTCTACAGCGCGGAGAATC<br>TCGCTCTCTCCAGGGGAAGCCGAAGTTTCCAAAAGGTCGTTGAT<br>CAAAGCTCGCCGCGTTGTTTCATCAAGCCTTACGGTCACCGTAA<br>CCAGCAAATCAATATCACTGTGTGGCTTCAGGCCGCCATCCACT<br>GCGGAGCCGTACAAATGTACGGCCAGCAACGTCGGTTCGAGAT<br>GGCGCTCGATGACGCCAACTACCTCTGATAGTTGAGTCGATACT<br>TCGGCGATCACCGCTTCCCTCATGATGTTTAACTTTGTTTTAGGG<br>CGACTGCCCTGCTGCGTAACATCGTTGCTGCTCCATAACATCAAA<br>CATCGACCCACGGCGTAACGCGCTTGCTGCTTGGATGCCCGAGG<br>CATAGACTGTACCCCAAAAAAACAGTCATAACAAGCCATGAAAA<br>CCGCCACTGCGCCGTTACCACCGCTGCGTTCGGTCAAGGTTCTG<br>GACCAGTTGCGTGAGCGCATACGCTACTTGCATTACAGCTTACG<br>AACCGAACAGGCTTATGTCCACTGGGTTCGTGCCTTCATCCGTTT<br>CCACGGTGTGCGTCACCCGGCAACCTTGGGCAGCAGCGAAGTC<br>GAGGCATTTCTGTCCTGGCTGGCGAACGAGCGCAAGGTTTCGG<br>TCTCCACGCATCGTCAGGCATTGGCGGCCTTGCTGTTCTTCTACG<br>GCAAGGTGCTGTGCACGGATCTGCCCTGGCTTCAGGAGATCGG<br>AAGACCTCGGCCGTCGCGGCGCTTGCCGGTGGTGCTGACCCCG<br>GATGAAGTGGTTCGCATCCTCGGTTTTCTGGAAGGCGAGCATCG<br>TTTGTTCGCCCAGCTTCTGTATGGAACGGGCATGCGGATCAGTG<br>AGGGTTTGCAACTGCGGGTCAAGGATCTGGATTTCGATCACGG<br>CACGATCATCGTGCGGGAGGGCAAGGGCTCCAAGGATCGGGCC<br>TTGATGTTACCCGAGAGCTTGGCACCCAGCCTGCGCGAGCAGG<br>GGAATTAATTCCCACGGGTTTTGCTGCCCGCAAACGGGCTGTTC<br>TGGTGTTGCTAGTTTGTTATCAGAATCGCAGATCCGGCTTCAGC<br>CGGTTTGCCGGCTGAAAGCGCTATTTCTTCCAGAATTGCCATGA<br>TTTTTTCCCCACGGGAGGCGTCACTGGCTCCCGTGTTGTCGGCA<br>GCTTTGATTCGATAAGCAGCATCGCCTGTTTCAGGCTGTCTATGT<br>GTGACTGTTGAGCTGTAACAAGTTGTCTCAGGTGTTCAATTTCAT<br>GTTCTAGTTGCTTTGTTTTACTGGTTTCACCTGTTCTATTAGGTGT<br>TACATGCTGTTCATCTGTTACATTGTCGATCTGTTCATGGTGAAC<br>AGCTTTTGAATGCACCAAAAACTCGTAAAAGCTCTGATGTATCTA<br>TCTTTTTTACACCGTTTTCATCTGTGCATATGGACAGTTTTCCCTT<br>TGATATGTAACGGTGAACAGTTGTTCTACTTTTGTTTGTTAGTCT<br>TGATGCTTCACTGATAGATACAAGAGCCATAAGAACCTCAGATC<br>CTTCCGTATTTAGCCAGTATGTTCTCTAGTGTGGTTCGTTGTTTTT<br>GCGTGAGCCATGAGAACGAACCATTGAGATCATACTTACTTTGC<br>ATGTCACTCAAAAATTTTGCCTCAAAACTGGTGAGCTGAATTTTT<br>GCAGTTAAAGCATCGTGTAGTGTTTTCTTAGTCCGTTATGTAGG<br>TAGGAATCTGATGTAATGGTTGTTGGTATTTTGTCACCATTCATT<br>TTTATCTGGTTGTTCTCAAGTTCGGTTACGAGATCCATTTGTCTA<br>TCTAGTTCAACTTGGAAAATCAACGTATCAGTCGGGCGGCCTCG<br>CTTATCAACCACCAATTTCATATTGCTGTAAGTGTTTAAATCTTTA<br>CTTATTGGTTTCAAAACCCATTGGTTAAGCCTTTTAAACTCATGG<br>TAGTTATTTTCAAGCATTAACATGAACTTAAATTCATCAAGGCTA<br>ATCTCTATATTTGCCTTGTGAGTTTTCTTTTGTGTTAGTTCTTTTA<br>ATAACCACTCATAAATCCTCATAGAGTATTTGTTTCAAAAGACT<br>TAACATGTTCCAGATTATATTTTATGAATTTTTTTAACTGGAAAA<br>GATAAGGCAATATCTCTTCACTAAAAACTAATTCTAATTTTTCGC<br>TTGAGAACTTGGCATAGTTTGTCCACTGGAAAATCTCAAAGCCT<br>TTAACCAAAGGATTCCTGATTTCCACAGTTCTCGTCATCAGCTCT<br>CTGGTTGCTTTAGCTAATACACCATAAGCATTTTCCCTACTGATG<br>TTCATCATCTGAGCGTATTGGTTATAAGTGAACGATACCGTCCGT<br>TCTTTCCTTGTAGGGTTTTCAATCGTGGGGTTGAGTAGTGCCAC<br>ACAGCATAAAATTAGCTTGGTTTCATGCTCCGTTAAGTCATAGC<br>GACTAATCGCTAGTTCATTTGCTTTGAAAACAACTAATTCAGACA<br>TACATCTCAATTGGTCTAGGTGATTTTAAT |
| 79 | Artificial sequence | p100.38 plasmid | GACGAAAGGGCCTCGTGATACGCCTATTTTTATAGGTTAATGTC<br>ATGATAATAATGGTTTCTTAGACGTCAGGTGGCACTTTTCGGGG<br>AAATGTGCGCGGAACCCCTATTTGTTTATTTTTCTAAATACATTC<br>AAATATGTATCCGCTCATGAGACAATAACCCTGATAAATGCTTC<br>AATAATATTGAAAAGGAAGAGTATGAGTATTCAACATTTCCGT<br>GTCGCCCTTATTCCCTTTTTGCGGCATTTTGCCTTCCTGTTTTTG<br>CTCACCCAGAAACGCTGGTGAAAGTAAAAGATGCTGAAGATCA<br>GTTGGGTGCACGAGTGGGTTACATCGAACTGGATCTCAACAGC<br>GGTAAGATCCTTGAGAGTTTTCGCCCCGAAGAACGTTTTCCAAT<br>GATGAGCACTTTTAAAGTTCTGCTATGTGGCGCGGTATTATCCC<br>GTATTGACGCCGGGCAAGAGCAACTCGGTCGCCGCATACACTAT<br>TCTCAGAATGACTTGGTTGAGTACTCACCAGTCACAGAAAAGCA |

SEQUENCE TABLE

| SEQ ID NO | Organism | Other Information | Sequence |
|---|---|---|---|
| | | | TCTTACGGATGGCATGACAGTAAGAGAATTATGCAGTGCTGCCA TAACCATGAGTGATAACACTGCGGCCAACTTACTTCTGACAACG ATCGGAGGACCGAAGGAGCTAACCGCTTTTTTGCACAACATGG GGGATCATGTAACTCGCCTTGATCGTTGGGAACCGGAGCTGAAT GAAGCCATACCAAACGACGAGCGTGACACCACGATGCCTGTAG CAATGGCAACAACGTTGCGCAAACTATTAACTGGCGAACTACTT ACTCTAGCTTCCCGGCAACAATTAATAGACTGGATGGAGGCGG ATAAAGTTGCAGGACCACTTCTGCGCTCGGCCCTTCCGGCTGGC TGGTTTATTGCTGATAAATCTGGAGCCGGTGAGCGTGGGTCTCG CGGTATCATTGCAGCACTGGGGCCAGATGGTAAGCCCTCCCGTA TCGTAGTTATCTACACGACGGGGAGTCAGGCAACTATGGATGA ACGAAATAGACAGATCGCTGAGATAGGTGCCTCACTGATTAAG CATTGGTAACTGTCAGACCAAGTTTACTCATATATACTTTAGATT GATTTAAAACTTCATTTTTAATTTGTGCATCCGAAGATCAGCAGT TCAACCTGTTGATAGTACGTACTAAGCTCTCATGTTTCACGTACT AAGCTCTCATGTTTAACGTACTAAGCTCTCATGTTTAACGAACTA AACCCTCATGGCTAACGTACTAAGCTCTCATGGCTAACGTACTA AGCTCTCATGTTTGAACAATAAAATTAATATAAATCAGCAACTTA AATAGCCTCTAAGGTTTTAAGTTTTATAAGAAAAAAAGAATAT ATAAGGCTTTTAAAGCTAGCTTTTAAGGTTTCACCATGTTCTTTC CTGCGTTATCCCTGATTCTGTGGATAACCGTATTACCGCCTTTG AGTGAGCTGATACCGCTCGCCGCAGCCGAACGACCGAGCGCAG CGAGTCAGTGAGCGAGGAAGCGGAAGAGCGCCCAATACGCAA ACCGCCTCTCCCCGCGCGTTGGCCGATTCATTAAGACAGCTGTCT CTTATACACATCTCAACCCTGAAGCTCTTGTTGGCTAGTGCGTAG TCGTTGGCAAGCTTTCCGCTGTTTCTGCATTCTTACGTTTTAGGA TGCATATGGCGGCCGCATAACTTCGTATAGCATACATTATACGA AGTTATCTAGAGTTGCATGCCTGCAGGTCCGCTTATTATCACTTA TTCAGGCGTAGCAACCAGGCGTTTAAGGGCACCAATAACTGCCT TAAAAAAATTACGCCCCGCCCTGCCACTCATCGCAGTACTGTTGT AATTCATTAAGCATTCTGCCGACATGGAAGCCATCACAAACGGC ATGATGAACCTGAATCGCCAGCGGCATCAGCACCTTGTCGCCTT GCGTATAATATTTGCCCATGGTGAAAACGGGGGCGAAGAAGTT GTCCATATTGGCCACGTTTAAATCAAAACTGGTGAAACTCACCC AGGGATTGGCTGAGACGAAAAACATATTCTCAATAAACCCTTTA GGGAAATAGGCCAGGTTTTCACCGTAACACGCCACATCTTGCGA ATATATGTGTAGAAACTGCCGGAAATCGTCGTGGTATTCACTCC AGAGCGATGAAAACGTTTCAGTTTGCTCATGGAAAACGGTGTA ACAAGGGTGAACACTATCCCATATCACCAGCTCACCGTCTTTCAT TGCCATACGGAATTCCGGATGAGCATTCATCAGGCGGGCAAGA ATGTGAATAAAGGCCGGATAAAACTTGTGCTTATTTTTCTTTACG GTCTTTAAAAAGGCCGTAATATCCAGCTGAACGGTCTGGTTATA GGTACATTGAGCAACTGACTGAAATGCCTCAAAATGTTCTTTAC GATGCCATTGGGATATATCAACGGTGGTATATCCAGTGATTTTTT TCTCCATTTTAGCTTCCTTAGCTCCTGAAAATCTCGATAACTCAAA AAATACGCCCGGTAGTGATCTTATTTCATTATGGTGAAAGTTGG AACCTCTTACGTGCCGATCAACGTCTCATTTTCGCCAAAAGTTGG CCCAGGGCTTCCCGGTATCAACAGGGACACCAGGATTTATTTAT TCTGCGAAGTGATCTTCCGTCACAGGTATTTATTCGACTCTAGAT AACTTCGTATAGCATACATTATACGAAGTTATGGATCCAGCTTAT CGATACCGTCAAACAAATCATAAAAAATTTATTTGCTTTCAGGAA AATTTTTCTGTATAATAGATTCAATTGCGATGACGACGAACACG CATTAAGGAGGTGAAGAGCTCGAATTCGAGCCAATATGCGAGA ACACCCGAGAAAATTCATCGATGATGGTTGAGATGTGTATAAGA GACAGCTGTCGTAATAGCGAAGAGGCCCGCACCGATCGCCCTTC CCAACAGTTGCGCAGCCTGAATGGCGAATGGCGCCTGATGCGG TATTTTCTCCTTACGCATCTGTGCGGTATTTCACACCGCATATGG TGCACTCTCAGTACAATCTGCTCTGATGCCGCATAGTTAAGCCA GCCCCGACACCCGCCAACACCCGCTGACGCGCCCTGACGGGCTT GTCTGCTCCCGGCATCCGCTTACAGACAAGCTGTGACCGTCTCC GGGAGCTGCATGTGTCAGAGGTTTTCACCGTCATCACCGAAACG CGCGA |
| 80 | Artificial sequence | pACYC-PTrc-sbm-ygfG plasmid 266-1348: lacI 1577-1769: PTrc 1800-3944: sbm 3967-4752: ygfG | cgaggccggccCCGCCAACACCCGCTGACGCGCCCTGACGGGCTTG TCTGCTCCCGGCATCCGCTTACAGACAAGCTGTGACCGTCTCCG GGAGCTGCATGTGTCAGAGGTTTTCACCGTCATCACCGAAACGC GCGAGGCAGCAGATCAATTCGCGCGCGAAGGCGAAGCGGCAT GCATTTACGTTGACACCATCGAATGGTGCAAAACCTTTCGCGGT ATGGCATGATAGCGCCCGGAAGAGAGTCAATTCAGGGTGGTGA ATGTGAAACCAGTAACGTTATACGATGTCGCAGAGTATGCCGGT GTCTCTTATCAGACCGTTTCCCGCGTGGTGAACCAGGCCAGCCA CGTTTCTGCGAAAACGCGGGAAAAAGTGGAAGCGGCGATGGC GGAGCTGAATTACATTCCCAACCGCGTGGCACAACAACTGGCG GGCAAACAGTCGTTGCTGATTGGCGTTGCCACCTCCAGTCTGGC |

SEQUENCE TABLE

| SEQ ID NO | Organism | Other Information | Sequence |
|---|---|---|---|
| | | 5208-6020: kanR 6347-7176: p15Aori | CCTGCACGCGCCGTCGCAAATTGTCGCGGCGATTAAATCTCGCG CCGATCAACTGGGTGCCAGCGTGGTGGTGTCGATGGTAGAACG AAGCGGCGTCGAAGCCTGTAAAGCGGCGGTGCACAATCTTCTC GCGCAACGCGTCAGTGGGCTGATCATTAACTATCCGCTGGATGA CCAGGATGCCATTGCTGTGGAAGCTGCCTGCACTAATGTTCCGG CGTTATTTCTTGATGTCTCTGACCAGACACCCATCAACAGTATTA TTTTCTCCCATGAAGACGGTACGCGACTGGGCGTGGAGCATCTG GTCGCATTGGGTCACCAGCAAATCGCGCTGTTAGCGGGCCCATT AAGTTCTGTCTCGGCGCGTCTGCGTCTGGCTGGCTGGCATAAAT ATCTCACTCGCAATCAAATTCAGCCGATAGCGGAACGGGAAGG CGACTGGAGTGCCATGTCCGGTTTTCAACAAACCATGCAAATGC TGAATGAGGGCATCGTTCCCACTGCGATGCTGGTTGCCAACGAT CAGATGGCGCTGGGCGCAATGCGCGCCATTACCGAGTCCGGGC TGCGCGTTGGTGCGGATATCTCGGTAGTGGGATACGACGATAC CGAAGACAGCTCATGTTATATCCCGCCGTCAACCACCATCAAAC AGGATTTTCGCCTGCTGGGGCAAACCAGCGTGGACCGCTTGCTG CAACTCTCTCAGGGCCAGGCGGTGAAGGGCAATCAGCTGTTGC CCGTCTCACTGGTGAAAAGAAAAACCACCCTGGCGCCCAATACG CAAACCGCCTCTCCCCGCGCGTTGGCCGATTCATTAATGCAGCT GGCACGACAGGTTTCCCGACTGGAAAGCGGGCAGTGAGCGCAA CGCAATTAATGTGAGTTAGCGCGAATTGATCTGGTTTGACAGCT TATCATCGACTGCACGGTGCACCAATGCTTCTGGCGTCAGGCAG CCATCGGAAGCTGTGGTATGGCTGTGCAGGTCGTAAATCACTGC ATAATTCGTGTCGCTCAAGGCGCACTCCCGTTCTGGATAATGTTT TTTGCGCCGACATCATAACGGTTCTGGCAAATATTCTGAAATGA GCTGTTGACAATTAATCATCCGGCTCGTATAATGTGTGGAATTG TGAGCGGATAACAATTTCACACAGGAAACAGCGCCGCTGAGAA AAAGCGAAGCGGCACTGCTCTTTAACAATTTATCAGACAATCTG TGTGGGCACTCGACCGGAATTATCGATTAACTTTATTATTAAAAA TTAAAGAGGTATATATTAATGTATCGATTAAATAAGGAGGAATA AAccatggCTAACGTGCAGGAGTGGCAACAGCTTGCCAACAAGG AATTGAGCCGTCGGGAGAAAACTGTCGACTCGCTGGTTCATCAA ACCGCGGAAGGGATCGCCATCAAGCCGCTGTATACCGAAGCCG ATCTCGATAATCTGGAGGTGACAGGTACCCTTCCTGGTTTGCCG CCCTACGTTCGTGGCCCGCGTGCCACTATGTATACCGCCCAACC GTGGACCATCCGTCAGTATGCTGGTTTTTCAACAGCAAAAGAGT CCAACGCTTTTTATCGCCGTAACCTGGCCGCCGGGCAAAAAGGT CTTTCCGTTGCGTTTGACCTTGCCACCCACCGTGGCTACGACTCC GATAACCCGCGCGTGGCGGGCGACGTCGGCAAAGCGGGCGTC GCTATCGACACCGTGGAAGATATGAAAGTCCTGTTCGACCAGAT CCCGCTGGATAAAATGTCGGTTTCGATGACCATGAATGGCGCAG TGCTACCAGTACTGGCGTTTTATATCGTCGCCGCAGAAGAGCAA GGTGTTACACCTGATAAACTGACCGGCACCATTCAAAACGATAT TCTCAAAGAGTACCTCTGCCGCAACACCTATATTTACCCACCAAA ACCGTCAATGCGCATTATCGCCGACATCATCGCCTGGTGTTCCG GCAACATGCCGCGATTTAATACCATCAGTATCAGCGGTTACCAC ATGGGTGAAGCGGGTGCCAACTGCGTGCAGCAGGTAGCATTTA CGCTCGCTGATGGGATTGAGTACATCAAAGCAGCAATCTCTGCC GGACTGAAAATTGATGACTTCGCTCCTCGCCTGTCGTTCTTCTTC GGCATCGGCATGGATCTGTTTATGAACGTCGCCATGTTGCGTGC GGCACGTTATTTATGGAGCGAAGCGGTCAGTGGATTTGGCGCA CAGGACCCGAAATCACTGGCGCTGCGTACCCACTGCCAGACCTC AGGCTGGAGCCTGACTGAACAGGATCCGTATAACAACGTTATCC GCACCACCATTGAAGCGCTGGCTGCGACGCTGGGCGGTACTCA GTCACTGCATACCAACGCCTTTGACGAAGCGCTTGGTTTGCCTA CCGATTTCTCAGCACGCATTGCCCGCAACACCCAGATCATCATCC AGGAAGAATCAGAACTCTGCCGCACCGTCGATCCACTGGCCGG ATCCTATTACATTGAGTCGCTGACCGATCAAATCGTCAAACAAG CCAGAGCTATTCCAACAGATCGACGAAGCCGGTGGCATGGC GAAAGCGATCGAAGCAGGTCTGCCAAAACGAATGATCGAAGAG GCCTCAGCGCGCGAACAGTCGCTGATCGACCAGGGCAAGCGTG TCATCGTTGGTGTCAACAAGTACAAACTGGATCACGAAGACGAA ACCGATGTACTTGAGATCGACAACGTGATGGTGCGTAACGAGC AAATTGCTTCGCTGGAACGCATTCGCGCCACCCGTGATGATGCC GCCGTAACCGCCGCGTTGAACGCCTGACTCACGCCGCACAGCA TAACGAAAACCTGCTGGCTGCCGCTGTTAATGCCGCTCGCGTTC GCGCCACCCTGGGTGAAATTCGATGCGCTGGAAGTCGCTTTC GACCGTTATCTGGTGCCAAGCCAGTGTGTTACCGGCGTGATTGC GCAAAGCTATCATCAGTCTGAGAAATCGGCCTCCGAGTTCGATG CCATTGTTGCGCAAACGGAGCAGTTCCTTGCCGACAATGGTCGT CGCCCGCGCATTCTGATCGCTAAGATGGGCCAGGATGACACG ATCGCGGCGCGAAAGTGATCGCCAGCGCCTATTCCGATCTCGGT TTCGACGTAGATTTAAGCCCGATGTTCTCTACACCTGAAGAGAT CGCCCGCCTGGCCGTAGAAAACGACGTTCACGTAGTGGGCGCA |

SEQUENCE TABLE

| SEQ ID NO | Organism | Other Information | Sequence |
|---|---|---|---|
| | | | TCCTCACTGGCTGCCGGTCATAAAACGCTGATCCCGGAACTGGT<br>CGAAGCGCTGAAAAAATGGGGACGCGAAGATATCTGCGTGGTC<br>GCGGGTGGCGTCATTCCGCCGCAGGATTACGCCTTCCTGCAAGA<br>GCGCGGCCGTGGCGGCGATTTATGGTCCAGGTACACCTATGCTC<br>GACAGTGTGCGCGACGTACTGAATCTGATAAGCCAGCATCATG<br>ATtaattctagaAAGGAGGAATAAACCatgTCTTATCAGTATGTTAA<br>CGTTGTCACTATCAACAAAGTGGCCGGTCATTGAGTTTAACTATG<br>GCCGAAAACTTAATGCCTTAAGTAAAGTCTTTATTGATGATCTTA<br>TGCAGGCGTTAAGCGATCTCAACCGGCCGGAAATTCGCTGTATC<br>tggggcgattcaggcctggtatgagtcagcaacaccttcttcacgaggcagacctca<br>gcgctagcggagtgtatactggctactatgttggcactgatgagggtgtcagtgaa<br>gtgcttcatgtggcaggagaaaaaaggctgcaccggtgcgtcagcagaatatgtga<br>tacaggatatattccgcttcctcgctcactgactcgctacgctcggtcgttcgactgcg<br>gcgagcggaaatggcttacgaacggggcggagatttcctggaagatgccaggaag<br>atacttaacagggaagtgagagggccgcgcaaagccgttttccataggctccgcc<br>ccctgacaagcatcacgaaatctgacgctcaaatcagtggtggcgaaacccgaca<br>ggactataaagataccaggcgtttccccctggcggctccctcgtgcgctctcctgttcc<br>tgcctttcggtttaccggtgtcattccgctgttatggccgcgtttgtctcattccacgcct<br>gacactcagttccgggtaggcagttcgctccaagctggactgtatgcacgaaccccc<br>cgttcagtccgaccgctgcgccttatccggtaactatcgtcttgagtccaacccggaa<br>agacatgcaaaagcaccactggcagcagccactggtaattgatttagaggagttag<br>tcttgaagtcatgcgccggttaaggctaaactgaaaggacaagttttggtgactgcg<br>ctcctccaagccagttacctcggttcaaagagttggtagctcagagaaccttcgaaa<br>aaccgccctgcaaggcggttttttcgttttcagagcaagagattacgcgcagaccaa<br>aacgatctcaagaagatcatcttattaaggggtctgacgctcagtggaacgaaaact<br>cacgttaagggattttggtcatgagattatcaaaaaggatcttcacctagatcctttta<br>aattaaaaatgaagttttaaatcaatctaaagtatatatgagtaaacttggtctgaca<br>gttaccaatgcttaatcagtgaggcacctatctcagcgatctgtctatttcgttcatcc<br>atagttgcctgactcccgtcgtgtagataactacgatacgggagggcttaccatctg<br>gccccagtgctgcaatgataccgcgagacccacgctcaccggctccagatttatcag<br>caataaaccagccagccggaagggccgagcgcagaagtggtcctgcaactttatcc<br>gcctccatccagtctattaattgttgccgggaagctagagtaagtagttcgccagtta<br>atagtttgcgcaacgttgttgccattgctgcaggcatcgtggtgtcacgctcgtcgttt<br>ggtatggcttcattcagctccggttcccaacgatcaaggcgagttacatgatcccca<br>tgttgtgcaaaaaagcggttagctccttcggtcctccgatcgttgtcagaagtaagtt<br>ggccgcagtgttatcactcatggttatggcagcactgcataattctcttactgtcatgc<br>catccgtaagatgcttttctgtgactggtgagt |
| 81 | Artificial sequence | Tn7tes plasmid | GGCCACGATGCGTCCGGCGTAGAGGATCTGCTCATGTTTGACA<br>GCTTATCATCGATGCATAATGTGCCTGTCAAATGGACGAAGCAG<br>GGATTCTGCAAACCCTATGCTACTCCGTCAAGCCGTCAATTGTCT<br>GATTCGTTACCAATTATGACAACTTGACGGCTACATCATTCACTT<br>TTTCTTCACAACCGGCACGGAACTCGCTCGGGCTGGCCCCGGTG<br>CATTTTTTAAATACCCGCGAGAAATAGAGTTGATCGTCAAAACC<br>AACATTGCGACCGACGGTGGCGATAGGCATCCGGGTGGTGCTC<br>AAAAGCAGCTTCGCCTGGCTGATACGTTGGTCCTCGCGCCAGCT<br>TAAGACGCTAATCCCTAACTGCTGGCGGAAAAGATGTGACAGA<br>CGCGACGGCGACAAGCAAACATGCTGTGCGACGCTGGCGATAT<br>CAAAATTGCTGTCTGCCAGGTGATCGCTGATGTACTGACAAGCC<br>TCGCGTACCCGATTATCCATCGGTGGATGGAGCGACTCGTTAAT<br>CGCTTCCATGCGCCGCAGTAACAATTGCTCAAGCAGATTTATCG<br>CCAGCAGCTCCGAATAGCGCCCTTCCCCTTGCCCGGCGTTAATG<br>ATTTGCCCAAACAGGTCGCTGAAATGCGGCTGGTGCGCTTCATC<br>CGGGCGAAAGAACCCCGTATTGGCAAATATTGACGGCCAGTTA<br>AGCCATTCATGCCAGTAGGCGCGCGGACGAAAGTAAACCCACT<br>GGTGATACCATTCGCGAGCCTCCGGATGACGACCGTAGTGATG<br>AATCTCTCCTGGCGGGAACAGCAAAATATCACCCGGTCGGCAAA<br>CAAATTCGTCCCTGATTTTTCACCACCCCCTGACCGCGAATGG<br>TGAGATTGAGAATATAACCTTTCATTCCCAGCGGTCGGTCGATA<br>AAAAAAATCGAGATAACCGTTGGCCTCAATCGGCGTTAAACCCGC<br>CACCAGATGGGCATTAAACGAGTATCCCGGCAGCAGGGGATCA<br>TTTTGCGCTTCAGCCATACTTTTCATACTCCCGCCATTCAGAGAA<br>GAAACCAATTGTCCATATTGCATCAGACATTGCCGTCACTGCGTC<br>TTTTACTGGCTCTTCTCGCTAACCAAACCGGTAACCCCGCTTATT<br>AAAAGCATTCTGTAACAAAGCGGGACAAAGCCATGACAAAAA<br>CGCGTAACAAAAGTGTCTATAATCACGGCAGAAAAGTCCACATT<br>GATTATTTGCACGGCGTCACACTTTGCTATGCCATAGCATTTTTA<br>TCCATAAGATTAGCGGATCCTACCTGACGCTTTTTATCGCAACTC<br>TCTACTGTTTCTCCATACCCGTTTTTTTGGGCTAGCGAATTCGAG<br>CTCGGTACCCAAGTCTTAAACTAGACAGAATAGTTGTAAACTGA<br>AATCAGTCCAGTTATGCTGTGAAAAAGCATACTGGACTTTTGTT<br>ATGGCTAAAGCAAACTCTTCATTTTCTGAAGTGCAAATTGCCCGT<br>CGTATTAAAGAGGGCGTGGCCAAGGGCATGGTAAAGACTATA<br>TTCCATGGCTAACAGTACAAGAAGTTCCTTCTTCAGGTCGTTCCC |

SEQUENCE TABLE

| SEQ ID NO | Organism | Other Information | Sequence |
|---|---|---|---|
| | | | ACCGTATTTATTCTCATAAGACGGGACGAGTCCATCATTTGCTAT
CTGACTTAGAGCTTGCTGTTTTTCTCAGTCTTGAGTGGGAGAGC
AGCGTGCTAGATATACGCGAGCAGTTCCCCTTATTACCTAGTGA
TACCAGGCAGATTGCAATAGATAGTGGTATTAAGCATCCTGTTA
TTCGTGGTGTAGATCAGGTTATGTCTACTGATTTTTTAGTGGACT
GCAAAGATGGTCCTTTTGAGCAGTTTGCTATTCAAGTCAAACCT
GCAGCAGCCTTACAAGACGAGCGTACCTTAGAAAAACTAGAACT
AGAGCGTCGCTATTGGCAGCAAAAGCAAATTCCTTGGTTCATTT
TTACTGATAAAGAAATAAATCCCGTAGTAAAAGAAAATATTGAA
TGGCTTTATTCAGTGAAAACAGAAGAAGTTTCTGCGGAGCTTTT
AGCACAACTATCCCCATTGGCCCATATCCTGCAAGAAAAAGGAG
ATGAAAACATTATCAATGTCTGTAAGCAGGTTGATATTGCTTAT
GATTTGGAGTTAGGCAAAACATTGAGTGAGATACGAGCCTTAA
CCGCAAATGGTTTTATTAAGTTCAATATTTATAAGTCTTTCAGGG
CAAATAAGTGTGCAGATCTCTGTATTAGCCAAGTAGTGAATATG
GAGGAGTTGCGCTATGTGGCAAATTAATGAGGTTGTGCTATTTG
ATAATGATCCGTATCGCATTTTGGCTATAGAGGATGGCCAAGTT
GTCTGGATGCAAATAAGCGCTGATAAAGGAGTTCCACAAGCTA
GGGCTGAGTTGTTGCTAATGCAGTATTTAGATGAAGGCCGCTTA
GTTAGAACTGATGACCCTTATGTACATCTTGATTTAGAAGAGCC
GTCTGTAGATTCTGTCAGCTTCCAGAAGCGCGAGGAGGATTATC
GAAAAATTCTTCCTATTATTAATAGTAAGGATCGTTTCGACCCTA
AAGTCAGAAGCGAACTCGTTGAGCATGTGGTCCAAGAACATAA
GGTTACTAAGGCTACAGTTTATAAGTTGTTACGCCGTTACTGGC
AGCGTGGTCAAACGCCTAATGCATTAATTCCTGACTACAAAAAC
AGCGGTGCACCAGGGGAAAGACGTTCAGCGACAGGAACAGCA
AAGATTGGCCGAGCCAGAGAATATGGTAAGGGTGAAGGAACC
AAGGTAACGCCCGAGATTGAACGCCTTTTTAGGTTGACCATAGA
AAAGCACCTGTTAAATCAAAAAGGTACAAAGACCACCGTTGCCT
ATAGACGATTTGTGGACTTGTTTGCTCAGTATTTTCCTCGCATTC
CCCAAGAGGATTACCCAACACTACGTCAGTTTCGTTATTTTTATG
ATCGAGAATACCCTAAAGCTCAGCGCTTAAAGTCTAGAGTTAAA
GCAGGGGTATATAAAAAAGACGTACGACCCTTAAGTAGTACAG
CCACTTCTCAGGCGTTAGGCCCTGGGAGTCGTTATGAGATTGAT
GCCACGATTGCTGATATTTATTTAGTGGATCATCATGATCGCCAA
AAAATCATAGGAAGACCAACGCTTTACATTGTGATTGATGTGTT
TAGTCGGATGATCACGGGCTTTTATATCGGCTTTGAAAATCCGT
CTTATGTGGTGGCGATGCAGGCTTTTGTAAATGCTTGCTCTGAC
AAAAACGGCCATTTGTGCCCAGCATGATATTGAGATTAGTAGCTC
AGACTGGCCGTGTGTAGGTTTGCCAGATGTGTTGCTAGCGGACC
GTGGCGAATTAATGAGTCATCAGGTCGAAGCCTTAGTTTCTAGT
TTTAATGTGCGAGTGGAAAGTGCTCCACCTAGACGTGGCGATGC
TAAAGGCATAGTGGAAAGCACTTTTAGAACACTACAAGCCGAG
TTTAAGTCCTTTGCACCTGGCATTGTAGAGGGCAGTCGGATCAA
AAGCCATGGTGAAACAGACTATAGGTTAGATGCATCTCTGTCGG
TATTTGAGTTCACACAAATTATTTTGCGTACGATCTTATTCAGAA
ATAACCATCTGGTGATGGATAAATACGATCGAGATGCTGATTTT
CCTACAGATTTACCGTCTATTCCTGTCCAGCTATGGCAATGGGGT
ATGCAGCATCGTACAGGTAGTTTAAGGGCTGTGGAGCAAGAGC
AGTTGCGAGTAGCGTTACTGCCTCGCCGAAAGGTCTCTATTTCTT
CATTTGGCGTTAATTTGTGGGGTTTGTATTACTCGGGGTCAGAG
ATTCTGCGTGAGGGTTGGTTGCAGCGGAGCACTGATATAGCTA
GACCTCAACATTTAGAAGCGGCTTATGACCCAGTGCTGGTTGAT
ACGATTTATTTGTTTCCGCAAGTTGGCAGCCGTGTATTTTGGCGC
TGTAATCTGACGGAACGTAGTCGGCAGTTTAAAGGTCTCTCATT
TTGGGAGGTTTGGGATATACAAGCACAAGAAAAACACAATAAA
GCCAATGCGAAGCAGGATGAGTTAACTAAACGCAGGGAGCTTG
AGGCGTTTATTCAGCAAACCATTCAGAAAGCGAATAAGTTAACG
CCCAGTACTACTGAGCCCAAATCAACACGCATTAAGCAGATTAA
AACTAATAAAAAGAAGCCGTGACCTCGGAGCGTAAAAAACGT
GCGGAGCATTTGAAGCCAAGCTCTTCAGGTGATGAGGCTAAAG
TTATTCCTTTCAACGCAGTGGAAGCGGATGATCAAGAAGATTAC
AGCCTACCCACATACGTGCCTGAATTATTTCAGGATCCACCAGA
AAAGGATGAGTCATGAGTGCTACCCGGATTCAAGCAGTTTATCG
TGATACGGGGTAGAGGCTTATCGTGATAATCCTTTTATCGAGG
CCTTACCACCATTACAAGAGTCAGTGAATAGTGCTGCATCACTG
AAATCCTCTTTACAGCTTACTTCCTCTGACTTGCAAAAGTCCCGT
GTTATCAGAGCTCATACCATTTGTCGTATTCCAGATGACTATTTT
CAGCCATTAGGTACGCATTTGCTACTAAGTGAGCGTATTTCGGT
CATGATTCGAGGTGGCTACGTAGGCAGAAATCCTAAAACAGGA
GATTTACAAAAGCATTTACAAAATGGTTATGAGCGTGTTCAAAC
GGGAGAGTTGGAGACATTTCGCTTTGAGGAGGCACGATCTACG
GCACAAAGCTTATTGTTAATTGGTTGTTCTGGTAGTGGGAAGAC
GACCTCTCTTCATCGTATTCTAGCCACGTATCCTCAGGTGATTTA |

SEQUENCE TABLE

| SEQ ID NO | Organism | Other Information | Sequence |
|---|---|---|---|
| | | | CCATCGTGAACTCAATGTAGAGCAGGTGGTGTATTTGAAAATAG ACTGCTCGCATAATGGTTCGCTAAAAGAAATCTGCTTGAATTTTT TCAGAGCGTTGGATCGAGCCTTGGGCTCGAACTATGAGCGTCGT TATGGCTTAAAACGTCATGGTATAGAAACCATGTTGGCTTTGAT GTCGCAAATAGCCAATGCACATGCTTTAGGGTTGTTGGTTATTG ATGAAATTCAGCATTTAAGCCGCTCTCGTTCGGGTGGATCTCAA GAGATGCTGAACTTTTTTGTGACGATGGTGAATATTATTGGCGT ACCAGTGATGTTGATTGGTACCCCTAAAGCACGAGAGATTTTTG AGGCTGATTTGCGGTCTGCACGTAGAGGGGCAGGGTTTGGAGC TATATTCTGGGATCCTATACAACAAACGCAACGTGGAAAGCCCA ATCAAGAGTGGATCGCTTTTACGGATAATCTTTGGCAATTACAG CTTTTACAACGCAAAGATGCGCTGTTATCGGATGAGGTCCGTGA TGTGTGGTATGAGCTAAGCCAAGGAGTGATGGACATTGTAGTA AAACTTTTTGTACTCGCTCAGCTCCGTGCGCTAGCTTTAGGCAAT GAGCGTATTACCGCTGGTTTATTGCGGCAAGTGTATCAAGATGA GTTAAAGCCTGTGCACCCCATGCTAGAGGCATTACGCTCGGGTA TCCCAGAACGCATTGCTCGTTATTCTGATCTAGTCGTTCCCGAGA TTGATAAACGGTTAATCCAACTTCAGCTAGATATCGCAGCGATA CAAGAACAAACACCAGAAGAAAAAGCCCTTCAAGAGTTAGATA CCGAAGATCAGCGTCATTTATATCTGATGCTGAAAGAGGATTAC GATTCAAGCCTGTTAATTCCCACTATTAAAAAGCGTTTAGCCAG AATCCAACGATGACAAGACAAAAGTTACTGCCTCTTGTTTTGCA GTGGTTGATGGAAGGCGAAACGGTAGTGTCAGAACTAGAAAA GCCCTCCAAGAGTAAAAAGGTTTCGGCTATAAAGGTAGTCAAG CCCAGCGACTGGGATAGCTTGCCTGATACGGATTTACGTTATAT CTATTCACAACGCCAACCTGAAAAAACCATGCATGAACGGTTAA AAGGGAAAGGGGTAATAGTGGATATGGCGAGCTTATTTAAACA AGCAGGTTAGCCATGAGAAACTTTCCTGTTCCGTACTCGAATGA GCTGATTTATAGCACTATTGCACGGGCAGGCGTTTATCAAGGGA TTGTTAGTCCTAAGCAGCTGTTGGATGAGGTGTATGGCAACCGC AAGGTGGTCGCTACCTTAGGTCTGCCCTCGCATTTAGGTGTGAT AGCAAGACATCTACATCAAACAGGACGTTACGCTGTTCAGCAGC TTATTTATGAGCATACCTTATTCCCTTTATATGCTCCGTTTGTAGG CAAGGAGCGCCGAGACGAAGCTATTCGGTTAATGGAGTACCAA GCGCAAGGTGCGGTGCATTTAATGCTAGGAGTCGCTGCTTCTAG AGTTAAGAGCGATAACCGCTTTAGATACTGCCCTGATTGCGTTG CTCTTCAGCTAAATAGGTATGGGGAAGCCTTTTGGCAACGAGAT TGGTATTTGCCCGCTTTGCCATATTGTCCAAAACACGGTGCTTTA GTCTTCTTTGATAGAGCTGTAGATGATCACCGACATCAATTTTGG GCTTTGGGTCATACTGAGCTGCTTTCAGACTACCCCAAAGACTCC CTATCTCAATTAACAGCACTAGCTGCTTATATAGCCCCTCTGTTA GATGCTCCACGAGCGCAAGAGCTTTCCCCAAGCCTTGAGCAGTG GACGCTGTTTTATCAGCGCTTAGCGCAGGATCTAGGGCTAACCA AAAGCAAGCACATTCGTCATGACTTGGTGGCGGAGAGAGTGAG GCAGACTTTTAGTGATGAGGCACTAGAGAAACTGGATTTAAAGT TGGCAGAGAACAAGGACACGTGTTGGCTGAAAAGTATATTCCG TAAGCATAGAAAAGCCTTTAGTTATTTACAGCATAGTATTGTGT GGCAAGCCTTATTGCCAAAACTAACGGTTATAGAAGCGCTACAG CAGGCAAGTGCTCTTACTGAGCACTCTATAACGACAAGACCTGT TAGCCAGTCTGTGCAACCTAACTCTGAAGATTTATCTGTTAAGCA TAAAGACTGGCAGCAACTAGTGCATAAATACCAAGGAATTAAG GCGGCAAGACAGTCTTTAGAGGGTGGGGTGCTATACGCTTGGC TTTACCGACATGACAGGGATTGGCTAGTTCACTGGAATCAACAG CATCAACAAGAGCGTCTGGCACCCGCCCCTAGAGTTGATTGGAA CCAAAGAGATCGAATTGCTGTACGACAACTATTAAGAATCATAA AGCGTCTAGATAGTAGCCTTGATCACCCAAGAGCGACATCGAGC TGGCTGTTAAAGCAAACTCCTAACGGAACCTCTCTTGCAAAAAA TCTACAGAAACTGCCTTTGGTAGCGCTTTGCTTAAAGCGTTACTC AGAGAGTGTGGAAGATTATCAAATTAGACGGATTAGCCAAGCT TTTATTAAGCTTAAACAGGAAGATGTTGAGCTTAGGCGCTGGCG ATTATTAAGAAGTGCAACGTTATCTAAAGAGCGGATAACTGAG GAAGCACAAAGATTCTTGGAAATGGTTTATGGGGAAGAGTGAG TGGTTAGGCTAGCTACATTTAATGACAATGTGCAGGTTGTACAT ATTGGTCATTTATTCCGTAACTCGGGTCATAAGGAGTGGCGTAT TTTTGTTTGGTTTAATCCAATGCAAGAACGGAAATGGACTCGAT TTACTCATTTGCCTTTATTAAGTCGAGCTAAGGTGGTTAACAGTA CAACAAAGCAAATAAATAAGGCGGATCGTGTGATTGAGTTTGA AGCATCGGATCTTCAACGAGCCAAAATAATCGATTTTCCTAATCT CTCGTCCTTTGCTTCCGTACGCAACAAGGATGGAGCGCAGAGTT CATTTATTTACGAAGCTGAAACACCATATAGCAAGACTCGTTATC ACATCCCACAGTTAGAGCTAGCTCGGTCATTATTTTTAGGGGAT CCTCTAGAGTCGACCTGCAGGCATGCAAGCTTGGCTGTTTTGGC GGATGAGAGAAGATTTTCAGCCTGATACAGATTAAATCAGAAC GCAGAAGCGGTCTGATAAAACAGAATTTGCCTGGCGGCAGTAG |

SEQUENCE TABLE

| SEQ ID NO | Organism | Other Information | Sequence |
|---|---|---|---|
| | | | CGCGGTGGTCCCACCTGACCCCATGCCGAACTCAGAAGTGAAAC<br>GCCGTAGCGCCGATGGTAGTGTGGGGTCTCCCCATGCGAGAGT<br>AGGGAACTGCCAGGCATCAAATAAAACGAAAGGCTCAGTCGAA<br>AGACTGGGCCTTTCGTTTTATCTGTTGTTTGTCGGTAACGCTCT<br>CCTGAGTAGGACAAATCCGCCGGGAGCGGATTTGAACGTTGCG<br>AAGCAACGGCCCGGAGGGTGGCGGGCAGGACGCCCGCCATAA<br>ACTGCCAGGCATCAAATTAAGCAGAAGGCCATCCTGACGGATG<br>GCCTTTTTGCGTTTCTACAAACTCTTTTGTTTATTTTTCTAAATAC<br>ATTCAAATATGTATCCGCTCATGAGACAATAACCCTGATAAATG<br>CTTCAATAATATTGAAAAGGAAGAGTATGAGTATTCAACATTT<br>CCGTGTCGCCCTTATTCCCTTTTTTGCGGCATTTTGCCTTCCTGTT<br>TTTGCTCACCCAGAAACGCTGGTGAAAGTAAAAGATGCTGAAG<br>ATCAGTTGGGTGCACGAGTGGGTTACATCGAACTGGATCTCAAC<br>AGCGGTAAGATCCTTGAGAGTTTTCGCCCCGAAGAACGTTTTCC<br>AATGATGAGCACTTTTAAAGTTCTGCTATGTGGCGCGGTATTAT<br>CCCGTGTTGACGCCGGGCAAGAGCAACTCGGTCGCCGCATACA<br>CTATTCTCAGAATGACTTGGTTGAGTACTCACCAGTCACAGAAA<br>AGCATCTTACGGATGGCATGACAGTAAGAGAATTATGCAGTGCT<br>GCCATAACCATGAGTGATAACACTGCGGCCAACTTACTTCTGAC<br>AACGATCGGAGGACCGAAGGAGCTAACCGCTTTTTTGCACAAC<br>ATGGGGGATCATGTAACTCGCCTTGATCGTTGGGAACCGGAGC<br>TGAATGAAGCCATACCAAACGACGAGCGTGACACCACGATGCC<br>TGCAGCAATGGCAACAACGTTGCGCAAACTATTAACTGGCGAAC<br>TACTTACTCTAGCTTCCCGGCAACAATTAATAGACTGGATGGAG<br>GCGGATAAAGTTGCAGGACCACTTCTGCGCTCGGCCCTTCCGGC<br>TGGCTGGTTTATTGCTGATAAATCTGGAGCCGGTGAGCGTGGG<br>TCTCGCGGTATCATTGCAGCACTGGGGCCAGATGGTAAGCCCTC<br>CCGTATCGTAGTTATCTACACGACGGGGAGTCAGGCAACTATGG<br>ATGAACGAAATAGACAGATCGCTGAGATAGGTGCCTCACTGATT<br>AAGCATTGGTAACTGTCAGACCAAGTTTACTCATATATACTTTAG<br>ATTGATTTACGCGCCCTGTAGCGGCGCATTAAGCGCGGCGGGT<br>GTGGTGGTTACGCGCAGCGTGACCGCTACACTTGCCAGCGCCCT<br>AGCGCCCGCTCCTTTCGCTTTCTTCCCTTCCTTTCTCGCCACGTTC<br>GCCGCCGGCCAGCCTCGCAGAGCAGGATTCCCGTTGAGCACCG<br>CCAGGTGCGAATAAGGGACAGTGAAGAAGGAACACCCGCTCGC<br>GGGTGGGCCTACTTCACCTATCCTGCCCGGCGGCATCACCGGCG<br>CCACAGGTGCGGTTGCTGGCGCCTATATCGCCGACATCACCGAT<br>GGGGAAGATCGGGCTCGCCACTTCGGGCTCATGAGCGCTTGTT<br>TCGGCGTGGGTATGGTGGCAGGCCCCGTGGCCGGGGGACTGTT<br>GGGCGCCATCTCCTTGCATGCACCATTCCTTGCGGCGGCGGTGC<br>TCAACGGCCTCAACCTACTACTGGGCTGCTTCCTAATGCAGGAG<br>TCGCATAAGGGAGAGCGTCGATCCCCGACAGTAAGACGGGTAA<br>GCCTGTTGATGATACCGCTGCCTTACTGGGTGCATTAGCCAGTC<br>TGAATGACCTGTCACGGGATAATCCGAAGTGGTCAGACTGGAA<br>AATCAGAGGGCAGGAACTGCTGAACAGCAAAAAGTCAGATAGC<br>ACCACATAGCAGACCCGCCATAAAACGCCCTGAGAAGCCCGTG<br>ACGGGCTTTTCTTGTATTATGGGTAGTTTCCTTGCATGAATCCAT<br>AAAAGGCGCCTGTAGTGCCATTTACCCCCATTCACTGCCAGAGC<br>CGTGAGCGCAGCGAACTGAATGTCACGAAAAAGACAGCGACTC<br>AGGTGCCTGATGGTCGGAGACAAAAGGAATATTCAGCGATTTG<br>CCCGAGCTTGCGAGGGTGCTACTTAAGCCTTTAGGGTTTTAAGG<br>TCTGTTTTGTAGAGGAGCAAACAGCGTTTGCGACATCCTTTTGTA<br>ATACTGCGGAACTGACTAAAGTAGTGAGTTATACACAGGGCTG<br>GGATCTATTCTTTTTATCTTTTTTTATTCTTTCTTTATTCTATAAATT<br>ATAACCACTTGAATATAAACAAAAAAAACACACAAAGGTCTAGC<br>GGAATTTACAGAGGGTCTAGCAGAATTTACAAGTTTTCCAGCAA<br>AGGTCTAGCAGAATTTACAGATACCCACAACTCAAAGGAAAAG<br>GACTAGTAATTATCATTGACTAGCCCATCTCAATTGGTATAGTGA<br>TTAAAATCACCTAGACCAATTGAGATGTATGTCTGAATTAGTTGT<br>TTTCAAAGCAAATGAACTAGCGATTAGTCGCTATGACTTAACGG<br>AGCATGAAACCAAGCTAATTTTATGCTGTGTGGCACTACTCAAC<br>CCCACGATTGAAAACCCTACAAGGAAAGAACGGACGGTATCGT<br>TCACTTATAACCAATACGTTCAGATGATGAACATCAGTAGGGAA<br>AATGCTTATGGTGTATTAGCTAAAGCAACCAGAGAGCTGATGAC<br>GAGAACTGTGGAAATCAGGAATCCTTTGGTTAAAGGCTTTGAG<br>ATTTTCCAGTGGACAAACTATGCCAAGTTCTCAAGCGAAAAATT<br>AGAATTAGTTTTTAGTGAAGAGATATTGCCTTATCTTTTCCAGTT<br>AAAAAAATTCATAAAATATAATCTGGAACATGTTAAGTCTTTTGA<br>AAACAAATACTCTATGAGGATTTATGAGTGGTTATTAAAGAAC<br>TAACACAAAAGAAAACTCACAAGGCAAATATAGAGATTAGCCTT<br>GATGAATTTAAGTTCATGTTAATGCTTGAAAATAACTACCATGA<br>GTTTAAAAGGCTTAACCAATGGGTTTTGAAACCAATAAGTAAAG<br>ATTTAAACACTTACAGCAATATGAAATTGGTGGTTGATAAGCGA<br>GGCCGCCCGACTGATACGTTGATTTTCCAAGTTGAACTAGATAG |

| SEQ ID NO | Organism | Other Information | Sequence |
|---|---|---|---|
| | | | ACAAATGGATCTCGTAACCGAACTTGAGAACAACCAGATAAAAA |
| | | | TGAATGGTGACAAAATACCAACAACCATTACATCAGATTCCTAC |
| | | | CTACATAACGGACTAAGAAAAACACTACACGATGCTTTAACTGC |
| | | | AAAAATTCAGCTCACCAGTTTTGAGGCAAAATTTTTGAGTGACA |
| | | | TGCAAAGTAAGTATGATCTCAATGGTTCGTTCTCATGGCTCACG |
| | | | CAAAAACAACGAACCACACTAGAGAACATACTGGCTAAATACG |
| | | | GAAGGATCTGAGGTTCTTATGGCTCTTGTATCTATCAGTGAAGC |
| | | | ATCAAGACTAACAAACAAAAGTAGAACAACTGTTCACCGTTACA |
| | | | TATCAAAGGGAAAACTGTCCATATGCACAGATGAAAACGGTGT |
| | | | AAAAAAGATAGATACATCAGAGCTTTTACGAGTTTTTGGTGCAT |
| | | | TTAAAGCTGTTCACCATGAACAGATCGACAATGTAACAGATGAA |
| | | | CAGCATGTAACACCTAATAGAACAGGTGAAACCAGTAAAACAA |
| | | | AGCAACTAGAACATGAAATTGAACACCTGAGACAACTTGTTACA |
| | | | GCTCAACAGTCACACATAGACAGCCTGAAACAGGCGATGCTGCT |
| | | | TATCGAATCAAAGCTGCCGACAACACGGGAGCCAGTGACGCCT |
| | | | CCCGTGGGGAAAAAATCATGGCAATTCTGGAAGAAATAGCGCT |
| | | | TTCAGCCTGTGGGCGGACAAAATAGTTGGGAACTGGGAGGGGT |
| | | | GGAAATGGAGTTTTTAAGGATTATTTAGGGAAGAGTGACAAAA |
| | | | TAGATGGGAACTGGGTGTAGCGTCGTAAGCTAATACGAAAATT |
| | | | AAAAATGACAAAATAGTTTGGAACTAGATTTCACTTATCTGGTT |
| | | | GGTCGACACTAGTATTACCCTGTTATCCCTAGATTTAAATGATAT |
| | | | CGGATCCTAGTAAGCCACGTTTTAATTAATCAGATGGGTCAATA |
| | | | GCGGCCGCCAATTCGCGCGCGAAGGCGAAGCGGCATGCATTTA |
| | | | CGTTGACACCATCGAATGGTGCAAAACCTTTCGCGGTATGGCAT |
| | | | GATAGCGCCCGGAAGAGAGTCAATTCAGGGTGGTGAATGTGAA |
| | | | ACCAGTAACGTTATACGATGTCGCAGAGTATGCCGGTGTCTCTT |
| | | | ATCAGACCGTTTCCCGCGTGGTGAACCAGGCCAGCCACGTTTCT |
| | | | GCGAAAACGCGGGAAAAAGTGGAAGCGGCGATGGCGGAGCTG |
| | | | AATTACATTCCCAACCGCGTGGCACAACAACTGGCGGGCAAACA |
| | | | GTCGTTGCTGATTGGCGTTGCCACCTCCAGTCTGGCCCTGCACG |
| | | | CGCCGTCGCAAATTGTCGCGGCGATTAAATCTCGCGCCGATCAA |
| | | | CTGGGTGCCAGCGTGGTGGTGTCGATGGTAGAACGAAGCGGC |
| | | | GTCGAAGCCTGTAAAGCGGCGGTGCACAATCTTCTCGCGCAAC |
| | | | GCGTCAGTGGGCTGATCATTAACTATCCGCTGGATGACCAGGAT |
| | | | GCCATTGCTGTGGAAGCTGCCTGCACTAATGTTCCGGCGTTATT |
| | | | TCTTGATGTCTCTGACCAGACACCCATCAACAGTATTATTTTCTCC |
| | | | CATGAAGACGGTACGCGACTGGGCGTGGAGCATCTGGTCGCAT |
| | | | TGGGTCACCAGCAAATCGCGCTGTTAGCGGGCCCATTAAGTTCT |
| | | | GTCTCGGCGCGTCTGCGTCTGGCTGGCTGGCATAAATATCTCAC |
| | | | TCGCAATCAAATTCAGCCGATAGCGGAACGGGAAGGCGACTGG |
| | | | AGTGCCATGTCCGGTTTTCAACAAACCATGCAAATGCTGAATGA |
| | | | GGGCATCGTTCCCACTGCGATGCTGGTTGCCAACGATCAGATGG |
| | | | CGCTGGGCGCAATGCGCGCCATTACCGAGTCCGGGCTGCGCGT |
| | | | TGGTGCGGATATCTCGGTAGTGGGATACGACGATACCGAAGAC |
| | | | AGCTCATGTTATATCCCGCCGTCAACCACCATCAAACAGGATTTT |
| | | | CGCCTGCTGGGGCAAACCAGCGTGGACCGCTTGCTGCAACTCTC |
| | | | TCAGGGCCAGGCGGTGAAGGGCAATCAGCTGTTGCCCGTCTCA |
| | | | CTGGTGAAAAGAAAAACCACCCTGGCGCCCAATACGCAAACCG |
| | | | CCTCTCCCCGCGCGTTGGCCGATTCATTAATGCAGCTGGCACGA |
| | | | CAGGTTTCCCGACTGGAAAGCGGGCAGTGAGCGCAACGCAATT |
| | | | AATGTGAGTTAGCGCGAATTGATCTGGTTTGACAGCTTATCATC |
| | | | GACTGCACGGTGCACCAATGCTTCTGGCGTCAGGCAGCCATCG |
| | | | GAAGCTGTGGTATGGCTGTGCAGGTCGTAAATCACTGCATAATT |
| | | | CGTGTCGCTCAAGGCGCACTCCCGTTCTGGATAATGTTTTTTGCG |
| | | | CCGACATCATAACGGTTCTGGCAAATATTCTGAAATGAGCTGTT |
| | | | GACAATTAATCATCCGGCTCGTATAATGTGTGGAATTGTGAGCG |
| | | | GATAACAATTTCACACAGGAAACAGCGCCGCTGAGAAAAAGCG |
| | | | AAGCGGCACTGCTCTTTAACAATTTATCAGACAATCTGTGTGGG |
| | | | CACTCGACCGGAATTATCGATTAACTTTATTATTAAAAATTAAAG |
| | | | AGGTATATATTAATGTATCGATTAAATAAGGAGGAATAAAccAT |
| | | | GGCGGACACGTTATTGATTCTGGGTGATAGCCTGAGCGCCGGG |
| | | | TATCGAATGTCTGCCAGCGCGGCCTGGCCTGCCTTGTTGAATGA |
| | | | TAAGTGGCAGAGTAAAACGTCGGTAGTTAATGCCAGCATCAGC |
| | | | GGCGACACCTCGCAACAAGGACTGGCGCGCCTTCCGGCTCTGCT |
| | | | GAAACAGCATCAGCCGCGTTGGGTGCTGGTTGAACTGGGCGGC |
| | | | AATGACGGTTTGCGTGGTTTTCAGCCACAGCAAACCGAGCAAAC |
| | | | GCTGCGCCAGATTTTGCAGGATGTCAAAGCCGCCAACGCTGAAC |
| | | | CATTGTTAATGCAAATACGTCTGCCTGCAAACTATGGTCGCCGTT |
| | | | ATAATGAAGCCTTTAGCGCCATTTACCCCAAACTCGCCAAAGAG |
| | | | TTTGATGTTCCGCTGCTGCCCTTTTTTATGGAAGAGGTCTACCTC |
| | | | AAGCCACAATGGATGCAGGATGACGGTATTCATCCCAACCGCG |
| | | | ACGCCCAGCCGTTTATTGCCGACTGGATGGCGAAGCAGTTGCA |
| | | | GCCTTTAGTAAATCATGACTCATAAtgactctagaaataatttaaatgga |
| | | | attcGAAGCTTGGGCCCGAACAAAAACTCATCTCAGAAGAGGAT |

SEQUENCE TABLE

| SEQ ID NO | Organism | Other Information | Sequence |
|---|---|---|---|
| | | | CTGAATAGCGCCGTCGACCATCATCATCATCATCATTGAGTTTAA ACGGTCTCCAGCTTGGCTGTTTTGGCGGATGAGAAGATTTTC AGCCTGATACAGATTAAATCAGAACGCAGAAGCGGTCTGATAA AACAGAATTTGCCTGGCGGCAGTAGCGCGGTGGTCCCACCTGA CCCCATGCCGAACTCAGAAGTGAAACGCCGTAGCGCCGATGGT AGTGTGGGGTCTCCCCATGCGAGAGTAGGGAACTGCCAGGCAT CAAATAAAACGAAAGGCTCAGTCGAAAGACTGGGCCTTTCGTTT TATCTGTTGTTTGTCGGTGAACGCTCTCCTGAttaattaagacgtcccg tcaagtcagcgtaatgcCCTAGGAGGCGCGCCACGGCCGCGTCGACC CCACGCCCCTCTTTAATACGACGGGCAATTTGCACTTCAGAAAAT GAAGAGTTTGCTTTAGCCATAACAAAAGTCCAGTATGCTTTTTCA CAGCATAACTGGACTGATTTCAGTTTACAACTATTCTGTCTAGTT TAAGACTTTATTGTCATAGTTTAGATCTATTTTGTTCAGTTTAAG ACTTTATTGTCCGCCCACA |
| 82 | Artificial sequence | Del-fadE-F primer | AAAAACAGCAACAATGTGAGCTTTGTTGTAATTATATTGTAAAC ATATTGATTCCGGGGATCCGTCGACC |
| 83 | Artificial sequence | Del-fadE-R primer | AAACGGAGCCTTTCGGCTCCGTTATTCATTTACGCGGCTTCAACT TTCCTGTAGGCTGGAGCTGCTTC |
| 84 | Artificial sequence | fadE-L2 primer | CGGGCAGGTGCTATGACCAGGAC |
| 85 | Artificial sequence | fadE-R1 primer | CGCGGCGTTGACCGGCAGCCTGG |
| 86 | Artificial sequence | Del-tonA-F primer | ATCATTCTCGTTTACGTTATCATTCACTTTACATCAGAGATATACC AATGATTCCGGGGATCCGTCGACC |
| 87 | Artificial sequence | Del-tonA-R primer | GCACGGAAATCCGTGCCCCAAAAGAGAAATTAGAAACGGAAGG TTGCGGTTGTAGGCTGGAGCTGCTTC |
| 88 | Artificial sequence | tonA-verF primer | CAACAGCAACCTGCTCAGCAA |
| 89 | Artificial sequence | tonA-verR primer | AAGCTGGAGCAGCAAAGCGTT |
| 90 | Artificial sequence | lacI-forward primer | GGCTGGCTGGCATAAATATCTC |
| 91 | Artificial sequence | lacZ-reverse primer | GCGTTAAAGTTGTTCTGCTTCATCAGCAGGATATCCTGCACCATC GTCTGGATTTTGAACTTTTGCTTTGCCACGGAAC |
| 92 | Artificial sequence | primer | TGAATTCCATGGCGCAACTCACTCTTCTTTTAGTCG |
| 93 | Artificial sequence | primer | CAGTACCTCGAGTCTTCGTATACATATGCGCTCAGTCAC |
| 94 | Artificial sequence | primer | CCTTGGGGCATATGAAAGCTG |
| 95 | Artificial sequence | primer | TTTAGTCATCTCGAGTGCACCTCACCTTT |
| 96 | Artificial sequence | pTrc_F primer | TTTCGCGAGGCCGGCCCCGCCAACACCCGCTGACG |
| 97 | Artificial sequence | pTrc_R primer | AAGGACGTCTTAATTAATCAGGAGAGCGTTCACCGACAA |
| 98 | Artificial sequence | LF302 primer | atatgacgtcGGCATCCGCTTACAGACA |
| 99 | Artificial sequence | LF303 primer | aattcttaagTCAGGAGAGCGTTCACCGACAA |
| 100 | Artificial sequence | TREE044 primer | GAGGAATAAACCATGAACGCAGGAATTTTAGGAGTAG |
| 101 | Artificial sequence | primer61 | CCCAAGCTTCGAATTCTTACTTACCCCAACGAATGATTAGG |

-continued

SEQUENCE TABLE

| SEQ ID NO | Organism | Other Information | Sequence |
|---|---|---|---|
| 102 | Artificial sequence | TREE025 primer | CCTGACAGTGCGGGCTTTTTTTTCGACCAAAGGTAACGAGGTA ACAACCGTGTAGGCTGGAGCTGCTTCG |
| 103 | Artificial sequence | TREE026 primer | GTATATATTAATGTATCGATTAAATAAGGAGGAATAAACCATGC GAGTGTTGAAGTTCGGCG |
| 104 | Artificial sequence | TREE027 primer | CTGATGTACCGCCGAACTTCAACACTCGCATGGTTTATTCCTCCT TATTTAATCGATAC |
| 105 | Artificial sequence | TREE028 primer | GCGCCCGTATTTCGTGGTGCTGATTAC |
| 106 | Artificial sequence | TREE029 primer | GTAATCAGCACCACGTAAATACGGGCGC |
| 107 | Artificial sequence | TREE030 primer | TCAGACTCCTAACTTCCATGAGAGG |
| 108 | Artificial sequence | Km_trc_over R primer | AATATTTGCCAGAACCGTTATGATGTCGGCATTCCGGGGATCCG TCGACC |
| 109 | Artificial sequence | Km_trc_over F primer | CTTCGAACTGCAGGTCGACGGATCCCCGGAATGCCGACATCATA ACGGTTCTGGC |
| 110 | Artificial sequence | EG238 primer | GCTGATCATTAACTATCCGCTGGATGACC |
| 111 | Artificial sequence | TREE017 primer | ACTGGAAAGCGGGCAGTGAGCGCAACGCAATTAATGTAAG |
| 112 | Artificial sequence | TREE018 primer | TCACTGCCCGCTTTCC |
| 113 | Artificial sequence | TREE019 primer | ACCGGCAGATCGTATGTAATATGCATGGTTTATTCCTCCTTATTT AATCGATACA |
| 114 | Artificial sequence | TREE020 primer | ATGCATATTACATACGATCTGCC |
| 115 | Artificial sequence | TREE021 primer | GGTCGACGGATCCCCGGAATTAAGCGTCAACGAAACCG |
| 116 | Artificial sequence | TREE022 primer | GAAGCAGCTCCAGCCTACACCAGACGATGGTGCAGGAT |
| 117 | Artificial sequence | TREE023 primer | GCAAAGACCAGACCGTTCATA |
| 118 | Artificial sequence | Kan/Chlor1 primer | ATTCCGGGGATCCGTCGACC |
| 119 | Artificial sequence | Kan/Chlor4 primer | TGTAGGCTGGAGCTGCTTCG |
| 120 | Artificial sequence | TREE133 primer | AAAAACAGCAACAATGTGAGCTTTGTTGTAATTATATTGTAAAC ATATTGTCCGCTGTTTCTGCATTCTTACgt |
| 121 | Artificial sequence | TREE134 primer | GATGACGACGAACACGCATTaagGAGGTGAATAAGGAGGAATA AcatATGAAAGCTGGCATTCTTGGTGTTG |
| 122 | Artificial sequence | TREE135 primer | GTAACGTCCAACACCAAGAATGCCAGCTTTCATatgTTATTCCTCC TTATTCACCTCcttAATGCGTGTTCG |
| 123 | Artificial sequence | TREE136 primer | AAACGGAGCCTTTCGGCTCCGTTATTCATTTACGCGGCTTCAACT TTCCGTTATCGGCCCCAGCGGATTG |
| 124 | Artificial sequence | TREE137 primer | CGCAGTTTGCAAGTGACGGTATATAACCGAAAAGTGACTGAGC GTACatgATTCCGGGGATCCGTCGACC |
| 125 | Artificial sequence | TREE138 primer | GCAAATTGCGTCATGTTTTAATCCTTATCCTAGAAACGAACCAGC GCGGATGTAGGCTGGAGCTGCTTCG |

SEQUENCE TABLE

| SEQ ID NO | Organism | Other Information | Sequence |
|---|---|---|---|
| 126 | Artificial sequence | TREE139 primer | GCAGCGACAAGTTCCTCAGC |
| 127 | Artificial sequence | TREE140 primer | CCGCAGAAGCTTCAGCAAACG |
| 128 | Artificial sequence | fadE-L2 primer | CGGGCAGGTGCTATGACCAGGAC |
| 129 | Artificial sequence | fadE-R2 primer | GGGCAGGATAAGCTCGGGAGG |
| 130 | Artificial sequence | Km_trc_over F primer | CTTCGAACTGCAGGTCGACGGATCCCCGGAATGCCGACATCATA ACGGTTCTGGC |
| 131 | Artificial sequence | Km_trc_over R primer | AATATTTGCCAGAACCGTTATGATGTCGGCATTCCGGGGATCCG TCGACC |
| 132 | Artificial sequence | TREE032 primer | GTATATATTAATGTATCGATTAAATAAGGAGGAATAAACCatgat ggtaaggatatttgatacaacac |
| 133 | Artificial sequence | TREE033 primer | ctaagtgttgtatcaaatatccttaccatcatGGTTTATTCCTCCTTATTTAAT CGATAC |
| 134 | Artificial sequence | TREE034 primer | gatttgttggctatagttagagaagttactggaaaattgTAACAAGGAAACCG TGTGATGTCGAAG |
| 135 | Artificial sequence | TREE035 primer | GTAATTCTTCGACATCACACGGTTTCCTTGTTAcaattttccagtaactt ctctaactatag |
| 136 | Artificial sequence | TREE104 primer | GGTAGCGAAGGTTTTGCCCGGC |
| 137 | Artificial sequence | TREE106 primer | GATTGGTGCCCCAGGTGACCTG |
| 138 | Artificial sequence | TREE146 primer | GAGTTGCAACGCAAAGCTCAACACAACGAAAACAACAAGGAAA CCGTGTGaGTGTAGGCTGGAGCTGCTTCG |
| 139 | Artificial sequence | TREE151 primer | CTTCCACGGCGTCGGCCTG |
| 140 | Artificial sequence | IFF primer | GGGTCAATAGCGGCCGCCAATTCGCGCGCGAAGGCG |
| 141 | Artificial sequence | IFR primer | TGGCGCGCCTCCTAGGGCATTACGCTGACTTGACGGG |
| 142 | Artificial sequence | ScpBC-KOfwd primer | GCTCAGTGAATTTATCCAGACGCAATATTTTGATTAAAGGAATTT TTATGATTCCGGGGATCCGTCGACC |
| 143 | Artificial sequence | ScpBC-KOrc primer | ATTGCTGAAGATCGTGACGGGACGAGTCATTAACCCAGCATCG AGCCGGTTGT AGGCTG GAGCTGCTTC |
| 144 | Artificial sequence | ScpBC check -60 fwd primer | CGGGTTCTGACTTGTAGCG |
| 145 | Artificial sequence | ScpBC check +60 rc primer | CCAACTTCGAAGCAATGATTGATG |

What is claimed is:

1. A recombinant *E. coli* host cell transformed with:
   (a) polynucleotides encoding polypeptides having enzymatic activity effective to produce an increased amount of propionyl-CoA in the recombinant *E. coli* host cell compared to the amount of propionyl-CoA produced in a parental *E. coli* host cell lacking or having a reduced amount of said enzymatic activity, wherein said polynucleotides encode polypeptides having aspartokinase activity, homoserine dehydrogenase activity, homoserine kinase activity, threonine synthase activity, and threonine deaminase activity,
   (b) a polynucleotide encoding a polypeptide having β-ketoacyl-ACP synthase activity that utilizes propionyl-CoA as a substrate and has 80% identity to SEQ ID NO:7, and
   (c) a polynucleotide encoding a polypeptide having thioesterase enzyme activity,
   wherein the recombinant *E. coli* host cell produces a fatty acid composition comprising odd-number chain length fatty acids and even numbered chain length fatty acids when cultured in the presence of a carbon source under conditions effective to express the polynucleotides according to (a), (b), and (c), and
   wherein at least 10% of the fatty acids in the fatty acid composition are odd-number chain length fatty acids.

2. The recombinant *E. coli* host cell of claim 1, wherein at least 20% of the fatty acids in the fatty acid composition are odd-number chain length fatty acids.

3. The recombinant *E. coli* host cell of claim 1, wherein the cell produces at least 100 mg/L odd-number chain length fatty acids when cultured in the presence of a carbon source under conditions effective to express the polynucleotides according to (a), (b), and (c).

4. A method of making a fatty acid composition comprising odd-number chain length fatty acids, the method comprising: obtaining the recombinant *E. coli* host cell of claim 1, culturing the recombinant *E. coli* host cell in a culture medium containing a carbon source under conditions effective to express polynucleotides encoding polypeptides having aspartokinase activity, homoserine dehydrogenase activity, homoserine kinase activity, threonine synthase activity, threonine deaminase activity, β-ketoacyl-ACP synthase activity, and thioesterase activity to produce a fatty acid composition comprising odd-number chain length fatty acids and even-numbered chain fatty acids, wherein at least 10% of the fatty acids in the composition are odd-number chain length fatty acids, and optionally recovering the composition from the culture medium.

5. A method of making a recombinant *E. coli* host cell which produces a higher proportion of odd-number chain length fatty acids than produced by a parental *E. coli* host cell, the method comprising:
   obtaining a parental *E. coli* host cell, and
   transforming the parental *E. coli* host cell with
   (a) polynucleotides encoding polypeptides having enzymatic activity effective to produce an increased amount propionyl-CoA in the recombinant *E. coli* host cell compared to the amount of propionyl-CoA produced in a parental *E. coli* host cell lacking or having a reduced amount of said enzymatic activity, wherein said polynucleotides encode polypeptides having aspartokinase activity, homoserine dehydrogenase activity, homoserine kinase activity, threonine synthase activity, and threonine deaminase activity,
(b) a polynucleotide encoding a polypeptide having β-ketoacyl-ACP synthase activity that utilizes propionyl-CoA as a substrate and has 80% identity to SEQ ID NO:7, and
(c) a polynucleotide encoding a polypeptide having thioesterase enzyme activity, wherein the recombinant E. coli host cell produces a higher proportion of odd-number chain length fatty acids when cultured in the presence of a carbon source under conditions effective to express the polynucleotides according to (a), (b), and (c), relative to the proportion of odd-number chain length fatty acids produced by the parental E. coli host cell cultured under the same conditions.

6. The method of claim 5,
wherein at least one polypeptide is exogenous to the parental E. coli host cell, or wherein expression of at least one endogenous polynucleotide is increased in the recombinant E. coli cell as compared to the expression of the polynucleotide in the parental E. coli cell.

* * * * *

SEQUENCE LISTING

<160> NUMBER OF SEQ ID NOS: 145

<210> SEQ ID NO 1
<211> LENGTH: 317
<212> TYPE: PRT
<213> ORGANISM: Escherichia coli
<220> FEATURE:
<223> OTHER INFORMATION: Beta ketoacyl-ACP synthase III

<400> SEQUENCE: 1

Met Tyr Thr Lys Ile Ile Gly Thr Gly Ser Tyr Leu Pro Glu Gln Val
1               5                   10                  15

Arg Thr Asn Ala Asp Leu Glu Lys Met Val Asp Thr Ser Asp Glu Trp
            20                  25                  30

Ile Val Thr Arg Thr Gly Ile Arg Glu Arg His Ile Ala Ala Pro Asn
        35                  40                  45

Glu Thr Val Ser Thr Met Gly Phe Glu Ala Ala Thr Arg Ala Ile Glu
    50                  55                  60

Met Ala Gly Ile Glu Lys Asp Gln Ile Gly Leu Ile Val Val Ala Thr
65                  70                  75                  80

Thr Ser Ala Thr His Ala Phe Pro Ser Ala Ala Cys Gln Ile Gln Ser
                85                  90                  95

Met Leu Gly Ile Lys Gly Cys Pro Ala Phe Asp Val Ala Ala Ala Cys
            100                 105                 110

Ala Gly Phe Thr Tyr Ala Leu Ser Val Ala Asp Gln Tyr Val Lys Ser
        115                 120                 125

Gly Ala Val Lys Tyr Ala Leu Val Val Gly Ser Asp Val Leu Ala Arg
    130                 135                 140

Thr Cys Asp Pro Thr Asp Arg Gly Thr Ile Ile Ile Phe Gly Asp Gly
145                 150                 155                 160

Ala Gly Ala Ala Val Leu Ala Ala Ser Glu Glu Pro Gly Ile Ile Ser
                165                 170                 175

Thr His Leu His Ala Asp Gly Ser Tyr Gly Glu Leu Leu Thr Leu Pro
            180                 185                 190

Asn Ala Asp Arg Val Asn Pro Glu Asn Ser Ile His Leu Thr Met Ala
        195                 200                 205

Gly Asn Glu Val Phe Lys Val Ala Val Thr Glu Leu Ala His Ile Val
    210                 215                 220

Asp Glu Thr Leu Ala Ala Asn Asn Leu Asp Arg Ser Gln Leu Asp Trp
225                 230                 235                 240

Leu Val Pro His Gln Ala Asn Leu Arg Ile Ile Ser Ala Thr Ala Lys
                245                 250                 255

Lys Leu Gly Met Ser Met Asp Asn Val Val Val Thr Leu Asp Arg His
            260                 265                 270

Gly Asn Thr Ser Ala Ala Ser Val Pro Cys Ala Leu Asp Glu Ala Val
        275                 280                 285

Arg Asp Gly Arg Ile Lys Pro Gly Gln Leu Val Leu Leu Glu Ala Phe
    290                 295                 300

Gly Gly Gly Phe Thr Trp Gly Ser Ala Leu Val Arg Phe
305                 310                 315

<210> SEQ ID NO 2
<211> LENGTH: 312
<212> TYPE: PRT
<213> ORGANISM: Bacillus subtilis
<220> FEATURE:
<223> OTHER INFORMATION: Beta ketoacyl-ACP synthase III (FabH1)

<400> SEQUENCE: 2

Met Lys Ala Gly Ile Leu Gly Val Gly Arg Tyr Ile Pro Glu Lys Val
1               5                   10                  15

Leu Thr Asn His Asp Leu Glu Lys Met Val Glu Thr Ser Asp Glu Trp
            20                  25                  30

Ile Arg Thr Arg Thr Gly Ile Glu Glu Arg Ile Ala Ala Asp Asp
            35                  40                  45

Val Phe Ser Ser His Met Ala Val Ala Ala Lys Asn Ala Leu Glu
 50                  55                  60

Gln Ala Glu Val Ala Ala Glu Asp Leu Asp Met Ile Leu Val Ala Thr
 65                  70                  75                  80

Val Thr Pro Asp Gln Ser Phe Pro Thr Val Ser Cys Met Ile Gln Glu
                 85                  90                  95

Gln Leu Gly Ala Lys Lys Ala Cys Ala Met Asp Ile Ser Ala Ala Cys
                100                 105                 110

Ala Gly Phe Met Tyr Gly Val Thr Gly Lys Gln Phe Ile Glu Ser
            115                 120                 125

Gly Thr Tyr Lys His Val Leu Val Val Gly Val Glu Lys Leu Ser Ser
            130                 135                 140

Ile Thr Asp Trp Glu Asp Arg Asn Thr Ala Val Leu Phe Gly Asp Gly
145                 150                 155                 160

Ala Gly Ala Ala Val Val Gly Pro Val Ser Asp Asp Arg Gly Ile Leu
                165                 170                 175

Ser Phe Glu Leu Gly Ala Asp Gly Thr Gly Gly Gln His Leu Tyr Leu
                180                 185                 190

Asn Glu Lys Arg His Thr Ile Met Asn Gly Arg Glu Val Phe Lys Phe
            195                 200                 205

Ala Val Arg Gln Met Gly Glu Ser Cys Val Asn Val Ile Glu Lys Ala
            210                 215                 220

Gly Leu Ser Lys Glu Asp Val Asp Phe Leu Ile Pro His Gln Ala Asn
225                 230                 235                 240

Ile Arg Ile Met Glu Ala Ala Arg Glu Arg Leu Glu Leu Pro Val Glu
                245                 250                 255

Lys Met Ser Lys Thr Val His Lys Tyr Gly Asn Thr Ser Ala Ala Ser
                260                 265                 270

Ile Pro Ile Ser Leu Val Glu Glu Leu Glu Ala Gly Lys Ile Lys Asp
            275                 280                 285

Gly Asp Val Val Met Val Gly Phe Gly Gly Gly Leu Thr Trp Gly
            290                 295                 300

Ala Ile Ala Ile Arg Trp Gly Arg
305                 310

<210> SEQ ID NO 3
<211> LENGTH: 325
<212> TYPE: PRT
<213> ORGANISM: Bacillus subtilis
<220> FEATURE:
<223> OTHER INFORMATION: Beta ketoacyl-ACP synthase III (FabH2)

<400> SEQUENCE: 3

Met Ser Lys Ala Lys Ile Thr Ala Ile Gly Thr Tyr Ala Pro Ser Arg
 1               5                  10                  15

Arg Leu Thr Asn Ala Asp Leu Glu Lys Ile Val Asp Thr Ser Asp Glu
            20                  25                  30

Trp Ile Val Gln Arg Thr Gly Met Arg Glu Arg Ile Ala Asp Glu
            35                  40                  45

His Gln Phe Thr Ser Asp Leu Cys Ile Glu Ala Val Lys Asn Leu Lys
            50                  55                  60

Ser Arg Tyr Lys Gly Thr Leu Asp Asp Val Asp Met Ile Leu Val Ala
 65                  70                  75                  80

Thr Thr Thr Ser Asp Tyr Ala Phe Pro Ser Thr Ala Cys Arg Val Gln
            85                  90                  95

Glu Tyr Phe Gly Trp Glu Ser Thr Gly Ala Leu Asp Ile Asn Ala Thr
            100                 105                 110

Cys Ala Gly Leu Thr Tyr Gly Leu His Leu Ala Asn Gly Leu Ile Thr
            115                 120                 125

Ser Gly Leu His Gln Lys Ile Leu Val Ile Ala Gly Glu Thr Leu Ser
        130                 135                 140

Lys Val Thr Asp Tyr Thr Asp Arg Thr Thr Cys Val Leu Phe Gly Asp
145                 150                 155                 160

Ala Ala Gly Ala Leu Leu Val Glu Arg Asp Glu Glu Thr Pro Gly Phe
                165                 170                 175

Leu Ala Ser Val Gln Gly Thr Ser Gly Asn Gly Gly Asp Ile Leu Tyr
            180                 185                 190

Arg Ala Gly Leu Arg Asn Glu Ile Asn Gly Val Gln Leu Val Gly Ser
            195                 200                 205

Gly Lys Met Val Gln Asn Gly Arg Glu Val Tyr Lys Trp Ala Ala Arg
        210                 215                 220

Thr Val Pro Gly Glu Phe Glu Arg Leu Leu His Lys Ala Gly Leu Ser
225                 230                 235                 240

Ser Asp Asp Leu Asp Trp Phe Val Pro His Ser Ala Asn Leu Arg Met
                245                 250                 255

Ile Glu Ser Ile Cys Glu Lys Thr Pro Phe Pro Ile Glu Lys Thr Leu
            260                 265                 270

Thr Ser Val Glu His Tyr Gly Asn Thr Ser Ser Val Ser Ile Val Leu
            275                 280                 285

Ala Leu Asp Leu Ala Val Lys Ala Gly Lys Leu Lys Lys Asp Gln Ile
        290                 295                 300

Val Leu Leu Phe Gly Phe Gly Gly Leu Thr Tyr Thr Gly Leu Leu
305                 310                 315                 320

Ile Lys Trp Gly Met
            325

<210> SEQ ID NO 4
<211> LENGTH: 320
<212> TYPE: PRT
<213> ORGANISM: Streptomyces coelicolor
<220> FEATURE:
<223> OTHER INFORMATION: Beta ketoacyl-ACP synthase III

<400> SEQUENCE: 4

Met Ala Arg Gly Ala Gly Arg Leu Thr Gly Ile Gly Val Tyr Arg Pro
1               5                   10                  15

Gly Gly Leu Leu Thr Ser Ala Glu Leu Asp Thr Arg Phe Gly His Glu
            20                  25                  30

Asp Gly Tyr Ile Glu Gln Ile Thr Gly Ile Arg Thr Arg Leu Lys Ala
        35                  40                  45

Asp Pro Asp Asp Thr Phe Val Glu Met Ala Ala Gln Ala Ala Asp Lys
    50                  55                  60

Ala Leu Ala His Ala Gly Val Leu Ala Glu Asp Leu Asp Cys Val Leu
65                  70                  75                  80

Phe Ser Ser Ala Ser Ser Val Gly Gln Ala Ser Cys Arg Ala Ala Ser
                85                  90                  95

Leu Thr His Arg Ile Gly Ala Gly Arg Ala Gly Gly Phe Asp Leu Asn
            100                 105                 110

Gly Gly Cys Ala Gly Phe Gly Tyr Gly Leu Thr Leu Ala Ser Gly Leu

```
                115                 120                 125
Ile Ala Ala Gln Gln Ala Arg Gln Ile Leu Val Val Ala Ala Glu Arg
        130                 135                 140

Leu Ser Asp Ile Thr Asp Pro Asp Asp Cys Gly Thr Val Met Val Phe
145                 150                 155                 160

Gly Asp Ala Ala Gly Ala Ala Val Val Ser Ala Ala Glu His Pro Gly
                165                 170                 175

Ile Gly Pro Ala Val Trp Gly Thr His Gly Pro Gly Glu Pro Trp Met
                180                 185                 190

Thr Ser Ala Pro Pro Lys Pro Gly Ala Ala Arg Pro Tyr Met His Met
                195                 200                 205

Asp Gly Thr Arg Val Val Arg Trp Phe Gly Ser Gln Met Pro Gln Val
        210                 215                 220

Ala Arg Asp Ala Leu Glu Ala Ala Gly Leu Thr Trp Asp Asp Ile Gly
225                 230                 235                 240

Ala Phe Val Pro His Gln Cys Asn Gly Arg Leu Ile Asp Ala Met Val
                245                 250                 255

Arg Arg Leu Arg Pro Pro Glu His Val Ala Ile Ala Arg Ser Ile Val
                260                 265                 270

Thr Asp Gly Asn Thr Ser Ser Ala Ser Ile Pro Leu Ala Leu Glu Ser
                275                 280                 285

Leu Leu Ala Ser Ala Thr Val Arg Pro Gly Asp Lys Ala Leu Leu Leu
                290                 295                 300

Gly Phe Gly Ala Gly Leu Thr Trp Cys Ala Gln Val Val Glu Leu Pro
305                 310                 315                 320

<210> SEQ ID NO 5
<211> LENGTH: 333
<212> TYPE: PRT
<213> ORGANISM: Streptomyces glaucescens
<220> FEATURE:
<223> OTHER INFORMATION: Beta ketoacyl-ACP synthase III

<400> SEQUENCE: 5

Met Ser Lys Ile Lys Pro Ala Lys Gly Ala Pro Tyr Ala Arg Ile Leu
1               5                   10                  15

Gly Val Gly Gly Tyr Arg Pro Thr Arg Val Val Pro Asn Glu Val Ile
                20                  25                  30

Leu Glu Thr Ile Asp Ser Ser Asp Glu Trp Ile Arg Ser Arg Ser Gly
            35                  40                  45

Ile Gln Thr Arg His Trp Ala Asn Asp Glu Glu Thr Val Ala Ala Met
    50                  55                  60

Ser Ile Glu Ala Ser Gly Lys Ala Ile Ala Asp Ala Gly Ile Thr Ala
65                  70                  75                  80

Ala Gln Val Gly Ala Val Ile Val Ser Thr Val Thr His Phe Lys Gln
                85                  90                  95

Thr Pro Ala Val Ala Thr Glu Ile Ala Asp Lys Leu Gly Thr Asn Lys
                100                 105                 110

Ala Ala Ala Phe Asp Ile Ser Ala Gly Cys Ala Gly Phe Gly Tyr Gly
                115                 120                 125

Leu Thr Leu Ala Lys Gly Met Ile Val Glu Gly Ser Ala Glu Tyr Val
            130                 135                 140

Leu Val Ile Gly Val Glu Arg Leu Ser Asp Leu Thr Asp Leu Glu Asp
145                 150                 155                 160

Arg Ala Thr Ala Phe Leu Phe Gly Asp Gly Ala Gly Ala Val Val Val
                165                 170                 175
```

```
Gly Pro Ser Asn Glu Pro Ala Ile Gly Pro Thr Ile Trp Gly Ser Glu
            180                 185                 190

Gly Asp Lys Ala Glu Thr Ile Lys Gln Thr Val Pro Trp Thr Asp Tyr
        195                 200                 205

Arg Glu Gly Gly Val Glu Arg Phe Pro Ala Ile Thr Gln Glu Gly Gln
    210                 215                 220

Ala Val Phe Arg Trp Ala Val Phe Glu Met Ala Lys Val Ala Gln Gln
225                 230                 235                 240

Ala Leu Asp Ala Ala Gly Val Ala Ala Asp Leu Asp Val Phe Ile
            245                 250                 255

Pro His Gln Ala Asn Glu Arg Ile Ile Asp Ser Met Val Lys Thr Leu
        260                 265                 270

Lys Leu Pro Glu Ser Val Thr Val Ala Arg Asp Val Arg Thr Thr Gly
            275                 280                 285

Asn Thr Ser Ala Ala Ser Ile Pro Leu Ala Met Glu Arg Leu Leu Ala
290                 295                 300

Thr Gly Glu Ala Lys Ser Gly Asp Thr Ala Leu Val Ile Gly Phe Gly
305                 310                 315                 320

Ala Gly Leu Val Tyr Ala Ala Ser Val Val Thr Leu Pro
                325                 330

<210> SEQ ID NO 6
<211> LENGTH: 335
<212> TYPE: PRT
<213> ORGANISM: Streptomyces avermitilis
<220> FEATURE:
<223> OTHER INFORMATION: Beta ketoacyl-ACP synthase III

<400> SEQUENCE: 6

Met Ser Gly Gly Arg Ala Ala Val Ile Thr Gly Ile Gly Gly Tyr Val
1               5                   10                  15

Pro Pro Asp Leu Val Thr Asn Asp Asp Leu Ala Gln Arg Leu Asp Thr
            20                  25                  30

Ser Asp Ala Trp Ile Arg Ser Arg Thr Gly Ile Ala Glu Arg His Val
        35                  40                  45

Ile Ala Pro Gly Thr Ala Thr Ser Asp Leu Ala Val Glu Ala Gly Leu
    50                  55                  60

Arg Ala Leu Lys Ser Ala Gly Asp Glu His Val Asp Ala Val Val Leu
65                  70                  75                  80

Ala Thr Thr Thr Pro Asp Gln Pro Cys Pro Ala Thr Ala Pro Gln Val
            85                  90                  95

Ala Ala Arg Leu Gly Leu Gly Gln Val Pro Ala Phe Asp Val Ala Ala
            100                 105                 110

Val Cys Ser Gly Phe Leu Phe Gly Leu Ala Thr Ala Ser Gly Leu Ile
        115                 120                 125

Ala Ala Gly Val Ala Asp Lys Val Leu Leu Val Ala Ala Asp Ala Phe
    130                 135                 140

Thr Thr Ile Ile Asn Pro Glu Asp Arg Thr Thr Ala Val Ile Phe Ala
145                 150                 155                 160

Asp Gly Ala Gly Ala Val Val Leu Arg Ala Gly Ala Ala Asp Glu Pro
                165                 170                 175

Gly Ala Val Gly Pro Leu Val Leu Gly Ser Asp Gly Glu Leu Ser His
            180                 185                 190

Leu Ile Glu Val Pro Ala Gly Gly Ser Arg Gln Arg Ser Ser Gly Pro
        195                 200                 205
```

-continued

Thr Thr Asp Pro Asp Asp Gln Tyr Phe Arg Met Leu Gly Arg Asp Thr
210                 215                 220

Tyr Arg His Ala Val Glu Arg Met Thr Asp Ala Ser Gln Arg Ala Ala
225                 230                 235                 240

Glu Leu Ala Asp Trp Arg Ile Asp Asp Val Asp Arg Phe Ala Ala His
            245                 250                 255

Gln Ala Asn Ala Arg Ile Leu Asp Ser Val Ala Glu Arg Leu Gly Val
        260                 265                 270

Pro Ala Glu Arg Gln Leu Thr Asn Ile Ala Arg Val Gly Asn Thr Gly
    275                 280                 285

Ala Ala Ser Ile Pro Leu Leu Ser Gln Ala Ala Ala Gly Arg
290                 295                 300

Leu Gly Ala Gly His Arg Val Leu Leu Thr Ala Phe Gly Gly Gly Leu
305                 310                 315                 320

Ser Trp Gly Ala Gly Thr Leu Val Trp Pro Glu Val Gln Pro Val
            325                 330                 335

<210> SEQ ID NO 7
<211> LENGTH: 312
<212> TYPE: PRT
<213> ORGANISM: Listeria monocytogenes
<220> FEATURE:
<223> OTHER INFORMATION: Beta ketoacyl-ACP synthase III

<400> SEQUENCE: 7

Met Asn Ala Gly Ile Leu Gly Val Gly Lys Tyr Val Pro Glu Lys Ile
1               5                   10                  15

Val Thr Asn Phe Asp Leu Glu Lys Ile Met Asp Thr Ser Asp Glu Trp
            20                  25                  30

Ile Arg Thr Arg Thr Gly Ile Glu Glu Arg Arg Ile Ala Arg Asp Asp
        35                  40                  45

Glu Tyr Thr His Asp Leu Ala Tyr Glu Ala Ala Lys Val Ala Ile Glu
    50                  55                  60

Asn Ala Gly Leu Thr Pro Asp Asp Ile Asp Leu Phe Ile Val Ala Thr
65                  70                  75                  80

Val Thr Gln Glu Ala Thr Phe Pro Ser Val Ala Asn Ile Ile Gln Asp
                85                  90                  95

Arg Leu Gly Ala Thr Asn Ala Ala Gly Met Asp Val Glu Ala Ala Cys
            100                 105                 110

Ala Gly Phe Thr Phe Gly Val Val Thr Ala Ala Gln Phe Ile Lys Thr
        115                 120                 125

Gly Ala Tyr Lys Asn Ile Val Val Gly Ala Asp Lys Leu Ser Lys
    130                 135                 140

Ile Thr Asn Trp Asp Asp Arg Ala Thr Ala Val Leu Phe Gly Asp Gly
145                 150                 155                 160

Ala Gly Ala Val Val Met Gly Pro Val Ser Asp Asp His Gly Leu Leu
                165                 170                 175

Ser Phe Asp Leu Gly Ser Asp Gly Ser Gly Gly Lys Tyr Leu Asn Leu
            180                 185                 190

Asp Glu Asn Lys Lys Ile Tyr Met Asn Gly Arg Glu Val Phe Arg Phe
        195                 200                 205

Ala Val Arg Gln Met Gly Glu Ala Ser Leu Arg Val Leu Glu Arg Ala
    210                 215                 220

Gly Leu Glu Lys Glu Glu Leu Asp Leu Leu Ile Pro His Gln Ala Asn
225                 230                 235                 240

Ile Arg Ile Met Glu Ala Ser Arg Glu Arg Leu Asn Leu Pro Glu Glu

```
                  245                 250                 255
Lys Leu Met Lys Thr Val His Lys Tyr Gly Asn Thr Ser Ser Ser Ser
            260                 265                 270

Ile Ala Leu Ala Leu Val Asp Ala Val Glu Glu Gly Arg Ile Lys Asp
            275                 280                 285

Asn Asp Asn Val Leu Leu Val Gly Phe Gly Gly Leu Thr Trp Gly
            290                 295                 300

Ala Leu Ile Ile Arg Trp Gly Lys
305                 310

<210> SEQ ID NO 8
<211> LENGTH: 312
<212> TYPE: PRT
<213> ORGANISM: Artificial Sequence
<220> FEATURE:
<223> OTHER INFORMATION: Description of Artificial Sequence: Synthetic
      L. monocytogenes beta ketoacyl-ACP synthase III variant
      polypeptide

<400> SEQUENCE: 8

Met Asn Ala Gly Ile Leu Gly Val Gly Lys Tyr Val P

Asn Asp Asn Val Leu Val Gly Phe Gly Gly Leu Thr Trp Gly
290                 295                 300

Ala Leu Ile Ile Arg Gly Gly Lys
305                 310

<210> SEQ ID NO 9
<211> LENGTH: 313
<212> TYPE: PRT
<213> ORGANISM: Staphylococcus aureus
<220> FEATURE:
<223> OTHER INFORMATION: Beta ketoacyl-ACP synthase III

<400> SEQUENCE: 9

Met Asn Val Gly Ile Lys Gly Phe Gly Ala Tyr Ala Pro Glu Lys Ile
1               5                   10                  15

Ile Asp Asn Ala Tyr Phe Glu Gln Phe Leu Asp Thr Ser Asp Glu Trp
            20                  25                  30

Ile Ser Lys Met Thr Gly Ile Lys Glu Arg His Trp Ala Asp Asp
        35                  40                  45

Gln Asp Thr Ser Asp Leu Ala Tyr Glu Ala Ser Leu Lys Ala Ile Ala
    50                  55                  60

Asp Ala Gly Ile Gln Pro Glu Asp Ile Asp Met Ile Ile Val Ala Thr
65                  70                  75                  80

Ala Thr Gly Asp Met Pro Phe Pro Thr Val Ala Asn Met Leu Gln Glu
                85                  90                  95

Arg Leu Gly Thr Gly Lys Val Ala Ser Met Asp Gln Leu Ala Ala Cys
            100                 105                 110

Ser Gly Phe Met Tyr Ser Met Ile Thr Ala Lys Gln Tyr Val Gln Ser
        115                 120                 125

Gly Asp Tyr His Asn Ile Leu Val Val Gly Ala Asp Lys Leu Ser Lys
    130                 135                 140

Ile Thr Asp Leu Thr Asp Arg Ser Thr Ala Val Leu Phe Gly Asp Gly
145                 150                 155                 160

Ala Gly Ala Val Ile Ile Gly Glu Val Ser Asp Gly Arg Gly Ile Ile
                165                 170                 175

Ser Tyr Glu Met Gly Ser Asp Gly Thr Gly Gly Lys His Leu Tyr Leu
            180                 185                 190

Asp Lys Asp Thr Gly Lys Leu Lys Met Asn Gly Arg Glu Val Phe Lys
        195                 200                 205

Phe Ala Val Arg Ile Met Gly Asp Ala Ser Thr Arg Val Val Glu Lys
    210                 215                 220

Ala Asn Leu Thr Ser Asp Asp Ile Asp Leu Phe Ile Pro His Gln Ala
225                 230                 235                 240

Asn Ile Arg Ile Met Glu Ser Ala Arg Glu Arg Leu Gly Ile Ser Lys
                245                 250                 255

Asp Lys Met Ser Val Ser Val Asn Lys Tyr Gly Asn Thr Ser Ala Ala
            260                 265                 270

Ser Ile Pro Leu Ser Ile Asp Gln Glu Leu Lys Asn Gly Lys Ile Lys
        275                 280                 285

Asp Asp Asp Thr Ile Val Leu Val Gly Phe Gly Gly Gly Leu Thr Trp
    290                 295                 300

Gly Ala Met Thr Ile Lys Trp Gly Lys
305                 310

<210> SEQ ID NO 10
<211> LENGTH: 324
<212> TYPE: PRT

```
<213> ORGANISM: Streptococcus pneumoniae
<220> FEATURE:
<223> OTHER INFORMATION: Beta ketoacyl-ACP synthase III

<400> SEQUENCE: 10
```

| | | | | | | | | | | | | | | | |
|---|---|---|---|---|---|---|---|---|---|---|---|---|---|---|---|
|Met|Ala|Phe|Ala|Lys|Ile|Ser|Gln|Val|Ala|His|Tyr|Val|Pro|Glu|Gln|
|1| | | |5| | | | |10| | | | |15| |
|Val|Val|Thr|Asn|His|Asp|Leu|Ala|Gln|Ile|Met|Asp|Thr|Asn|Asp|Glu|
| | | |20| | | | |25| | | | |30| | |
|Trp|Ile|Ser|Ser|Arg|Thr|Gly|Ile|Arg|Gln|Arg|His|Ile|Ser|Arg|Thr|
| | | | |35| | | | |40| | | | |45| |
|Glu|Ser|Thr|Ser|Asp|Leu|Ala|Thr|Glu|Val|Ala|Lys|Lys|Leu|Met|Ala|
| |50| | | | |55| | | | |60| | | | |
|Lys|Ala|Gly|Ile|Thr|Gly|Glu|Glu|Leu|Asp|Phe|Ile|Ile|Leu|Ala|Thr|
|65| | | | |70| | | | |75| | | | |80|
|Ile|Thr|Pro|Asp|Ser|Met|Met|Pro|Ser|Thr|Ala|Ala|Arg|Val|Gln|Ala|
| | | | |85| | | | |90| | | | |95| |
|Asn|Ile|Gly|Ala|Asn|Lys|Ala|Phe|Ala|Phe|Asp|Leu|Thr|Ala|Ala|Cys|
| | | |100| | | | |105| | | | |110| | |
|Ser|Gly|Phe|Val|Phe|Ala|Leu|Ser|Thr|Ala|Glu|Lys|Phe|Ile|Ala|Ser|
| | | |115| | | | |120| | | | |125| | |
|Gly|Arg|Phe|Gln|Lys|Gly|Leu|Val|Ile|Gly|Ser|Glu|Thr|Leu|Ser|Lys|
| |130| | | | |135| | | | |140| | | | |
|Ala|Val|Asp|Trp|Ser|Asp|Arg|Ser|Thr|Ala|Val|Leu|Phe|Gly|Asp|Gly|
|145| | | | |150| | | | |155| | | | |160|
|Ala|Gly|Gly|Val|Leu|Leu|Glu|Ala|Ser|Glu|Gln|Glu|His|Phe|Leu|Ala|
| | | | |165| | | | |170| | | | |175| |
|Glu|Ser|Leu|Asn|Ser|Asp|Gly|Ser|Arg|Ser|Glu|Cys|Leu|Thr|Tyr|Gly|
| | | |180| | | | |185| | | | |190| | |
|His|Ser|Gly|Leu|His|Ser|Pro|Phe|Ser|Asp|Gln|Glu|Ser|Ala|Asp|Ser|
| | | |195| | | | |200| | | | |205| | |
|Phe|Leu|Lys|Met|Asp|Gly|Arg|Thr|Val|Phe|Asp|Phe|Ala|Ile|Arg|Asp|
| |210| | | | |215| | | | |220| | | | |
|Val|Ala|Lys|Ser|Ile|Lys|Gln|Thr|Ile|Asp|Glu|Ser|Pro|Ile|Glu|Val|
|225| | | | |230| | | | |235| | | | |240|
|Thr|Asp|Leu|Asp|Tyr|Leu|Leu|Leu|His|Gln|Ala|Asn|Asp|Arg|Ile|Leu|
| | | | |245| | | | |250| | | | |255| |
|Asp|Lys|Met|Ala|Arg|Lys|Ile|Gly|Val|Asp|Arg|Ala|Lys|Leu|Pro|Ala|
| | | |260| | | | |265| | | | |270| | |
|Asn|Met|Met|Glu|Tyr|Gly|Asn|Thr|Ser|Ala|Ala|Ser|Ile|Pro|Ile|Leu|
| | | |275| | | | |280| | | | |285| | |
|Leu|Ser|Glu|Cys|Val|Glu|Gln|Gly|Leu|Ile|Pro|Leu|Asp|Gly|Ser|Gln|
| |290| | | | |295| | | | |300| | | | |
|Thr|Val|Leu|Leu|Ser|Gly|Phe|Gly|Gly|Gly|Leu|Thr|Trp|Gly|Thr|Leu|
|305| | | | |310| | | | |315| | | | |320|
|Ile|Leu|Thr|Ile| | | | | | | | | | | | |

```
<210> SEQ ID NO 11
<211> LENGTH: 325
<212> TYPE: PRT
<213> ORGANISM: Streptococcus mutans
<220> FEATURE:
<223> OTHER INFORMATION: Beta ketoacyl-ACP synthase III

<400> SEQUENCE: 11
```

| | | | | | | | | | | | | | | | |
|---|---|---|---|---|---|---|---|---|---|---|---|---|---|---|---|
|Met|Thr|Phe|Ala|Lys|Ile|Ser|Gln|Ala|Ala|Tyr|Tyr|Val|Pro|Ser|Gln|
|1| | | |5| | | | |10| | | | |15| |

Val Val Thr Asn Asp Asp Leu Ser Lys Ile Met Asp Thr Ser Asp Glu
            20                  25                  30

Trp Ile Thr Ser Arg Thr Gly Ile Arg Glu Arg Arg Ile Ser Gln Ser
            35                  40                  45

Glu Asp Thr Ser Asp Leu Ala Ser Gln Val Ala Lys Glu Leu Leu Lys
 50                  55                  60

Lys Ala Ser Leu Lys Ala Lys Glu Ile Asp Phe Ile Ile Val Ala Thr
 65                  70                  75                  80

Ile Thr Pro Asp Ala Met Met Pro Ser Thr Ala Ala Cys Val Gln Ala
            85                  90                  95

Lys Ile Gly Ala Val Asn Ala Phe Ala Phe Asp Leu Thr Ala Ala Cys
            100                 105                 110

Ser Gly Phe Ile Phe Ala Leu Ser Ala Ala Glu Lys Met Ile Lys Ser
            115                 120                 125

Gly Gln Tyr Gln Lys Gly Leu Val Ile Gly Ala Glu Val Leu Ser Lys
130                 135                 140

Ile Ile Asp Trp Ser Asp Arg Thr Thr Ala Val Leu Phe Gly Asp Gly
145                 150                 155                 160

Ala Gly Gly Val Leu Leu Glu Ala Asp Ser Ser Glu His Phe Leu Phe
            165                 170                 175

Glu Ser Ile His Ser Asp Gly Ser Arg Gly Glu Ser Leu Thr Ser Gly
            180                 185                 190

Glu His Ala Val Ser Ser Pro Phe Ser Gln Val Asp Lys Lys Asp Asn
            195                 200                 205

Cys Phe Leu Lys Met Asp Gly Arg Ala Ile Phe Asp Phe Ala Ile Arg
210                 215                 220

Asp Val Ser Lys Ser Ile Ser Met Leu Ile Arg Lys Ser Asp Met Pro
225                 230                 235                 240

Val Glu Ala Ile Asp Tyr Phe Leu Leu His Gln Ala Asn Ile Arg Ile
            245                 250                 255

Leu Asp Lys Met Ala Lys Lys Ile Gly Ala Asp Arg Glu Lys Phe Pro
            260                 265                 270

Ala Asn Met Met Lys Tyr Gly Asn Thr Ser Ala Ala Ser Ile Pro Ile
            275                 280                 285

Leu Leu Ala Glu Cys Val Glu Asn Gly Thr Ile Glu Leu Asn Gly Ser
            290                 295                 300

His Thr Val Leu Leu Ser Gly Phe Gly Gly Gly Leu Thr Trp Gly Ser
305                 310                 315                 320

Leu Ile Val Lys Ile
            325

<210> SEQ ID NO 12
<211> LENGTH: 325
<212> TYPE: PRT
<213> ORGANISM: Lactococcus lactis
<220> FEATURE:
<223> OTHER INFORMATION: Beta ketoacyl-ACP synthase III

<400> SEQUENCE: 12

Met Thr Phe Ala Lys Ile Thr Gln Val Ala His Tyr Val Pro Glu Asn
1               5                   10                  15

Val Val Ser Asn Asp Asp Leu Ser Lys Ile Met Asp Thr Asn Asp Glu
            20                  25                  30

Trp Ile Tyr Ser Arg Thr Gly Ile Lys Asn Arg His Ile Ser Thr Gly
            35                  40                  45

```
Glu Asn Thr Ser Asp Leu Ala Ala Lys Val Ala Lys Gln Leu Ile Ser
     50                  55                  60

Asp Ser Asn Leu Ser Pro Glu Thr Ile Asp Phe Ile Ile Val Ala Thr
 65                  70                  75                  80

Val Thr Pro Asp Ser Leu Met Pro Ser Thr Ala Ala Arg Val Gln Ala
                 85                  90                  95

Gln Val Gly Ala Val Asn Ala Phe Ala Tyr Asp Leu Thr Ala Ala Cys
            100                 105                 110

Ser Gly Phe Val Phe Ala Leu Ser Thr Ala Glu Lys Leu Ile Ser Ser
        115                 120                 125

Gly Ala Tyr Gln Arg Gly Leu Val Ile Gly Ala Glu Val Phe Ser Lys
    130                 135                 140

Val Ile Asp Trp Ser Asp Arg Ser Thr Ala Val Leu Phe Gly Asp Gly
145                 150                 155                 160

Ala Ala Gly Val Leu Ile Glu Ala Gly Ala Ser Gln Pro Leu Ile Ile
                165                 170                 175

Ala Glu Lys Met Gln Thr Asp Gly Ser Arg Gly Asn Ser Leu Leu Ser
            180                 185                 190

Ser Tyr Ala Asp Ile Gln Thr Pro Phe Ala Ser Val Ser Tyr Glu Ser
        195                 200                 205

Ser Asn Leu Ser Met Glu Gly Arg Ala Ile Phe Asp Phe Ala Val Arg
    210                 215                 220

Asp Val Pro Lys Asn Ile Gln Ala Thr Leu Glu Lys Ala Asn Leu Ser
225                 230                 235                 240

Ala Glu Glu Val Asp Tyr Tyr Leu Leu His Gln Ala Asn Ser Arg Ile
                245                 250                 255

Leu Asp Lys Met Ala Lys Lys Leu Gly Val Thr Arg Gln Lys Phe Leu
            260                 265                 270

Gln Asn Met Gln Glu Tyr Gly Asn Thr Ser Ala Ala Ser Ile Pro Ile
        275                 280                 285

Leu Leu Ser Glu Ser Val Lys Asn Gly Ile Phe Ser Leu Asp Gly Gln
    290                 295                 300

Thr Lys Val Val Leu Thr Gly Phe Gly Gly Gly Leu Thr Trp Gly Thr
305                 310                 315                 320

Ala Ile Ile Asn Leu
            325

<210> SEQ ID NO 13
<211> LENGTH: 300
<212> TYPE: PRT
<213> ORGANISM: Propionibacterium freudenreichii
<220> FEATURE:
<223> OTHER INFORMATION: subsp. shermanii, Beta ketoacyl-ACP synthase
      III

<400> SEQUENCE: 13

Met Ile Asp Ser Thr Pro Glu Trp Ile Glu Gln Arg Thr Gly Ile Arg
 1               5                  10                  15

Glu Arg Arg Trp Ala Thr Lys Asp Glu Thr Val Leu Ser Met Ala Thr
             20                  25                  30

Asp Ala Gly Arg Lys Ala Leu Asp Met Ala Gly Val Lys Pro Glu Gln
         35                  40                  45

Val Gly Ala Ile Ile Val Ser Thr Val Ser His His Ile Pro Ser Pro
     50                  55                  60

Gly Leu Ser Asp Tyr Leu Ala Glu Leu Gly Cys Pro Ala Pro Ala
 65                  70                  75                  80
```

```
Thr Phe Asp Ile Ser Ala Ala Cys Ala Gly Phe Cys Tyr Ala Leu Thr
                85                  90                  95

Leu Ala Glu Ser Ile Val Arg Ala Gly His Ala Gly Lys Asp Gly Phe
            100                 105                 110

Val Leu Ile Val Gly Val Glu Arg Leu Ser Asp Met Thr Asn Met Asp
        115                 120                 125

Asp Arg Gly Thr Asp Phe Leu Phe Gly Asp Gly Ala Gly Ala Ala Val
    130                 135                 140

Val Gly Pro Ser Asp Thr Pro Ala Ile Gly Pro Ala Val Trp Gly Ser
145                 150                 155                 160

Lys Pro Ala Asn Val Lys Thr Ile Glu Ile Gln Ser Trp Thr Glu Ala
                165                 170                 175

Asp Lys Asn Pro Thr Gly Phe Pro Leu Ile Gln Met Asp Gly His Thr
            180                 185                 190

Val Phe Lys Trp Ala Leu Ser Glu Val Ala Asp His Ala Ala Glu Ala
        195                 200                 205

Ile Asp Ala Ala Gly Ile Thr Pro Glu Gln Leu Asp Ile Phe Leu Pro
    210                 215                 220

His Gln Ala Asn Asp Arg Ile Thr Asp Ala Ile Ile Arg His Leu His
225                 230                 235                 240

Leu Pro Asp Ser Val Ser Val Cys Arg Asp Ile Ala Glu Met Gly Asn
                245                 250                 255

Thr Ser Ala Ala Ser Ile Pro Ile Ala Met Asp Ala Met Ile Arg Glu
            260                 265                 270

Gly Arg Ala Lys Ser Gly Gln Thr Ala Leu Ile Ile Gly Phe Gly Ala
        275                 280                 285

Gly Leu Val Tyr Ala Gly Arg Val Val Val Leu Pro
    290                 295                 300

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      FabH motif peptide
<220> FEATURE:
<221> NAME/KEY: MOD_RES
<222> LOCATION: (3)..(3)
<223> OTHER INFORMATION: Asn or Ser
<220> FEATURE:
<221> NAME/KEY: MOD_RES
<222> LOCATION: (5)..(5)
<223> OTHER INFORMATION: Ala or Glu
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (10)..(10)
<223> OTHER INFORMATION: Met or Arg
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (15)..(15)
<223> OTHER INFORMATION: Asn or Glu
<220> FEATURE:
<221> NAME/KEY: MOD_RES
<222> LOCATION: (17)..(17)
<223> OTHER INFORMATION: Arg or His

<400> SEQUENCE: 14
```

```
Asp Thr Xaa Asp Xaa Trp Ile Xaa Xaa Xaa Thr Gly Ile Xaa Xaa Arg
1               5                   10                  15

Xaa

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: Synthetic
      FabH motif peptide
<220> FEATURE:
<221> NAME/KEY: MOD_RES
<222> LOCATION: (1)..(1)
<223> OTHER INFORMATION: Ser or Ala
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (7)..(7)
<223> OTHER INFORMATION: Ala or Val
<220> FEATURE:
<221> NAME/KEY: MOD_RES
<222> LOCATION: (9)..(9)
<223> OTHER INFORMATION: Ala or Ser
<220> FEATURE:
<221> NAME/KEY: MOD_RES
<222> LOCATION: (12)..(14)
<223> OTHER INFORMATION: Any amino acid
<220> FEATURE:
<221> NAME/KEY: MOD_RES
<222> LOCATION: (15)..(15)
<223> OTHER INFORMATION: Met or Leu
<220> FEATURE:
<221> NAME/KEY: MOD_RES
<222> LOCATION: (16)..(17)
<223> OTHER INFORMATION: Any amino acid

<400> SEQUENCE: 15

Xaa Xaa Asp Xaa Xaa Ala Xaa Cys Xaa Gly Phe Xaa Xaa Xaa Xaa Xaa
1               5                   10                  15

Xaa Ala

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      FabH motif peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Ala or Ile
<220> FEATURE:
<221> NAME/KEY: MOD_RES
<222> LOCATION: (6)..(6)
<223> OTHER INFORMATION: Ile or Val
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
```

```
<222> LOCATION: (9)..(9)
<223> OTHER INFORMATION: Ala or Gly
<220> FEATURE:
<221> NAME/KEY: MOD_RES
<222> LOCATION: (13)..(14)
<223> OTHER INFORMATION: Ala or Gly
<220> FEATURE:
<221> NAME/KEY: MOD_RES
<222> LOCATION: (15)..(15)
<223> OTHER INFORMATION: Ala or Val

<400> SEQUENCE: 16

Asp Arg Xaa Thr Xaa Xaa Xaa Phe Xaa Asp Gly Ala Xaa Xaa Xaa
1               5                   10                  15

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      FabH motif peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (8)..(8)
<223> OTHER INFORMATION: Met or Leu

<400> SEQUENCE: 17

His Gln Ala Asn Xaa Arg Ile Xaa
1               5

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic
      FabH motif peptide
<220> FEATURE:
<221> NAME/KEY: MOD_RES
<222> LOCATION: (4)..(4)
<223> OTHER INFORMATION: Gly or Ser
<220> FEATURE:
<221> NAME/KEY: MOD_RES
<222> LOCATION: (8)..(8)
<223> OTHER INFORMATION: Val or Ile
<220> FEATURE:
<221> NAME/KEY: MOD_RES
<222> LOCATION: (10)..(11)
<223> OTHER INFORMATION: Any amino acid
<220> FEATURE:
<221> NAME/KEY: MOD_RES
<222> LOCATION: (12)..(12)
<223> OTHER INFORMATION: Ile or Leu
<220> FEATURE:
<221> NAME/KEY: MOD_RES
<222> LOCATION: (13)..(18)
<223> OTHER INFORMATION: Any amino acid

<400> SEQUENCE: 18

Gly Asn Thr Xaa Ala Ala Ser Xaa Pro Xaa Xaa Xaa Xaa Xaa Xaa
1               5                   10                  15

Xaa Xaa Gly

<210> SEQ ID NO 19
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      FabH motif peptide
<220> FEATURE:
<221> NAME/KEY: MOD_RES
<222> LOCATION: (1)..(1)
<223> OTHER INFORMATION: Ile or Val
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (10)..(10)
<223> OTHER INFORMATION: Leu or Phe
<220> FEATURE:
<221> NAME/KEY: MOD_RES
<222> LOCATION: (11)..(11)
<223> OTHER INFORMATION: Thr or Ser

<400> SEQUENCE: 19

Xaa Xaa Leu Xaa Xaa Phe Gly Gly Gly Xaa Xaa Trp Gly
1               5                   10

<210> SEQ ID NO 20
<211> LENGTH: 820
<212> TYPE: PRT
<213> ORGANISM: Escherichia coli
<220> FEATURE:
<223> OTHER INFORMATION: Aspartate kinase / Homoserine dehydrogenase
      (ThrA)

<400> SEQUENCE: 20

Met Arg Val Leu Lys Phe Gly Gly Thr Ser Val Ala Asn Ala Glu Arg
1               5                   10                  15

Phe Leu Arg Val Ala Asp Ile Leu Glu Ser Asn Ala Arg Gln Gly Gln
                20                  25                  30

Val Ala Thr Val Leu Ser Ala Pro Ala Lys Ile Thr Asn His Leu Val
            35                  40                  45

Ala Met Ile Glu Lys Thr Ile Ser Gly Gln Asp Ala Leu Pro Asn Ile
        50                  55                  60

Ser Asp Ala Glu Arg Ile Phe Ala Glu Leu Leu Thr Gly Leu Ala Ala
65                  70                  75                  80

Ala Gln Pro Gly Phe Pro Leu Ala Gln Leu Lys Thr Phe Val Asp Gln
                85                  90                  95

Glu Phe Ala Gln Ile Lys His Val Leu His Gly Ile Ser Leu Leu Gly
            100                 105                 110

Gln Cys Pro Asp Ser Ile Asn Ala Ala Leu Ile Cys Arg Gly Glu Lys
        115                 120                 125

Met Ser Ile Ala Ile Met Ala Gly Val Leu Glu Ala Arg Gly His Asn
130                 135                 140

Val Thr Val Ile Asp Pro Val Glu Lys Leu Leu Ala Val Gly His Tyr
145                 150                 155                 160

Leu Glu Ser Thr Val Asp Ile Ala Glu Ser Thr Arg Arg Ile Ala Ala
                165                 170                 175

Ser Arg Ile Pro Ala Asp His Met Val Leu Met Ala Gly Phe Thr Ala
            180                 185                 190

Gly Asn Glu Lys Gly Glu Leu Val Val Leu Gly Arg Asn Gly Ser Asp
        195                 200                 205

Tyr Ser Ala Ala Val Leu Ala Ala Cys Leu Arg Ala Asp Cys Cys Glu
210                 215                 220
```

```
Ile Trp Thr Asp Val Asp Gly Val Tyr Thr Cys Asp Pro Arg Gln Val
225                 230                 235                 240

Pro Asp Ala Arg Leu Leu Lys Ser Met Ser Tyr Gln Glu Ala Met Glu
            245                 250                 255

Leu Ser Tyr Phe Gly Ala Lys Val Leu His Pro Arg Thr Ile Thr Pro
                260                 265                 270

Ile Ala Gln Phe Gln Ile Pro Cys Leu Ile Lys Asn Thr Gly Asn Pro
            275                 280                 285

Gln Ala Pro Gly Thr Leu Ile Gly Ala Ser Arg Asp Glu Asp Glu Leu
        290                 295                 300

Pro Val Lys Gly Ile Ser Asn Leu Asn Asn Met Ala Met Phe Ser Val
305                 310                 315                 320

Ser Gly Pro Gly Met Lys Gly Met Val Gly Met Ala Ala Arg Val Phe
                325                 330                 335

Ala Ala Met Ser Arg Ala Arg Ile Ser Val Val Leu Ile Thr Gln Ser
            340                 345                 350

Ser Ser Glu Tyr Ser Ile Ser Phe Cys Val Pro Gln Ser Asp Cys Val
        355                 360                 365

Arg Ala Glu Arg Ala Met Gln Glu Glu Phe Tyr Leu Glu Leu Lys Glu
    370                 375                 380

Gly Leu Leu Glu Pro Leu Ala Val Thr Glu Arg Leu Ala Ile Ile Ser
385                 390                 395                 400

Val Val Gly Asp Gly Met Arg Thr Leu Arg Gly Ile Ser Ala Lys Phe
                405                 410                 415

Phe Ala Ala Leu Ala Arg Ala Asn Ile Asn Ile Val Ala Ile Ala Gln
            420                 425                 430

Gly Ser Ser Glu Arg Ser Ile Ser Val Val Val Asn Asn Asp Asp Ala
        435                 440                 445

Thr Thr Gly Val Arg Val Thr His Gln Met Leu Phe Asn Thr Asp Gln
    450                 455                 460

Val Ile Glu Val Phe Val Ile Gly Val Gly Gly Val Gly Gly Ala Leu
465                 470                 475                 480

Leu Glu Gln Leu Lys Arg Gln Gln Ser Trp Leu Lys Asn Lys His Ile
                485                 490                 495

Asp Leu Arg Val Cys Gly Val Ala Asn Ser Lys Ala Leu Leu Thr Asn
            500                 505                 510

Val His Gly Leu Asn Leu Glu Asn Trp Gln Glu Glu Leu Ala Gln Ala
        515                 520                 525

Lys Glu Pro Phe Asn Leu Gly Arg Leu Ile Arg Leu Val Lys Glu Tyr
    530                 535                 540

His Leu Leu Asn Pro Val Ile Val Asp Cys Thr Ser Ser Gln Ala Val
545                 550                 555                 560

Ala Asp Gln Tyr Ala Asp Phe Leu Arg Glu Gly Phe His Val Val Thr
                565                 570                 575

Pro Asn Lys Lys Ala Asn Thr Ser Ser Met Asp Tyr Tyr His Gln Leu
            580                 585                 590

Arg Tyr Ala Ala Glu Lys Ser Arg Arg Lys Phe Leu Tyr Asp Thr Asn
        595                 600                 605

Val Gly Ala Gly Leu Pro Val Ile Glu Asn Leu Gln Asn Leu Leu Asn
    610                 615                 620

Ala Gly Asp Glu Leu Met Lys Phe Ser Gly Ile Leu Ser Gly Ser Leu
625                 630                 635                 640

Ser Tyr Ile Phe Gly Lys Leu Asp Glu Gly Met Ser Phe Ser Glu Ala
```

```
                    645                 650                 655
Thr Thr Leu Ala Arg Glu Met Gly Tyr Thr Glu Pro Asp Pro Arg Asp
            660                 665                 670

Asp Leu Ser Gly Met Asp Val Ala Arg Lys Leu Leu Ile Leu Ala Arg
            675                 680                 685

Glu Thr Gly Arg Glu Leu Glu Leu Ala Asp Ile Glu Ile Glu Pro Val
            690                 695                 700

Leu Pro Ala Glu Phe Asn Ala Glu Gly Asp Val Ala Ala Phe Met Ala
705                 710                 715                 720

Asn Leu Ser Gln Leu Asp Asp Leu Phe Ala Ala Arg Val Ala Lys Ala
            725                 730                 735

Arg Asp Glu Gly Lys Val Leu Arg Tyr Val Gly Asn Ile Asp Glu Asp
            740                 745                 750

Gly Val Cys Arg Val Lys Ile Ala Glu Val Asp Gly Asn Asp Pro Leu
            755                 760                 765

Phe Lys Val Lys Asn Gly Glu Asn Ala Leu Ala Phe Tyr Ser His Tyr
            770                 775                 780

Tyr Gln Pro Leu Pro Leu Val Leu Arg Gly Tyr Gly Ala Gly Asn Asp
785                 790                 795                 800

Val Thr Ala Ala Gly Val Phe Ala Asp Leu Leu Arg Thr Leu Ser Trp
            805                 810                 815

Lys Leu Gly Val
            820

<210> SEQ ID NO 21
<211> LENGTH: 820
<212> TYPE: PRT
<213> ORGANISM: Artificial Sequence
<220> FEATURE:
<223> OTHER INFORMATION: Description of Artificial Sequence: Synthetic
      Escherichia coli ThrA S345F variant polypeptide

<400> SEQUENCE: 21

Met Arg Val Leu Lys Phe Gly Gly Thr Ser Val Ala Asn Ala Glu Arg
1               5                   10                  15

Phe Leu Arg Val Ala Asp Ile Leu Glu Ser Asn Ala Arg Gln Gly Gln
            20                  25                  30

Val Ala Thr Val Leu Ser Ala Pro Ala Lys Ile Thr Asn His Leu Val
        35                  40                  45

Ala Met Ile Glu Lys Thr Ile Ser Gly Gln Asp Ala Leu Pro Asn Ile
    50                  55                  60

Ser Asp Ala Glu Arg Ile Phe Ala Glu Leu Leu Thr Gly Leu Ala Ala
65                  70                  75                  80

Ala Gln Pro Gly Phe Pro Leu Ala Gln Leu Lys Thr Phe Val Asp Gln
            85                  90                  95

Glu Phe Ala Gln Ile Lys His Val Leu His Gly Ile Ser Leu Leu Gly
            100                 105                 110

Gln Cys Pro Asp Ser Ile Asn Ala Ala Leu Ile Cys Arg Gly Glu Lys
        115                 120                 125

Met Ser Ile Ala Ile Met Ala Gly Val Leu Glu Ala Arg Gly His Asn
    130                 135                 140

Val Thr Val Ile Asp Pro Val Glu Lys Leu Leu Ala Val Gly His Tyr
145                 150                 155                 160

Leu Glu Ser Thr Val Asp Ile Ala Glu Ser Thr Arg Arg Ile Ala Ala
            165                 170                 175

Ser Arg Ile Pro Ala Asp His Met Val Leu Met Ala Gly Phe Thr Ala
```

```
                180                 185                 190
Gly Asn Glu Lys Gly Glu Leu Val Val Leu Gly Arg Asn Gly Ser Asp
            195                 200                 205

Tyr Ser Ala Ala Val Leu Ala Ala Cys Leu Arg Ala Asp Cys Cys Glu
        210                 215                 220

Ile Trp Thr Asp Val Asp Gly Val Tyr Thr Cys Asp Pro Arg Gln Val
225                 230                 235                 240

Pro Asp Ala Arg Leu Leu Lys Ser Met Ser Tyr Gln Glu Ala Met Glu
                245                 250                 255

Leu Ser Tyr Phe Gly Ala Lys Val Leu His Pro Arg Thr Ile Thr Pro
            260                 265                 270

Ile Ala Gln Phe Gln Ile Pro Cys Leu Ile Lys Asn Thr Gly Asn Pro
        275                 280                 285

Gln Ala Pro Gly Thr Leu Ile Gly Ala Ser Arg Asp Glu Asp Glu Leu
    290                 295                 300

Pro Val Lys Gly Ile Ser Asn Leu Asn Asn Met Ala Met Phe Ser Val
305                 310                 315                 320

Ser Gly Pro Gly Met Lys Gly Met Val Gly Met Ala Ala Arg Val Phe
                325                 330                 335

Ala Ala Met Ser Arg Ala Arg Ile Phe Val Val Leu Ile Thr Gln Ser
            340                 345                 350

Ser Ser Glu Tyr Ser Ile Ser Phe Cys Val Pro Gln Ser Asp Cys Val
        355                 360                 365

Arg Ala Glu Arg Ala Met Gln Glu Glu Phe Tyr Leu Glu Leu Lys Glu
    370                 375                 380

Gly Leu Leu Glu Pro Leu Ala Val Thr Glu Arg Leu Ala Ile Ile Ser
385                 390                 395                 400

Val Val Gly Asp Gly Met Arg Thr Leu Arg Gly Ile Ser Ala Lys Phe
                405                 410                 415

Phe Ala Ala Leu Ala Arg Ala Asn Ile Asn Ile Val Ala Ile Ala Gln
            420                 425                 430

Gly Ser Ser Glu Arg Ser Ile Ser Val Val Val Asn Asn Asp Asp Ala
        435                 440                 445

Thr Thr Gly Val Arg Val Thr His Gln Met Leu Phe Asn Thr Asp Gln
    450                 455                 460

Val Ile Glu Val Phe Val Ile Gly Val Gly Val Gly Gly Ala Leu
465                 470                 475                 480

Leu Glu Gln Leu Lys Arg Gln Gln Ser Trp Leu Lys Asn Lys His Ile
                485                 490                 495

Asp Leu Arg Val Cys Gly Val Ala Asn Ser Lys Ala Leu Leu Thr Asn
            500                 505                 510

Val His Gly Leu Asn Leu Glu Asn Trp Gln Glu Glu Leu Ala Gln Ala
        515                 520                 525

Lys Glu Pro Phe Asn Leu Gly Arg Leu Ile Arg Leu Val Lys Glu Tyr
    530                 535                 540

His Leu Leu Asn Pro Val Ile Val Asp Cys Thr Ser Ser Gln Ala Val
545                 550                 555                 560

Ala Asp Gln Tyr Ala Asp Phe Leu Arg Glu Gly Phe His Val Val Thr
                565                 570                 575

Pro Asn Lys Lys Ala Asn Thr Ser Ser Met Asp Tyr His Gln Leu
            580                 585                 590

Arg Tyr Ala Ala Glu Lys Ser Arg Arg Lys Phe Leu Tyr Asp Thr Asn
        595                 600                 605
```

-continued

```
Val Gly Ala Gly Leu Pro Val Ile Glu Asn Leu Gln Asn Leu Leu Asn
            610             615                 620

Ala Gly Asp Glu Leu Met Lys Phe Ser Gly Ile Leu Ser Gly Ser Leu
625                 630                 635                 640

Ser Tyr Ile Phe Gly Lys Leu Asp Glu Gly Met Ser Phe Ser Glu Ala
                645                 650                 655

Thr Thr Leu Ala Arg Glu Met Gly Tyr Thr Glu Pro Asp Pro Arg Asp
            660                 665                 670

Asp Leu Ser Gly Met Asp Val Ala Arg Lys Leu Leu Ile Leu Ala Arg
        675                 680                 685

Glu Thr Gly Arg Glu Leu Glu Leu Ala Asp Ile Glu Ile Glu Pro Val
690                 695                 700

Leu Pro Ala Glu Phe Asn Ala Glu Gly Asp Val Ala Ala Phe Met Ala
705                 710                 715                 720

Asn Leu Ser Gln Leu Asp Asp Leu Phe Ala Ala Arg Val Ala Lys Ala
                725                 730                 735

Arg Asp Glu Gly Lys Val Leu Arg Tyr Val Gly Asn Ile Asp Glu Asp
            740                 745                 750

Gly Val Cys Arg Val Lys Ile Ala Glu Val Asp Gly Asn Asp Pro Leu
        755                 760                 765

Phe Lys Val Lys Asn Gly Glu Asn Ala Leu Ala Phe Tyr Ser His Tyr
770                 775                 780

Tyr Gln Pro Leu Pro Leu Val Leu Arg Gly Tyr Gly Ala Gly Asn Asp
785                 790                 795                 800

Val Thr Ala Ala Gly Val Phe Ala Asp Leu Leu Arg Thr Leu Ser Trp
                805                 810                 815

Lys Leu Gly Val
            820

<210> SEQ ID NO 22
<211> LENGTH: 404
<212> TYPE: PRT
<213> ORGANISM: Bacillus subtilis
<220> FEATURE:
<223> OTHER INFORMATION: Aspartate kinase

<400> SEQUENCE: 22

Met Lys Ile Ile Val Gln Lys Phe Gly Gly Thr Ser Val Lys Asp Asp
1               5                   10                  15

Lys Gly Arg Lys Leu Ala Leu Gly His Ile Lys Glu Ala Ile Ser Glu
            20                  25                  30

Gly Tyr Lys Val Val Val Val Ser Ala Met Gly Arg Lys Gly Asp
        35                  40                  45

Pro Tyr Ala Thr Asp Ser Leu Leu Gly Leu Leu Tyr Gly Asp Gln Ser
    50                  55                  60

Ala Ile Ser Pro Arg Glu Gln Asp Leu Leu Leu Ser Cys Gly Glu Thr
65                  70                  75                  80

Ile Ser Ser Val Val Phe Thr Ser Met Leu Leu Asp Asn Gly Val Lys
                85                  90                  95

Ala Ala Ala Leu Thr Gly Ala Gln Ala Gly Phe Leu Thr Asn Asp Gln
            100                 105                 110

His Thr Asn Ala Lys Ile Glu Met Lys Pro Glu Arg Leu Phe Ser
        115                 120                 125

Val Leu Ala Asn His Asp Ala Val Val Val Ala Gly Phe Gln Gly Ala
    130                 135                 140

Thr Glu Lys Gly Asp Thr Thr Thr Ile Gly Arg Gly Gly Ser Asp Thr
```

```
                145                 150                 155                 160
Ser Ala Ala Ala Leu Gly Ala Ala Val Asp Ala Glu Tyr Ile Asp Ile
                    165                 170                 175

Phe Thr Asp Val Glu Gly Val Met Thr Ala Asp Pro Arg Val Val Glu
            180                 185                 190

Asn Ala Lys Pro Leu Pro Val Thr Tyr Thr Glu Ile Cys Asn Leu
        195                 200                 205

Ala Tyr Gln Gly Ala Lys Val Ile Ser Pro Arg Ala Val Glu Ile Ala
    210                 215                 220

Met Gln Ala Lys Val Pro Ile Arg Val Arg Ser Thr Tyr Ser Asn Asp
225                 230                 235                 240

Lys Gly Thr Leu Val Thr Ser His His Ser Lys Val Gly Ser Asp
                245                 250                 255

Val Phe Glu Arg Leu Ile Thr Gly Ile Ala His Val Lys Asp Val Thr
                260                 265                 270

Gln Phe Lys Val Pro Ala Lys Ile Gly Gln Tyr Asn Val Gln Thr Glu
            275                 280                 285

Val Phe Lys Ala Met Ala Asn Ala Gly Ile Ser Val Asp Phe Phe Asn
        290                 295                 300

Ile Thr Pro Ser Glu Ile Val Tyr Thr Val Ala Gly Asn Lys Thr Glu
305                 310                 315                 320

Thr Ala Gln Arg Ile Leu Met Asp Met Gly Tyr Asp Pro Met Val Thr
                325                 330                 335

Arg Asn Cys Ala Lys Val Ser Ala Val Gly Ala Gly Ile Met Gly Val
                340                 345                 350

Pro Gly Val Thr Ser Lys Ile Val Ser Ala Leu Ser Glu Lys Glu Ile
            355                 360                 365

Pro Ile Leu Gln Ser Ala Asp Ser His Thr Thr Ile Trp Val Leu Val
        370                 375                 380

His Glu Ala Asp Met Val Pro Ala Val Asn Ala Leu His Glu Val Phe
385                 390                 395                 400

Glu Leu Ser Lys

<210> SEQ ID NO 23
<211> LENGTH: 411
<212> TYPE: PRT
<213> ORGANISM: Pseudomonas putida
<220> FEATURE:
<223> OTHER INFORMATION: Aspartate kinase

<400> SEQUENCE: 23

Met Ala Leu Ile Val Gln Lys Phe Gly Gly Thr Ser Val Gly Ser Ile
1               5                   10                  15

Glu Arg Ile Glu Gln Val Ala Glu Lys Val Lys Lys His Arg Glu Ala
            20                  25                  30

Gly Asp Asp Leu Val Val Val Leu Ser Ala Met Ser Gly Glu Thr Asn
        35                  40                  45

Arg Leu Ile Asp Leu Ala Lys Gln Ile Thr Asp Gln Pro Val Pro Arg
    50                  55                  60

Glu Leu Asp Val Ile Val Ser Thr Gly Glu Gln Val Thr Ile Ala Leu
65                  70                  75                  80

Leu Thr Met Ala Leu Ile Lys Arg Gly Val Pro Ala Val Ser Tyr Thr
                85                  90                  95

Gly Asn Gln Val Arg Ile Leu Asp Ser Ser His Asn Lys Ala Arg
            100                 105                 110
```

Ile Leu Gln Ile Asp Asp Gln Lys Ile Arg Ala Asp Leu Lys Glu Gly
                115                 120                 125

Arg Val Val Val Ala Gly Phe Gln Gly Val Asp Glu His Gly Ser
    130                 135                 140

Ile Thr Thr Leu Gly Arg Gly Gly Ser Asp Thr Thr Gly Val Ala Leu
145                 150                 155                 160

Ala Ala Ala Leu Lys Ala Asp Glu Cys Gln Ile Tyr Thr Asp Val Asp
                165                 170                 175

Gly Val Tyr Thr Thr Asp Pro Arg Val Val Pro Gln Ala Arg Arg Leu
                180                 185                 190

Glu Lys Ile Thr Phe Glu Glu Met Leu Glu Met Ala Ser Leu Gly Ser
                195                 200                 205

Lys Val Leu Gln Ile Arg Ser Val Glu Phe Ala Gly Lys Tyr Asn Val
                210                 215                 220

Pro Leu Arg Val Leu His Ser Phe Lys Glu Gly Pro Gly Thr Leu Ile
225                 230                 235                 240

Thr Ile Asp Glu Glu Ser Met Glu Gln Pro Ile Ile Ser Gly Ile
                245                 250                 255

Ala Phe Asn Arg Asp Glu Ala Lys Leu Thr Ile Arg Gly Val Pro Asp
                260                 265                 270

Thr Pro Gly Val Ala Phe Lys Ile Leu Gly Pro Ile Ser Ala Ser Asn
                275                 280                 285

Ile Glu Val Asp Met Ile Val Gln Asn Val Ala His Asp Asn Thr Thr
                290                 295                 300

Asp Phe Thr Phe Thr Val His Arg Asn Glu Tyr Glu Lys Ala Gln Ser
305                 310                 315                 320

Val Leu Glu Asn Thr Ala Arg Glu Ile Gly Ala Arg Glu Val Ile Gly
                325                 330                 335

Asp Thr Lys Ile Ala Lys Val Ser Ile Val Gly Val Gly Met Arg Ser
                340                 345                 350

His Ala Gly Val Ala Ser Cys Met Phe Glu Ala Leu Ala Lys Glu Ser
                355                 360                 365

Ile Asn Ile Gln Met Ile Ser Thr Ser Glu Ile Lys Val Ser Val Val
                370                 375                 380

Leu Glu Glu Lys Tyr Leu Glu Leu Ala Val Arg Ala Leu His Thr Ala
385                 390                 395                 400

Phe Asp Leu Asp Ala Pro Ala Arg Gln Gly Glu
                405                 410

<210> SEQ ID NO 24
<211> LENGTH: 527
<212> TYPE: PRT
<213> ORGANISM: Saccharomyces cerevisiae
<220> FEATURE:
<223> OTHER INFORMATION: Aspartate kinase

<400> SEQUENCE: 24

Met Pro Met Asp Phe Gln Pro Thr Ser Ser His Ser Asn Trp Val Val
1               5                   10                  15

Gln Lys Phe Gly Gly Thr Ser Val Gly Lys Phe Pro Val Gln Ile Val
                20                  25                  30

Asp Asp Ile Val Lys His Tyr Ser Lys Pro Asp Gly Pro Asn Asn Asn
                35                  40                  45

Val Ala Val Val Cys Ser Ala Arg Ser Ser Tyr Thr Lys Ala Glu Gly
            50                  55                  60

Thr Thr Ser Arg Leu Leu Lys Cys Cys Asp Leu Ala Ser Gln Glu Ser

-continued

```
                65                  70                  75                  80
Glu Phe Gln Asp Ile Ile Glu Val Ile Arg Gln Asp His Ile Asp Asn
                    85                  90                  95
Ala Asp Arg Phe Ile Leu Asn Pro Ala Leu Gln Ala Lys Leu Val Asp
                100                 105                 110
Asp Thr Asn Lys Glu Leu Glu Leu Val Lys Lys Tyr Leu Asn Ala Ser
                115                 120                 125
Lys Val Leu Gly Glu Val Ser Ser Arg Thr Val Asp Leu Val Met Ser
            130                 135                 140
Cys Gly Glu Lys Leu Ser Cys Leu Phe Met Thr Ala Leu Cys Asn Asp
145                 150                 155                 160
Arg Gly Cys Lys Ala Lys Tyr Val Asp Leu Ser His Ile Val Pro Ser
                    165                 170                 175
Asp Phe Ser Ala Ser Ala Leu Asp Asn Ser Phe Tyr Thr Phe Leu Val
                180                 185                 190
Gln Ala Leu Lys Glu Lys Leu Ala Pro Phe Val Ser Ala Lys Glu Arg
                195                 200                 205
Ile Val Pro Val Phe Thr Gly Phe Gly Leu Val Pro Thr Gly Leu
            210                 215                 220
Leu Asn Gly Val Gly Arg Gly Tyr Thr Asp Leu Cys Ala Ala Leu Ile
225                 230                 235                 240
Ala Val Ala Val Asn Ala Asp Glu Leu Gln Val Trp Lys Glu Val Asp
                    245                 250                 255
Gly Ile Phe Thr Ala Asp Pro Arg Lys Val Pro Glu Ala Arg Leu Leu
                260                 265                 270
Asp Ser Val Thr Pro Glu Glu Ala Ser Glu Leu Thr Tyr Tyr Gly Ser
                275                 280                 285
Glu Val Ile His Pro Phe Thr Met Glu Gln Val Ile Arg Ala Lys Ile
            290                 295                 300
Pro Ile Arg Ile Lys Asn Val Gln Asn Pro Leu Gly Asn Gly Thr Ile
305                 310                 315                 320
Ile Tyr Pro Asp Asn Val Ala Lys Lys Gly Glu Ser Thr Pro Pro His
                    325                 330                 335
Pro Pro Glu Asn Leu Ser Ser Ser Phe Tyr Glu Lys Arg Lys Arg Gly
                340                 345                 350
Ala Thr Ala Ile Thr Thr Lys Asn Asp Ile Phe Val Ile Asn Ile His
                355                 360                 365
Ser Asn Lys Lys Thr Leu Ser His Gly Phe Leu Ala Gln Ile Phe Thr
            370                 375                 380
Ile Leu Asp Lys Tyr Lys Leu Val Asp Leu Ile Ser Thr Ser Glu
385                 390                 395                 400
Val His Val Ser Met Ala Leu Pro Ile Pro Asp Ala Asp Ser Leu Lys
                    405                 410                 415
Ser Leu Arg Gln Ala Glu Glu Lys Leu Arg Ile Leu Gly Ser Val Asp
                420                 425                 430
Ile Thr Lys Lys Leu Ser Ile Val Ser Leu Val Gly Lys His Met Lys
                435                 440                 445
Gln Tyr Ile Gly Ile Ala Gly Thr Met Phe Thr Thr Leu Ala Glu Glu
            450                 455                 460
Gly Ile Asn Ile Glu Met Ile Ser Gln Gly Ala Asn Glu Ile Asn Ile
465                 470                 475                 480
Ser Cys Val Ile Asn Glu Ser Asp Ser Ile Lys Ala Leu Gln Cys Ile
                    485                 490                 495
```

```
His Ala Lys Leu Leu Ser Glu Arg Thr Asn Thr Ser Asn Gln Phe Glu
            500                 505                 510

His Ala Ile Asp Glu Arg Leu Glu Gln Leu Lys Arg Leu Gly Ile
            515                 520                 525

<210> SEQ ID NO 25
<211> LENGTH: 433
<212> TYPE: PRT
<213> ORGANISM: Bacillus subtilis
<220> FEATURE:
<223> OTHER INFORMATION: Homoserine dehydrogenase

<400> SEQUENCE: 25

Met Lys Ala Ile Arg Val Gly Leu Leu Gly Leu Gly Thr Val Gly Ser
1               5                   10                  15

Gly Val Val Lys Ile Ile Gln Asp His Gln Asp Lys Leu Met His Gln
            20                  25                  30

Val Gly Cys Pro Val Thr Ile Lys Lys Val Leu Val Lys Asp Leu Glu
        35                  40                  45

Lys Lys Arg Glu Val Asp Leu Pro Lys Glu Val Leu Thr Thr Glu Val
    50                  55                  60

Tyr Asp Val Ile Asp Asp Pro Asp Val Asp Val Ile Glu Val Ile
65                  70                  75                  80

Gly Gly Val Glu Gln Thr Lys Gln Tyr Leu Val Asp Ala Leu Arg Ser
                85                  90                  95

Lys Lys His Val Val Thr Ala Asn Lys Asp Leu Met Ala Val Tyr Gly
            100                 105                 110

Ser Glu Leu Leu Ala Glu Ala Lys Glu Asn Gly Cys Asp Ile Tyr Phe
        115                 120                 125

Glu Ala Ser Val Ala Gly Gly Ile Pro Ile Leu Arg Thr Leu Glu Glu
    130                 135                 140

Gly Leu Ser Ser Asp Arg Ile Thr Lys Met Met Gly Ile Val Asn Gly
145                 150                 155                 160

Thr Thr Asn Phe Ile Leu Thr Lys Met Ile Lys Glu Lys Ser Pro Tyr
                165                 170                 175

Glu Glu Val Leu Lys Glu Ala Gln Asp Leu Gly Phe Ala Glu Ala Asp
            180                 185                 190

Pro Thr Ser Asp Val Glu Gly Leu Asp Ala Ala Arg Lys Met Ala Ile
        195                 200                 205

Leu Ala Arg Leu Gly Phe Ser Met Asn Val Asp Leu Glu Asp Val Lys
    210                 215                 220

Val Lys Gly Ile Ser Gln Ile Thr Asp Glu Asp Ile Ser Phe Ser Lys
225                 230                 235                 240

Arg Leu Gly Tyr Thr Met Lys Leu Ile Gly Ile Ala Gln Arg Asp Gly
                245                 250                 255

Ser Lys Ile Glu Val Ser Val Gln Pro Thr Leu Leu Pro Asp His His
            260                 265                 270

Pro Leu Ser Ala Val His Asn Glu Phe Asn Ala Val Tyr Val Tyr Gly
        275                 280                 285

Glu Ala Val Gly Glu Thr Met Phe Tyr Gly Pro Gly Ala Gly Ser Met
    290                 295                 300

Pro Thr Ala Thr Ser Val Val Ser Asp Leu Val Ala Val Met Lys Asn
305                 310                 315                 320

Met Arg Leu Gly Val Thr Gly Asn Ser Phe Val Gly Pro Gln Tyr Glu
                325                 330                 335

Lys Asn Met Lys Ser Pro Ser Asp Ile Tyr Ala Gln Gln Phe Leu Arg
```

-continued

```
                    340                 345                 350
Ile His Val Lys Asp Glu Val Gly Ser Phe Ser Lys Ile Thr Ser Val
                355                 360                 365

Phe Ser Glu Arg Gly Val Ser Phe Glu Lys Ile Leu Gln Leu Pro Ile
        370                 375                 380

Lys Gly His Asp Glu Leu Ala Glu Ile Val Ile Val Thr His His Thr
385                 390                 395                 400

Ser Glu Ala Asp Phe Ser Asp Ile Leu Gln Asn Leu Asn Asp Leu Glu
                405                 410                 415

Val Val Gln Glu Val Lys Ser Thr Tyr Arg Val Glu Gly Asn Gly Trp
                420                 425                 430

Ser

<210> SEQ ID NO 26
<211> LENGTH: 434
<212> TYPE: PRT
<213> ORGANISM: Artificial Sequence
<220> FEATURE:
<223> OTHER INFORMATION: Description of Artificial Sequence: Synthetic
      Pseudomonas putida homoserine dehydrogenase polypeptide

<400> SEQUENCE: 26

Met Lys Pro Val Lys Val Gly Ile Cys Gly Leu Gly Thr Val Gly Gly
1               5                   10                  15

Gly Thr Phe Asn Val Leu Gln Arg Asn Ala Glu Glu Ile Ala Arg Arg
                20                  25                  30

Ala Gly Arg Gly Ile Glu Val Ala Gln Ile Ala Met Arg Ser Gln Asn
            35                  40                  45

Pro Asn Cys Gln Ile Thr Gly Thr Pro Ile Thr Ala Asp Val Phe Glu
    50                  55                  60

Val Ala Ser Asn Pro Glu Ile Asp Ile Val Ile Glu Leu Ile Gly Gly
65                  70                  75                  80

Tyr Thr Ile Ala Arg Asp Leu Val Leu Lys Ala Ile Glu Asn Gly Lys
                85                  90                  95

His Val Val Thr Ala Asn Lys Ala Leu Ile Ala Val His Gly Asn Glu
                100                 105                 110

Ile Phe Ala Lys Ala Arg Glu Lys Gly Val Ile Val Ala Phe Glu Ala
            115                 120                 125

Ala Val Ala Gly Gly Ile Pro Val Ile Lys Ala Ile Arg Glu Gly Leu
    130                 135                 140

Ser Ala Asn Arg Ile Asn Trp Leu Ala Gly Ile Ile Asn Gly Thr Gly
145                 150                 155                 160

Asn Phe Ile Leu Thr Glu Met Arg Glu Lys Gly Arg Ala Phe Pro Asp
                165                 170                 175

Val Leu Ala Glu Ala Gln Ala Leu Gly Tyr Ala Glu Ala Asp Pro Thr
                180                 185                 190

Phe Asp Val Glu Gly Ile Asp Ala Ala His Lys Leu Thr Ile Leu Ala
            195                 200                 205

Ser Ile Ala Phe Gly Ile Pro Leu Gln Phe Asp Lys Ala Tyr Thr Glu
    210                 215                 220

Gly Ile Thr Gln Leu Thr Thr Ala Asp Val Asn Tyr Ala Glu Ala Leu
225                 230                 235                 240

Gly Tyr Arg Ile Lys His Leu Gly Val Ala Arg Arg Thr Ala Glu Gly
                245                 250                 255

Ile Glu Leu Arg Val His Pro Thr Leu Ile Pro Ala Asp Arg Leu Ile
                260                 265                 270
```

```
Ala Asn Val Asn Gly Val Met Asn Ala Val Met Val Asn Gly Asp Ala
            275                 280                 285

Ala Gly Ser Thr Leu Tyr Tyr Gly Ala Gly Ala Gly Met Glu Pro Thr
        290                 295                 300

Ala Ser Ser Val Val Gly Asp Leu Val Asp Val Arg Ala Met Thr
305                 310                 315                 320

Ser Asp Pro Glu Asn Arg Val Pro His Leu Ala Phe Gln Pro Asp Ser
                325                 330                 335

Leu Ser Ala His Pro Ile Leu Pro Ile Glu Ala Cys Glu Ser Ala Tyr
            340                 345                 350

Tyr Leu Arg Ile Gln Ala Lys Asp His Pro Gly Val Leu Ala Gln Val
        355                 360                 365

Ala Ser Ile Leu Ser Glu Arg Gly Ile Asn Ile Glu Ser Ile Met Gln
    370                 375                 380

Lys Glu Ala Glu Gln Asp Gly Leu Val Pro Met Ile Leu Val Thr
385                 390                 395                 400

His Gly Val Val Glu Gln Arg Ile Asn Asp Ala Ile Val Ala Leu Glu
                405                 410                 415

Ala Leu Gln Asp Val Val Gly Lys Val Val Arg Ile Arg Val Glu Gln
            420                 425                 430

Leu Asn

<210> SEQ ID NO 27
<211> LENGTH: 359
<212> TYPE: PRT
<213> ORGANISM: Saccharomyces cerevisiae
<220> FEATURE:
<223> OTHER INFORMATION: Homoserine dehydrogenase

<400> SEQUENCE: 27

Met Ser Thr Lys Val Val Asn Val Ala Val Ile Gly Ala Gly Val Val
1               5                   10                  15

Gly Ser Ala Phe Leu Asp Gln Leu Leu Ala Met Lys Ser Thr Ile Thr
            20                  25                  30

Tyr Asn Leu Val Leu Leu Ala Glu Ala Glu Arg Ser Leu Ile Ser Lys
        35                  40                  45

Asp Phe Ser Pro Leu Asn Val Gly Ser Asp Trp Lys Ala Ala Leu Ala
    50                  55                  60

Ala Ser Thr Thr Lys Thr Leu Pro Leu Asp Asp Leu Ile Ala His Leu
65                  70                  75                  80

Lys Thr Ser Pro Lys Pro Val Ile Leu Val Asp Asn Thr Ser Ser Ala
                85                  90                  95

Tyr Ile Ala Gly Phe Tyr Thr Lys Phe Val Glu Asn Gly Ile Ser Ile
            100                 105                 110

Ala Thr Pro Asn Lys Lys Ala Phe Ser Ser Asp Leu Ala Thr Trp Lys
        115                 120                 125

Ala Leu Phe Ser Asn Lys Pro Thr Asn Gly Phe Val Tyr His Glu Ala
    130                 135                 140

Thr Val Gly Ala Gly Leu Pro Ile Ile Ser Phe Leu Arg Glu Ile Ile
145                 150                 155                 160

Gln Thr Gly Asp Glu Val Glu Lys Ile Glu Gly Ile Phe Ser Gly Thr
                165                 170                 175

Leu Ser Tyr Ile Phe Asn Glu Phe Ser Thr Ser Gln Ala Asn Asp Val
            180                 185                 190

Lys Phe Ser Asp Val Val Lys Val Ala Lys Lys Leu Gly Tyr Thr Glu
```

```
              195                 200                 205
Pro Asp Pro Arg Asp Asp Leu Asn Gly Leu Asp Val Ala Arg Lys Val
210                 215                 220

Thr Ile Val Gly Arg Ile Ser Gly Val Glu Val Glu Ser Pro Thr Ser
225                 230                 235                 240

Phe Pro Val Gln Ser Leu Ile Pro Lys Pro Leu Glu Ser Val Lys Ser
                    245                 250                 255

Ala Asp Glu Phe Leu Glu Lys Leu Ser Asp Tyr Asp Lys Asp Leu Thr
                260                 265                 270

Gln Leu Lys Lys Glu Ala Ala Thr Glu Asn Lys Val Leu Arg Phe Ile
            275                 280                 285

Gly Lys Val Asp Val Ala Thr Lys Ser Val Ser Val Gly Ile Glu Lys
        290                 295                 300

Tyr Asp Tyr Ser His Pro Phe Ala Ser Leu Lys Gly Ser Asp Asn Val
305                 310                 315                 320

Ile Ser Ile Lys Thr Lys Arg Tyr Thr Asn Pro Val Val Ile Gln Gly
                    325                 330                 335

Ala Gly Ala Gly Ala Ala Val Thr Ala Ala Gly Val Leu Gly Asp Val
                340                 345                 350

Ile Lys Ile Ala Gln Arg Leu
            355

<210> SEQ ID NO 28
<211> LENGTH: 310
<212> TYPE: PRT
<213> ORGANISM: Escherichia coli
<220> FEATURE:
<223> OTHER INFORMATION: Homoserine kinase

<400> SEQUENCE: 28

Met Val Lys Val Tyr Ala Pro Ala Ser Ser Ala Asn Met Ser Val Gly
1               5                   10                  15

Phe Asp Val Leu Gly Ala Ala Val Thr Pro Val Asp Gly Ala Leu Leu
                20                  25                  30

Gly Asp Val Val Thr Val Glu Ala Ala Glu Thr Phe Ser Leu Asn Asn
            35                  40                  45

Leu Gly Arg Phe Ala Asp Lys Leu Pro Ser Glu Pro Arg Glu Asn Ile
    50                  55                  60

Val Tyr Gln Cys Trp Glu Arg Phe Cys Gln Glu Leu Gly Lys Gln Ile
65                  70                  75                  80

Pro Val Ala Met Thr Leu Glu Lys Asn Met Pro Ile Gly Ser Gly Leu
                85                  90                  95

Gly Ser Ser Ala Cys Ser Val Val Ala Ala Leu Met Ala Met Asn Glu
                100                 105                 110

His Cys Gly Lys Pro Leu Asn Asp Thr Arg Leu Leu Ala Leu Met Gly
            115                 120                 125

Glu Leu Glu Gly Arg Ile Ser Gly Ser Ile His Tyr Asp Asn Val Ala
        130                 135                 140

Pro Cys Phe Leu Gly Gly Met Gln Leu Met Ile Glu Glu Asn Asp Ile
145                 150                 155                 160

Ile Ser Gln Gln Val Pro Gly Phe Asp Glu Trp Leu Trp Val Leu Ala
                    165                 170                 175

Tyr Pro Gly Ile Lys Val Ser Thr Ala Glu Ala Arg Ala Ile Leu Pro
                180                 185                 190

Ala Gln Tyr Arg Arg Gln Asp Cys Ile Ala His Gly Arg His Leu Ala
            195                 200                 205
```

```
Gly Phe Ile His Ala Cys Tyr Ser Arg Gln Pro Glu Leu Ala Ala Lys
    210                 215                 220

Leu Met Lys Asp Val Ile Ala Glu Pro Tyr Arg Glu Arg Leu Leu Pro
225                 230                 235                 240

Gly Phe Arg Gln Ala Arg Gln Ala Val Ala Glu Ile Gly Ala Val Ala
                245                 250                 255

Ser Gly Ile Ser Gly Ser Gly Pro Thr Leu Phe Ala Leu Cys Asp Lys
            260                 265                 270

Pro Glu Thr Ala Gln Arg Val Ala Asp Trp Leu Gly Lys Asn Tyr Leu
        275                 280                 285

Gln Asn Gln Glu Gly Phe Val His Ile Cys Arg Leu Asp Thr Ala Gly
    290                 295                 300

Ala Arg Val Leu Glu Asn
305                 310

<210> SEQ ID NO 29
<211> LENGTH: 309
<212> TYPE: PRT
<213> ORGANISM: Bacillus subtilis
<220> FEATURE:
<223> OTHER INFORMATION: Homoserine kinase

<400> SEQUENCE: 29

Met Asn Glu Ala Asp Met Leu Phe Ser Val Thr Val Pro Gly Ser Thr
1               5                   10                  15

Ala Asn Leu Gly Pro Gly Phe Asp Ser Val Gly Met Ala Leu Ser Arg
            20                  25                  30

Tyr Leu Lys Leu Thr Val Phe Glu Ser Asp Lys Trp Ser Phe Glu Ala
        35                  40                  45

Glu Thr Glu Thr Val Ala Gly Ile Pro Ala Gly Thr Asp Asn Leu Ile
    50                  55                  60

Tyr Gln Val Ala Lys Arg Thr Ala Asp Leu Tyr Gly Lys Glu Met Pro
65                  70                  75                  80

Pro Val His Val Lys Val Trp Ser Asp Ile Pro Leu Ala Arg Gly Leu
                85                  90                  95

Gly Ser Ser Ala Ala Ala Ile Val Ala Ala Ile Glu Leu Ala Asp Glu
            100                 105                 110

Leu Cys Gly Leu Lys Leu Ser Glu Ala Asp Lys Leu His Leu Ala Ser
        115                 120                 125

Leu Glu Glu Gly His Pro Asp Asn Ala Gly Ala Ser Leu Val Gly Gly
    130                 135                 140

Leu Val Ile Gly Leu His Glu Asp Asp Glu Thr Gln Met Ile Arg Val
145                 150                 155                 160

Pro Asn Ala Asp Ile Asp Val Val Val Ile Pro Phe Tyr Glu Val
                165                 170                 175

Leu Thr Arg Asp Ala Arg Asp Val Leu Pro Lys Glu Phe Pro Tyr Ala
            180                 185                 190

Asp Ala Val Lys Ala Ser Ala Val Ser Asn Ile Leu Ile Ala Ala Ile
        195                 200                 205

Met Ser Lys Asp Trp Pro Leu Val Gly Lys Ile Met Lys Lys Asp Met
    210                 215                 220

Phe His Gln Pro Tyr Arg Ala Met Leu Val Pro Glu Leu Ser Lys Val
225                 230                 235                 240

Glu His Val Ala Glu Met Lys Gly Ala Tyr Gly Thr Ala Leu Ser Gly
                245                 250                 255
```

```
Ala Gly Pro Thr Ile Leu Val Met Thr Glu Lys Gly Lys Gly Glu
        260                 265                 270

Leu Lys Glu Gln Leu Ala Leu His Phe Pro His Cys Glu Val Asp Ala
    275                 280                 285

Leu Thr Val Pro Lys Glu Gly Ser Ile Ile Glu Arg Asn Pro Leu Tyr
    290                 295                 300

Gln Val Lys Ser Val
305

<210> SEQ ID NO 30
<211> LENGTH: 316
<212> TYPE: PRT
<213> ORGANISM: Pseudomonas putida
<220> FEATURE:
<223> OTHER INFORMATION: Homoserine kinase

<400> SEQUENCE: 30

Met Ser Val Phe Thr Pro Val Thr Arg Pro Glu Leu Glu Thr Phe Leu
1               5                   10                  15

Ala Pro Tyr Glu Leu Gly Arg Leu Leu Asp Phe Gln Gly Ile Ala Ala
            20                  25                  30

Gly Thr Glu Asn Ser Asn Phe Val Ser Leu Glu Gln Gly Glu Phe
        35                  40                  45

Val Leu Thr Leu Ile Glu Arg Gly Pro Ser Glu Asp Met Pro Phe Phe
50                  55                  60

Ile Glu Leu Leu Asp Thr Leu His Gly Ala Asp Met Pro Val Pro Tyr
65                  70                  75                  80

Ala Ile Arg Asp Arg Asp Gly Asn Gly Leu Arg Glu Leu Cys Gly Lys
                85                  90                  95

Pro Ala Leu Leu Gln Pro Arg Leu Ser Gly Lys His Ile Lys Ala Pro
            100                 105                 110

Asn Asn Gln His Cys Ala Gln Val Gly Glu Leu Leu Ala His Ile His
        115                 120                 125

Leu Ala Thr Arg Glu His Ile Ile Glu Arg Arg Thr Asp Arg Gly Leu
    130                 135                 140

Asp Trp Met Leu Ala Ser Gly Val Glu Leu Leu Pro Arg Leu Thr Ala
145                 150                 155                 160

Glu Gln Ala Ala Leu Leu Gln Pro Ala Leu Asp Glu Ile Ser Ala His
                165                 170                 175

Lys Ala Gln Ile Leu Ala Leu Pro Arg Ala Asn Leu His Ala Asp Leu
            180                 185                 190

Phe Arg Asp Asn Val Met Phe Glu Gly Thr His Leu Thr Gly Val Ile
        195                 200                 205

Asp Phe Tyr Asn Ala Cys Ser Gly Pro Met Leu Tyr Asp Ile Ala Ile
    210                 215                 220

Thr Val Asn Asp Trp Cys Leu Asp Glu Gln Gly Ala Val Asp Val Pro
225                 230                 235                 240

Arg Ala Gln Ala Leu Leu Ala Ala Tyr Ala Ala Leu Arg Pro Phe Thr
                245                 250                 255

Ala Ala Glu Ala Glu Leu Trp Pro Glu Met Leu Arg Val Gly Cys Val
            260                 265                 270

Arg Phe Trp Leu Ser Arg Leu Ile Ala Ala Glu Ser Phe Ala Gly Met
        275                 280                 285

Asp Val Met Ile His Asp Pro Ser Glu Phe Glu Val Arg Leu Ala Gln
    290                 295                 300

Arg Gln Gln Val Ala Leu His Leu Pro Phe Ala Leu
```

<210> SEQ ID NO 31
<211> LENGTH: 357
<212> TYPE: PRT
<213> ORGANISM: Saccharomyces cerevisiae
<220> FEATURE:
<223> OTHER INFORMATION: Homoserine kinase

<400> SEQUENCE: 31

```
Met Val Arg Ala Phe Lys Ile Lys Val Pro Ala Ser Ser Ala Asn Ile
1               5                   10                  15

Gly Pro Gly Tyr Asp Val Leu Gly Val Gly Leu Ser Leu Phe Leu Glu
            20                  25                  30

Leu Asp Val Thr Ile Asp Ser Ser Gln Ala Gln Glu Thr Asn Asp Asp
        35                  40                  45

Pro Asn Asn Cys Lys Leu Ser Tyr Thr Lys Glu Ser Glu Gly Tyr Ser
    50                  55                  60

Thr Val Pro Leu Arg Ser Asp Ala Asn Leu Ile Thr Arg Thr Ala Leu
65                  70                  75                  80

Tyr Val Leu Arg Cys Asn Asn Ile Arg Asn Phe Pro Ser Gly Thr Lys
                85                  90                  95

Val His Val Ser Asn Pro Ile Pro Leu Gly Arg Gly Leu Gly Ser Ser
            100                 105                 110

Gly Ala Ala Val Val Ala Gly Val Ile Leu Gly Asn Glu Val Ala Gln
        115                 120                 125

Leu Gly Phe Ser Lys Gln Arg Met Leu Asp Tyr Cys Leu Met Ile Glu
    130                 135                 140

Arg His Pro Asp Asn Ile Thr Ala Ala Met Met Gly Gly Phe Cys Gly
145                 150                 155                 160

Ser Phe Leu Arg Asp Leu Thr Pro Gln Glu Val Glu Arg Arg Glu Ile
                165                 170                 175

Pro Leu Ala Glu Val Leu Pro Glu Pro Ser Gly Gly Glu Asp Thr Gly
            180                 185                 190

Leu Val Pro Pro Leu Pro Pro Thr Asp Ile Gly Arg His Val Lys Tyr
        195                 200                 205

Gln Trp Asn Pro Ala Ile Lys Cys Ile Ala Ile Pro Gln Phe Glu
    210                 215                 220

Leu Ser Thr Ala Asp Ser Arg Gly Val Leu Pro Lys Ala Tyr Pro Thr
225                 230                 235                 240

Gln Asp Leu Val Phe Asn Leu Gln Arg Leu Ala Val Leu Thr Thr Ala
                245                 250                 255

Leu Thr Met Asp Pro Pro Asn Ala Asp Leu Ile Tyr Pro Ala Met Gln
            260                 265                 270

Asp Arg Val His Gln Pro Tyr Arg Lys Thr Leu Ile Pro Gly Leu Thr
        275                 280                 285

Glu Ile Leu Ser Cys Val Thr Pro Ser Thr Tyr Pro Gly Leu Leu Gly
    290                 295                 300

Ile Cys Leu Ser Gly Ala Gly Pro Thr Ile Leu Ala Leu Ala Thr Glu
305                 310                 315                 320

Asn Phe Glu Glu Ile Ser Gln Glu Ile Ile Asn Arg Phe Ala Lys Asn
                325                 330                 335

Gly Ile Lys Cys Ser Trp Lys Leu Leu Glu Pro Ala Tyr Asp Gly Ala
            340                 345                 350

Ser Val Glu Gln Gln
        355
```

<210> SEQ ID NO 32
<211> LENGTH: 428
<212> TYPE: PRT
<213> ORGANISM: Escherichia coli
<220> FEATURE:
<223> OTHER INFORMATION: Threonine synthase

<400> SEQUENCE: 32

```
Met Lys Leu Tyr Asn Leu Lys Asp His Asn Glu Gln Val Ser Phe Ala
1               5                   10                  15

Gln Ala Val Thr Gln Gly Leu Gly Lys Asn Gln Gly Leu Phe Phe Pro
            20                  25                  30

His Asp Leu Pro Glu Phe Ser Leu Thr Glu Ile Asp Glu Met Leu Lys
        35                  40                  45

Leu Asp Phe Val Thr Arg Ser Ala Lys Ile Leu Ser Ala Phe Ile Gly
    50                  55                  60

Asp Glu Ile Pro Gln Glu Ile Leu Glu Glu Arg Val Arg Ala Ala Phe
65                  70                  75                  80

Ala Phe Pro Ala Pro Val Ala Asn Val Glu Ser Asp Val Gly Cys Leu
                85                  90                  95

Glu Leu Phe His Gly Pro Thr Leu Ala Phe Lys Asp Phe Gly Gly Arg
            100                 105                 110

Phe Met Ala Gln Met Leu Thr His Ile Ala Gly Asp Lys Pro Val Thr
        115                 120                 125

Ile Leu Thr Ala Thr Ser Gly Asp Thr Gly Ala Ala Val Ala His Ala
    130                 135                 140

Phe Tyr Gly Leu Pro Asn Val Lys Val Val Ile Leu Tyr Pro Arg Gly
145                 150                 155                 160

Lys Ile Ser Pro Leu Gln Glu Lys Leu Phe Cys Thr Leu Gly Gly Asn
                165                 170                 175

Ile Glu Thr Val Ala Ile Asp Gly Asp Phe Asp Ala Cys Gln Ala Leu
            180                 185                 190

Val Lys Gln Ala Phe Asp Asp Glu Glu Leu Lys Val Ala Leu Gly Leu
        195                 200                 205

Asn Ser Ala Asn Ser Ile Asn Ile Ser Arg Leu Leu Ala Gln Ile Cys
    210                 215                 220

Tyr Tyr Phe Glu Ala Val Ala Gln Leu Pro Gln Glu Thr Arg Asn Gln
225                 230                 235                 240

Leu Val Val Ser Val Pro Ser Gly Asn Phe Gly Asp Leu Thr Ala Gly
                245                 250                 255

Leu Leu Ala Lys Ser Leu Gly Leu Pro Val Lys Arg Phe Ile Ala Ala
            260                 265                 270

Thr Asn Val Asn Asp Thr Val Pro Arg Phe Leu His Asp Gly Gln Trp
        275                 280                 285

Ser Pro Lys Ala Thr Gln Ala Thr Leu Ser Asn Ala Met Asp Val Ser
    290                 295                 300

Gln Pro Asn Asn Trp Pro Arg Val Glu Glu Leu Phe Arg Arg Lys Ile
305                 310                 315                 320

Trp Gln Leu Lys Glu Leu Gly Tyr Ala Ala Val Asp Asp Glu Thr Thr
                325                 330                 335

Gln Gln Thr Met Arg Glu Leu Lys Glu Leu Gly Tyr Thr Ser Glu Pro
            340                 345                 350

His Ala Ala Val Ala Tyr Arg Ala Leu Arg Asp Gln Leu Asn Pro Gly
        355                 360                 365
```

-continued

Glu Tyr Gly Leu Phe Leu Gly Thr Ala His Pro Ala Lys Phe Lys Glu
        370                 375                 380

Ser Val Glu Ala Ile Leu Gly Glu Thr Leu Asp Leu Pro Lys Glu Leu
385                 390                 395                 400

Ala Glu Arg Ala Asp Leu Pro Leu Leu Ser His Asn Leu Pro Ala Asp
                405                 410                 415

Phe Ala Ala Leu Arg Lys Leu Met Met Asn His Gln
                420                 425

<210> SEQ ID NO 33
<211> LENGTH: 352
<212> TYPE: PRT
<213> ORGANISM: Bacillus subtilis
<220> FEATURE:
<223> OTHER INFORMATION: Threonine synthase

<400> SEQUENCE: 33

Met Trp Lys Gly Leu Ile His Gln Tyr Lys Glu Phe Leu Pro Val Thr
1               5                   10                  15

Asp Gln Thr Pro Ala Leu Thr Leu His Glu Gly Asn Thr Pro Leu Ile
                20                  25                  30

His Leu Pro Lys Leu Ser Glu Gln Leu Gly Ile Glu Leu His Val Lys
            35                  40                  45

Thr Glu Gly Val Asn Pro Thr Gly Ser Phe Lys Asp Arg Gly Met Val
        50                  55                  60

Met Ala Val Ala Lys Ala Lys Glu Gly Asn Asp Thr Ile Met Cys
65                  70                  75                  80

Ala Ser Thr Gly Asn Thr Ser Ala Ala Ala Ala Tyr Ala Ala Arg
                85                  90                  95

Ala Asn Met Lys Cys Ile Val Ile Ile Pro Asn Gly Lys Ile Ala Phe
                100                 105                 110

Gly Lys Leu Ala Gln Ala Val Met Tyr Gly Ala Glu Ile Ile Ala Ile
            115                 120                 125

Asp Gly Asn Phe Asp Asp Ala Leu Lys Ile Val Arg Ser Ile Cys Glu
        130                 135                 140

Lys Ser Pro Ile Ala Leu Val Asn Ser Val Asn Pro Tyr Arg Ile Glu
145                 150                 155                 160

Gly Gln Lys Thr Ala Ala Phe Glu Val Cys Glu Gln Leu Gly Glu Ala
                165                 170                 175

Pro Asp Val Leu Ala Ile Pro Val Gly Asn Ala Gly Asn Ile Thr Ala
                180                 185                 190

Tyr Trp Lys Gly Phe Lys Glu Tyr His Glu Lys Asn Gly Thr Gly Leu
            195                 200                 205

Pro Lys Met Arg Gly Phe Glu Ala Glu Gly Ala Ala Ile Val Arg
        210                 215                 220

Asn Glu Val Ile Glu Asn Pro Glu Thr Ile Ala Thr Ala Ile Arg Ile
225                 230                 235                 240

Gly Asn Pro Ala Ser Trp Asp Lys Ala Val Lys Ala Ala Glu Glu Ser
                245                 250                 255

Asn Gly Lys Ile Asp Glu Val Thr Asp Asp Glu Ile Leu His Ala Tyr
                260                 265                 270

Gln Leu Ile Ala Arg Val Glu Gly Val Phe Ala Glu Pro Gly Ser Cys
            275                 280                 285

Ala Ser Ile Ala Gly Val Leu Lys Gln Val Lys Ser Gly Glu Ile Pro
        290                 295                 300

Lys Gly Ser Lys Val Val Ala Val Leu Thr Gly Asn Gly Leu Lys Asp

```
                305                 310                 315                 320
Pro Asn Thr Ala Val Asp Ile Ser Glu Ile Lys Pro Val Thr Leu Pro
                    325                 330                 335

Thr Asp Glu Asp Ser Ile Leu Glu Tyr Val Lys Gly Ala Ala Arg Val
                340                 345                 350

<210> SEQ ID NO 34
<211> LENGTH: 481
<212> TYPE: PRT
<213> ORGANISM: Corynebacterium glutamicum
<220> FEATURE:
<223> OTHER INFORMATION: Threonine synthase

<400> SEQUENCE: 34

Met Asp Tyr Ile Ser Thr Arg Asp Ala Ser Arg Thr Pro Ala Arg Phe
1               5                   10                  15

Ser Asp Ile Leu Leu Gly Gly Leu Ala Pro Asp Gly Gly Leu Tyr Leu
                20                  25                  30

Pro Ala Thr Tyr Pro Gln Leu Asp Asp Ala Gln Leu Ser Lys Trp Arg
                35                  40                  45

Glu Val Leu Ala Asn Gly Tyr Ala Ala Leu Ala Ala Glu Val Ile
 50                 55                  60

Ser Leu Phe Val Asp Asp Ile Pro Val Glu Asp Ile Lys Ala Ile Thr
65                  70                  75                  80

Ala Arg Ala Tyr Thr Tyr Pro Lys Phe Asn Ser Glu Asp Ile Val Pro
                85                  90                  95

Val Thr Glu Leu Glu Asp Asn Ile Tyr Leu Gly His Leu Ser Glu Gly
                100                 105                 110

Pro Thr Ala Ala Phe Lys Asp Met Ala Met Gln Leu Leu Gly Glu Leu
            115                 120                 125

Phe Glu Tyr Glu Leu Arg Arg Arg Asn Glu Thr Ile Asn Ile Leu Gly
    130                 135                 140

Ala Thr Ser Gly Asp Thr Gly Ser Ser Ala Glu Tyr Ala Met Arg Gly
145                 150                 155                 160

Arg Glu Gly Ile Arg Val Phe Met Leu Thr Pro Ala Gly Arg Met Thr
                165                 170                 175

Pro Phe Gln Gln Ala Gln Met Phe Gly Leu Asp Asp Pro Asn Ile Phe
                180                 185                 190

Asn Ile Ala Leu Asp Gly Val Phe Asp Asp Cys Gln Asp Val Val Lys
            195                 200                 205

Ala Val Ser Ala Asp Ala Glu Phe Lys Lys Asp Asn Arg Ile Gly Ala
    210                 215                 220

Val Asn Ser Ile Asn Trp Ala Arg Leu Met Ala Gln Val Val Tyr Tyr
225                 230                 235                 240

Val Ser Ser Trp Ile Arg Thr Thr Thr Ser Asn Asp Gln Lys Val Ser
                245                 250                 255

Phe Ser Val Pro Thr Gly Asn Phe Gly Asp Ile Cys Ala Gly His Ile
                260                 265                 270

Ala Arg Gln Met Gly Leu Pro Ile Asp Arg Leu Ile Val Ala Thr Asn
            275                 280                 285

Glu Asn Asp Val Leu Asp Glu Phe Phe Arg Thr Gly Asp Tyr Arg Val
    290                 295                 300

Arg Ser Ser Ala Asp Thr His Glu Thr Ser Ser Pro Ser Met Asp Ile
305                 310                 315                 320

Ser Arg Ala Ser Asn Phe Glu Arg Phe Ile Phe Asp Leu Leu Gly Arg
                325                 330                 335
```

```
Asp Ala Thr Arg Val Asn Asp Leu Phe Gly Thr Gln Val Arg Gln Gly
        340                 345                 350

Gly Phe Ser Leu Ala Asp Asp Ala Asn Phe Glu Lys Ala Ala Ala Glu
        355                 360                 365

Tyr Gly Phe Ala Ser Gly Arg Ser Thr His Ala Asp Arg Val Ala Thr
370                 375                 380

Ile Ala Asp Val His Ser Arg Leu Asp Val Leu Ile Asp Pro His Thr
385                 390                 395                 400

Ala Asp Gly Val His Val Ala Arg Gln Trp Arg Asp Glu Val Asn Thr
                405                 410                 415

Pro Ile Ile Val Leu Glu Thr Ala Leu Pro Val Lys Phe Ala Asp Thr
                420                 425                 430

Ile Val Glu Ala Ile Gly Glu Ala Pro Gln Thr Pro Glu Arg Phe Ala
                435                 440                 445

Ala Ile Met Asp Ala Pro Phe Lys Val Ser Asp Leu Pro Asn Asp Thr
        450                 455                 460

Asp Ala Val Lys Gln Tyr Ile Val Asp Ala Ile Ala Asn Thr Ser Val
465                 470                 475                 480

Lys

<210> SEQ ID NO 35
<211> LENGTH: 329
<212> TYPE: PRT
<213> ORGANISM: Escherichia coli
<220> FEATURE:
<223> OTHER INFORMATION: Threonine deaminase (TdcB)

<400> SEQUENCE: 35

Met His Ile Thr Tyr Asp Leu Pro Val Ala Ile Asp Asp Ile Ile Glu
1               5                   10                  15

Ala Lys Gln Arg Leu Ala Gly Arg Ile Tyr Lys Thr Gly Met Pro Arg
            20                  25                  30

Ser Asn Tyr Phe Ser Glu Arg Cys Lys Gly Glu Ile Phe Leu Lys Phe
        35                  40                  45

Glu Asn Met Gln Arg Thr Gly Ser Phe Lys Ile Arg Gly Ala Phe Asn
    50                  55                  60

Lys Leu Ser Ser Leu Thr Asp Ala Glu Lys Arg Lys Gly Val Val Ala
65                  70                  75                  80

Cys Ser Ala Gly Asn His Ala Gln Gly Val Ser Leu Ser Cys Ala Met
                85                  90                  95

Leu Gly Ile Asp Gly Lys Val Val Met Pro Lys Gly Ala Pro Lys Ser
            100                 105                 110

Lys Val Ala Ala Thr Cys Asp Tyr Ser Ala Glu Val Val Leu His Gly
        115                 120                 125

Asp Asn Phe Asn Asp Thr Ile Ala Lys Val Ser Glu Ile Val Glu Met
    130                 135                 140

Glu Gly Arg Ile Phe Ile Pro Pro Tyr Asp Asp Pro Lys Val Ile Ala
145                 150                 155                 160

Gly Gln Gly Thr Ile Gly Leu Glu Ile Met Glu Asp Leu Tyr Asp Val
                165                 170                 175

Asp Asn Val Ile Val Pro Ile Gly Gly Gly Gly Leu Ile Ala Gly Ile
            180                 185                 190

Ala Val Ala Ile Lys Ser Ile Asn Pro Thr Ile Arg Val Ile Gly Val
        195                 200                 205

Gln Ser Glu Asn Val His Gly Met Ala Ala Ser Phe His Ser Gly Glu
```

```
                    210                 215                 220
Ile Thr Thr His Arg Thr Thr Gly Thr Leu Ala Asp Gly Cys Asp Val
225                 230                 235                 240

Ser Arg Pro Gly Asn Leu Thr Tyr Glu Ile Val Arg Glu Leu Val Asp
                    245                 250                 255

Asp Ile Val Leu Val Ser Glu Asp Glu Ile Arg Asn Ser Met Ile Ala
                260                 265                 270

Leu Ile Gln Arg Asn Lys Val Thr Glu Gly Ala Gly Ala Leu Ala
            275                 280                 285

Cys Ala Ala Leu Leu Ser Gly Lys Leu Asp Gln Tyr Ile Gln Asn Arg
290                 295                 300

Lys Thr Val Ser Ile Ile Ser Gly Gly Asn Ile Asp Leu Ser Arg Val
305                 310                 315                 320

Ser Gln Ile Thr Gly Phe Val Asp Ala
                325

<210> SEQ ID NO 36
<211> LENGTH: 514
<212> TYPE: PRT
<213> ORGANISM: Escherichia coli
<220> FEATURE:
<223> OTHER INFORMATION: Threonine deaminase (IlvA)

<400> SEQUENCE: 36

Met Ala Asp Ser Gln Pro Leu Ser Gly Ala Pro Glu Gly Ala Glu Tyr
1               5                   10                  15

Leu Arg Ala Val Leu Arg Ala Pro Val Tyr Glu Ala Ala Gln Val Thr
                20                  25                  30

Pro Leu Gln Lys Met Glu Lys Leu Ser Ser Arg Leu Asp Asn Val Ile
            35                  40                  45

Leu Val Lys Arg Glu Asp Arg Gln Pro Val His Ser Phe Lys Leu Arg
50                  55                  60

Gly Ala Tyr Ala Met Met Ala Gly Leu Thr Glu Glu Gln Lys Ala His
65                  70                  75                  80

Gly Val Ile Thr Ala Ser Ala Gly Asn His Ala Gln Gly Val Ala Phe
                85                  90                  95

Ser Ser Ala Arg Leu Gly Val Lys Ala Leu Ile Val Met Pro Thr Ala
            100                 105                 110

Thr Ala Asp Ile Lys Val Asp Ala Val Arg Gly Phe Gly Gly Glu Val
            115                 120                 125

Leu Leu His Gly Ala Asn Phe Asp Glu Ala Lys Ala Lys Ala Ile Glu
130                 135                 140

Leu Ser Gln Gln Gln Gly Phe Thr Trp Val Pro Pro Phe Asp His Pro
145                 150                 155                 160

Met Val Ile Ala Gly Gln Gly Thr Leu Ala Leu Glu Leu Leu Gln Gln
                165                 170                 175

Asp Ala His Leu Asp Arg Val Phe Val Pro Val Gly Gly Gly Gly Leu
            180                 185                 190

Ala Ala Gly Val Ala Val Leu Ile Lys Gln Leu Met Pro Gln Ile Lys
            195                 200                 205

Val Ile Ala Val Glu Ala Glu Asp Ser Ala Cys Leu Lys Ala Ala Leu
210                 215                 220

Asp Ala Gly His Pro Val Asp Leu Pro Arg Val Gly Leu Phe Ala Glu
225                 230                 235                 240

Gly Val Ala Val Lys Arg Ile Gly Asp Glu Thr Phe Arg Leu Cys Gln
                245                 250                 255
```

```
Glu Tyr Leu Asp Asp Ile Ile Thr Val Asp Ser Asp Ala Ile Cys Ala
            260                 265                 270

Ala Met Lys Asp Leu Phe Glu Asp Val Arg Ala Val Ala Glu Pro Ser
            275                 280                 285

Gly Ala Leu Ala Leu Ala Gly Met Lys Lys Tyr Ile Ala Leu His Asn
        290                 295                 300

Ile Arg Gly Glu Arg Leu Ala His Ile Leu Ser Gly Ala Asn Val Asn
305                 310                 315                 320

Phe His Gly Leu Arg Tyr Val Ser Glu Arg Cys Glu Leu Gly Glu Gln
                325                 330                 335

Arg Glu Ala Leu Leu Ala Val Thr Ile Pro Glu Glu Lys Gly Ser Phe
            340                 345                 350

Leu Lys Phe Cys Gln Leu Leu Gly Gly Arg Ser Val Thr Glu Phe Asn
            355                 360                 365

Tyr Arg Phe Ala Asp Ala Lys Asn Ala Cys Ile Phe Val Gly Val Arg
        370                 375                 380

Leu Ser Arg Gly Leu Glu Glu Arg Lys Glu Ile Leu Gln Met Leu Asn
385                 390                 395                 400

Asp Gly Gly Tyr Ser Val Val Asp Leu Ser Asp Asp Glu Met Ala Lys
                405                 410                 415

Leu His Val Arg Tyr Met Val Gly Gly Arg Pro Ser His Pro Leu Gln
            420                 425                 430

Glu Arg Leu Tyr Ser Phe Glu Phe Pro Glu Ser Pro Gly Ala Leu Leu
            435                 440                 445

Arg Phe Leu Asn Thr Leu Gly Thr Tyr Trp Asn Ile Ser Leu Phe His
        450                 455                 460

Tyr Arg Ser His Gly Thr Asp Tyr Gly Arg Val Leu Ala Ala Phe Glu
465                 470                 475                 480

Leu Gly Asp His Glu Pro Asp Phe Glu Thr Arg Leu Asn Glu Leu Gly
                485                 490                 495

Tyr Asp Cys His Asp Glu Thr Asn Asn Pro Ala Phe Arg Phe Phe Leu
            500                 505                 510

Ala Gly

<210> SEQ ID NO 37
<211> LENGTH: 422
<212> TYPE: PRT
<213> ORGANISM: Bacillus subtilis
<220> FEATURE:
<223> OTHER INFORMATION: Threonine deaminase (IlvA)

<400> SEQUENCE: 37

Met Lys Pro Leu Leu Lys Glu Asn Ser Leu Ile Gln Val Lys Asp Ile
1               5                   10                  15

Leu Lys Ala His Gln Asn Val Lys Asp Val Val Ile His Thr Pro Leu
            20                  25                  30

Gln Arg Asn Asp Arg Leu Ser Glu Arg Tyr Glu Cys Asn Ile Tyr Leu
        35                  40                  45

Lys Arg Glu Asp Leu Gln Val Val Arg Ser Phe Lys Leu Arg Gly Ala
    50                  55                  60

Tyr His Lys Met Lys Gln Leu Ser Glu Gln Thr Glu Asn Gly Val
65                  70                  75                  80

Val Cys Ala Ser Ala Gly Asn His Ala Gln Gly Val Ala Phe Ser Cys
                85                  90                  95

Lys His Leu Gly Ile His Gly Lys Ile Phe Met Pro Ser Thr Thr Pro
```

```
                  100                 105                 110
Arg Gln Lys Val Ser Gln Val Glu Leu Phe Gly Lys Gly Phe Ile Asp
        115                 120                 125

Ile Ile Leu Thr Gly Asp Thr Phe Asp Asp Ala Tyr Lys Ser Ala Ala
        130                 135                 140

Glu Cys Cys Glu Ala Glu Ser Arg Thr Phe Ile His Pro Phe Asp Asp
145                 150                 155                 160

Pro Asp Val Met Ala Gly Gln Gly Thr Leu Ala Val Glu Ile Leu Asn
                165                 170                 175

Asp Ile Asp Thr Glu Pro His Phe Leu Phe Ala Ser Val Gly Gly Gly
                180                 185                 190

Gly Leu Leu Ser Gly Val Gly Thr Tyr Leu Lys Asn Val Ser Pro Asp
        195                 200                 205

Thr Lys Val Ile Ala Val Glu Pro Ala Gly Ala Ala Ser Tyr Phe Glu
        210                 215                 220

Ser Asn Lys Ala Gly His Val Val Thr Leu Asp Lys Ile Asp Lys Phe
225                 230                 235                 240

Val Asp Gly Ala Ala Val Lys Lys Ile Gly Glu Glu Thr Phe Arg Thr
                245                 250                 255

Leu Glu Thr Val Val Asp Asp Ile Leu Leu Val Pro Glu Gly Lys Val
                260                 265                 270

Cys Thr Ser Ile Leu Glu Leu Tyr Asn Glu Cys Ala Val Val Ala Glu
        275                 280                 285

Pro Ala Gly Ala Leu Ser Val Ala Ala Leu Asp Leu Tyr Lys Asp Gln
        290                 295                 300

Ile Lys Gly Lys Asn Val Val Cys Val Val Ser Gly Gly Asn Asn Asp
305                 310                 315                 320

Ile Gly Arg Met Gln Glu Met Lys Glu Arg Ser Leu Ile Phe Glu Gly
                325                 330                 335

Leu Gln His Tyr Phe Ile Val Asn Phe Pro Gln Arg Ala Gly Ala Leu
                340                 345                 350

Arg Glu Phe Leu Asp Glu Val Leu Gly Pro Asn Asp Asp Ile Thr Arg
        355                 360                 365

Phe Glu Tyr Thr Lys Lys Asn Asn Lys Ser Asn Gly Pro Ala Leu Val
        370                 375                 380

Gly Ile Glu Leu Gln Asn Lys Ala Asp Tyr Gly Pro Leu Ile Glu Arg
385                 390                 395                 400

Met Asn Lys Lys Pro Phe His Tyr Val Glu Val Asn Lys Asp Glu Asp
                405                 410                 415

Leu Phe His Leu Leu Ile
                420

<210> SEQ ID NO 38
<211> LENGTH: 436
<212> TYPE: PRT
<213> ORGANISM: Corynebacterium glutamicum
<220> FEATURE:
<223> OTHER INFORMATION: Threonine deaminase (IlvA)

<400> SEQUENCE: 38

Met Ser Glu Thr Tyr Val Ser Glu Lys Ser Pro Gly Val Met Ala Ser
1               5                   10                  15

Gly Ala Glu Leu Ile Arg Ala Ala Asp Ile Gln Thr Ala Gln Ala Arg
                20                  25                  30

Ile Ser Ser Val Ile Ala Pro Thr Pro Leu Gln Tyr Cys Pro Arg Leu
        35                  40                  45
```

Ser Glu Glu Thr Gly Ala Glu Ile Tyr Leu Lys Arg Glu Asp Leu Gln
 50                  55                  60

Asp Val Arg Ser Tyr Lys Ile Arg Gly Ala Leu Asn Ser Gly Ala Gln
 65                  70                  75                  80

Leu Thr Gln Glu Gln Arg Asp Ala Gly Ile Val Ala Ala Ser Ala Gly
                 85                  90                  95

Asn His Ala Gln Gly Val Ala Tyr Val Cys Lys Ser Leu Gly Val Gln
                100                 105                 110

Gly Arg Ile Tyr Val Pro Val Gln Thr Pro Lys Gln Lys Arg Asp Arg
            115                 120                 125

Ile Met Val His Gly Gly Glu Phe Val Ser Leu Val Thr Gly Asn
            130                 135                 140

Asn Phe Asp Glu Ala Ser Ala Ala His Glu Asp Ala Glu Arg Thr
145                 150                 155                 160

Gly Ala Thr Leu Ile Glu Pro Phe Asp Ala Arg Asn Thr Val Ile Gly
                165                 170                 175

Gln Gly Thr Val Ala Ala Glu Ile Leu Ser Gln Leu Thr Ser Met Gly
            180                 185                 190

Lys Ser Ala Asp His Val Met Val Pro Val Gly Gly Gly Leu Leu
            195                 200                 205

Ala Gly Val Val Ser Tyr Met Ala Asp Met Ala Pro Arg Thr Ala Ile
210                 215                 220

Val Gly Ile Glu Pro Ala Gly Ala Ala Ser Met Gln Ala Ala Leu His
225                 230                 235                 240

Asn Gly Gly Pro Ile Thr Leu Glu Thr Val Asp Pro Phe Val Asp Gly
                245                 250                 255

Ala Ala Val Lys Arg Val Gly Asp Leu Asn Tyr Thr Ile Val Glu Lys
                260                 265                 270

Asn Gln Gly Arg Val His Met Met Ser Ala Thr Glu Gly Ala Val Cys
                275                 280                 285

Thr Glu Met Leu Asp Leu Tyr Gln Asn Glu Gly Ile Ile Ala Glu Pro
    290                 295                 300

Ala Gly Ala Leu Ser Ile Ala Gly Leu Lys Glu Met Ser Phe Ala Pro
305                 310                 315                 320

Gly Ser Val Val Val Cys Ile Ile Ser Gly Gly Asn Asn Asp Val Leu
                325                 330                 335

Arg Tyr Ala Glu Ile Ala Glu Arg Ser Leu Val His Arg Gly Leu Lys
                340                 345                 350

His Tyr Phe Leu Val Asn Phe Pro Gln Lys Pro Gly Gln Leu Arg His
            355                 360                 365

Phe Leu Glu Asp Ile Leu Gly Pro Asp Asp Ile Thr Leu Phe Glu
    370                 375                 380

Tyr Leu Lys Arg Asn Asn Arg Glu Thr Gly Thr Ala Leu Val Gly Ile
385                 390                 395                 400

His Leu Ser Glu Ala Ser Gly Leu Asp Ser Leu Leu Glu Arg Met Glu
                405                 410                 415

Glu Ser Ala Ile Asp Ser Arg Arg Leu Glu Pro Gly Thr Pro Glu Tyr
            420                 425                 430

Glu Tyr Leu Thr
            435

<210> SEQ ID NO 39
<211> LENGTH: 310
<212> TYPE: PRT

<213> ORGANISM: Corynebacterium glutamicum
<220> FEATURE:
<223> OTHER INFORMATION: Threonine deaminase (TdcB)

<400> SEQUENCE: 39

Met Leu Thr Leu Asn Asp Val Ile Thr Ala Gln Gln Arg Thr Ala Pro
1               5                   10                  15

His Val Arg Arg Thr Pro Leu Phe Glu Ala Asp Pro Ile Asp Gly Thr
            20                  25                  30

Gln Ile Trp Ile Lys Ala Glu Phe Leu Gln Lys Cys Gly Val Phe Lys
        35                  40                  45

Thr Arg Gly Ala Phe Asn Arg Gln Leu Ala Ala Ser Glu Asn Gly Leu
    50                  55                  60

Leu Asp Pro Thr Val Gly Ile Val Ala Ala Ser Gly Gly Asn Ala Gly
65                  70                  75                  80

Leu Ala Asn Ala Phe Ala Ala Ser Leu Ser Val Pro Ala Thr Val
                85                  90                  95

Leu Val Pro Glu Thr Ala Pro Gln Val Lys Val Asp Arg Leu Lys Gln
            100                 105                 110

Tyr Gly Ala Thr Val Gln Gln Ile Gly Ser Glu Tyr Ala Glu Ala Phe
        115                 120                 125

Glu Ala Ala Gln Thr Phe Glu Ser Glu Thr Gly Ala Leu Phe Cys His
    130                 135                 140

Ala Tyr Asp Gln Pro Asp Ile Ala Ala Gly Ala Gly Val Ile Gly Leu
145                 150                 155                 160

Glu Ile Val Glu Asp Leu Pro Asp Val Asp Thr Ile Val Val Ala Val
                165                 170                 175

Gly Gly Gly Gly Leu Tyr Ala Gly Ile Ala Ala Val Val Ala Ala His
            180                 185                 190

Asp Ile Lys Val Val Ala Val Glu Pro Ser Lys Ile Pro Thr Leu His
        195                 200                 205

Asn Ser Leu Ile Ala Gly Gln Pro Val Asp Val Asn Val Ser Gly Ile
    210                 215                 220

Ala Ala Asp Ser Leu Gly Ala Arg Gln Ile Gly Arg Glu Ala Phe Asp
225                 230                 235                 240

Ile Ala Thr Ala His Pro Pro Ile Gly Val Leu Val Asp Asp Glu Ala
                245                 250                 255

Ile Ile Ala Ala Arg Arg His Leu Trp Asp Asn Tyr Arg Ile Pro Ala
            260                 265                 270

Glu His Gly Ala Ala Ala Ala Leu Ala Ser Leu Thr Ser Gly Ala Tyr
        275                 280                 285

Lys Pro Ala Ala Asp Glu Lys Val Ala Val Ile Val Cys Gly Ala Asn
    290                 295                 300

Thr Asp Leu Thr Thr Leu
305                 310

<210> SEQ ID NO 40
<211> LENGTH: 491
<212> TYPE: PRT
<213> ORGANISM: Methanocaldococcus jannaschii
<220> FEATURE:
<223> OTHER INFORMATION: Citramalate synthase

<400> SEQUENCE: 40

Met Met Val Arg Ile Phe Asp Thr Thr Leu Arg Asp Gly Glu Gln Thr
1               5                   10                  15

Pro Gly Val Ser Leu Thr Pro Asn Asp Lys Leu Glu Ile Ala Lys Lys

```
                20                  25                  30
Leu Asp Glu Leu Gly Val Asp Val Ile Glu Ala Gly Ser Ala Ile Thr
             35                  40                  45

Ser Lys Gly Glu Arg Glu Gly Ile Lys Leu Ile Thr Lys Glu Gly Leu
 50                  55                  60

Asn Ala Glu Ile Cys Ser Phe Val Arg Ala Leu Pro Val Asp Ile Asp
 65                  70                  75                  80

Ala Ala Leu Glu Cys Asp Val Asp Ser Val His Leu Val Val Pro Thr
                 85                  90                  95

Ser Pro Ile His Met Lys Tyr Lys Leu Arg Lys Thr Glu Asp Glu Val
                100                 105                 110

Leu Glu Thr Ala Leu Lys Ala Val Glu Tyr Ala Lys Glu His Gly Leu
            115                 120                 125

Ile Val Glu Leu Ser Ala Glu Asp Ala Thr Arg Ser Asp Val Asn Phe
        130                 135                 140

Leu Ile Lys Leu Phe Asn Glu Gly Lys Val Gly Ala Asp Arg Val
145                 150                 155                 160

Cys Val Cys Asp Thr Val Gly Val Leu Thr Pro Gln Lys Ser Gln Glu
                165                 170                 175

Leu Phe Lys Lys Ile Thr Glu Asn Val Asn Leu Pro Val Ser Val His
                180                 185                 190

Cys His Asn Asp Phe Gly Met Ala Thr Ala Asn Thr Cys Ser Ala Val
            195                 200                 205

Leu Gly Gly Ala Val Gln Cys His Val Thr Val Asn Gly Ile Gly Glu
        210                 215                 220

Arg Ala Gly Asn Ala Ser Leu Glu Glu Val Val Ala Ala Leu Lys Ile
225                 230                 235                 240

Leu Tyr Gly Tyr Asp Thr Lys Ile Lys Met Glu Lys Leu Tyr Glu Val
                245                 250                 255

Ser Arg Ile Val Ser Arg Leu Met Lys Leu Pro Val Pro Pro Asn Lys
                260                 265                 270

Ala Ile Val Gly Asp Asn Ala Phe Ala His Glu Ala Gly Ile His Val
            275                 280                 285

Asp Gly Leu Ile Lys Asn Thr Glu Thr Tyr Glu Pro Ile Lys Pro Glu
        290                 295                 300

Met Val Gly Asn Arg Arg Ile Ile Leu Gly Lys His Ser Gly Arg
305                 310                 315                 320

Lys Ala Leu Lys Tyr Lys Leu Asp Leu Met Gly Ile Asn Val Ser Asp
                325                 330                 335

Glu Gln Leu Asn Lys Ile Tyr Glu Arg Val Lys Glu Phe Gly Asp Leu
            340                 345                 350

Gly Lys Tyr Ile Ser Asp Ala Asp Leu Leu Ala Ile Val Arg Glu Val
        355                 360                 365

Thr Gly Lys Leu Val Glu Glu Lys Ile Lys Leu Asp Glu Leu Thr Val
            370                 375                 380

Val Ser Gly Asn Lys Ile Thr Pro Ile Ala Ser Val Lys Leu His Tyr
385                 390                 395                 400

Lys Gly Glu Asp Ile Thr Leu Ile Glu Thr Ala Tyr Gly Val Gly Pro
                405                 410                 415

Val Asp Ala Ala Ile Asn Ala Val Arg Lys Ala Ile Ser Gly Val Ala
            420                 425                 430

Asp Ile Lys Leu Val Glu Tyr Arg Val Glu Ala Ile Gly Gly Gly Thr
        435                 440                 445
```

```
Asp Ala Leu Ile Glu Val Val Lys Leu Arg Lys Gly Thr Glu Ile
            450                 455                 460

Val Glu Val Arg Lys Ser Asp Ala Asp Ile Ile Arg Ala Ser Val Asp
465                 470                 475                 480

Ala Val Met Glu Gly Ile Asn Met Leu Leu Asn
                485                 490
```

<210> SEQ ID NO 41
<211> LENGTH: 372
<212> TYPE: PRT
<213> ORGANISM: Artificial Sequence
<220> FEATURE:
<223> OTHER INFORMATION: Description of Artificial Sequence: Synthetic
      M. jannaschii Citramalate synthase variant polypeptide

<400> SEQUENCE: 41

```
Met Met Val Arg Ile Phe Asp Thr Thr Leu Arg Asp Gly Glu Gln Thr
1               5                   10                  15

Pro Gly Val Ser Leu Thr Pro Asn Asp Lys Leu Glu Ile Ala Lys Lys
            20                  25                  30

Leu Asp Glu Leu Gly Val Asp Val Ile Glu Ala Gly Ser Ala Val Thr
        35                  40                  45

Ser Lys Gly Glu Arg Glu Gly Ile Lys Leu Ile Thr Lys Glu Gly Leu
    50                  55                  60

Asn Ala Glu Ile Cys Ser Phe Val Arg Ala Leu Pro Val Asp Ile Asp
65                  70                  75                  80

Ala Ala Leu Glu Cys Asp Val Asp Ser Val His Leu Val Val Pro Thr
                85                  90                  95

Ser Pro Ile His Met Lys Tyr Lys Leu Arg Lys Thr Glu Asp Glu Val
            100                 105                 110

Leu Val Thr Ala Leu Lys Ala Val Glu Tyr Ala Lys Glu Gln Gly Leu
        115                 120                 125

Ile Val Glu Leu Ser Ala Glu Asp Ala Thr Arg Ser Asp Val Asn Phe
    130                 135                 140

Leu Ile Lys Leu Phe Asn Glu Gly Glu Lys Val Gly Ala Asp Arg Val
145                 150                 155                 160

Cys Val Cys Asp Thr Val Gly Val Leu Thr Pro Gln Lys Ser Gln Glu
                165                 170                 175

Leu Phe Lys Lys Ile Thr Glu Asn Val Asn Leu Pro Val Ser Val His
            180                 185                 190

Cys His Asn Asp Phe Gly Met Ala Thr Ala Asn Ala Cys Ser Ala Val
        195                 200                 205

Leu Gly Gly Ala Val Gln Cys His Val Thr Val Asn Gly Ile Gly Glu
    210                 215                 220

Arg Ala Gly Asn Ala Ser Leu Glu Glu Val Val Ala Ala Ser Lys Ile
225                 230                 235                 240

Leu Tyr Gly Tyr Asp Thr Lys Ile Lys Met Glu Lys Leu Tyr Glu Val
                245                 250                 255

Ser Arg Ile Val Ser Arg Leu Met Lys Leu Pro Val Pro Pro Asn Lys
            260                 265                 270

Ala Ile Val Gly Asp Asn Ala Phe Ala His Glu Ala Gly Ile His Val
        275                 280                 285

Asp Gly Leu Ile Lys Asn Thr Glu Thr Tyr Glu Pro Ile Lys Pro Glu
    290                 295                 300

Met Val Gly Asn Arg Arg Arg Ile Ile Leu Gly Lys His Ser Gly Arg
305                 310                 315                 320
```

```
Lys Ala Leu Lys Tyr Lys Leu Asp Leu Met Gly Ile Asn Val Ser Asp
                325                 330                 335

Glu Gln Leu Asn Lys Ile Tyr Glu Arg Val Lys Glu Phe Gly Asp Leu
            340                 345                 350

Gly Lys Tyr Ile Ser Asp Ala Asp Leu Leu Ala Ile Val Arg Glu Val
            355                 360                 365

Thr Gly Lys Leu
    370

<210> SEQ ID NO 42
<211> LENGTH: 516
<212> TYPE: PRT
<213> ORGANISM: Leptospira interrogans
<220> FEATURE:
<223> OTHER INFORMATION: Citramalate synthase

<400> SEQUENCE: 42

Met Thr Lys Val Glu Thr Arg Leu Glu Ile Leu Asp Val Thr Leu Arg
1               5                   10                  15

Asp Gly Glu Gln Thr Arg Gly Val Ser Phe Ser Thr Ser Glu Lys Leu
            20                  25                  30

Asn Ile Ala Lys Phe Leu Leu Gln Lys Leu Asn Val Asp Arg Val Glu
        35                  40                  45

Ile Ala Ser Ala Arg Val Ser Lys Gly Glu Leu Glu Thr Val Gln Lys
50                  55                  60

Ile Met Glu Trp Ala Ala Thr Glu Gln Leu Thr Glu Arg Ile Glu Ile
65                  70                  75                  80

Leu Gly Phe Val Asp Gly Asn Lys Thr Val Asp Trp Ile Lys Asp Ser
                85                  90                  95

Gly Ala Lys Val Leu Asn Leu Leu Thr Lys Gly Ser Leu His His Leu
            100                 105                 110

Glu Lys Gln Leu Gly Lys Thr Pro Lys Glu Phe Phe Thr Asp Val Ser
        115                 120                 125

Phe Val Ile Glu Tyr Ala Ile Lys Ser Gly Leu Lys Ile Asn Val Tyr
130                 135                 140

Leu Glu Asp Trp Ser Asn Gly Phe Arg Asn Ser Pro Asp Tyr Val Lys
145                 150                 155                 160

Ser Leu Val Glu His Leu Ser Lys Glu His Ile Glu Arg Ile Phe Leu
                165                 170                 175

Pro Asp Thr Leu Gly Val Leu Ser Pro Glu Glu Thr Phe Gln Gly Val
            180                 185                 190

Asp Ser Leu Ile Gln Lys Tyr Pro Asp Ile His Phe Glu Phe His Gly
        195                 200                 205

His Asn Asp Tyr Asp Leu Ser Val Ala Asn Ser Leu Gln Ala Ile Arg
210                 215                 220

Ala Gly Val Lys Gly Leu His Ala Ser Ile Asn Gly Leu Gly Glu Arg
225                 230                 235                 240

Ala Gly Asn Thr Pro Leu Glu Ala Leu Val Thr Thr Ile His Asp Lys
                245                 250                 255

Ser Asn Ser Lys Thr Asn Ile Asn Glu Ile Ala Ile Thr Glu Ala Ser
            260                 265                 270

Arg Leu Val Glu Val Phe Ser Gly Lys Arg Ile Ser Ala Asn Arg Pro
        275                 280                 285

Ile Val Gly Glu Asp Val Phe Thr Gln Thr Ala Gly Val His Ala Asp
290                 295                 300

Gly Asp Lys Lys Gly Asn Leu Tyr Ala Asn Pro Ile Leu Pro Glu Arg
```

```
                    305                 310                 315                 320
            Phe Gly Arg Lys Arg Ser Tyr Ala Leu Gly Lys Leu Ala Gly Lys Ala
                            325                 330                 335

Ser Ile Ser Glu Asn Val Lys Gln Leu Gly Met Val Leu Ser Glu Val
                            340                 345                 350

Val Leu Gln Lys Val Leu Glu Arg Val Ile Glu Leu Gly Asp Gln Asn
                            355                 360                 365

Lys Leu Val Thr Pro Glu Asp Leu Pro Phe Ile Ile Ala Asp Val Ser
                            370                 375                 380

Gly Arg Thr Gly Glu Lys Val Leu Thr Ile Lys Ser Cys Asn Ile His
            385                 390                 395                 400

Ser Gly Ile Gly Ile Arg Pro His Ala Gln Ile Glu Leu Glu Tyr Gln
                            405                 410                 415

Gly Lys Ile His Lys Glu Ile Ser Glu Gly Asp Gly Tyr Asp Ala
                            420                 425                 430

Phe Met Asn Ala Leu Thr Lys Ile Thr Asn Arg Leu Gly Ile Ser Ile
                            435                 440                 445

Pro Lys Leu Ile Asp Tyr Glu Val Arg Ile Pro Pro Gly Gly Lys Thr
                            450                 455                 460

Asp Ala Leu Val Glu Thr Arg Ile Thr Trp Asn Lys Ser Leu Asp Leu
            465                 470                 475                 480

Glu Glu Asp Gln Thr Phe Lys Thr Met Gly Val His Pro Asp Gln Thr
                            485                 490                 495

Val Ala Ala Val His Ala Thr Glu Lys Met Leu Asn Gln Ile Leu Gln
                            500                 505                 510

Pro Trp Gln Ile
                    515

<210> SEQ ID NO 43
<211> LENGTH: 386
<212> TYPE: PRT
<213> ORGANISM: Artificial Sequence
<220> FEATURE:
<223> OTHER INFORMATION: Description of Artificial Sequence: Synthetic
      Leptospira inter -continued

```
Leu Glu Asp Trp Ser Asn Gly Phe Arg Asn Ser Pro Asp Tyr Val Lys
145                 150                 155                 160

Ser Leu Val Glu His Leu Ser Lys Glu His Ile Glu Arg Ile Phe Leu
                165                 170                 175

Pro Asp Thr Leu Gly Val Leu Ser Pro Glu Glu Thr Phe Gln Gly Val
            180                 185                 190

Asp Ser Leu Ile Gln Lys Tyr Pro Asp Ile His Phe Glu Phe His Gly
        195                 200                 205

His Asn Asp Tyr Asp Leu Ser Val Ala Asn Ser Leu Gln Ala Ile Arg
210                 215                 220

Ala Gly Val Lys Gly Leu His Ala Ser Ile Asn Gly Leu Gly Glu Arg
225                 230                 235                 240

Ala Gly Asn Thr Pro Leu Glu Ala Leu Val Thr Thr Ile His Asp Lys
                245                 250                 255

Ser Asn Ser Lys Thr Asn Ile Asn Glu Ile Ala Ile Thr Glu Ala Ser
                260                 265                 270

Arg Leu Val Glu Val Phe Ser Gly Lys Arg Ile Ser Ala Asn Arg Pro
                275                 280                 285

Ile Val Gly Glu Asp Val Phe Thr Gln Thr Ala Gly Val His Ala Asp
290                 295                 300

Gly Asp Lys Lys Gly Asn Leu Tyr Ala Asn Pro Ile Leu Pro Glu Arg
305                 310                 315                 320

Phe Gly Arg Lys Arg Ser Tyr Ala Leu Gly Lys Leu Ala Gly Lys Ala
                325                 330                 335

Ser Ile Ser Glu Asn Val Lys Gln Leu Gly Met Val Leu Ser Glu Val
                340                 345                 350

Val Leu Gln Lys Val Leu Glu Arg Val Ile Glu Leu Gly Asp Gln Asn
                355                 360                 365

Lys Leu Val Thr Pro Glu Asp Leu Pro Phe Ile Ile Ala Asp Val Ser
                370                 375                 380

Gly Arg
385

<210> SEQ ID NO 44
<211> LENGTH: 466
<212> TYPE: PRT
<213> ORGANISM: Escherichia coli
<220> FEATURE:
<223> OTHER INFORMATION: Isopropylmalate isomerase large subunit

<400> SEQUENCE: 44

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
                20                  25                  30

His Glu Val Thr Ser Pro Gln Ala Phe Asp Gly Leu Arg Ala His Gly
            35                  40                  45

Arg Pro Val Arg Gln Pro Gly Lys Thr Phe Ala Thr Met Asp His Asn
        50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
```

```
                115             120             125
Ser His Thr Ala Thr His Gly Ala Phe Gly Ala Leu Ala Phe Gly Ile
        130                 135                 140
Gly Thr Ser Glu Val Glu His Val Leu Ala Thr Gln Thr Leu Lys Gln
145                 150                 155                 160
Gly Arg Ala Lys Thr Met Lys Ile Glu Val Gln Gly Lys Ala Ala Pro
                165                 170                 175
Gly Ile Thr Ala Lys Asp Ile Val Leu Ala Ile Ile Gly Lys Thr Gly
                180                 185                 190
Ser Ala Gly Gly Thr Gly His Val Val Glu Phe Cys Gly Glu Ala Ile
                195                 200                 205
Arg Asp Leu Ser Met Glu Gly Arg Met Thr Leu Cys Asn Met Ala Ile
210                 215                 220
Glu Met Gly Ala Lys Ala Gly Leu Val Ala Pro Asp Glu Thr Thr Phe
225                 230                 235                 240
Asn Tyr Val Lys Gly Arg Leu His Ala Pro Lys Gly Lys Asp Phe Asp
                245                 250                 255
Asp Ala Val Ala Tyr Trp Lys Thr Leu Gln Thr Asp Glu Gly Ala Thr
                260                 265                 270
Phe Asp Thr Val Val Thr Leu Gln Ala Glu Glu Ile Ser Pro Gln Val
                275                 280                 285
Thr Trp Gly Thr Asn Pro Gly Gln Val Ile Ser Val Asn Asp Asn Ile
290                 295                 300
Pro Asp Pro Ala Ser Phe Ala Asp Pro Val Glu Arg Ala Ser Ala Glu
305                 310                 315                 320
Lys Ala Leu Ala Tyr Met Gly Leu Lys Pro Gly Ile Pro Leu Thr Glu
                325                 330                 335
Val Ala Ile Asp Lys Val Phe Ile Gly Ser Cys Thr Asn Ser Arg Ile
                340                 345                 350
Glu Asp Leu Arg Ala Ala Ala Glu Ile Ala Lys Gly Arg Lys Val Ala
                355                 360                 365
Pro Gly Val Gln Ala Leu Val Val Pro Gly Ser Gly Pro Val Lys Ala
370                 375                 380
Gln Ala Glu Ala Glu Gly Leu Asp Lys Ile Phe Ile Glu Ala Gly Phe
385                 390                 395                 400
Glu Trp Arg Leu Pro Gly Cys Ser Met Cys Leu Ala Met Asn Asn Asp
                405                 410                 415
Arg Leu Asn Pro Gly Glu Arg Cys Ala Ser Thr Ser Asn Arg Asn Phe
                420                 425                 430
Glu Gly Arg Gln Gly Arg Gly Gly Arg Thr His Leu Val Ser Pro Ala
                435                 440                 445
Met Ala Ala Ala Ala Val Thr Gly His Phe Ala Asp Ile Arg Asn
    450                 455                 460
Ile Lys
465

<210> SEQ ID NO 45
<211> LENGTH: 201
<212> TYPE: PRT
<213> ORGANISM: Escherichia coli
<220> FEATURE:
<223> OTHER INFORMATION: Isopropylmalate isomerase small subunit

<400> SEQUENCE: 45

Met Ala Glu Lys Phe Ile Lys His Thr Gly Leu Val Val Pro Leu Asp
1               5                   10                  15
```

```
Ala Ala Asn Val Asp Thr Asp Ala Ile Ile Pro Lys Gln Phe Leu Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu His Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 46
<211> LENGTH: 472
<212> TYPE: PRT
<213> ORGANISM: Bacillus subtilis
<220> FEATURE:
<223> OTHER INFORMATION: Isopropylmalate isomerase large subunit

<400> SEQUENCE: 46

Met Met Pro Arg Thr Ile Ile Glu Lys Ile Trp Asp Gln His Ile Val
1               5                   10                  15

Lys His Gly Glu Gly Lys Pro Asp Leu Leu Tyr Ile Asp Leu His Leu
            20                  25                  30

Ile His Glu Val Thr Ser Pro Gln Ala Phe Glu Gly Leu Arg Gln Lys
        35                  40                  45

Gly Arg Lys Val Arg Arg Pro Gln Asn Thr Phe Ala Thr Met Asp His
    50                  55                  60

Asn Ile Pro Thr Val Asn Arg Phe Glu Ile Lys Asp Glu Val Ala Lys
65                  70                  75                  80

Arg Gln Val Thr Ala Leu Glu Arg Asn Cys Glu Glu Phe Gly Val Arg
                85                  90                  95

Leu Ala Asp Leu His Ser Val Asp Gln Gly Ile Val His Val Val Gly
            100                 105                 110

Pro Glu Leu Gly Leu Thr Leu Pro Gly Lys Thr Ile Val Cys Gly Asp
        115                 120                 125

Ser His Thr Ser Thr His Gly Ala Phe Gly Ala Leu Ala Phe Gly Ile
    130                 135                 140

Gly Thr Ser Glu Val Glu His Val Leu Ser Thr Gln Thr Leu Trp Gln
145                 150                 155                 160

Gln Arg Pro Lys Thr Leu Glu Val Arg Val Asp Gly Thr Leu Gln Lys
                165                 170                 175
```

Gly Val Thr Ala Lys Asp Val Ile Leu Ala Val Ile Gly Lys Tyr Gly
                180                 185                 190

Val Lys Phe Gly Thr Gly Tyr Val Ile Glu Tyr Thr Gly Glu Val Phe
            195                 200                 205

Arg Asn Met Thr Met Asp Glu Arg Met Thr Val Cys Asn Met Ser Ile
210                 215                 220

Glu Ala Gly Ala Arg Ala Gly Leu Ile Ala Pro Asp Glu Val Thr Phe
225                 230                 235                 240

Glu Tyr Cys Lys Asn Arg Lys Tyr Thr Pro Lys Gly Glu Glu Phe Asp
                245                 250                 255

Lys Ala Val Glu Glu Trp Lys Ala Leu Arg Thr Asp Pro Gly Ala Val
            260                 265                 270

Tyr Asp Lys Ser Ile Val Leu Asp Gly Asn Lys Ile Ser Pro Met Val
        275                 280                 285

Thr Trp Gly Ile Asn Pro Gly Met Val Leu Pro Val Asp Ser Glu Val
        290                 295                 300

Pro Ala Pro Glu Ser Phe Ser Ala Glu Asp Lys Lys Glu Ala Ile
305                 310                 315                 320

Arg Ala Tyr Glu Tyr Met Gly Leu Thr Pro His Gln Lys Ile Glu Asp
                325                 330                 335

Ile Lys Val Glu His Val Phe Ile Gly Ser Cys Thr Asn Ser Arg Met
            340                 345                 350

Thr Asp Leu Arg Gln Ala Ala Asp Met Ile Lys Gly Lys Lys Val Ala
        355                 360                 365

Asp Ser Val Arg Ala Ile Val Val Pro Gly Ser Gln Ser Val Lys Leu
        370                 375                 380

Gln Ala Glu Lys Glu Gly Leu Asp Gln Ile Phe Leu Glu Ala Gly Phe
385                 390                 395                 400

Glu Trp Arg Glu Ser Gly Cys Ser Met Cys Leu Ser Met Asn Asn Asp
                405                 410                 415

Val Val Pro Glu Gly Glu Arg Cys Ala Ser Thr Ser Asn Arg Asn Phe
            420                 425                 430

Glu Gly Arg Gln Gly Lys Gly Ala Arg Thr His Leu Val Ser Pro Ala
        435                 440                 445

Met Ala Ala Met Ala Ala Ile His Gly His Phe Val Asp Val Arg Lys
450                 455                 460

Phe Tyr Gln Glu Lys Thr Val Val
465                 470

<210> SEQ ID NO 47
<211> LENGTH: 199
<212> TYPE: PRT
<213> ORGANISM: Bacillus subtilis
<220> FEATURE:
<223> OTHER INFORMATION: Isopropylmalate isomerase small subunit

<400> SEQUENCE: 47

Met Glu Pro Leu Lys Ser His Thr Gly Lys Ala Ala Val Leu Asn Arg
1               5                   10                  15

Ile Asn Val Asp Thr Asp Gln Ile Ile Pro Lys Gln Phe Leu Lys Arg
            20                  25                  30

Ile Glu Arg Thr Gly Tyr Gly Arg Phe Ala Phe Asp Trp Arg Tyr
        35                  40                  45

Asp Ala Asn Gly Glu Pro Asn Pro Glu Phe Glu Leu Asn Gln Pro Val
50                  55                  60

Tyr Gln Gly Ala Ser Ile Leu Ile Ala Gly Glu Asn Phe Gly Cys Gly

```
              65                  70                  75                  80
Ser Ser Arg Glu His Ala Pro Trp Ala Leu Asp Asp Tyr Gly Phe Lys
                  85                  90                  95

Ile Ile Ile Ala Pro Ser Phe Ala Asp Ile Phe His Gln Asn Cys Phe
            100                 105                 110

Lys Asn Gly Met Leu Pro Ile Arg Met Pro Tyr Asp Asn Trp Lys Gln
            115                 120                 125

Leu Val Gly Gln Tyr Glu Asn Gln Ser Leu Gln Met Thr Val Asp Leu
            130                 135                 140

Glu Asn Gln Leu Ile His Asp Ser Glu Gly Asn Gln Ile Ser Phe Glu
145                 150                 155                 160

Val Asp Pro His Trp Lys Glu Met Leu Ile Asn Gly Tyr Asp Glu Ile
                165                 170                 175

Ser Leu Thr Leu Leu Glu Asp Glu Ile Lys Gln Phe Glu Ser Gln
            180                 185                 190

Arg Ser Ser Trp Leu Gln Ala
            195

<210> SEQ ID NO 48
<211> LENGTH: 363
<212> TYPE: PRT
<213> ORGANISM: Escherichia coli
<220> FEATURE:
<223> OTHER INFORMATION: Beta-isopropylmalate dehydrogenase

<400> SEQUENCE: 48

Met Ser Lys Asn Tyr His Ile Ala Val Leu Pro Gly Asp Gly Ile Gly
1               5                   10                  15

Pro Glu Val Met Thr Gln Ala Leu Lys Val Leu Asp Ala Val Arg Asn
            20                  25                  30

Arg Phe Ala Met Arg Ile Thr Thr Ser His Tyr Asp Val Gly Gly Ala
        35                  40                  45

Ala Ile Asp Asn His Gly Gln Pro Leu Pro Pro Ala Thr Val Glu Gly
    50                  55                  60

Cys Glu Gln Ala Asp Ala Val Leu Phe Gly Ser Val Gly Gly Pro Lys
65                  70                  75                  80

Trp Glu His Leu Pro Pro Asp Gln Gln Pro Glu Arg Gly Ala Leu Leu
                85                  90                  95

Pro Leu Arg Lys His Phe Lys Leu Phe Ser Asn Leu Arg Pro Ala Lys
            100                 105                 110

Leu Tyr Gln Gly Leu Glu Ala Phe Cys Pro Leu Arg Ala Asp Ile Ala
            115                 120                 125

Ala Asn Gly Phe Asp Ile Leu Cys Val Arg Glu Leu Thr Gly Gly Ile
            130                 135                 140

Tyr Phe Gly Gln Pro Lys Gly Arg Glu Gly Ser Gly Gln Tyr Glu Lys
145                 150                 155                 160

Ala Phe Asp Thr Glu Val Tyr His Arg Phe Glu Ile Glu Arg Ile Ala
                165                 170                 175

Arg Ile Ala Phe Glu Ser Ala Arg Lys Arg Arg His Lys Val Thr Ser
            180                 185                 190

Ile Asp Lys Ala Asn Val Leu Gln Ser Ser Ile Leu Trp Arg Glu Ile
            195                 200                 205

Val Asn Glu Ile Ala Thr Glu Tyr Pro Asp Val Glu Leu Ala His Met
            210                 215                 220

Tyr Ile Asp Asn Ala Thr Met Gln Leu Ile Lys Asp Pro Ser Gln Phe
225                 230                 235                 240
```

```
Asp Val Leu Leu Cys Ser Asn Leu Phe Gly Asp Ile Leu Ser Asp Glu
            245                 250                 255

Cys Ala Met Ile Thr Gly Ser Met Gly Met Leu Pro Ser Ala Ser Leu
            260                 265                 270

Asn Glu Gln Gly Phe Gly Leu Tyr Glu Pro Ala Gly Ser Ala Pro
            275                 280                 285

Asp Ile Ala Gly Lys Asn Ile Ala Asn Pro Ile Ala Gln Ile Leu Ser
            290                 295                 300

Leu Ala Leu Leu Leu Arg Tyr Ser Leu Asp Ala Asp Ala Ala Cys
305                 310                 315                 320

Ala Ile Glu Arg Ala Ile Asn Arg Ala Leu Glu Gly Ile Arg Thr
            325                 330                 335

Gly Asp Leu Ala Arg Gly Ala Ala Val Ser Thr Asp Glu Met Gly
            340                 345                 350

Asp Ile Ile Ala Arg Tyr Val Ala Glu Gly Val
            355                 360
```

<210> SEQ ID NO 49
<211> LENGTH: 365
<212> TYPE: PRT
<213> ORGANISM: Bacillus subtilis
<220> FEATURE:
<223> OTHER INFORMATION: Beta-isopropylmalate dehydrogenase

<400> SEQUENCE: 49

```
Met Lys Lys Arg Ile Ala Leu Leu Pro Gly Asp Gly Ile Gly Pro Glu
1               5                   10                  15

Val Leu Glu Ser Ala Thr Asp Val Leu Lys Ser Val Ala Glu Arg Phe
            20                  25                  30

Asn His Glu Phe Glu Phe Glu Tyr Gly Leu Ile Gly Gly Ala Ala Ile
            35                  40                  45

Asp Glu His His Asn Pro Leu Pro Glu Glu Thr Val Ala Ala Cys Lys
        50                  55                  60

Asn Ala Asp Ala Ile Leu Leu Gly Ala Val Gly Gly Pro Lys Trp Asp
65                  70                  75                  80

Gln Asn Pro Ser Glu Leu Arg Pro Glu Lys Gly Leu Leu Ser Ile Arg
                85                  90                  95

Lys Gln Leu Asp Leu Phe Ala Asn Leu Arg Pro Val Lys Val Phe Glu
            100                 105                 110

Ser Leu Ser Asp Ala Ser Pro Leu Lys Lys Glu Tyr Ile Asp Asn Val
        115                 120                 125

Asp Phe Val Ile Val Arg Glu Leu Thr Gly Gly Leu Tyr Phe Gly Gln
    130                 135                 140

Pro Ser Lys Arg Tyr Val Asn Thr Glu Gly Glu Gln Glu Ala Val Asp
145                 150                 155                 160

Thr Leu Phe Tyr Lys Arg Thr Glu Ile Glu Arg Val Ile Arg Glu Gly
                165                 170                 175

Phe Lys Met Ala Ala Ala Arg Lys Gly Lys Val Thr Ser Val Asp Lys
            180                 185                 190

Ala Asn Val Leu Glu Ser Ser Arg Leu Trp Arg Glu Val Ala Glu Asp
        195                 200                 205

Val Ala Gln Glu Phe Pro Asp Val Lys Leu Glu His Met Leu Val Asp
    210                 215                 220

Asn Ala Ala Met Gln Leu Ile Tyr Ala Pro Asn Gln Phe Asp Val Val
225                 230                 235                 240
```

Val Thr Glu Asn Met Phe Gly Asp Ile Leu Ser Asp Glu Ala Ser Met
                245                 250                 255

Leu Thr Gly Ser Leu Gly Met Leu Pro Ser Ala Ser Leu Ser Ser Ser
            260                 265                 270

Gly Leu His Leu Phe Glu Pro Val His Gly Ser Ala Pro Asp Ile Ala
        275                 280                 285

Gly Lys Gly Met Ala Asn Pro Phe Ala Ala Ile Leu Ser Ala Ala Met
290                 295                 300

Leu Leu Arg Thr Ser Phe Gly Leu Glu Glu Ala Lys Ala Val Glu
305                 310                 315                 320

Asp Ala Val Asn Lys Val Leu Ala Ser Gly Lys Arg Thr Arg Asp Leu
                325                 330                 335

Ala Arg Ser Glu Glu Phe Ser Ser Thr Gln Ala Ile Thr Glu Glu Val
            340                 345                 350

Lys Ala Ala Ile Met Ser Glu Asn Thr Ile Ser Asn Val
        355                 360                 365

<210> SEQ ID NO 50
<211> LENGTH: 364
<212> TYPE: PRT
<213> ORGANISM: Saccharomyces cerevisiae
<220> FEATURE:
<223> OTHER INFORMATION: Beta-isopropylmalate dehydrogenase

<400> SEQUENCE: 50

Met Ser Ala Pro Lys Lys Ile Val Val Leu Pro Gly Asp His Val Gly
1               5                   10                  15

Gln Glu Ile Thr Ala Glu Ala Ile Lys Val Leu Lys Ala Ile Ser Asp
            20                  25                  30

Val Arg Ser Asn Val Lys Phe Asp Phe Glu Asn His Leu Ile Gly Gly
        35                  40                  45

Ala Ala Ile Asp Ala Thr Gly Val Pro Leu Pro Asp Glu Ala Leu Glu
    50                  55                  60

Ala Ser Lys Lys Ala Asp Ala Val Leu Leu Gly Ala Val Gly Gly Pro
65                  70                  75                  80

Lys Trp Gly Thr Gly Ser Val Arg Pro Glu Gln Gly Leu Leu Lys Ile
                85                  90                  95

Arg Lys Glu Leu Gln Leu Tyr Ala Asn Leu Arg Pro Cys Asn Phe Ala
            100                 105                 110

Ser Asp Ser Leu Leu Asp Leu Ser Pro Ile Lys Pro Gln Phe Ala Lys
        115                 120                 125

Gly Thr Asp Phe Val Val Val Arg Glu Leu Val Gly Gly Ile Tyr Phe
    130                 135                 140

Gly Lys Arg Lys Glu Asp Asp Gly Asp Gly Val Ala Trp Asp Ser Glu
145                 150                 155                 160

Gln Tyr Thr Val Pro Glu Val Gln Arg Ile Thr Arg Met Ala Ala Phe
                165                 170                 175

Met Ala Leu Gln His Glu Pro Pro Leu Pro Ile Trp Ser Leu Asp Lys
            180                 185                 190

Ala Asn Val Leu Ala Ser Ser Arg Leu Trp Arg Lys Thr Val Glu Glu
        195                 200                 205

Thr Ile Lys Asn Glu Phe Pro Thr Leu Lys Val Gln His Gln Leu Ile
    210                 215                 220

Asp Ser Ala Ala Met Ile Leu Val Lys Asn Pro Thr His Leu Asn Gly
225                 230                 235                 240

Ile Ile Ile Thr Ser Asn Met Phe Gly Asp Ile Ile Ser Asp Glu Ala

```
                     245                 250                 255
Ser Val Ile Pro Gly Ser Leu Gly Leu Leu Pro Ser Ala Ser Leu Ala
                260                 265                 270

Ser Leu Pro Asp Lys Asn Thr Ala Phe Gly Leu Tyr Glu Pro Cys His
            275                 280                 285

Gly Ser Ala Pro Asp Leu Pro Lys Asn Lys Val Asn Pro Ile Ala Thr
        290                 295                 300

Ile Leu Ser Ala Ala Met Met Leu Lys Leu Ser Leu Asn Leu Pro Glu
305                 310                 315                 320

Glu Gly Lys Ala Ile Glu Asp Ala Val Lys Lys Val Leu Asp Ala Gly
                325                 330                 335

Ile Arg Thr Gly Asp Leu Gly Gly Ser Asn Ser Thr Thr Glu Val Gly
            340                 345                 350

Asp Ala Val Ala Glu Glu Val Lys Lys Ile Leu Ala
        355                 360

<210> SEQ ID NO 51
<211> LENGTH: 714
<212> TYPE: PRT
<213> ORGANISM: Escherichia coli
<220> FEATURE:
<223> OTHER INFORMATION: Methylmalonyl-CoA mutase

<400> SEQUENCE: 51

Met Ser Asn Val Gln Glu Trp Gln Gln Leu Ala Asn Lys Glu Leu Ser
1               5                   10                  15

Arg Arg Glu Lys Thr Val Asp Ser Leu Val His Gln Thr Ala Glu Gly
                20                  25                  30

Ile Ala Ile Lys Pro Leu Tyr Thr Glu Ala Asp Leu Asp Asn Leu Glu
            35                  40                  45

Val Thr Gly Thr Leu Pro Gly Leu Pro Pro Tyr Val Arg Gly Pro Arg
        50                  55                  60

Ala Thr Met Tyr Thr Ala Gln Pro Trp Thr Ile Arg Gln Tyr Ala Gly
65                  70                  75                  80

Phe Ser Thr Ala Lys Glu Ser Asn Ala Phe Tyr Arg Arg Asn Leu Ala
                85                  90                  95

Ala Gly Gln Lys Gly Leu Ser Val Ala Phe Asp Leu Ala Thr His Arg
            100                 105                 110

Gly Tyr Asp Ser Asp Asn Pro Arg Val Ala Gly Asp Val Gly Lys Ala
        115                 120                 125

Gly Val Ala Ile Asp Thr Val Glu Asp Met Lys Val Leu Phe Asp Gln
    130                 135                 140

Ile Pro Leu Asp Lys Met Ser Val Ser Met Thr Met Asn Gly Ala Val
145                 150                 155                 160

Leu Pro Val Leu Ala Phe Tyr Ile Val Ala Ala Glu Glu Gln Gly Val
                165                 170                 175

Thr Pro Asp Lys Leu Thr Gly Thr Ile Gln Asn Asp Ile Leu Lys Glu
            180                 185                 190

Tyr Leu Cys Arg Asn Thr Tyr Ile Tyr Pro Pro Lys Pro Ser Met Arg
        195                 200                 205

Ile Ile Ala Asp Ile Ile Ala Trp Cys Ser Gly Asn Met Pro Arg Phe
    210                 215                 220

Asn Thr Ile Ser Ile Ser Gly Tyr His Met Gly Glu Ala Gly Ala Asn
225                 230                 235                 240

Cys Val Gln Gln Val Ala Phe Thr Leu Ala Asp Gly Ile Glu Tyr Ile
                245                 250                 255
```

```
Lys Ala Ala Ile Ser Ala Gly Leu Lys Ile Asp Asp Phe Ala Pro Arg
                260                 265                 270

Leu Ser Phe Phe Phe Gly Ile Gly Met Asp Leu Phe Met Asn Val Ala
            275                 280                 285

Met Leu Arg Ala Ala Arg Tyr Leu Trp Ser Glu Ala Val Ser Gly Phe
        290                 295                 300

Gly Ala Gln Asp Pro Lys Ser Leu Ala Leu Arg Thr His Cys Gln Thr
305                 310                 315                 320

Ser Gly Trp Ser Leu Thr Glu Gln Asp Pro Tyr Asn Asn Val Ile Arg
                325                 330                 335

Thr Thr Ile Glu Ala Leu Ala Ala Thr Leu Gly Gly Thr Gln Ser Leu
            340                 345                 350

His Thr Asn Ala Phe Asp Glu Ala Leu Gly Leu Pro Thr Asp Phe Ser
        355                 360                 365

Ala Arg Ile Ala Arg Asn Thr Gln Ile Ile Gln Glu Glu Ser Glu
370                 375                 380

Leu Cys Arg Thr Val Asp Pro Leu Ala Gly Ser Tyr Tyr Ile Glu Ser
385                 390                 395                 400

Leu Thr Asp Gln Ile Val Lys Gln Ala Arg Ala Ile Ile Gln Gln Ile
            405                 410                 415

Asp Glu Ala Gly Gly Met Ala Lys Ala Ile Glu Ala Gly Leu Pro Lys
        420                 425                 430

Arg Met Ile Glu Glu Ala Ser Ala Arg Glu Gln Ser Leu Ile Asp Gln
            435                 440                 445

Gly Lys Arg Val Ile Val Gly Val Asn Lys Tyr Lys Leu Asp His Glu
        450                 455                 460

Asp Glu Thr Asp Val Leu Glu Ile Asp Asn Val Met Val Arg Asn Glu
465                 470                 475                 480

Gln Ile Ala Ser Leu Glu Arg Ile Arg Ala Thr Arg Asp Asp Ala Ala
            485                 490                 495

Val Thr Ala Ala Leu Asn Ala Leu Thr His Ala Ala Gln His Asn Glu
        500                 505                 510

Asn Leu Leu Ala Ala Ala Val Asn Ala Ala Arg Val Arg Ala Thr Leu
        515                 520                 525

Gly Glu Ile Ser Asp Ala Leu Glu Val Ala Phe Asp Arg Tyr Leu Val
        530                 535                 540

Pro Ser Gln Cys Val Thr Gly Val Ile Ala Gln Ser Tyr His Gln Ser
545                 550                 555                 560

Glu Lys Ser Ala Ser Glu Phe Asp Ala Ile Val Ala Gln Thr Glu Gln
            565                 570                 575

Phe Leu Ala Asp Asn Gly Arg Arg Pro Arg Ile Leu Ile Ala Lys Met
        580                 585                 590

Gly Gln Asp Gly His Asp Arg Gly Ala Lys Val Ile Ala Ser Ala Tyr
        595                 600                 605

Ser Asp Leu Gly Phe Asp Val Asp Leu Ser Pro Met Phe Ser Thr Pro
        610                 615                 620

Glu Glu Ile Ala Arg Leu Ala Val Glu Asn Asp Val His Val Val Gly
625                 630                 635                 640

Ala Ser Ser Leu Ala Ala Gly His Lys Thr Leu Ile Pro Glu Leu Val
                645                 650                 655

Glu Ala Leu Lys Lys Trp Gly Arg Glu Asp Ile Cys Val Val Ala Gly
            660                 665                 670

Gly Val Ile Pro Pro Gln Asp Tyr Ala Phe Leu Gln Glu Arg Gly Val
```

-continued

```
                675                 680                 685
Ala Ala Ile Tyr Gly Pro Gly Thr Pro Met Leu Asp Ser Val Arg Asp
    690                 695                 700

Val Leu Asn Leu Ile Ser Gln His His Asp
705                 710

<210> SEQ ID NO 52
<211> LENGTH: 714
<212> TYPE: PRT
<213> ORGANISM: Salmonella enterica
<220> FEATURE:
<223> OTHER INFORMATION: Methylmalonyl-CoA mutase

<400> SEQUENCE: 52

Met Ala Asn Leu Gln Ala Trp Gln Thr Leu Ala Asn Asn Glu Leu Ser
1               5                   10                  15

Arg Arg Glu Lys Thr Val Glu Ser Leu Ile Arg Gln Thr Ala Glu Gly
                20                  25                  30

Ile Ala Val Lys Pro Leu Tyr Thr Glu Ala Asp Leu Asn Asn Leu Glu
            35                  40                  45

Val Thr Gly Thr Leu Pro Gly Leu Pro Pro Tyr Val Arg Gly Pro Arg
        50                  55                  60

Ala Thr Met Tyr Thr Ala Gln Pro Trp Thr Ile Arg Gln Tyr Ala Gly
65                  70                  75                  80

Phe Ser Thr Ala Lys Glu Ser Asn Ala Phe Tyr Arg Arg Asn Leu Ala
                85                  90                  95

Ala Gly Gln Lys Gly Leu Ser Val Ala Phe Asp Leu Ala Thr His Arg
            100                 105                 110

Gly Tyr Asp Ser Asp Asn Pro Arg Val Ala Gly Asp Val Gly Lys Ala
        115                 120                 125

Gly Val Ala Ile Asp Thr Val Glu Asp Met Lys Val Leu Phe Asp Gln
    130                 135                 140

Ile Pro Leu Asp Lys Met Ser Val Ser Met Thr Met Asn Gly Ala Val
145                 150                 155                 160

Leu Pro Val Met Ala Phe Tyr Ile Val Ala Ala Glu Glu Gln Gly Val
                165                 170                 175

Ser Pro Glu Gln Leu Thr Gly Thr Ile Gln Asn Asp Ile Leu Lys Glu
            180                 185                 190

Tyr Leu Cys Arg Asn Thr Tyr Ile Tyr Pro Pro Lys Pro Ser Met Arg
        195                 200                 205

Ile Ile Ala Asp Ile Ile Ala Trp Cys Ser Gly Asn Met Pro Arg Phe
    210                 215                 220

Asn Thr Ile Ser Ile Ser Gly Tyr His Met Gly Glu Ala Gly Ala Asn
225                 230                 235                 240

Cys Val Gln Gln Val Ala Phe Thr Leu Ala Asp Gly Ile Glu Tyr Ile
                245                 250                 255

Lys Ala Ala Leu Ser Ala Gly Leu Lys Ile Asp Asp Phe Ala Pro Arg
            260                 265                 270

Leu Ser Phe Phe Phe Gly Ile Gly Met Asp Leu Phe Met Asn Val Ala
        275                 280                 285

Met Leu Arg Ala Ala Arg Tyr Leu Trp Ser Glu Ala Val Ser Gly Phe
    290                 295                 300

Gly Ala Thr Asn Pro Lys Ser Leu Ala Leu Arg Thr His Cys Gln Thr
305                 310                 315                 320

Ser Gly Trp Ser Leu Thr Glu Gln Asp Pro Tyr Asn Asn Ile Ile Arg
                325                 330                 335
```

```
Thr Thr Ile Glu Ala Leu Gly Ala Thr Leu Gly Gly Thr Gln Ser Leu
            340                 345                 350

His Thr Asn Ala Phe Asp Glu Ala Leu Gly Leu Pro Thr Asp Phe Ser
            355                 360                 365

Ala Arg Ile Ala Arg Asn Thr Gln Ile Ile Gln Glu Glu Ser Ser
            370                 375                 380

Ile Cys Arg Thr Val Asp Pro Leu Ala Gly Ser Tyr Tyr Val Glu Ser
385                 390                 395                 400

Leu Thr Asp Gln Ile Val Lys Gln Ala Arg Ala Ile Ile Lys Gln Ile
                405                 410                 415

Asp Ala Ala Gly Gly Met Ala Lys Ala Ile Glu Ala Gly Leu Pro Lys
                420                 425                 430

Arg Met Ile Glu Glu Ala Ser Arg Glu Gln Ser Leu Ile Asp Gln
            435                 440                 445

Gly Glu Arg Val Ile Val Gly Val Asn Lys Tyr Lys Leu Glu Lys Glu
            450                 455                 460

Asp Glu Thr Ala Val Leu Glu Ile Asp Asn Val Lys Val Arg Asn Glu
465                 470                 475                 480

Gln Ile Ala Ala Leu Glu Arg Ile Arg Ala Thr Arg Asp Asn Arg Ala
                485                 490                 495

Val Asn Ala Ala Leu Gln Ala Leu Thr His Ala Ala Gln His His Glu
            500                 505                 510

Asn Leu Leu Ala Ala Val Glu Ala Arg Val Arg Ala Thr Leu
            515                 520                 525

Gly Glu Ile Ser Asp Ala Leu Glu Ala Phe Asp Arg Tyr Leu Val
            530                 535                 540

Pro Ser Gln Cys Val Thr Gly Val Ile Ala Gln Ser Tyr His Gln Ser
545                 550                 555                 560

Asp Lys Ser Ala Gly Glu Phe Asp Ala Ile Val Ala Gln Thr Gln Gln
                565                 570                 575

Phe Leu Ala Asp Thr Gly Arg Arg Pro Arg Ile Leu Ile Ala Lys Met
            580                 585                 590

Gly Gln Asp Gly His Asp Arg Gly Ala Lys Val Ile Ala Ser Ala Tyr
            595                 600                 605

Ser Asp Leu Gly Phe Asp Val Asp Leu Ser Pro Met Phe Ser Thr Pro
610                 615                 620

Asp Glu Ile Ala Arg Leu Ala Val Glu Asn Asp Val His Val Ile Gly
625                 630                 635                 640

Ala Ser Ser Leu Ala Ala Gly His Lys Thr Leu Ile Pro Glu Leu Val
                645                 650                 655

Ala Ala Leu Lys Lys Trp Gly Arg Glu Asp Ile Cys Val Val Ala Gly
            660                 665                 670

Gly Val Ile Pro Pro Gln Asp Tyr Ala Phe Leu Lys Ala His Gly Val
            675                 680                 685

Ala Ala Ile Tyr Gly Pro Gly Thr Pro Met Leu Glu Ser Val Arg Asp
            690                 695                 700

Val Leu Ala Arg Ile Ser Gln His His Asp
705                 710

<210> SEQ ID NO 53
<211> LENGTH: 638
<212> TYPE: PRT
<213> ORGANISM: Propionibacterium freudenreichii
<220> FEATURE:
<223> OTHER INFORMATION: Methylmalonyl-CoA mutase beta (small) subunit
```

```
<400> SEQUENCE: 53

Met Ser Ser Thr Asp Gln Gly Thr Asn Pro Ala Asp Thr Asp Leu
1               5                   10                  15

Thr Pro Thr Thr Leu Ser Leu Ala Gly Asp Phe Pro Lys Ala Thr Glu
            20                  25                  30

Glu Gln Trp Glu Arg Glu Val Glu Lys Val Leu Asn Arg Gly Arg Pro
            35                  40                  45

Pro Glu Lys Gln Leu Thr Phe Ala Glu Cys Leu Lys Arg Leu Thr Val
 50                  55                  60

His Thr Val Asp Gly Ile Asp Ile Val Pro Met Tyr Arg Pro Lys Asp
 65                  70                  75                  80

Ala Pro Lys Lys Leu Gly Tyr Pro Gly Val Ala Pro Phe Thr Arg Gly
                85                  90                  95

Thr Thr Val Arg Asn Gly Asp Met Asp Ala Trp Asp Val Arg Ala Leu
            100                 105                 110

His Glu Asp Pro Asp Glu Lys Phe Thr Arg Lys Ala Ile Leu Glu Gly
            115                 120                 125

Leu Glu Arg Gly Val Thr Ser Leu Leu Leu Arg Val Asp Pro Asp Ala
130                 135                 140

Ile Ala Pro Glu His Leu Asp Glu Val Leu Ser Asp Val Leu Leu Glu
145                 150                 155                 160

Met Thr Lys Val Glu Val Phe Ser Arg Tyr Asp Gln Gly Ala Ala Ala
                165                 170                 175

Glu Ala Leu Val Ser Val Tyr Glu Arg Ser Asp Lys Pro Ala Lys Asp
            180                 185                 190

Leu Ala Leu Asn Leu Gly Leu Asp Pro Ile Ala Phe Ala Ala Leu Gln
            195                 200                 205

Gly Thr Glu Pro Asp Leu Thr Val Leu Gly Asp Trp Val Arg Arg Leu
210                 215                 220

Ala Lys Phe Ser Pro Asp Ser Arg Ala Val Thr Ile Asp Ala Asn Ile
225                 230                 235                 240

Tyr His Asn Ala Gly Ala Gly Asp Val Ala Glu Leu Ala Trp Ala Leu
                245                 250                 255

Ala Thr Gly Ala Glu Tyr Val Arg Ala Leu Val Glu Gln Gly Phe Thr
            260                 265                 270

Ala Thr Glu Ala Phe Asp Thr Ile Asn Phe Arg Val Thr Ala Thr His
            275                 280                 285

Asp Gln Phe Leu Thr Ile Ala Arg Leu Arg Ala Leu Arg Glu Ala Trp
290                 295                 300

Ala Arg Ile Gly Glu Val Phe Gly Val Asp Glu Asp Lys Arg Gly Ala
305                 310                 315                 320

Arg Gln Asn Ala Ile Thr Ser Trp Arg Asp Val Thr Arg Glu Asp Pro
                325                 330                 335

Tyr Val Asn Ile Leu Arg Gly Ser Ile Ala Thr Phe Ser Ala Ser Val
            340                 345                 350

Gly Gly Ala Glu Ser Ile Thr Thr Leu Pro Phe Thr Gln Ala Leu Gly
            355                 360                 365

Leu Pro Glu Asp Asp Phe Pro Leu Arg Ile Ala Arg Asn Thr Gly Ile
370                 375                 380

Val Leu Ala Glu Glu Val Asn Ile Gly Arg Val Asn Asp Pro Ala Gly
385                 390                 395                 400

Gly Ser Tyr Tyr Val Glu Ser Leu Thr Arg Ser Leu Ala Asp Ala Ala
                405                 410                 415
```

```
Trp Lys Glu Phe Gln Glu Val Glu Lys Leu Gly Gly Met Ser Lys Ala
                420                 425                 430

Val Met Thr Glu His Val Thr Lys Val Leu Asp Ala Cys Asn Ala Glu
            435                 440                 445

Arg Ala Lys Arg Leu Ala Asn Arg Lys Gln Pro Ile Thr Ala Val Ser
450                 455                 460

Glu Phe Pro Met Ile Gly Ala Arg Ser Ile Glu Thr Lys Pro Phe Pro
465                 470                 475                 480

Ala Ala Pro Ala Arg Lys Gly Leu Ala Trp His Arg Asp Ser Glu Val
                485                 490                 495

Phe Glu Gln Leu Met Asp Arg Ser Thr Ser Val Ser Glu Arg Pro Lys
            500                 505                 510

Val Phe Leu Ala Cys Leu Gly Thr Arg Arg Asp Phe Gly Gly Arg Glu
        515                 520                 525

Gly Phe Ser Ser Pro Val Trp His Ile Ala Gly Ile Asp Thr Pro Gln
    530                 535                 540

Val Glu Gly Gly Thr Thr Ala Glu Ile Val Glu Ala Phe Lys Lys Ser
545                 550                 555                 560

Gly Ala Gln Val Ala Asp Leu Cys Ser Ser Ala Lys Val Tyr Ala Gln
                565                 570                 575

Gln Gly Leu Glu Val Ala Lys Ala Leu Lys Ala Gly Ala Lys Ala
            580                 585                 590

Leu Tyr Leu Ser Gly Ala Phe Lys Glu Phe Gly Asp Ala Ala Glu
        595                 600                 605

Ala Glu Lys Leu Ile Asp Gly Arg Leu Phe Met Gly Met Asp Val Val
610                 615                 620

Asp Thr Leu Ser Ser Thr Leu Asp Ile Leu Gly Val Ala Lys
625                 630                 635

<210> SEQ ID NO 54
<211> LENGTH: 728
<212> TYPE: PRT
<213> ORGANISM: Propionibacterium freudenreichii
<220> FEATURE:
<223> OTHER INFORMATION: Methylmalonyl-CoA mutase alpha (large) subunit

<400> SEQUENCE: 54

Met Ser Thr Leu Pro Arg Phe Asp Ser Val Asp Leu Gly Asn Ala Pro
1               5                   10                  15

Val Pro Ala Asp Ala Ala Gln Arg Phe Glu Glu Leu Ala Ala Lys Ala
            20                  25                  30

Gly Thr Glu Glu Ala Trp Glu Thr Ala Glu Gln Ile Pro Val Gly Thr
        35                  40                  45

Leu Phe Asn Glu Asp Val Tyr Lys Asp Met Asp Trp Leu Asp Thr Tyr
    50                  55                  60

Ala Gly Ile Pro Pro Phe Val His Gly Pro Tyr Ala Thr Met Tyr Ala
65                  70                  75                  80

Phe Arg Pro Trp Thr Ile Arg Gln Tyr Ala Gly Phe Ser Thr Ala Lys
                85                  90                  95

Glu Ser Asn Ala Phe Tyr Arg Arg Asn Leu Ala Ala Gly Gln Lys Gly
            100                 105                 110

Leu Ser Val Ala Phe Asp Leu Pro Thr His Arg Gly Tyr Asp Ser Asp
        115                 120                 125

Asn Pro Arg Val Ala Gly Asp Val Gly Met Ala Gly Val Ala Ile Asp
    130                 135                 140
```

-continued

```
Ser Ile Tyr Asp Met Arg Glu Leu Phe Ala Gly Ile Pro Leu Asp Gln
145                 150                 155                 160

Met Ser Val Ser Met Thr Met Asn Gly Ala Val Leu Pro Ile Leu Ala
            165                 170                 175

Leu Tyr Val Val Thr Ala Glu Glu Gln Gly Val Lys Pro Glu Gln Leu
        180                 185                 190

Ala Gly Thr Ile Gln Asn Asp Ile Leu Lys Glu Phe Met Val Arg Asn
    195                 200                 205

Thr Tyr Ile Tyr Pro Gln Pro Ser Met Arg Ile Ile Ser Glu Ile
210                 215                 220

Phe Ala Tyr Thr Ser Ala Asn Met Pro Lys Trp Asn Ser Ile Ser Ile
225                 230                 235                 240

Ser Gly Tyr His Met Gln Glu Ala Gly Ala Thr Ala Asp Ile Glu Met
            245                 250                 255

Ala Tyr Thr Leu Ala Asp Gly Val Asp Tyr Ile Arg Ala Gly Glu Ser
        260                 265                 270

Val Gly Leu Asn Val Asp Gln Phe Ala Pro Arg Leu Ser Phe Phe Trp
    275                 280                 285

Gly Ile Gly Met Asn Phe Phe Met Glu Val Ala Lys Leu Arg Ala Ala
290                 295                 300

Arg Met Leu Trp Ala Lys Leu His Gln Phe Gly Pro Lys Asn Pro
305                 310                 315                 320

Lys Ser Met Ser Leu Arg Thr His Ser Gln Thr Ser Gly Trp Ser Leu
            325                 330                 335

Thr Ala Gln Asp Val Tyr Asn Asn Val Val Arg Thr Cys Ile Glu Ala
        340                 345                 350

Met Ala Ala Thr Gln Gly His Thr Gln Ser Leu His Thr Asn Ser Leu
    355                 360                 365

Asp Glu Ala Ile Ala Leu Pro Thr Asp Phe Ser Ala Arg Ile Ala Arg
370                 375                 380

Asn Thr Gln Leu Phe Leu Gln Gln Glu Ser Gly Thr Thr Arg Val Ile
385                 390                 395                 400

Asp Pro Trp Ser Gly Ser Ala Tyr Val Glu Glu Leu Thr Trp Asp Leu
            405                 410                 415

Ala Arg Lys Ala Trp Gly His Ile Gln Glu Val Glu Lys Val Gly Gly
        420                 425                 430

Met Ala Lys Ala Ile Glu Lys Gly Ile Pro Lys Met Arg Ile Glu Glu
    435                 440                 445

Ala Ala Ala Arg Thr Gln Ala Arg Ile Asp Ser Gly Arg Gln Pro Leu
450                 455                 460

Ile Gly Val Asn Lys Tyr Arg Leu Glu His Glu Pro Pro Leu Asp Val
465                 470                 475                 480

Leu Lys Val Asp Asn Ser Thr Val Leu Ala Glu Gln Lys Ala Lys Leu
            485                 490                 495

Val Lys Leu Arg Ala Glu Arg Asp Pro Glu Lys Val Lys Ala Ala Leu
        500                 505                 510

Asp Lys Ile Thr Trp Ala Ala Asn Pro Asp Lys Asp Pro Asp
515                 520                 525

Arg Asn Leu Leu Lys Leu Cys Ile Asp Ala Gly Arg Ala Met Ala Thr
530                 535                 540

Val Gly Glu Met Ser Asp Ala Leu Glu Lys Val Phe Gly Arg Tyr Thr
545                 550                 555                 560

Ala Gln Ile Arg Thr Ile Ser Gly Val Tyr Ser Lys Glu Val Lys Asn
            565                 570                 575
```

```
Thr Pro Glu Val Glu Glu Ala Arg Glu Leu Val Glu Phe Glu Gln
            580                 585                 590

Ala Glu Gly Arg Arg Pro Arg Ile Leu Leu Ala Lys Met Gly Gln Asp
        595                 600                 605

Gly His Asp Arg Gly Gln Lys Val Ile Ala Thr Ala Tyr Ala Asp Leu
        610                 615                 620

Gly Phe Asp Val Asp Val Gly Pro Leu Phe Gln Thr Pro Glu Glu Thr
625                 630                 635                 640

Ala Arg Gln Ala Val Glu Ala Asp Val His Val Val Gly Val Ser Ser
        645                 650                 655

Leu Ala Gly Gly His Leu Thr Leu Val Pro Ala Leu Arg Lys Glu Leu
        660                 665                 670

Asp Lys Leu Gly Arg Pro Asp Ile Leu Ile Thr Val Gly Gly Val Ile
        675                 680                 685

Pro Glu Gln Asp Phe Asp Glu Leu Arg Lys Asp Gly Ala Val Glu Ile
        690                 695                 700

Tyr Thr Pro Gly Thr Val Ile Pro Glu Ser Ala Ile Ser Leu Val Lys
705                 710                 715                 720

Lys Leu Arg Ala Ser Leu Asp Ala
                725

<210> SEQ ID NO 55
<211> LENGTH: 678
<212> TYPE: PRT
<213> ORGANISM: Bacillus megaterium
<220> FEATURE:
<223> OTHER INFORMATION: Methylmalonyl-CoA mutase beta (small) subunit

<400> SEQUENCE: 55

Met Lys Thr Asn Thr Leu Ser Phe His Glu Phe Thr Arg Thr Pro Lys
1               5                   10                  15

Glu Asp Trp Ala Gln Glu Val Ser Lys Asn Thr Ala Ile Ser Ser Lys
            20                  25                  30

Glu Thr Leu Glu Asn Ile Phe Leu Lys Pro Leu Tyr Phe Glu Ser Asp
        35                  40                  45

Thr Ala His Leu Asp Tyr Leu Gln Gln Ser Pro Ala Gly Ile Asp Tyr
    50                  55                  60

Leu Arg Gly Ala Gly Lys Glu Ser Tyr Ile Leu Gly Glu Trp Glu Ile
65                  70                  75                  80

Thr Gln Lys Ile Asp Leu Pro Ser Ile Lys Glu Ser Asn Lys Leu Leu
                85                  90                  95

Leu His Ser Leu Arg Asn Gly Gln Asn Thr Ala Ala Phe Thr Cys Ser
            100                 105                 110

Glu Ala Met Arg Gln Gly Lys Asp Ile Asp Glu Ala Thr Glu Ala Glu
        115                 120                 125

Val Ala Ser Gly Ala Thr Ile Ser Thr Leu Glu Asp Val Ala His Leu
    130                 135                 140

Phe Gln His Val Ala Leu Glu Ala Val Pro Leu Phe Leu Asn Thr Gly
145                 150                 155                 160

Cys Thr Ser Val Pro Leu Leu Ser Phe Leu Lys Ala Tyr Cys Val Asp
                165                 170                 175

His Asn Phe Asn Met Arg Gln Leu Lys Gly Thr Val Gly Met Asp Pro
            180                 185                 190

Leu Gly Thr Leu Ala Glu Tyr Gly Arg Val Pro Leu Ser Thr Arg Asp
        195                 200                 205
```

-continued

```
Leu Tyr Asp His Leu Ala Tyr Ala Thr Arg Leu Ala His Ser Asn Val
    210                 215                 220
Pro Glu Leu Lys Thr Ile Ile Val Ser Ser Ile Pro Tyr His Asn Ser
225                 230                 235                 240
Gly Ala Asn Ala Val Gln Glu Leu Ala Tyr Met Leu Ala Thr Gly Val
                245                 250                 255
Gln Tyr Ile Asp Glu Cys Ile Lys Arg Gly Leu Ser Leu His Gln Val
            260                 265                 270
Leu Pro His Met Thr Phe Ser Phe Ser Val Ser Ser His Leu Phe Met
        275                 280                 285
Glu Ile Ser Lys Leu Arg Ala Phe Arg Met Leu Trp Ala Asn Val Val
    290                 295                 300
Arg Ala Phe Asp Asp Thr Ala Val Ser Val Pro Phe Ile His Thr Glu
305                 310                 315                 320
Thr Ser His Leu Thr Gln Ser Lys Glu Asp Met Tyr Thr Asn Ala Leu
                325                 330                 335
Arg Ser Thr Val Gln Ala Phe Ala Ser Ile Val Gly Gly Ala Asp Ser
            340                 345                 350
Leu His Ile Glu Pro Tyr Asp Ser Val Thr Ser Ser Ser Gln Phe
        355                 360                 365
Ala His Arg Leu Ala Arg Asn Thr His Leu Ile Leu Gln His Glu Thr
    370                 375                 380
His Ile Ser Lys Val Met Asp Pro Ala Gly Gly Ser Trp Tyr Val Glu
385                 390                 395                 400
Ala Tyr Thr His Glu Leu Met Thr Lys Ala Trp Glu Leu Phe Gly Asn
                405                 410                 415
Ile Glu Asp His Gly Gly Met Glu Glu Ala Leu Lys Gln Gly Arg Ile
            420                 425                 430
Gln Asp Glu Val Glu Gln Met Lys Val Lys Arg Gln Glu Asp Ile Glu
        435                 440                 445
Cys Arg Ile Glu Arg Leu Ile Gly Val Thr His Tyr Ala Pro Lys Gln
    450                 455                 460
Gln Asp Ala Ser Gln Glu Ile Lys Ser Thr Pro Phe Lys Lys Glu Glu
465                 470                 475                 480
Ile Lys Met Asp Lys Tyr Ser Asp Gln Asn Ala Ser Glu Phe Ser Ser
                485                 490                 495
Asn Leu Ser Leu Glu Asp Tyr Thr Lys Leu Ala Ser Lys Gly Val Thr
            500                 505                 510
Ala Gly Trp Met Leu Lys Gln Met Ala Lys Gln Thr Gln Pro Asp Ser
        515                 520                 525
Val Val Pro Leu Thr Lys Trp Arg Ala Ala Glu Lys Phe Glu Lys Ile
530                 535                 540
Arg Val Tyr Thr Lys Gly Met Ser Ile Gly Ile Met Glu Leu Thr Asp
545                 550                 555                 560
Pro Ser Ser Arg Lys Lys Ala Glu Ile Ala Arg Ser Leu Phe Glu Ser
                565                 570                 575
Ala Gly Phe Ala Cys Glu Thr Ile Lys Asn Ile Asp Ser Tyr Val Glu
            580                 585                 590
Ile Ala Asp Trp Met Asn Glu Gln Lys His Glu Ala Tyr Val Ile Cys
        595                 600                 605
Gly Ser Asp Glu Leu Val Glu Lys Leu Leu Thr Lys Ala Met Thr Tyr
    610                 615                 620
Phe Glu Glu Asp Ser Val Tyr Val Tyr Val Val Gly Glu Glu His Val
625                 630                 635                 640
```

```
Ser Arg Lys Thr Gln Trp Gln Gln Lys Gly Val Met Ser Val Ile His
            645                 650                 655

Pro Lys Thr Asn Val Ile Gln Cys Val Lys Lys Leu Leu Cys Ala Leu
            660                 665                 670

Glu Val Glu Val His Val
            675

<210> SEQ ID NO 56
<211> LENGTH: 716
<212> TYPE: PRT
<213> ORGANISM: Bacillus megaterium
<220> FEATURE:
<223> OTHER INFORMATION: Methylmalonyl-CoA mutase alpha (large) subunit

<400> SEQUENCE: 56

Met Tyr Lys Lys Pro Ser Phe Ser Asn Ile Pro Leu Ser Phe Ser Lys
1               5                   10                  15

Gln Gln Arg Glu Asp Val Thr Gln Ser Ser Tyr Thr Ala Phe Gln
            20                  25                  30

Thr Asn Glu Gln Ile Glu Leu Lys Ser Val Tyr Thr Lys Lys Asp Arg
            35                  40                  45

Asp Asn Leu Asp Phe Ile His Phe Ala Pro Gly Val Pro Pro Phe Val
        50                  55                  60

Arg Gly Pro Tyr Ala Thr Met Tyr Val Asn Arg Pro Trp Thr Ile Arg
65                  70                  75                  80

Gln Tyr Ala Gly Tyr Ser Thr Ala Glu Glu Ser Asn Ala Phe Tyr Arg
                85                  90                  95

Arg Asn Leu Ala Ala Gly Gln Lys Gly Leu Ser Val Ala Phe Asp Leu
            100                 105                 110

Ala Thr His Arg Gly Tyr Asp Ser Asp His Pro Arg Val Val Gly Asp
            115                 120                 125

Val Gly Lys Ala Gly Val Ala Ile Asp Ser Met Met Asp Met Lys Gln
        130                 135                 140

Leu Phe Glu Gly Ile Pro Leu Asp Gln Met Ser Val Ser Met Thr Met
145                 150                 155                 160

Asn Gly Ala Val Leu Pro Ile Leu Ala Phe Tyr Ile Val Thr Ala Glu
                165                 170                 175

Glu Gln Gly Val Lys Lys Glu Lys Leu Ala Gly Thr Ile Gln Asn Asp
            180                 185                 190

Ile Leu Lys Glu Tyr Met Val Arg Asn Thr Tyr Ile Tyr Pro Pro Glu
        195                 200                 205

Met Ser Met Arg Ile Ile Ala Asp Ile Phe Lys Tyr Thr Ala Glu Tyr
    210                 215                 220

Met Pro Lys Phe Asn Ser Ile Ser Ile Ser Gly Tyr His Met Gln Glu
225                 230                 235                 240

Ala Gly Ala Pro Ala Asp Leu Glu Leu Ala Tyr Thr Leu Ala Asp Gly
                245                 250                 255

Leu Glu Tyr Val Arg Thr Gly Leu Lys Ala Gly Ile Thr Ile Asp Ala
            260                 265                 270

Phe Ala Pro Arg Leu Ser Phe Phe Trp Ala Ile Gly Met Asn Tyr Phe
        275                 280                 285

Met Glu Val Ala Lys Met Arg Ala Gly Arg Leu Leu Trp Ala Lys Leu
    290                 295                 300

Met Lys Gln Phe Glu Pro Asp Asn Pro Lys Ser Leu Ala Leu Arg Thr
305                 310                 315                 320
```

```
His Ser Gln Thr Ser Gly Trp Ser Leu Thr Glu Gln Asp Pro Phe Asn
            325                 330                 335

Asn Val Ile Arg Thr Cys Val Glu Ala Leu Ala Ala Val Ser Gly His
            340                 345                 350

Thr Gln Ser Leu His Thr Asn Ala Leu Asp Glu Ala Ile Ala Leu Pro
            355                 360                 365

Thr Asp Phe Ser Ala Arg Ile Ala Arg Asn Thr Gln Leu Tyr Leu Gln
370                 375                 380

Asn Glu Thr Glu Ile Cys Ser Val Ile Asp Pro Trp Gly Gly Ser Tyr
385                 390                 395                 400

Tyr Val Glu Ser Leu Thr Asn Glu Leu Met Ile Lys Ala Trp Lys His
                405                 410                 415

Leu Glu Glu Ile Glu Gln Leu Gly Gly Met Thr Lys Ala Ile Glu Ala
            420                 425                 430

Gly Val Pro Lys Met Lys Ile Glu Glu Ala Ala Arg Arg Gln Ala
            435                 440                 445

Arg Ile Asp Ser Gln Ala Glu Ile Ile Val Gly Val Asn Gln Phe Gln
    450                 455                 460

Pro Glu Gln Glu Pro Leu Asp Ile Leu Asp Ile Asp Asn Thr Ala
465                 470                 475                 480

Val Arg Met Lys Gln Leu Glu Lys Leu Lys Lys Ile Arg Ser Glu Arg
                485                 490                 495

Asn Glu Gln Ala Val Ile Glu Ala Leu Asn Arg Leu Thr Asn Cys Ala
            500                 505                 510

Lys Thr Gly Glu Gly Asn Leu Leu Ala Phe Ala Val Glu Ala Ala Arg
            515                 520                 525

Ala Arg Ala Thr Leu Gly Glu Ile Ser Glu Ala Ile Glu Lys Val Ala
530                 535                 540

Gly Arg His Gln Ala Thr Ser Lys Ser Val Ser Gly Val Tyr Ser Ala
545                 550                 555                 560

Glu Phe Val His Arg Asp Gln Ile Glu Glu Val Arg Lys Leu Thr Ala
                565                 570                 575

Glu Phe Leu Glu Gly Glu Gly Arg Arg Pro Arg Ile Leu Val Ala Lys
            580                 585                 590

Met Gly Gln Asp Gly His Asp Arg Gly Ser Lys Val Ile Ser Thr Ala
            595                 600                 605

Phe Ala Asp Leu Gly Phe Asp Val Asp Ile Gly Pro Leu Phe Gln Thr
610                 615                 620

Pro Gln Glu Thr Ala Arg Gln Ala Val Glu Asn Asp Val His Val Ile
625                 630                 635                 640

Gly Ile Ser Ser Leu Ala Ala Gly His Lys Thr Leu Leu Pro Gln Leu
                645                 650                 655

Val Asp Glu Leu Lys Lys Leu Glu Arg Asp Ile Val Val Ile Val
            660                 665                 670

Gly Gly Val Ile Pro Lys Gln Asp Tyr Ser Phe Leu Leu Glu His Gly
            675                 680                 685

Ala Ser Ala Ile Phe Gly Pro Gly Thr Val Ile Pro Lys Ala Ala Val
            690                 695                 700

Ser Val Leu His Glu Ile Lys Lys Arg Leu Glu Glu
705                 710                 715

<210> SEQ ID NO 57
<211> LENGTH: 616
<212> TYPE: PRT
<213> ORGANISM: Corynebacterium glutamicum
```

```
<220> FEATURE:
<223> OTHER INFORMATION: Methylmalonyl-CoA mutase beta (small) subunit

<400> SEQUENCE: 57

Met Thr Asp Leu Thr Lys Thr Ala Val Pro Glu Glu Leu Ser Glu Asn
1               5                   10                  15

Leu Glu Thr Trp Tyr Lys Ala Val Ala Gly Val Phe Ala Arg Thr Gln
            20                  25                  30

Lys Lys Asp Ile Gly Asp Ile Ala Val Asp Val Trp Lys Lys Leu Ile
        35                  40                  45

Val Thr Thr Pro Asp Gly Val Asp Ile Asn Pro Leu Tyr Thr Arg Ala
    50                  55                  60

Asp Glu Ser Gln Arg Lys Phe Thr Glu Val Pro Gly Glu Phe Pro Phe
65                  70                  75                  80

Thr Arg Gly Thr Thr Val Asp Gly Glu Arg Val Gly Trp Gly Val Thr
                85                  90                  95

Glu Thr Phe Gly His Asp Ser Pro Lys Asn Ile Asn Ala Ala Val Leu
            100                 105                 110

Asn Ala Leu Asn Ser Gly Thr Thr Thr Leu Gly Phe Glu Phe Ser Glu
        115                 120                 125

Glu Phe Thr Ala Ala Asp Leu Lys Val Ala Leu Glu Gly Val Tyr Leu
    130                 135                 140

Asn Met Ala Pro Leu Leu Ile His Ala Gly Gly Ser Thr Ser Glu Val
145                 150                 155                 160

Ala Ala Ala Leu Tyr Thr Leu Ala Glu Glu Ala Gly Thr Phe Phe Ala
                165                 170                 175

Ala Leu Thr Leu Gly Ser Arg Pro Leu Thr Ala Gln Val Asp Gly Ser
            180                 185                 190

His Ser Asp Thr Ile Glu Glu Ala Val Gln Leu Ala Val Asn Ala Ser
        195                 200                 205

Lys Arg Ala Asn Val Arg Ala Ile Leu Val Asp Gly Ser Ser Phe Ser
    210                 215                 220

Asn Gln Gly Ala Ser Asp Ala Gln Glu Ile Gly Leu Ser Ile Ala Ala
225                 230                 235                 240

Gly Val Asp Tyr Val Arg Arg Leu Val Asp Ala Gly Leu Ser Thr Glu
                245                 250                 255

Ala Ala Leu Lys Gln Val Ala Phe Arg Phe Ala Val Thr Asp Glu Gln
            260                 265                 270

Phe Ala Gln Ile Ser Lys Leu Arg Val Ala Arg Arg Leu Trp Ala Arg
        275                 280                 285

Val Cys Glu Val Leu Gly Phe Pro Glu Leu Ala Val Ala Pro Gln His
    290                 295                 300

Ala Val Thr Ala Arg Ala Met Phe Ser Gln Arg Asp Pro Trp Val Asn
305                 310                 315                 320

Met Leu Arg Ser Thr Val Ala Ala Phe Ala Ala Gly Val Gly Gly Ala
                325                 330                 335

Thr Asp Val Glu Val Arg Thr Phe Asp Asp Ala Ile Pro Asp Gly Val
            340                 345                 350

Pro Gly Val Ser Arg Asn Phe Ala His Arg Ile Ala Arg Asn Thr Asn
        355                 360                 365

Leu Leu Leu Leu Glu Glu Ser His Leu Gly His Val Val Asp Pro Ala
    370                 375                 380

Gly Gly Ser Tyr Phe Val Glu Ser Phe Thr Asp Asp Leu Ala Glu Lys
385                 390                 395                 400
```

```
Ala Trp Ala Val Phe Ser Gly Ile Glu Ala Glu Gly Tyr Ser Ala
            405                 410                 415

Ala Cys Ala Ser Gly Thr Val Thr Ala Met Leu Asp Gln Thr Trp Glu
        420                 425                 430

Gln Thr Arg Ala Asp Val Ala Ser Arg Lys Lys Leu Thr Gly Ile
        435                 440                 445

Asn Glu Phe Pro Asn Leu Ala Glu Ser Pro Leu Pro Ala Asp Arg Arg
450                 455                 460

Val Glu Pro Ala Gly Val Arg Arg Trp Ala Ala Asp Phe Glu Ala Leu
465                 470                 475                 480

Arg Asn Arg Ser Asp Ala Phe Leu Glu Lys Asn Gly Ala Arg Pro Gln
                485                 490                 495

Ile Thr Met Ile Pro Leu Gly Pro Leu Ser Lys His Asn Ile Arg Thr
                500                 505                 510

Gly Phe Thr Ser Asn Leu Leu Ala Ser Gly Gly Ile Glu Ala Ile Asn
                515                 520                 525

Pro Gly Gln Leu Val Pro Gly Thr Asp Ala Phe Ala Glu Ala Ala Gln
        530                 535                 540

Ala Ala Gly Ile Val Val Val Cys Gly Thr Asp Gln Glu Tyr Ala Glu
545                 550                 555                 560

Thr Gly Glu Gly Ala Val Glu Lys Leu Arg Glu Ala Gly Val Glu Arg
                565                 570                 575

Ile Leu Leu Ala Gly Ala Pro Lys Ser Phe Glu Gly Ser Ala His Ala
                580                 585                 590

Pro Asp Gly Tyr Leu Asn Met Thr Ile Asp Ala Ala Ala Thr Leu Ala
        595                 600                 605

Asp Leu Leu Asp Ala Leu Gly Ala
610                 615

<210> SEQ ID NO 58
<211> LENGTH: 737
<212> TYPE: PRT
<213> ORGANISM: Corynebacterium glutamicum
<220> FEATURE:
<223> OTHER INFORMATION: Methylmalonyl-CoA mutase alpha (large) subunit

<400> SEQUENCE: 58

Met Thr Ser Ile Pro Asn Phe Ser Asp Ile Pro Leu Thr Ala Glu Thr
1               5                   10                  15

Arg Ala Ser Glu Ser His Asn Val Asp Ala Gly Lys Val Trp Asn Thr
                20                  25                  30

Pro Glu Gly Ile Asp Val Lys Arg Val Phe Thr Gln Ala Asp Arg Asp
            35                  40                  45

Glu Ala Gln Ala Ala Gly His Pro Val Asp Ser Leu Pro Gly Gln Lys
        50                  55                  60

Pro Phe Met Arg Gly Pro Tyr Pro Thr Met Tyr Thr Asn Gln Pro Trp
65                  70                  75                  80

Thr Ile Arg Gln Tyr Ala Gly Phe Ser Thr Ala Ala Glu Ser Asn Ala
                85                  90                  95

Phe Tyr Arg Arg Asn Leu Ala Ala Gly Gln Lys Gly Leu Ser Val Ala
                100                 105                 110

Phe Asp Leu Ala Thr His Arg Gly Tyr Asp Ser Asp Asn Glu Arg Val
            115                 120                 125

Val Gly Asp Val Gly Met Ala Gly Val Ala Ile Asp Ser Ile Leu Asp
        130                 135                 140

Met Arg Gln Leu Phe Asp Gly Ile Asp Leu Ser Ser Val Ser Val Ser
```

```
              145                 150                 155                 160
Met Thr Met Asn Gly Ala Val Leu Pro Ile Leu Ala Phe Tyr Ile Val
                    165                 170                 175

Ala Ala Glu Glu Gln Gly Val Gly Pro Glu Gln Leu Ala Gly Thr Ile
            180                 185                 190

Gln Asn Asp Ile Leu Lys Glu Phe Met Val Arg Asn Thr Tyr Ile Tyr
                195                 200                 205

Pro Pro Lys Pro Ser Met Arg Ile Ile Ser Asn Ile Phe Glu Tyr Thr
            210                 215                 220

Ser Leu Lys Met Pro Arg Phe Asn Ser Ile Ser Ile Ser Gly Tyr His
225                 230                 235                 240

Ile Gln Glu Ala Gly Ala Thr Ala Asp Leu Glu Leu Ala Tyr Thr Leu
                245                 250                 255

Ala Asp Gly Ile Glu Tyr Ile Arg Ala Gly Lys Glu Val Gly Leu Asp
                260                 265                 270

Val Asp Lys Phe Ala Pro Arg Leu Ser Phe Phe Trp Gly Ile Ser Met
            275                 280                 285

Tyr Thr Phe Met Glu Ile Ala Lys Leu Arg Ala Gly Arg Leu Leu Trp
        290                 295                 300

Ser Glu Leu Val Ala Lys Phe Asp Pro Lys Asn Ala Lys Ser Gln Ser
305                 310                 315                 320

Leu Arg Thr His Ser Gln Thr Ser Gly Trp Ser Leu Thr Ala Gln Asp
                325                 330                 335

Val Tyr Asn Asn Val Ala Arg Thr Ala Ile Glu Ala Met Ala Ala Thr
                340                 345                 350

Gln Gly His Thr Gln Ser Leu His Thr Asn Ala Leu Asp Glu Ala Leu
            355                 360                 365

Ala Leu Pro Thr Asp Phe Ser Ala Arg Ile Ala Arg Asn Thr Gln Leu
370                 375                 380

Leu Leu Gln Gln Glu Ser Gly Thr Val Arg Pro Val Asp Pro Trp Ala
385                 390                 395                 400

Gly Ser Tyr Tyr Val Glu Trp Leu Thr Asn Glu Leu Ala Asn Arg Ala
                405                 410                 415

Arg Lys His Ile Asp Glu Val Glu Glu Ala Gly Gly Met Ala Gln Ala
                420                 425                 430

Thr Ala Gln Gly Ile Pro Lys Leu Arg Ile Glu Glu Ser Ala Ala Arg
            435                 440                 445

Thr Gln Ala Arg Ile Asp Ser Gly Arg Gln Ala Leu Ile Gly Val Asn
        450                 455                 460

Arg Tyr Val Ala Glu Glu Asp Glu Glu Ile Glu Val Leu Lys Val Asp
465                 470                 475                 480

Asn Thr Lys Val Arg Ala Glu Gln Leu Ala Lys Leu Ala Gln Leu Lys
                485                 490                 495

Ala Glu Arg Asn Asp Ala Glu Val Lys Ala Ala Leu Asp Ala Leu Thr
            500                 505                 510

Ala Ala Ala Arg Asn Glu His Lys Glu Pro Gly Asp Leu Asp Gln Asn
        515                 520                 525

Leu Leu Lys Leu Ala Val Asp Ala Ala Arg Ala Lys Ala Thr Ile Gly
    530                 535                 540

Glu Ile Ser Asp Ala Leu Glu Val Val Phe Gly Arg His Glu Ala Glu
545                 550                 555                 560

Ile Arg Thr Leu Ser Gly Val Tyr Lys Asp Glu Val Gly Lys Glu Gly
                565                 570                 575
```

```
Thr Val Ser Asn Val Glu Arg Ala Ile Ala Leu Ala Asp Ala Phe Glu
                580                 585                 590

Ala Glu Glu Gly Arg Arg Pro Arg Ile Phe Ile Ala Lys Met Gly Gln
            595                 600                 605

Asp Gly His Asp Arg Gly Gln Lys Val Val Ala Ser Ala Tyr Ala Asp
        610                 615                 620

Leu Gly Met Asp Val Asp Val Gly Pro Leu Phe Gln Thr Pro Ala Glu
625                 630                 635                 640

Ala Ala Arg Ala Ala Val Asp Ala Asp Val His Val Val Gly Met Ser
                645                 650                 655

Ser Leu Ala Ala Gly His Leu Thr Leu Leu Pro Glu Leu Lys Lys Glu
                660                 665                 670

Leu Ala Ala Leu Gly Arg Asp Asp Ile Leu Val Thr Val Gly Gly Val
                675                 680                 685

Ile Pro Pro Gly Asp Phe Gln Asp Leu Tyr Asp Met Gly Ala Ala Ala
                690                 695                 700

Ile Tyr Pro Pro Gly Thr Val Ile Ala Glu Ser Ala Ile Asp Leu Ile
705                 710                 715                 720

Thr Arg Leu Ala Ala His Leu Gly Phe Asp Leu Asp Val Asp Val Asn
                725                 730                 735

Glu

<210> SEQ ID NO 59
<211> LENGTH: 261
<212> TYPE: PRT
<213> ORGANISM: Escherichia coli
<220> FEATURE:
<223> OTHER INFORMATION: Methylmalonyl-CoA decarboxylase

<400> SEQUENCE: 59

Met Ser Tyr Gln Tyr Val Asn Val Val Thr Ile Asn Lys Val Ala Val
1               5                   10                  15

Ile Glu Phe Asn Tyr Gly Arg Lys Leu Asn Ala Leu Ser Lys Val Phe
                20                  25                  30

Ile Asp Asp Leu Met Gln Ala Leu Ser Asp Leu Asn Arg Pro Glu Ile
            35                  40                  45

Arg Cys Ile Ile Leu Arg Ala Pro Ser Gly Ser Lys Val Phe Ser Ala
    50                  55                  60

Gly His Asp Ile His Glu Leu Pro Ser Gly Gly Arg Asp Pro Leu Ser
65              70                  75                  80

Tyr Asp Asp Pro Leu Arg Gln Ile Thr Arg Met Ile Gln Lys Phe Pro
                85                  90                  95

Lys Pro Ile Ile Ser Met Val Glu Gly Ser Val Trp Gly Gly Ala Phe
                100                 105                 110

Glu Met Ile Met Ser Ser Asp Leu Ile Ile Ala Ala Ser Thr Ser Thr
                115                 120                 125

Phe Ser Met Thr Pro Val Asn Leu Gly Val Pro Tyr Asn Leu Val Gly
            130                 135                 140

Ile His Asn Leu Thr Arg Asp Ala Gly Phe His Ile Val Lys Glu Leu
145                 150                 155                 160

Ile Phe Thr Ala Ser Pro Ile Thr Ala Gln Arg Ala Leu Ala Val Gly
                165                 170                 175

Ile Leu Asn His Val Val Glu Val Glu Glu Leu Glu Asp Phe Thr Leu
            180                 185                 190

Gln Met Ala His His Ile Ser Glu Lys Ala Pro Leu Ala Ile Ala Val
        195                 200                 205
```

```
Ile Lys Glu Glu Leu Arg Val Leu Gly Glu Ala His Thr Met Asn Ser
    210                 215                 220
Asp Glu Phe Glu Arg Ile Gln Gly Met Arg Arg Ala Val Tyr Asp Ser
225                 230                 235                 240
Glu Asp Tyr Gln Glu Gly Met Asn Ala Phe Leu Glu Lys Arg Lys Pro
                245                 250                 255
Asn Phe Val Gly His
            260

<210> SEQ ID NO 60
<211> LENGTH: 261
<212> TYPE: PRT
<213> ORGANISM: Salmonella enterica
<220> FEATURE:
<223> OTHER INFORMATION: Methylmalonyl-CoA decarboxylase

<400> SEQUENCE: 60

Met Ser Tyr Gln Tyr Val Asn Val Ile Ile Gln Lys Val Ala Val
1               5                   10                  15
Ile Glu Phe Asn Tyr Ala Arg Lys Leu Asn Ala Leu Ser Lys Val Phe
                20                  25                  30
Ile Asp Asp Leu Met Gln Ala Leu Ser Asp Leu Ser Arg Pro Glu Ile
            35                  40                  45
Arg Cys Ile Ile Leu Arg Ala Pro Ser Gly Ala Lys Val Phe Ser Ala
    50                  55                  60
Gly His Asp Ile His Glu Leu Pro Ser Gly Arg Arg Asp Pro Leu Ser
65                  70                  75                  80
Tyr Asp Asp Pro Leu Arg Gln Ile Thr Arg Leu Ile Gln Lys Tyr Pro
                85                  90                  95
Lys Pro Val Ile Ser Met Val Glu Gly Ser Val Trp Gly Gly Ala Phe
                100                 105                 110
Glu Met Ile Met Ser Ser Asp Leu Ile Ile Ala Ala Ser Thr Ser Thr
            115                 120                 125
Phe Ser Met Thr Pro Val Asn Leu Gly Val Pro Tyr Asn Leu Val Gly
130                 135                 140
Ile His Asn Leu Thr Arg Asp Ala Gly Phe His Ile Val Lys Glu Leu
145                 150                 155                 160
Ile Phe Thr Ala Ser Pro Ile Thr Ala Gln Arg Ala Leu Ala Val Gly
                165                 170                 175
Ile Leu Asn His Val Val Glu Ala Asp Glu Leu Glu Asp Phe Thr Leu
            180                 185                 190
Gln Met Ala His His Ile Ser Glu Lys Ala Pro Leu Ala Ile Ala Val
        195                 200                 205
Ile Lys Glu Glu Leu Arg Val Leu Gly Glu Ala His Thr Met Asn Ser
    210                 215                 220
Asp Glu Phe Glu Arg Ile Gln Gly Met Arg Arg Ala Val Tyr Asp Ser
225                 230                 235                 240
Glu Asp Tyr Gln Glu Gly Met Asn Ala Phe Leu Glu Lys Arg Lys Pro
                245                 250                 255
His Phe Val Gly His
            260

<210> SEQ ID NO 61
<211> LENGTH: 261
<212> TYPE: PRT
<213> ORGANISM: Yersinia enterocolitica
<220> FEATURE:
```

<223> OTHER INFORMATION: Methylmalonyl-CoA decarboxylase

<400> SEQUENCE: 61

```
Met Ser Tyr Gln Tyr Val Lys Val Leu Ile Ala Asn Arg Val Gly Ile
1               5                   10                  15

Ile Glu Phe Asn His Ala Arg Lys Leu Asn Ala Leu Ser Lys Val Phe
            20                  25                  30

Met Asp Asp Leu Met Leu Ala Leu His Asp Leu Asn Asn Thr Asp Ile
        35                  40                  45

Arg Cys Ile Ile Leu Arg Ala Ala Glu Gly Ser Lys Val Phe Ser Ala
    50                  55                  60

Gly His Asp Ile His Glu Leu Pro Thr Gly Arg Arg Asp Pro Leu Ser
65                  70                  75                  80

Tyr Asp Asp Pro Leu Arg Gln Ile Thr Arg Ala Ile Gln Lys Tyr Pro
                85                  90                  95

Lys Pro Ile Ile Ser Met Val Glu Gly Ser Val Trp Gly Gly Ala Phe
            100                 105                 110

Glu Met Ile Met Ser Ser Asp Ile Ile Ala Cys Arg Asn Ser Thr
        115                 120                 125

Phe Ser Met Thr Pro Val Asn Leu Gly Val Pro Tyr Asn Leu Val Gly
    130                 135                 140

Ile His Asn Leu Ile Arg Asp Ala Gly Phe His Ile Val Lys Glu Leu
145                 150                 155                 160

Ile Phe Thr Ala Ala Pro Ile Thr Ala Glu Arg Ala Leu Ser Val Gly
                165                 170                 175

Ile Leu Asn His Val Val Glu Pro Ser Glu Leu Glu Asp Phe Thr Leu
            180                 185                 190

Lys Leu Ala His Val Ile Ser Glu Lys Ala Pro Leu Ala Ile Ala Val
        195                 200                 205

Ile Lys Glu Glu Leu Arg Val Leu Gly Glu Ala His Thr Met Asn Ser
    210                 215                 220

Asp Glu Phe Glu Arg Ile Gln Gly Met Arg Arg Ala Val Tyr Asp Ser
225                 230                 235                 240

Asn Asp Tyr Gln Glu Gly Met Ser Ala Phe Met Glu Lys Arg Lys Pro
                245                 250                 255

Asn Phe Leu Gly Arg
            260
```

<210> SEQ ID NO 62
<211> LENGTH: 611
<212> TYPE: PRT
<213> ORGANISM: Propionibacterium freudenreichii
<220> FEATURE:
<223> OTHER INFORMATION: Methylmalonyl-CoA carboxyl transferase

<400> SEQUENCE: 62

```
Met Ala Glu Asn Asn Asn Leu Lys Leu Ala Ser Thr Met Glu Gly Arg
1               5                   10                  15

Val Glu Gln Leu Ala Glu Gln Arg Gln Val Ile Glu Ala Gly Gly Gly
            20                  25                  30

Glu Arg Arg Val Glu Lys Gln His Ser Gln Gly Lys Gln Thr Ala Arg
        35                  40                  45

Glu Arg Leu Asn Asn Leu Leu Asp Pro His Ser Phe Asp Glu Val Gly
    50                  55                  60

Ala Phe Arg Lys His Arg Thr Thr Leu Phe Gly Met Asp Lys Ala Val
65                  70                  75                  80
```

```
Val Pro Ala Asp Gly Val Val Thr Gly Arg Gly Thr Ile Leu Gly Arg
                85                  90                  95
Pro Val His Ala Ala Ser Gln Asp Phe Thr Val Met Gly Gly Ser Ala
            100                 105                 110
Gly Glu Thr Gln Ser Thr Lys Val Val Glu Thr Met Glu Gln Ala Leu
        115                 120                 125
Leu Thr Gly Thr Pro Phe Leu Phe Phe Tyr Asp Ser Gly Gly Ala Arg
    130                 135                 140
Ile Gln Glu Gly Ile Asp Ser Leu Ser Gly Tyr Gly Lys Met Phe Phe
145                 150                 155                 160
Ala Asn Val Lys Leu Ser Gly Val Val Pro Gln Ile Ala Ile Ile Ala
                165                 170                 175
Gly Pro Cys Ala Gly Gly Ala Ser Tyr Ser Pro Ala Leu Thr Asp Phe
            180                 185                 190
Ile Ile Met Thr Lys Lys Ala His Met Phe Ile Thr Gly Pro Gln Val
        195                 200                 205
Ile Lys Ser Val Thr Gly Glu Asp Val Thr Ala Asp Glu Leu Gly Gly
    210                 215                 220
Ala Glu Ala His Met Ala Ile Ser Gly Asn Ile His Phe Val Ala Glu
225                 230                 235                 240
Asp Asp Asp Ala Ala Glu Leu Ile Ala Lys Lys Leu Leu Ser Phe Leu
                245                 250                 255
Pro Gln Asn Asn Thr Glu Glu Ala Ser Phe Val Asn Pro Asn Asn Asp
            260                 265                 270
Val Ser Pro Asn Thr Glu Leu Arg Asp Ile Val Pro Ile Asp Gly Lys
        275                 280                 285
Lys Gly Tyr Asp Val Arg Asp Val Ile Ala Lys Ile Val Asp Trp Gly
    290                 295                 300
Asp Tyr Leu Glu Val Lys Ala Gly Tyr Ala Thr Asn Leu Val Thr Ala
305                 310                 315                 320
Phe Ala Arg Val Asn Gly Arg Ser Val Gly Ile Val Ala Asn Gln Pro
                325                 330                 335
Ser Val Met Ser Gly Cys Leu Asp Ile Asn Ala Ser Asp Lys Ala Ala
            340                 345                 350
Glu Phe Val Asn Phe Cys Asp Ser Phe Asn Ile Pro Leu Val Gln Leu
        355                 360                 365
Val Asp Val Pro Gly Phe Leu Pro Gly Val Gln Gln Glu Tyr Gly Gly
    370                 375                 380
Ile Ile Arg His Gly Ala Lys Met Leu Tyr Ala Tyr Ser Glu Ala Thr
385                 390                 395                 400
Val Pro Lys Ile Thr Val Val Leu Arg Lys Ala Tyr Gly Gly Ser Tyr
                405                 410                 415
Leu Ala Met Cys Asn Arg Asp Leu Gly Ala Asp Ala Val Tyr Ala Trp
            420                 425                 430
Pro Ser Ala Glu Ile Ala Val Met Gly Ala Glu Gly Ala Ala Asn Val
        435                 440                 445
Ile Phe Arg Lys Glu Ile Lys Ala Ala Asp Pro Asp Ala Met Arg
    450                 455                 460
Ala Glu Lys Ile Glu Glu Tyr Gln Asn Ala Phe Asn Thr Pro Tyr Val
465                 470                 475                 480
Ala Ala Ala Arg Gly Gln Val Asp Asp Val Ile Asp Pro Ala Asp Thr
                485                 490                 495
Arg Arg Lys Ile Ala Ser Ala Leu Glu Met Tyr Ala Thr Lys Arg Gln
            500                 505                 510
```

```
Thr Arg Pro Ala Lys Lys Pro Trp Lys Leu Pro Leu Leu Ser Glu Glu
        515                 520                 525

Glu Ile Met Ala Asp Glu Glu Lys Asp Leu Met Ile Ala Thr Leu
    530                 535                 540

Asn Lys Arg Val Ala Ser Leu Glu Ser Glu Leu Gly Ser Leu Gln Ser
545                 550                 555                 560

Asp Thr Gln Gly Val Thr Glu Asp Val Leu Thr Ala Ile Ser Ala Val
                565                 570                 575

Ala Ala Tyr Leu Gly Asn Asp Gly Ser Ala Glu Val Val His Phe Ala
            580                 585                 590

Pro Ser Pro Asn Trp Val Arg Glu Gly Arg Arg Ala Leu Gln Asn His
        595                 600                 605

Ser Ile Arg
    610

<210> SEQ ID NO 63
<211> LENGTH: 148
<212> TYPE: PRT
<213> ORGANISM: Propionibacterium freundenreichii
<220> FEATURE:
<223> OTHER INFORMATION: Methylmalonyl-CoA epimerase

<400> SEQUENCE: 63

Met Ser Asn Glu Asp Leu Phe Ile Cys Ile Asp His Val Ala Tyr Ala
1               5                   10                  15

Cys Pro Asp Ala Asp Glu Ala Ser Lys Tyr Tyr Gln Glu Thr Phe Gly
            20                  25                  30

Trp His Glu Leu His Arg Glu Glu Asn Pro Glu Gln Gly Val Val Glu
        35                  40                  45

Ile Met Met Ala Pro Ala Ala Lys Leu Thr Glu His Met Thr Gln Val
    50                  55                  60

Gln Val Met Ala Pro Leu Asn Asp Glu Ser Thr Val Ala Lys Trp Leu
65                  70                  75                  80

Ala Lys His Asn Gly Arg Ala Gly Leu His His Met Ala Trp Arg Val
                85                  90                  95

Asp Asp Ile Asp Ala Val Ser Ala Thr Leu Arg Glu Arg Gly Val Gln
            100                 105                 110

Leu Leu Tyr Asp Glu Pro Lys Leu Gly Thr Gly Gly Asn Arg Ile Asn
        115                 120                 125

Phe Met His Pro Lys Ser Gly Lys Gly Val Leu Ile Glu Leu Thr Gln
    130                 135                 140

Tyr Pro Lys Asn
145

<210> SEQ ID NO 64
<211> LENGTH: 208
<212> TYPE: PRT
<213> ORGANISM: Escherichia coli
<220> FEATURE:
<223> OTHER INFORMATION: Thioesterase (TesA)

<400> SEQUENCE: 64

Met Met Asn Phe Asn Asn Val Phe Arg Trp His Leu Pro Phe Leu Phe
1               5                   10                  15

Leu Val Leu Leu Thr Phe Arg Ala Ala Ala Ala Asp Thr Leu Leu Ile
            20                  25                  30

Leu Gly Asp Ser Leu Ser Ala Gly Tyr Arg Met Ser Ala Ser Ala Ala
        35                  40                  45
```

```
Trp Pro Ala Leu Leu Asn Asp Lys Trp Gln Ser Lys Thr Ser Val Val
     50                  55                  60

Asn Ala Ser Ile Ser Gly Asp Thr Ser Gln Gln Gly Leu Ala Arg Leu
 65                  70                  75                  80

Pro Ala Leu Leu Lys Gln His Gln Pro Arg Trp Val Leu Val Glu Leu
                 85                  90                  95

Gly Gly Asn Asp Gly Leu Arg Gly Phe Gln Pro Gln Gln Thr Glu Gln
            100                 105                 110

Thr Leu Arg Gln Ile Leu Gln Asp Val Lys Ala Ala Asn Ala Glu Pro
        115                 120                 125

Leu Leu Met Gln Ile Arg Leu Pro Ala Asn Tyr Gly Arg Arg Tyr Asn
130                 135                 140

Glu Ala Phe Ser Ala Ile Tyr Pro Lys Leu Ala Lys Glu Phe Asp Val
145                 150                 155                 160

Pro Leu Leu Pro Phe Phe Met Glu Glu Val Tyr Leu Lys Pro Gln Trp
                165                 170                 175

Met Gln Asp Asp Gly Ile His Pro Asn Arg Asp Ala Gln Pro Phe Ile
            180                 185                 190

Ala Asp Trp Met Ala Lys Gln Leu Gln Pro Leu Val Asn His Asp Ser
        195                 200                 205

<210> SEQ ID NO 65
<211> LENGTH: 183
<212> TYPE: PRT
<213> ORGANISM: Artificial Sequence
<220> FEATURE:
<223> OTHER INFORMATION: Description of Artificial Sequence: Synthetic
      Escherichia coli Thioesterase (TesA) mutant polypeptide

<400> SEQUENCE: 65

Met Ala Asp Thr Leu Leu Ile Leu Gly Asp Ser Leu Ser Ala Gly Tyr
 1               5                  10                  15

Arg Met Ser Ala Ser Ala Ala Trp Pro Ala Leu Leu Asn Asp Lys Trp
            20                  25                  30

Gln Ser Lys Thr Ser Val Val Asn Ala Ser Ile Ser Gly Asp Thr Ser
        35                  40                  45

Gln Gln Gly Leu Ala Arg Leu Pro Ala Leu Leu Lys Gln His Gln Pro
    50                  55                  60

Arg Trp Val Leu Val Glu Leu Gly Gly Asn Asp Gly Leu Arg Gly Phe
 65                  70                  75                  80

Gln Pro Gln Gln Thr Glu Gln Thr Leu Arg Gln Ile Leu Gln Asp Val
                85                  90                  95

Lys Ala Ala Asn Ala Glu Pro Leu Leu Met Gln Ile Arg Leu Pro Ala
            100                 105                 110

Asn Tyr Gly Arg Arg Tyr Asn Glu Ala Phe Ser Ala Ile Tyr Pro Lys
        115                 120                 125

Leu Ala Lys Glu Phe Asp Val Pro Leu Leu Pro Phe Phe Met Glu Glu
    130                 135                 140

Val Tyr Leu Lys Pro Gln Trp Met Gln Asp Asp Gly Ile His Pro Asn
145                 150                 155                 160

Arg Asp Ala Gln Pro Phe Ile Ala Asp Trp Met Ala Lys Gln Leu Gln
                165                 170                 175

Pro Leu Val Asn His Asp Ser
            180

<210> SEQ ID NO 66
```

```
<211> LENGTH: 286
<212> TYPE: PRT
<213> ORGANISM: Escherichia coli
<220> FEATURE:
<223> OTHER INFORMATION: Thioesterase (TesB)

<400> SEQUENCE: 66

Met Ser Gln Ala Leu Lys Asn Leu Leu Thr Leu Leu Asn Leu Glu Lys
1               5                   10                  15

Ile Glu Glu Gly Leu Phe Arg Gly Gln Ser Glu Asp Leu Gly Leu Arg
            20                  25                  30

Gln Val Phe Gly Gly Gln Val Gly Gln Ala Leu Tyr Ala Ala Lys
        35                  40                  45

Glu Thr Val Pro Glu Glu Arg Leu Val His Ser Phe His Ser Tyr Phe
50                  55                  60

Leu Arg Pro Gly Asp Ser Lys Lys Pro Ile Ile Tyr Asp Val Glu Thr
65                  70                  75                  80

Leu Arg Asp Gly Asn Ser Phe Ser Ala Arg Arg Val Ala Ala Ile Gln
            85                  90                  95

Asn Gly Lys Pro Ile Phe Tyr Met Thr Ala Ser Phe Gln Ala Pro Glu
        100                 105                 110

Ala Gly Phe Glu His Gln Lys Thr Met Pro Ser Ala Pro Ala Pro Asp
    115                 120                 125

Gly Leu Pro Ser Glu Thr Gln Ile Ala Gln Ser Leu Ala His Leu Leu
130                 135                 140

Pro Pro Val Leu Lys Asp Lys Phe Ile Cys Asp Arg Pro Leu Glu Val
145                 150                 155                 160

Arg Pro Val Glu Phe His Asn Pro Leu Lys Gly His Val Ala Glu Pro
            165                 170                 175

His Arg Gln Val Trp Ile Arg Ala Asn Gly Ser Val Pro Asp Asp Leu
        180                 185                 190

Arg Val His Gln Tyr Leu Leu Gly Tyr Ala Ser Asp Leu Asn Phe Leu
    195                 200                 205

Pro Val Ala Leu Gln Pro His Gly Ile Gly Phe Leu Glu Pro Gly Ile
210                 215                 220

Gln Ile Ala Thr Ile Asp His Ser Met Trp Phe His Arg Pro Phe Asn
225                 230                 235                 240

Leu Asn Glu Trp Leu Leu Tyr Ser Val Glu Ser Thr Ser Ala Ser Ser
            245                 250                 255

Ala Arg Gly Phe Val Arg Gly Glu Phe Tyr Thr Gln Asp Gly Val Leu
        260                 265                 270

Val Ala Ser Thr Val Gln Glu Gly Val Met Arg Asn His Asn
    275                 280                 285

<210> SEQ ID NO 67
<211> LENGTH: 362
<212> TYPE: PRT
<213> ORGANISM: Arabidopsis thaliana
<220> FEATURE:
<223> OTHER INFORMATION: Thioesterase (FatA)

<400> SEQUENCE: 67

Met Leu Lys Leu Ser Cys Asn Val Thr Asp Ser Lys Leu Gln Arg Ser
1               5                   10                  15

Leu Leu Phe Phe Ser His Ser Tyr Arg Ser Asp Pro Val Asn Phe Ile
            20                  25                  30

Arg Arg Arg Ile Val Ser Cys Ser Gln Thr Lys Lys Thr Gly Leu Val
        35                  40                  45
```

Pro Leu Arg Ala Val Val Ser Ala Asp Gln Gly Ser Val Val Gln Gly
            50                  55                  60

Leu Ala Thr Leu Ala Asp Gln Leu Arg Leu Gly Ser Leu Thr Glu Asp
65                  70                  75                  80

Gly Leu Ser Tyr Lys Glu Lys Phe Val Val Arg Ser Tyr Glu Val Gly
                85                  90                  95

Ser Asn Lys Thr Ala Thr Val Glu Thr Ile Ala Asn Leu Leu Gln Glu
            100                 105                 110

Val Gly Cys Asn His Ala Gln Ser Val Gly Phe Ser Thr Asp Gly Phe
        115                 120                 125

Ala Thr Thr Thr Thr Met Arg Lys Leu His Leu Ile Trp Val Thr Ala
130                 135                 140

Arg Met His Ile Glu Ile Tyr Lys Tyr Pro Ala Trp Gly Asp Val Val
145                 150                 155                 160

Glu Ile Glu Thr Trp Cys Gln Ser Glu Gly Arg Ile Gly Thr Arg Arg
                165                 170                 175

Asp Trp Ile Leu Lys Asp Ser Val Thr Gly Glu Val Thr Gly Arg Ala
            180                 185                 190

Thr Ser Lys Trp Val Met Met Asn Gln Asp Thr Arg Arg Leu Gln Lys
        195                 200                 205

Val Ser Asp Asp Val Arg Asp Glu Tyr Leu Val Phe Cys Pro Gln Glu
210                 215                 220

Pro Arg Leu Ala Phe Pro Glu Glu Asn Asn Arg Ser Leu Lys Lys Ile
225                 230                 235                 240

Pro Lys Leu Glu Asp Pro Ala Gln Tyr Ser Met Ile Gly Leu Lys Pro
                245                 250                 255

Arg Arg Ala Asp Leu Asp Met Asn Gln His Val Asn Asn Val Thr Tyr
            260                 265                 270

Ile Gly Trp Val Leu Glu Ser Ile Pro Gln Glu Ile Val Asp Thr His
        275                 280                 285

Glu Leu Gln Val Ile Thr Leu Asp Tyr Arg Arg Glu Cys Gln Gln Asp
290                 295                 300

Asp Val Val Asp Ser Leu Thr Thr Thr Thr Ser Glu Ile Gly Gly Thr
305                 310                 315                 320

Asn Gly Ser Ala Thr Ser Gly Thr Gln Gly His Asn Asp Ser Gln Phe
                325                 330                 335

Leu His Leu Leu Arg Leu Ser Gly Asp Gly Gln Glu Ile Asn Arg Gly
            340                 345                 350

Thr Thr Leu Trp Arg Lys Lys Pro Ser Ser
        355                 360

<210> SEQ ID NO 68
<211> LENGTH: 412
<212> TYPE: PRT
<213> ORGANISM: Arabidopsis thaliana
<220> FEATURE:
<223> OTHER INFORMATION: Thioesterase (FatB)

<400> SEQUENCE: 68

Met Val Ala Thr Ser Ala Thr Ser Ser Phe Phe Pro Val Pro Ser Ser
1               5                   10                  15

Ser Leu Asp Pro Asn Gly Lys Gly Asn Lys Ile Gly Ser Thr Asn Leu
            20                  25                  30

Ala Gly Leu Asn Ser Ala Pro Asn Ser Gly Arg Met Lys Val Lys Pro
        35                  40                  45

```
Asn Ala Gln Ala Pro Pro Lys Ile Asn Gly Lys Lys Val Gly Leu Pro
 50                  55                  60
Gly Ser Val Asp Ile Val Arg Thr Asp Thr Glu Thr Ser Ser His Pro
 65                  70                  75                  80
Ala Pro Arg Thr Phe Ile Asn Gln Leu Pro Asp Trp Ser Met Leu Leu
                 85                  90                  95
Ala Ala Ile Thr Thr Ile Phe Leu Ala Ala Glu Lys Gln Trp Met Met
                100                 105                 110
Leu Asp Trp Lys Pro Arg Arg Ser Asp Met Leu Val Asp Pro Phe Gly
            115                 120                 125
Ile Gly Arg Ile Val Gln Asp Gly Leu Val Phe Arg Gln Asn Phe Ser
130                 135                 140
Ile Arg Ser Tyr Glu Ile Gly Ala Asp Arg Ser Ala Ser Ile Glu Thr
145                 150                 155                 160
Val Met Asn His Leu Gln Glu Thr Ala Leu Asn His Val Lys Thr Ala
                165                 170                 175
Gly Leu Leu Gly Asp Gly Phe Gly Ser Thr Pro Glu Met Phe Lys Lys
                180                 185                 190
Asn Leu Ile Trp Val Val Thr Arg Met Gln Val Val Val Asp Lys Tyr
            195                 200                 205
Pro Thr Trp Gly Asp Val Val Glu Val Asp Thr Trp Val Ser Gln Ser
210                 215                 220
Gly Lys Asn Gly Met Arg Arg Asp Trp Leu Val Arg Asp Cys Asn Thr
225                 230                 235                 240
Gly Glu Thr Leu Thr Arg Ala Ser Ser Val Trp Val Met Met Asn Lys
                245                 250                 255
Leu Thr Arg Arg Leu Ser Lys Ile Pro Glu Glu Val Arg Gly Glu Ile
                260                 265                 270
Glu Pro Tyr Phe Val Asn Ser Asp Pro Val Leu Ala Glu Asp Ser Arg
            275                 280                 285
Lys Leu Thr Lys Ile Asp Asp Lys Thr Ala Asp Tyr Val Arg Ser Gly
            290                 295                 300
Leu Thr Pro Arg Trp Ser Asp Leu Asp Val Asn Gln His Val Asn Asn
305                 310                 315                 320
Val Lys Tyr Ile Gly Trp Ile Leu Glu Ser Ala Pro Val Gly Ile Met
                325                 330                 335
Glu Arg Gln Lys Leu Lys Ser Met Thr Leu Glu Tyr Arg Arg Glu Cys
                340                 345                 350
Gly Arg Asp Ser Val Leu Gln Ser Leu Thr Ala Val Thr Gly Cys Asp
            355                 360                 365
Ile Gly Asn Leu Ala Thr Ala Gly Asp Val Glu Cys Gln His Leu Leu
            370                 375                 380
Arg Leu Gln Asp Gly Ala Glu Val Val Arg Gly Arg Thr Glu Trp Ser
385                 390                 395                 400
Ser Lys Thr Pro Thr Thr Thr Trp Gly Thr Ala Pro
                405                 410

<210> SEQ ID NO 69
<211> LENGTH: 382
<212> TYPE: PRT
<213> ORGANISM: Umbellularia californica
<220> FEATURE:
<223> OTHER INFORMATION: Thioesterase (FatB)

<400> SEQUENCE: 69

Met Ala Thr Thr Ser Leu Ala Ser Ala Phe Cys Ser Met Lys Ala Val
```

```
                1               5              10              15
Met Leu Ala Arg Asp Gly Arg Gly Met Lys Pro Arg Ser Ser Asp Leu
                    20                  25                  30

Gln Leu Arg Ala Gly Asn Ala Pro Thr Ser Leu Lys Met Ile Asn Gly
                    35                  40                  45

Thr Lys Phe Ser Tyr Thr Glu Ser Leu Lys Arg Leu Pro Asp Trp Ser
    50                  55                  60

Met Leu Phe Ala Val Ile Thr Thr Ile Phe Ser Ala Ala Glu Lys Gln
65                      70                  75                  80

Trp Thr Asn Leu Glu Trp Lys Pro Lys Pro Lys Leu Pro Gln Leu Leu
                    85                  90                  95

Asp Asp His Phe Gly Leu His Gly Leu Val Phe Arg Arg Thr Phe Ala
                    100                 105                 110

Ile Arg Ser Tyr Glu Val Gly Pro Asp Arg Ser Thr Ser Ile Leu Ala
                    115                 120                 125

Val Met Asn His Met Gln Glu Ala Thr Leu Asn His Ala Lys Ser Val
                    130                 135                 140

Gly Ile Leu Gly Asp Gly Phe Gly Thr Thr Leu Glu Met Ser Lys Arg
145                     150                 155                 160

Asp Leu Met Trp Val Val Arg Arg Thr His Val Ala Val Glu Arg Tyr
                        165                 170                 175

Pro Thr Trp Gly Asp Thr Val Glu Val Glu Cys Trp Ile Gly Ala Ser
                    180                 185                 190

Gly Asn Asn Gly Met Arg Arg Asp Phe Leu Val Arg Asp Cys Lys Thr
                    195                 200                 205

Gly Glu Ile Leu Thr Arg Cys Thr Ser Leu Ser Val Leu Met Asn Thr
                    210                 215                 220

Arg Thr Arg Arg Leu Ser Thr Ile Pro Asp Glu Val Arg Gly Glu Ile
225                     230                 235                 240

Gly Pro Ala Phe Ile Asp Asn Val Ala Val Lys Asp Asp Glu Ile Lys
                    245                 250                 255

Lys Leu Gln Lys Leu Asn Asp Ser Thr Ala Asp Tyr Ile Gln Gly Gly
                    260                 265                 270

Leu Thr Pro Arg Trp Asn Asp Leu Asp Val Asn Gln His Val Asn Asn
                    275                 280                 285

Leu Lys Tyr Val Ala Trp Val Phe Glu Thr Val Pro Asp Ser Ile Phe
                    290                 295                 300

Glu Ser His His Ile Ser Ser Phe Thr Leu Glu Tyr Arg Arg Glu Cys
305                     310                 315                 320

Thr Arg Asp Ser Val Leu Arg Ser Leu Thr Thr Val Ser Gly Gly Ser
                    325                 330                 335

Ser Glu Ala Gly Leu Val Cys Asp His Leu Leu Gln Leu Glu Gly Gly
                    340                 345                 350

Ser Glu Val Leu Arg Ala Arg Thr Glu Trp Arg Pro Lys Leu Thr Asp
                    355                 360                 365

Ser Phe Arg Gly Ile Ser Val Ile Pro Ala Glu Pro Arg Val
                    370                 375                 380
```

<210> SEQ ID NO 70
<211> LENGTH: 376
<212> TYPE: PRT
<213> ORGANISM: Cuphea hookeriana
<220> FEATURE:
<223> OTHER INFORMATION: Thioesterase (FatA1)

<400> SEQUENCE: 70

```
Met Leu Lys Leu Ser Cys Asn Ala Ala Thr Asp Gln Ile Leu Ser Ser
  1               5                  10                  15

Ala Val Ala Gln Thr Ala Leu Trp Gly Gln Pro Arg Asn Arg Ser Phe
             20                  25                  30

Ser Met Ser Ala Arg Arg Gly Ala Val Cys Cys Ala Pro Pro Ala
         35                  40                  45

Ala Gly Lys Pro Pro Ala Met Thr Ala Val Ile Pro Lys Asp Gly Val
         50                  55                  60

Ala Ser Ser Gly Ser Gly Ser Leu Ala Asp Gln Leu Arg Leu Gly Ser
 65                  70                  75                  80

Arg Thr Gln Asn Gly Leu Ser Tyr Thr Glu Lys Phe Ile Val Arg Cys
                 85                  90                  95

Tyr Glu Val Gly Ile Asn Lys Thr Ala Thr Val Glu Thr Met Ala Asn
                100                 105                 110

Leu Leu Gln Glu Val Gly Cys Asn His Ala Gln Ser Val Gly Phe Ser
            115                 120                 125

Thr Asp Gly Phe Ala Thr Thr Pro Thr Met Arg Lys Leu Asn Leu Ile
            130                 135                 140

Trp Val Thr Ala Arg Met His Ile Glu Ile Tyr Lys Tyr Pro Ala Trp
145                 150                 155                 160

Ser Asp Val Val Glu Ile Glu Thr Trp Cys Gln Ser Glu Gly Arg Ile
                165                 170                 175

Gly Thr Arg Arg Asp Trp Ile Leu Lys Asp Tyr Gly Asn Gly Glu Val
            180                 185                 190

Ile Gly Arg Ala Thr Ser Lys Trp Val Met Met Asn Gln Asn Thr Arg
            195                 200                 205

Arg Leu Gln Lys Val Asp Asp Ser Val Arg Glu Glu Tyr Met Val Phe
            210                 215                 220

Cys Pro Arg Glu Pro Arg Leu Ser Phe Pro Glu Glu Asn Asn Arg Ser
225                 230                 235                 240

Leu Arg Lys Ile Ser Lys Leu Glu Asp Pro Ala Glu Tyr Ser Arg Leu
                245                 250                 255

Gly Leu Thr Pro Arg Arg Ala Asp Leu Asp Met Asn Gln His Val Asn
            260                 265                 270

Asn Val Ala Tyr Ile Gly Trp Ala Leu Glu Ser Val Pro Gln Glu Ile
            275                 280                 285

Ile Asp Ser Tyr Glu Leu Glu Thr Ile Thr Leu Asp Tyr Arg Arg Glu
            290                 295                 300

Cys Gln Gln Asp Asp Val Val Asp Ser Leu Thr Ser Val Leu Ser Asp
305                 310                 315                 320

Glu Glu Ser Gly Thr Leu Pro Glu Leu Lys Gly Thr Asn Gly Ser Ala
            325                 330                 335

Ser Thr Pro Leu Lys Arg Asp His Asp Gly Ser Arg Gln Phe Leu His
            340                 345                 350

Leu Leu Arg Leu Ser Pro Asp Gly Leu Glu Ile Asn Arg Gly Arg Thr
            355                 360                 365

Glu Trp Arg Lys Lys Ser Thr Lys
            370                 375

<210> SEQ ID NO 71
<211> LENGTH: 415
<212> TYPE: PRT
<213> ORGANISM: Cuphea hookeriana
<220> FEATURE:
<223> OTHER INFORMATION: Thioesterase (FatB2)
```

<400> SEQUENCE: 71

```
Met Val Ala Ala Ala Ser Ser Ala Phe Phe Pro Val Pro Ala Pro
  1               5                  10                  15

Gly Ala Ser Pro Lys Pro Gly Lys Phe Gly Asn Trp Pro Ser Ser Leu
             20                  25                  30

Ser Pro Ser Phe Lys Pro Lys Ser Ile Pro Asn Gly Gly Phe Gln Val
             35                  40                  45

Lys Ala Asn Asp Ser Ala His Pro Lys Ala Asn Gly Ser Ala Val Ser
 50                  55                  60

Leu Lys Ser Gly Ser Leu Asn Thr Gln Glu Asp Thr Ser Ser Ser Pro
 65                  70                  75                  80

Pro Pro Arg Thr Phe Leu His Gln Leu Pro Asp Trp Ser Arg Leu Leu
                 85                  90                  95

Thr Ala Ile Thr Thr Val Phe Val Lys Ser Lys Arg Pro Asp Met His
                100                 105                 110

Asp Arg Lys Ser Lys Arg Pro Asp Met Leu Val Asp Ser Phe Gly Leu
            115                 120                 125

Glu Ser Thr Val Gln Asp Gly Leu Val Phe Arg Gln Ser Phe Ser Ile
130                 135                 140

Arg Ser Tyr Glu Ile Gly Thr Asp Arg Thr Ala Ser Ile Glu Thr Leu
145                 150                 155                 160

Met Asn His Leu Gln Glu Thr Ser Leu Asn His Cys Lys Ser Thr Gly
                165                 170                 175

Ile Leu Leu Asp Gly Phe Gly Arg Thr Leu Glu Met Cys Lys Arg Asp
            180                 185                 190

Leu Ile Trp Val Val Ile Lys Met Gln Ile Lys Val Asn Arg Tyr Pro
195                 200                 205

Ala Trp Gly Asp Thr Val Glu Ile Asn Thr Arg Phe Ser Arg Leu Gly
            210                 215                 220

Lys Ile Gly Met Gly Arg Asp Trp Leu Ile Ser Asp Cys Asn Thr Gly
225                 230                 235                 240

Glu Ile Leu Val Arg Ala Thr Ser Ala Tyr Ala Met Met Asn Gln Lys
                245                 250                 255

Thr Arg Arg Leu Ser Lys Leu Pro Tyr Glu Val His Gln Glu Ile Val
            260                 265                 270

Pro Leu Phe Val Asp Ser Pro Val Ile Glu Asp Ser Asp Leu Lys Val
            275                 280                 285

His Lys Phe Lys Val Lys Thr Gly Asp Ser Ile Gln Lys Gly Leu Thr
290                 295                 300

Pro Gly Trp Asn Asp Leu Asp Val Asn Gln His Val Ser Asn Val Lys
305                 310                 315                 320

Tyr Ile Gly Trp Ile Leu Glu Ser Met Pro Thr Glu Val Leu Glu Thr
                325                 330                 335

Gln Glu Leu Cys Ser Leu Ala Leu Glu Tyr Arg Arg Glu Cys Gly Arg
            340                 345                 350

Asp Ser Val Leu Glu Ser Val Thr Ala Met Asp Pro Ser Lys Val Gly
            355                 360                 365

Val Arg Ser Gln Tyr Gln His Leu Leu Arg Leu Glu Asp Gly Thr Ala
370                 375                 380

Ile Val Asn Gly Ala Thr Glu Trp Arg Pro Lys Asn Ala Gly Ala Asn
385                 390                 395                 400

Gly Ala Ile Ser Thr Gly Lys Thr Ser Asn Gly Asn Ser Val Ser
                405                 410                 415
```

<210> SEQ ID NO 72
<211> LENGTH: 394
<212> TYPE: PRT
<213> ORGANISM: Cuphea hookeriana
<220> FEATURE:
<223> OTHER INFORMATION: thioesterase (FatB3)

<400> SEQUENCE: 72

```
Met Val Ala Ala Ala Ser Ser Ala Phe Phe Ser Val Pro Thr Pro
1               5                   10                  15

Gly Ile Ser Pro Lys Pro Gly Lys Phe Gly Asn Gly Gly Phe Gln Val
            20                  25                  30

Lys Ala Asn Ala Asn Ala His Pro Ser Leu Lys Ser Gly Ser Leu Glu
            35                  40                  45

Thr Glu Asp Asp Thr Ser Ser Ser Pro Pro Arg Thr Phe Ile
    50                  55                  60

Asn Gln Leu Pro Asp Trp Ser Met Leu Leu Ser Ala Ile Thr Thr Ile
65                  70                  75                  80

Phe Gly Ala Ala Glu Lys Gln Trp Met Met Leu Asp Arg Lys Ser Lys
                85                  90                  95

Arg Pro Asp Met Leu Met Glu Pro Phe Gly Val Asp Ser Ile Val Gln
                100                 105                 110

Asp Gly Val Phe Phe Arg Gln Ser Phe Ser Ile Arg Ser Tyr Glu Ile
                115                 120                 125

Gly Ala Asp Arg Thr Thr Ser Ile Glu Thr Leu Met Asn Met Phe Gln
            130                 135                 140

Glu Thr Ser Leu Asn His Cys Lys Ser Asn Gly Leu Leu Asn Asp Gly
145                 150                 155                 160

Phe Gly Arg Thr Pro Glu Met Cys Lys Lys Gly Leu Ile Trp Val Val
                165                 170                 175

Thr Lys Met Gln Val Glu Val Asn Arg Tyr Pro Ile Trp Gly Asp Ser
                180                 185                 190

Ile Glu Val Asn Thr Trp Val Ser Glu Ser Gly Lys Asn Gly Met Gly
            195                 200                 205

Arg Asp Trp Leu Ile Ser Asp Cys Ser Thr Gly Glu Ile Leu Val Arg
    210                 215                 220

Ala Thr Ser Val Trp Ala Met Met Asn Gln Lys Thr Arg Arg Leu Ser
225                 230                 235                 240

Lys Phe Pro Phe Glu Val Arg Gln Glu Ile Ala Pro Asn Phe Val Asp
                245                 250                 255

Ser Val Pro Val Ile Glu Asp Asp Arg Lys Leu His Lys Leu Asp Val
                260                 265                 270

Lys Thr Gly Asp Ser Ile His Asn Gly Leu Thr Pro Arg Trp Asn Asp
            275                 280                 285

Leu Asp Val Asn Gln His Val Asn Asn Val Lys Tyr Ile Gly Trp Ile
    290                 295                 300

Leu Lys Ser Val Pro Thr Asp Val Phe Glu Ala Gln Glu Leu Cys Gly
305                 310                 315                 320

Val Thr Leu Glu Tyr Arg Arg Glu Cys Gly Arg Asp Ser Val Met Glu
                325                 330                 335

Ser Val Thr Ala Met Asp Pro Ser Lys Glu Gly Asp Arg Ser Val Tyr
            340                 345                 350

Gln His Leu Leu Arg Leu Glu Asp Gly Ala Asp Ile Ala Ile Gly Arg
    355                 360                 365
```

```
Thr Glu Trp Arg Pro Lys Asn Ala Gly Ala Asn Gly Ala Ile Ser Thr
    370                 375                 380

Gly Lys Thr Ser Asn Arg Asn Ser Val Ser
385                 390

<210> SEQ ID NO 73
<211> LENGTH: 4559
<212> TYPE: DNA
<213> ORGANISM: Artificial Sequence
<220> FEATURE:
<223> OTHER INFORMATION: Description of Artificial Sequence: Synthetic
      pDG2 plasmid polynucleotide

<400> SEQUENCE: 73
ggggaattgt gagcggataa caattcccct gtagaaataa ttttgtttaa ctttaataag     60
gagatatacc atggcgcaac tcactcttct tttagtcggc aattccgacg ccatcacgcc    120
attacttgct aaagctgact ttgaacaacg ttcgcgtctg cagattattc ctgcgcagtc    180
agttatcgcc agtgatgccc ggccttcgca agctatccgc gccagtcgtg ggagttcaat    240
gcgcgtggcc ctggagctgg tgaaagaagg tcgagcgcaa gcctgtgtca gtgccggtaa    300
taccggggcg ctgatgggc tggcaaaatt attactcaag cccctggagg ggattgagcg    360
tccggcgctg gtgacggtat taccacatca gcaaagggc aaaacggtgg tccttgactt    420
aggggccaac gtcgattgtg acagcacaat gctggtgcaa tttgccatta tgggctcagt    480
tctggctgaa gaggtggtgg aaattcccaa tcctcgcgtg gcgttgctca atattggtga    540
agaagaagta aagggtctcg acagtattcg ggatgcctca gcggtgctta aacaatccc    600 ttctatcaat tatatcggct atcttgaagc caatgagttg ttaactggca agacagatgt    660
gctggtttgt gacggcttta caggaaatgt cacattaaag acgatggaag tgttgtcag    720 gatgttcctt tctctgctga atctcagggg tgaagggaaa aaacggtcgt ggtggctact    780
gttattaaag cgttggctac aaaagagcct gacgaggcga ttcagtcacc tcaaccccga    840
ccagtataac ggcgcctgtc tgttaggatt gcgcggcacg gtgataaaaa gtcatggtgc    900
agccaatcag cgagcttttg cggtcgcgat tgaacaggca gtgcaggcgg tgcagcgaca    960
agttcctcag cgaattgccg ctcgcctgga atctgtatac cagctggtt tgagctgct    1020 ggacggtggc aaaagcggaa ctctgcggta gcaggacgct gccagcgaac tcgcagtttg    1080
caagtgacgg tatataaccg aaaagtgact gagcgcatat gtatacgaag actcgagtct    1140
ggtaaagaaa ccgctgctgc gaaatttgaa cgccagcaca tggactcgtc tactagcgca    1200
gcttaattaa cctaggctgc tgccaccgct gagcaataac tagcataacc ccttggggcc    1260
tctaaacggg tcttgagggg ttttttgctg aaacctcagg catttgagaa gcacacggtc    1320
acactgcttc cggtagtcaa taaaccgta aaccagcaat agcataagc ggctatttaa    1380 cgaccctgcc ctgaaccgac gacccgggtca tcgtggccgg atcttgcggc ccctcggctt    1440
gaacgaattg ttagacatta tttgccgact accttggtga tctcgccttt cacgtagtgg    1500
acaaattctt ccaactgatc tgcgcgcgag gccaagcgat cttcttcttg tccaagataa    1560
gcctgtctag cttcaagtat gacgggctga tactgggccg gcaggcgctc cattgcccag    1620
tcggcagcga catccttcgg cgcgattttg ccggttactg cgctgtacca aatgcgggac    1680
aacgtaagca ctacatttcg ctcatcgcca gcccagtcgg gcggcgagtt ccatagcgtt    1740
aaggtttcat ttagcgcctc aaatagatcc tgttcaggaa ccggatcaaa gagttcctcc    1800
gccgctggac ctaccaaggc aacgctatgt tctcttgctt ttgtcagcaa gatagccaga    1860
tcaatgtcga tcgtggctgg ctcgaagata cctgcaagaa tgtcattgcg ctgccattct    1920
```

```
ccaaattgca gttcgcgctt agctggataa cgccacggaa tgatgtcgtc gtgcacaaca    1980
atggtgactt ctacagcgcg gagaatctcg ctctctccag gggaagccga agtttccaaa    2040
aggtcgttga tcaaagctcg ccgcgttgtt tcatcaagcc ttacggtcac cgtaaccagc    2100
aaatcaatat cactgtgtgg cttcaggccg ccatccactg cggagccgta caaatgtacg    2160
gccagcaacg tcggttcgag atggcgctcg atgacgccaa ctacctctga tagttgagtc    2220
gatacttcgg cgatcaccgc ttccctcata ctcttccttt ttcaatatta ttgaagcatt    2280
tatcagggtt attgtctcat gagcggatac atatttgaat gtatttagaa aaataaacaa    2340
atagctagct cactcggtcg ctacgctccg ggcgtgagac tgcggcgggc gctgcggaca    2400
catacaaagt tacccacaga ttccgtggat aagcagggga ctaacatgtg aggcaaaaca    2460
gcagggccgc gccggtggcg ttttccata ggctccgccc tcctgccaga gttcacataa     2520
acagacgctt ttccggtgca tctgtgggag ccgtgaggct caaccatgaa tctgacagta    2580
cgggcgaaac ccgacaggac ttaaagatcc ccaccgtttc cggcgggtcg ctccctcttg    2640
cgctctcctg ttccgaccct gccgtttacc ggatacctgt tccgcctttc tcccttacgg    2700
gaagtgtggc gctttctcat agctcacaca ctggtatctc ggctcggtgt aggtcgttcg    2760
ctccaagctg ggctgtaagc aagaactccc cgttcagccc gactgctgcg ccttatccgg    2820
taactgttca cttgagtcca acccggaaaa gcacggtaaa acgccactgg cagcagccat    2880
tggtaactgg gagttcgcag aggatttgtt tagctaaaca cgcggttgct cttgaagtgt    2940
gcgccaaagt ccggctacac tggaaggaca gatttggttg ctgtgctctg cgaaagccag    3000
ttaccacggt taagcagttc cccaactgac ttaaccttcg atcaaaccac ctccccaggt    3060 ggtttttcg tttacagggc aaaagattac gcgcagaaaa aaggatctc aagaagatcc      3120 tttgatcttt tctactgaac cgctctagat ttcagtgcaa tttatctctt caaatgtagc    3180
acctgaagtc agccccatac gatataagtt gtaattctca tgttagtcat gccccgcgcc    3240
caccggaagg agctgactgg gttgaaggct ctcaagggca tcggtcgaga tcccggtgcc    3300
taatgagtga gctaacttac attaattgcg ttgcgctcac tgcccgcttt ccagtcggga    3360
aacctgtcgt gccagctgca ttaatgaatc ggccaacgcg cggggagagg cggtttgcgt    3420
attgggcgcc agggtggttt ttcttttcac cagtgagacg ggcaacagct gattgccctt    3480
caccgcctgg ccctgagaga gttgcagcaa gcggtccacg ctggtttgcc ccagcaggcg    3540
aaaatcctgt ttgatggtgg ttaacggcgg gatataacat gagctgtctt cggtatcgtc    3600
gtatcccact accgagatgt ccgcaccaac gcgcagcccg gactcggtaa tggcgcgcat    3660
tgcgcccagc gccatctgat cgttggcaac cagcatcgca gtgggaacga tgccctcatt    3720
cagcatttgc atggtttgtt gaaaaccgga catggcactc cagtcgcctt cccgttccgc    3780
tatcggctga atttgattgc gagtgagata tttatgccag ccagcagac gcagacgcgc     3840 cgagacagaa cttaatgggc ccgctaacag cgcgatttgc tggtgaccca atgcgaccag    3900
atgctccacg cccagtcgcg taccgtcttc atgggagaaa ataatactgt tgatgggtgt    3960
ctggtcgaga acatcaagaa ataacgccgg aacattagtg caggcagctt ccacagcaat    4020
ggcatcctgg tcatccagcg gatagttaat gatcagccca ctgacgcgtt gcgcgagaag    4080
attgtgcacc gccgctttac aggcttcgac gccgcttcgt tctaccatcg acaccaccac    4140
gctggcaccc agttgatcgg cgcgagattt aatcgccgcg acaatttgcg acggcgcgtg    4200
cagggccaga ctgaggtgg caacgccaat cagcaacgac tgtttgcccg ccagttgttg      4260
tgccacgcgg ttgggaatgt aattcagctc cgccatcgcc gcttccactt tttcccgcgt    4320
```

```
tttcgcagaa acgtggctgg cctggttcac cacgcgggaa acggtctgat aagagacacc    4380
ggcatactct gcgacatcgt ataacgttac tggtttcaca ttcaccaccc tgaattgact    4440
ctcttccggg cgctatcatg ccataccgcg aaaggttttg cgccattcga tggtgtccgg    4500
gatctcgacg ctctccctta tgcgactcct gcattaggaa attaatacga ctcactata     4559
```

<210> SEQ ID NO 74
<211> LENGTH: 5502
<212> TYPE: DNA
<213> ORGANISM: Artificial Sequence
<220> FEATURE:
<223> OTHER INFORMATION: Description of Artificial Sequence: Synthetic
      pDG6 plasmid polynucleotide

<400> SEQUENCE: 74

```
ggggaattgt gagcggataa caattcccct gtagaaataa ttttgtttaa ctttaataag      60
gagatatacc atggcgcaac tcactcttct tttagtcggc aattccgacg ccatcacgcc     120
attacttgct aaagctgact ttgaacaacg ttcgcgtctg cagattattc ctgcgcagtc     180
agttatcgcc agtgatgccc ggccttcgca agctatccgc gccagtcgtg ggagttcaat     240
gcgcgtggcc ctggagctgg tgaaagaagg tcgagcgcaa gcctgtgtca gtgccggtaa     300
taccggggcg ctgatggggc tggcaaaatt attactcaag cccctggagg ggattgagcg     360
tccggcgctg gtgacggtat taccacatca gcaaagggc aaaacggtgg tccttgactt     420
aggggccaac gtcgattgtg acagcacaat gctggtgcaa tttgccatta tgggctcagt     480
tctggctgaa gaggtggtgg aaattcccaa tcctcgcgtg gcgttgctca atattggtga     540
agaagaagta aagggtctcg acagtattcg ggatgcctca gcggtgctta aacaatccc     600 ttctatcaat tatatcggct atcttgaagc caatgagttg ttaactggca agacagatgt     660
gctggtttgt gacggcttta caggaaatgt cacattaaag acgatggaag tgttgtcag     720 gatgttcctt tctctgctga aatctcaggg tgaagggaaa aaacggtcgt ggtggctact     780
gttattaaag cgttggctac aaaagagcct gacgaggcga ttcagtcacc tcaaccccga     840
ccagtataac ggcgcctgtc tgttaggatt gcgcggcacg tgataaaaa gtcatggtgc     900 agccaatcag cgagcttttg cggtcgcgat tgaacaggca gtgcaggcgg tgcagcgaca     960
agttcctcag cgaattgccg ctcgcctgga atctgtatac ccagctggtt ttgagctgct    1020
ggacggtggc aaaagcggaa ctctgcggta gcaggacgct gccagcgaac tcgcagtttg    1080
caagtgacgg tatataaccg aaaagtgact gagcgcatat gaaagctggc attcttggtg    1140
ttggacgtta cattcctgag aaggttttaa caaatcatga tcttgaaaaa atggttgaaa    1200
cttctgacga gtggattcgt acaagaacag gaatagaaga aagaagaatc gcagcagatg    1260
atgtgttttc atcacacatg gctgttgcag cagcgaaaaa tgcgctggaa caagctgaag    1320
tggctgctga ggatctggat atgatctcgg ttgcaactgt tacacctgat cagtcattcc    1380
ctacggtgtc ttgtatgatt caagaacaac tcggcgcgaa gaaagcgtgt gctatggata    1440
tcagcgcggc ttgtgcgggc ttcatgtacg gggttgtaac cggtaaacaa tttattgaat    1500
ccggaaccta caagcatgtt ctagttgttg gtgtagagaa gctctcaagc attaccgact    1560
gggaagaccg caatacagcc gttctgtttg gagacggagc aggcgctgcg gtagtcgggc    1620
cagtcagtga tgacagagga atcctttcat ttgaactagg agccgacggc acaggcggtc    1680
agcacttgta tctgaatgaa aaacgacata caatcatgaa tggacgagaa gttttcaaat    1740
ttgcagtccg ccaaatggga gaatcatgcg taaatgtcat tgaaaaagcc ggactttcaa    1800
```

```
aagaggatgt ggacttttg attccgcatc aggcgaacat ccgtatcatg gaagctgctc    1860
gcgagcgttt agagcttcct gtcgaaaaga tgtctaaaac tgttcataaa tatggaaata    1920
cttctgccgc atccattccg atctctcttg tagaagaatt ggaagccggt aaaatcaaag    1980
acggcgatgt ggtcgttatg gtagggttcg gcggaggact aacatggggc gccattgcaa    2040
tccgctgggg ccgataaaaa aaaggtgagg tgcactcgag tctggtaaag aaaccgctgc    2100
tgcgaaattt gaacgccagc acatggactc gtctactagc gcagcttaat taacctaggc    2160
tgctgccacc gctgagcaat aactagcata ccccttggg gcctctaaac gggtcttgag    2220
gggttttttg ctgaaacctc aggcatttga aagcacacg gtcacactgc ttccggtagt    2280
caataaaccg gtaaaccagc aatagacata agcggctatt taacgaccct gccctgaacc    2340
gacgaccggg tcatcgtggc cggatcttgc ggcccctcgg cttgaacgaa ttgttagaca    2400
ttatttgccg actaccttgg tgatctcgcc tttcacgtag tggacaaatt cttccaactg    2460
atctgcgcgc gaggccaagc gatcttcttc ttgtccaaga taagcctgtc tagcttcaag    2520
tatgacgggc tgatactggg ccggcaggcg ctccattgcc cagtcggcag cgacatcctt    2580
cggcgcgatt ttgccggtta ctgcgctgta ccaaatgcgg gacaacgtaa gcactacatt    2640
tcgctcatcg ccagcccagt cgggcggcga gttccatagc gttaaggttt catttagcgc    2700
ctcaaataga tcctgttcag gaaccggatc aaagagttcc tccgccgctg gacctaccaa    2760
ggcaacgcta tgttctcttg cttttgtcag caagatagcc agatcaatgt cgatcgtggc    2820
tggctcgaag atacctgcaa gaatgtcatt gcgctgccat tctccaaatt gcagttcgcg    2880
cttagctgga taacgccacg gaatgatgtc gtcgtgcaca acaatggtga cttctacagc    2940
gcggagaatc tcgctctctc caggggaagc cgaagtttcc aaaaggtcgt tgatcaaagc    3000
tcgccgcgtt gtttcatcaa gccttacggt caccgtaacc agcaaatcaa tatcactgtg    3060
tggcttcagg ccgccatcca ctgcggagcc gtacaaatgt acggccagca acgtcggttc    3120
gagatggcgc tcgatgacgc caactacctc tgatagttga gtcgatactt cggcgatcac    3180
cgcttccctc atactcttcc tttttcaata ttattgaagc atttatcagg gttattgtct    3240
catgagcgga tacatatttg aatgtattta gaaaaataaa caaatagcta gctcactcgg    3300
tcgctacgct ccgggcgtga gactgcggcg ggcgctgcgg acacatacaa agttacccac    3360
agattccgtg gataagcagg ggactaacat gtgaggcaaa acagcagggc cgcgccggtg    3420 gcgttttcc ataggctccg ccctcctgcc agagttcaca taaacagacg cttttccggt    3480
gcatctgtgg gagccgtgag gctcaaccat gaatctgaca gtacgggcga acccgacag    3540 gacttaaaga tccccaccgt ttccggcggg tcgctccctc ttgcgctctc ctgttccgac    3600
cctgccgttt accggatacc tgttccgcct ttctccctta cgggaagtgt ggcgctttct    3660
catagctcac acactggtat ctcggctcgg tgtaggtcgt tcgctccaag ctgggctgta    3720
agcaagaact ccccgttcag cccgactgct gcgccttatc cggtaactgt tcacttgagt    3780
ccaacccgga aaagcacggt aaaacgccac tggcagcagc cattggtaac tgggagttcg    3840
cagaggattt gtttagctaa acacgcgtt gctcttgaag tgtgcgccaa agtccggcta    3900
cactggaagg acagatttgg ttgctgtgct ctgcgaaagc cagttaccac ggttaagcag    3960
ttccccaact gacttaacct tcgatcaaac cacctcccca ggtggttttt tcgtttacag    4020
ggcaaaagat tacgcgcaga aaaaaaggat ctcaagaaga tccttttgatc ttttctactg    4080 aaccgctcta gatttcagtg caatttatct cttcaaatgt agcacctgaa gtcagcccca    4140
tacgatataa gttgtaattc tcatgttagt catgccccgc gcccaccgga aggagctgac    4200
```

-continued

```
tgggttgaag gctctcaagg gcatcggtcg agatcccggt gcctaatgag tgagctaact    4260
tacattaatt gcgttgcgct cactgcccgc tttccagtcg ggaaacctgt cgtgccagct    4320
gcattaatga atcggccaac gcgcgggag aggcggtttg cgtattgggc gccagggtgg     4380
ttttttcttt caccagtgag acgggcaaca gctgattgcc cttcaccgcc tggccctgag    4440
agagttgcag caagcggtcc acgctggttt gccccagcag gcgaaaatcc tgtttgatgg    4500
tggttaacgg cgggatataa catgagctgt cttcggtatc gtcgtatccc actaccgaga    4560
tgtccgcacc aacgcgcagc ccggactcgg taatggcgcg cattgcgccc agcgccatct    4620
gatcgttggc aaccagcatc gcagtgggaa cgatgccctc attcagcatt tgcatggttt    4680
gttgaaaacc ggacatggca ctccagtcgc cttcccgttc cgctatcggc tgaatttgat    4740
tgcgagtgag atatttatgc cagccagcca gacgcagacg cgccgagaca gaacttaatg    4800
ggcccgctaa cagcgcgatt tgctggtgac ccaatgcgac cagatgctcc acgcccagtc    4860
gcgtaccgtc ttcatgggag aaaataatac tgttgatggg tgtctggtca gagacatcaa    4920
gaaataacgc cggaacatta gtgcaggcag cttccacagc aatggcatcc tggtcatcca    4980
gcggatagtt aatgatcagc ccactgacgc gttgcgcgag aagattgtgc accgccgctt    5040
tacaggcttc gacgccgctt cgttctacca tcgacaccac cacgctggca cccagttgat    5100
cggcgcgaga tttaatcgcc gcgacaattt gcgacgcgc gtgcagggcc agactggagg     5160
tggcaacgcc aatcagcaac gactgtttgc ccgccagttg ttgtgccacg cggttgggaa    5220
tgtaattcag ctccgccatc gccgcttcca ctttttcccg cgttttcgca gaaacgtggc    5280
tggcctggtt caccacgcgg gaaacggtct gataagagac accggcatac tctgcgacat    5340
cgtataacgt tactggtttc acattcacca ccctgaattg actctcttcc gggcgctatc    5400
atgccatacc gcgaaaggtt ttgcgccatt cgatggtgtc cgggatctcg acgctctccc    5460
ttatgcgact cctgcattag gaaattaata cgactcacta ta                       5502
```

<210> SEQ ID NO 75
<211> LENGTH: 5733
<212> TYPE: DNA
<213> ORGANISM: Artificial Sequence
<220> FEATURE:
<223> OTHER INFORMATION: Description of Artificial Sequence: Synthetic pACYC-PTrc vector polynucleotide

<400> SEQUENCE: 75

```
actcaccagt cacagaaaag catcttacgg atggcatgac agtaagagaa ttatgcagtg      60
ctgccataac catgagtgat aacactgcgg ccaacttact tctgacaacg atcggaggac     120
cgaaggagct aaccgctttt ttgcacaaca tgggggatca tgtaactcgc cttgatcgtt     180
gggaaccgga gctgaatgaa gccataccaa acgacgagcg tgacaccacg atgcctgcag    240
caatggcaac aacgttgcgc aaactattaa ctggcgaact acttactcta gcttcccggc    300
aacaattaat agactggatg gaggcggata agttgcagg accacttctg cgctcggccc      360
ttccggctgg ctggtttatt gctgataaat ctggagccgg tgagcgtggg tctcgcggta    420
tcattgcagc actggggcca gatggtaagc cctcccgtat cgtagttatc tacacgacgg    480
ggagtcaggc aactatggat gaacgaaata gacagatcgc tgagataggt gcctcactga    540
ttaagcattg gtaactgtca gaccaagttt actcatatat actttagatt gatttaaaac    600
ttcatttta atttaaaagg atctaggtga agatccttt tgataatctc atgaccaaaa       660
tcccttaacg tgagttttcg ttccactgag cgtcagaccc cttaataaga tgatcttctt    720
gagatcgttt ggtctgcgc gtaatctctt gctctgaaaa cgaaaaaacc gccttgcagg     780
```

```
gcggttttc  gaaggttctc  tgagctacca  actctttgaa  ccgaggtaac  tggcttggag     840
gagcgcagtc  accaaaactt  gtcctttcag  tttagcctta  accggcgcat  gacttcaaga    900
ctaactcctc  taaatcaatt  accagtggct  gctgccagtg  gtgcttttgc  atgtctttcc    960
gggttggact  caagacgata  gttaccggat  aaggcgcagc  ggtcggactg  aacgggggt    1020
tcgtgcatac  agtccagctt  ggagcgaact  gcctacccgg  aactgagtgt  caggcgtgga   1080
atgagacaaa  cgcggccata  acagcggaat  gacaccggta  aaccgaaagg  caggaacagg   1140
agagcgcacg  agggagccgc  cagggggaaa  cgcctggtat  ctttatagtc  ctgtcgggtt   1200
tcgccaccac  tgatttgagc  gtcagatttc  gtgatgcttg  tcaggggggc  ggagcctatg   1260
gaaaaacggc  tttgccgcgg  ccctctcact  tccctgttaa  gtatcttcct  ggcatcttcc   1320
aggaaatctc  cgcccgttc   gtaagccatt  tccgctcgcc  gcagtcgaac  gaccgagcgt   1380
agcgagtcag  tgagcgagga  agcgaatat   atcctgtatc  acatattctg  ctgacgcacc   1440
ggtgcagcct  ttttctcct   gccacatgaa  gcacttcact  gacaccctca  tcagtgccaa   1500
catagtaagc  cagtatacac  tccgctagcg  ctgaggtctg  cctcgtgaag  aaggtgttgc   1560
tgactcatac  caggcctgaa  tcgccccatc  atccagccag  aaagtgaggg  agccacggtt   1620
gatgagagct  tgttgtagg   tggaccagtt  ggtgattttg  aacttttgct  ttgccacgga   1680
acggtctgcg  ttgtcgggaa  gatgcgtgat  ctgatccttc  aactcagcaa  aagttcgatt   1740
tattcaacaa  agccacgttg  tgtctcaaaa  tctctgatgt  acattgcac   aagataaaaa   1800
tatatcatca  tgaacaataa  aactgtctgc  ttacataaac  agtaatacaa  ggggtgttat   1860
gagccatatt  caacgggaaa  cgtcttgctc  gaggccgcga  ttaaattcca  acatggatgc   1920
tgatttatat  gggtataaat  gggctcgcga  taatgtcggg  caatcaggtg  cgacaatcta   1980
tcgattgtat  gggaagcccg  atgcgccaga  gttgtttctg  aaacatggca  aaggtagcgt   2040
tgccaatgat  gttacagatg  agatggtcag  actaaactgg  ctgacggaat  ttatgcctct   2100
tccgaccatc  aagcatttta  tccgtactcc  tgatgatgca  tggttactca  ccactgcgat   2160
ccccgggaaa  acagcattcc  aggtattaga  agaatatcct  gattcaggtg  aaaatattgt   2220
tgatgcgctg  gcagtgttcc  tgcgccggtt  gcattcgatt  cctgtttgta  attgtccttt   2280
taacagcgat  cgcgtatttc  gtctcgctca  ggcgcaatca  cgaatgaata  acggtttggt   2340
tgatgcgagt  gattttgatg  acgagcgtaa  tggctggcct  gttgaacaag  tctggaaaga   2400
aatgcataag  cttttgccat  tctcaccgga  ttcagtcgtc  actcatggtg  atttctcact   2460
tgataaccttt  atttttgacg  aggggaaatt  aataggttgt  attgatgttg  gacgagtcgg   2520
aatcgcagac  cgataccagg  atcttgccat  cctatggaac  tgcctcggtg  agttttctcc   2580
ttcattacag  aaacggcttt  ttcaaaaata  tggtattgat  aatcctgata  tgaataaatt   2640
gcagtttcat  ttgatgctcg  atgagttttt  ctaatcagaa  ttggttaatt  ggttgtaaca   2700
ctggcagagc  attacgctga  cttgacggga  cggcggcttt  gttgaataaa  tcgaactttt   2760
gctgagttga  aggatcagat  cacgcatctt  cccgacaacg  cagaccgttc  cgtggcaaag   2820
caaaagttca  aaatcaccaa  ctggtccacc  tacaacaaag  ctctcatcaa  ccgtggctcc   2880
ctcactttct  ggctggatga  tggggcgatt  caggcctggt  atgagtcagc  aacaccttct   2940
tcacgaggca  gacctcagcg  ctcaaagatg  caggggtaaa  agctaaccgc  atctttaccg   3000
acaaggcatc  cggcagttca  acagatcggg  aagggctgga  tttgctgagg  atgaaggtgg   3060
aggaaggtga  tgtcattctg  gtgaagaagc  tcgaccgtct  tggccgcgac  accgccgaca   3120
tgatccaact  gataaaagag  tttgatgctc  agggtgtagc  ggttcggttt  attgacgacg   3180
```

```
ggatcagtac cgacggtgat atggggcaaa tggtggtcac catcctgtcg gctgtggcac    3240
aggctgaacg ccggaggatc ctagagcgca cgaatgaggg ccgacaggaa gcaaagctga    3300
aaggaatcaa atttggccgc aggcgtaccg tggacaggaa cgtcgtgctg acgcttcatc    3360
agaagggcac tggtgcaacg gaaattgctc atcagctcag tattgcccgc tccacggttt    3420
ataaaattct tgaagacgaa agggcctcgt gatacgccta tttttatagg ttaatgtcat    3480
gataataatg gtttcttaga cgtcttaatt aatcaggaga gcgttcaccg acaaacaaca    3540
gataaaacga aaggcccagt ctttcgactg agcctttcgt tttatttgat gcctggcagt    3600
tccctactct cgcatgggga dacccacac taccatcggc gctacggcgt ttcacttctg    3660
agttcggcat ggggtcaggt gggaccaccg cgctactgcc gccaggcaaa ttctgtttta    3720
tcagaccgct tctgcgttct gatttaatct gtatcaggct gaaaatcttc tctcatccgc    3780
caaaacagcc aagctggaga ccgtttaaac tcaatgatga tgatgatgat ggtcgacggc    3840
gctattcaga tcctcttctg agatgagttt ttgttcgggc ccaagcttcg aattcccata    3900
tggtaccagc tgcagatctc gagctcggat ccatggttta ttcctcctta tttaatcgat    3960
acattaatat atacctcttt aatttttaat aataaagtta atcgataatt ccggtcgagt    4020
gcccacacag attgtctgat aaattgttaa agagcagtgc cgcttcgctt tttctcagcg    4080
gcgctgtttc ctgtgtgaaa ttgttatccg ctcacaattc cacacattat acgagccgga    4140
tgattaattg tcaacagctc atttcagaat atttgccaga accgttatga tgtcggcgca    4200
aaaaacatta tccagaacgg gagtgcgcct tgagcgacac gaattatgca gtgatttacg    4260
acctgcacag ccataccaca gcttccgatg gctgcctgac gccagaagca ttggtgcacc    4320
gtgcagtcga tgataagctg tcaaaccaga tcaattcgcg ctaactcaca ttaattgcgt    4380
tgcgctcact gcccgctttc cagtcgggaa acctgtcgtg ccagctgcat taatgaatcg    4440
gccaacgcgc ggggagaggc ggtttgcgta ttgggcgcca gggtggtttt tcttttcacc    4500
agtgagacgg gcaacagctg attgcccttc accgcctggc cctgagagag ttgcagcaag    4560
cggtccacgc tggtttgccc cagcaggcga aaatcctgtt tgatggtggt tgacggcggg    4620
atataacatg agctgtcttc ggtatcgtcg tatcccacta ccgagatatc cgcaccaacg    4680
cgcagcccgg actcggtaat ggcgcgcatt gcgcccagcg ccatctgatc gttggcaacc    4740
agcatcgcag tgggaacgat gccctcattc agcatttgca tggtttgttg aaaaccggac    4800
atggcactcc agtcgccttc ccgttccgct atcggctgaa tttgattgcg agtgagatat    4860
ttatgccagc cagccagacg cagacgcgcc gagacagaac ttaatgggcc cgctaacagc    4920
gcgatttgct ggtgacccaa tgcgaccaga tgctccacgc ccagtcgcgt accgtcttca    4980
tgggagaaaa taatactgtt gatgggtgtc tggtcagaga catcaagaaa taacgccgga    5040
acattagtgc aggcagcttc cacagcaatg gcatcctggt catccagcgg atagttaatg    5100
atcagcccac tgacgcgttg cgcgagaaga ttgtgcaccg ccgctttaca ggcttcgacg    5160
ccgcttcgtt ctaccatcga caccaccacg ctggcaccca gttgatcggc gcgagattta    5220
atcgccgcga caatttgcga cggcgcgtgc agggccagac tggaggtggc aacgccaatc    5280
agcaacgact gtttgcccgc cagttgttgt gccacgcggt tgggaatgta attcagctcc    5340
gccatcgccg cttccacttt ttcccgcgtt ttcgcagaaa cgtggctggc ctggttcacc    5400
acgcgggaaa cggtctgata agagacaccg gcatactctg cgacatcgta acgttact     5460 ggtttcacat tcaccaccct gaattgactc tcttccgggc gctatcatgc cataccgcga    5520
aaggttttgc accattcgat ggtgtcaacg taaatgcatg ccgcttcgcc ttcgcgcgcg    5580
```

```
aattgatctg ctgcctcgcg cgtttcggtg atgacggtga aaacctctga cacatgcagc    5640
tcccggagac ggtcacagct tgtctgtaag cggatgccgg gagcagacaa gcccgtcagg    5700
gcgcgtcagc gggtgttggc ggggccggcc tcg                                 5733

<210> SEQ ID NO 76
<211> LENGTH: 193
<212> TYPE: DNA
<213> ORGANISM: Artificial Sequence
<220> FEATURE:
<223> OTHER INFORMATION: Description of Artificial Sequence: Synthetic
      PTrc promoter polynucleotide

<400> SEQUENCE: 76
ctgttgacaa ttaatcatcc ggctcgtata atgtgtggaa ttgtgagcgg ataacaattt     60
cacacaggaa acagcgccgc tgagaaaaag cgaagcggca ctgctcttta acaatttatc    120
agacaatctg tgtgggcact cgaccggaat tatcgattaa ctttattatt aaaaattaaa    180
gaggtatata tta                                                       193

<210> SEQ ID NO 77
<211> LENGTH: 193
<212> TYPE: DNA
<213> ORGANISM: Artificial Sequence
<220> FEATURE:
<223> OTHER INFORMATION: Description of Artificial Sequence: Synthetic
      PTrc2 promoter polynucleotide

<400> SEQUENCE: 77
ctgttgacaa ttaatcatcc ggctcgtgta atgtgtggaa ttgtgagcgg ataacaattt     60
cacacaggaa acagcgccgc tgagaaaaag cgaagcggca ctgctcttta acaatttatc    120
agacaatctg tgtgggcact cgaccggaat tatcgattaa ctttattatt aaaaattaaa    180
gaggtatata tta                                                       193

<210> SEQ ID NO 78
<211> LENGTH: 5978
<212> TYPE: DNA
<213> ORGANISM: Artificial Sequence
<220> FEATURE:
<223> OTHER INFORMATION: Description of Artificial Sequence: Synthetic
      pDS80 plasmid polynucleotide

<400> SEQUENCE: 78
cactatacca attgagatgg gctagtcaat gataattact agtccttttc ctttgagttg     60
tgggtatctg taaattctgc tagaccttg ctggaaaact tgtaaattct gctagaccct    120
ctgtaaattc cgctagacct ttgtgtgttt ttttgttta tattcaagtg gttataattt    180
atagaataaa gaaagaataa aaaagataaa aagaataga tcccagccct gtgtataact    240
cactacttta gtcagttccg cagtattaca aaaggatgtc gcaaacgctg tttgctcctc    300
tacaaaacag accttaaaac cctaaaggcg tcggcatccg cttacagaca agctgtgacc    360
gtctccggga gctgcatgtg tcagaggttt tcaccgtcat caccgaaacg cgcgaggcag    420
cagatcaatt cgcgcgcgaa ggcgaagcgg catgcattta cgttgacacc atcgaatggt    480
gcaaaacctt tcgcggtatg gcatgatagc gcccggaaga gagtcaattc agggtggtga    540
atgtgaaacc agtaacgtta tacgatgtcg cagagtatgc cggtgtctct tatcagaccg    600
tttcccgcgt ggtgaaccag gccagccacg tttctgcgaa aacgcgggaa aaagtggaag    660
cggcgatggc ggagctgaat tacattccca accgcgtggc acaacaactg gcgggcaaac    720
```

```
agtcgttgct gattggcgtt gccacctcca gtctggccct gcacgcgccg tcgcaaattg    780
tcgcggcgat taaatctcgc gccgatcaac tgggtgccag cgtggtggtg tcgatggtag    840
aacgaagcgg cgtcgaagcc tgtaaagcgg cggtgcacaa tcttctcgcg caacgcgtca    900
gtgggctgat cattaactat ccgctggatg accaggatgc cattgctgtg gaagctgcct    960
gcactaatgt tccggcgtta tttcttgatg tctctgacca dacacccatc aacagtatta   1020
ttttctccca tgaagacggt acgcgactgg gcgtggagca tctggtcgca ttgggtcacc   1080
agcaaatcgc gctgttagcg ggcccattaa gttctgtctc ggcgcgtctg cgtctggctg   1140
gctggcataa atatctcact cgcaatcaaa ttcagccgat agcggaacgg gaaggcgact   1200
ggagtgccat gtccggtttt caacaaacca tgcaaatgct gaatgagggc atcgttccca   1260
ctgcgatgct ggttgccaac gatcagatgg cgctgggcgc aatgcgcgcc attaccgagt   1320
ccgggctgcg cgttggtgcg gatatctcgg tagtgggata cgacgatacc gaagacagct   1380
catgttatat cccgccgtta accaccatca aacaggattt tcgcctgctg ggcaaaacca   1440
gcgtggaccg cttgctgcaa ctctctcagg gccaggcggt gaagggcaat cagctgttgc   1500
ccgtctcact ggtgaaaaga aaaccaccc tggcgcccaa tacgcaaacc gcctctcccc    1560
gcgcgttggc cgattcatta atgcagctgg cacgacaggt ttcccgactg gaaagcgggc   1620
agtgagcgca acgcaattaa tgtaagttag cgcgaattga tctggtttga cagcttatca   1680
tcgactgcac ggtgcaccaa tgcttctggc gtcaggcagc catcggaagc tgtggtatgg   1740
ctgtgcaggt cgtaaatcac tgcataattc gtgtcgctca aggcgcactc ccgttctgga   1800
taatgttttt tgcgccgaca tcataacggt tctggcaaat attttcagat ctctcaccta   1860
ccaaacaatg cccccctgca aaaataaat tcatataaaa aacatacaga taaccatctg    1920
cggtgataaa ttatctctgg cggtgttgac ataaatacca ctggcggtga tactgagcac   1980
agaatattca cacaggaaac agcgccgctg agaaaaagcg aagcggcact gctctttaac   2040
aatttatcag acaatctgtg tgggcactcg accggaatta tcgattaact ttattattaa   2100
aaattaaaga ggtatatatt aatgtatcga ttaaataagg aggaataaac catggatccg   2160
agctcgagat ctgcagctgg taccatatgg gaattcgaag cttgggcccg aacaaaaact   2220
catctcagaa gaggatctga atagcgccgt cgaccatcat catcatcatc attgagttta   2280
aacggtctcc agcttggctg ttttggcgga tgagagaaga ttttcagcct gatacagatt   2340
aaatcagaac gcagaagcgg tctgataaaa cagaatttgc ctggcggcag tagcgcggtg   2400
gtcccacctg accccatgcc gaactcagaa gtgaaacgcc gtagcgccga tggtagtgtg   2460
gggtctcccc atgcgagagt agggaactgc caggcatcaa ataaaacgaa aggctcagtc   2520
gaaagactgg gcctttcgtt ttatctgttg tttgtcggtg aacgctctcc tgacgcctga   2580
tgcggtattt tctccttacg catctgtgcg gtatttcaca ccgcatatgg tgcactctca   2640
gtacaatctg ctctgatgcc gcatagttaa gccagcccg acacccgcca cacccgctg    2700
acgagcttag taaagccctc gctagatttt aatgcggatg ttgcgattac ttcgccaact   2760
attgcgataa caagaaaaag ccagcctttc atgatatatc tcccaatttg tgtagggctt   2820
attatgcacg cttaaaaata taaaaagcag acttgacctg atagtttggc tgtgagcaat   2880
tatgtgctta gtgcatctaa cgcttgagtt aagccgcgcc gcgaagcggc gtcggcttga   2940
acgaattgtt agacattatt tgccgactac cttggtgatc tcgcctttca cgtagtggac   3000
aaattcttcc aactgatctg cgcgcgaggc caagcgatct tcttcttgtc caagataagc   3060
ctgtctagct tcaagtatga cgggctgata ctgggccggc aggcgctcca ttgcccagtc   3120
```

```
ggcagcgaca tccttcggcg cgattttgcc ggttactgcg ctgtaccaaa tgcgggacaa    3180
cgtaagcact acatttcgct catcgccagc ccagtcgggc ggcgagttcc atagcgttaa    3240
ggtttcattt agcgcctcaa atagatcctg ttcaggaacc ggatcaaaga gttcctccgc    3300
cgctggacct accaaggcaa cgctatgttc tcttgctttt gtcagcaaga tagccagatc    3360
aatgtcgatc gtggctggct cgaagatacc tgcaagaatg tcattgcgct gccattctcc    3420
aaattgcagt tcgcgcttag ctggataacg ccacggaatg atgtcgtcgt gcacaacaat    3480
ggtgacttct acagcgcgga gaatctcgct ctctccaggg gaagccgaag tttccaaaag    3540
gtcgttgatc aaagctcgcc gcgttgtttc atcaagcctt acggtcaccg taaccagcaa    3600
atcaatatca ctgtgtggct tcaggccgcc atccactgcg gagccgtaca aatgtacggc    3660
cagcaacgtc ggttcgagat ggcgctcgat gacgccaact acctctgata gttgagtcga    3720
tacttcggcg atcaccgctt ccctcatgat gtttaacttt gttttagggc gactgccctg    3780
ctgcgtaaca tcgttgctgc tccataacat caaacatcga cccacggcgt aacgcgcttg    3840
ctgcttggat gcccgaggca tagactgtac cccaaaaaaa cagtcataac aagccatgaa    3900
aaccgccact cgcgccgttac caccgctgcg ttcggtcaag gttctggacc agttgcgtga    3960
gcgcatacgc tacttgcatt acagcttacg aaccgaacag gcttatgtcc actgggttcg    4020
tgccttcatc cgtttccacg gtgtgcgtca cccggcaacc ttgggcagca gcgaagtcga    4080
ggcatttctg tcctggctgg cgaacgagcg caaggtttcg gtctccacgc atcgtcaggc    4140
attggcggcc ttgctgttct tctacggcaa ggtgctgtgc acggatctgc cctggcttca    4200
ggagatcgga agacctcggc cgtcgcggcg cttgccggtg gtgctgaccc cggatgaagt    4260
ggttcgcatc ctcggttttc tggaaggcga gcatcgtttg ttcgcccagc ttctgtatgg    4320
aacgggcatg cggatcagtg agggtttgca actgcgggtc aaggatctgg atttcgatca    4380
cggcacgatc atcgtgcggg agggcaaggg ctccaaggat cgggccttga tgttacccga    4440
gagcttggca cccagcctgc gcgagcaggg gaattaattc ccacgggttt tgctgcccgc    4500
aaacgggctg ttctggtgtt gctagtttgt tatcagaatc gcagatccgg cttcagccgg    4560
tttgccggct gaaagcgcta tttcttccag aattgccatg atttttttcc cacgggaggc    4620
gtcactggct cccgtgttgt cggcagcttt gattcgataa gcagcatcgc ctgtttcagg    4680
ctgtctatgt gtgactgttg agctgtaaca agttgtctca ggtgttcaat tcatgttct    4740 agttgctttg ttttactggt ttcacctgtt ctattaggtg ttacatgctg ttcatctgtt    4800
acattgtcga tctgttcatg gtgaacagct ttgaatgcac caaaaactcg taaaagctct    4860
gatgtatcta tctttttttac accgttttca tctgtgcata tggacagttt tcccttttgat  4920 atgtaacggt gaacagttgt tctacttttg tttgttagtc ttgatgcttc actgatagat    4980
acaagagcca taagaacctc agatccttcc gtatttagcc agtatgttct ctagtgtggt    5040
tcgttgtttt tgcgtgagcc atgagaacga accattgaga tcatacttac tttgcatgtc    5100
actcaaaaat tttgcctcaa aactggtgag ctgaatttt gcagttaaag catcgtgtag     5160
tgtttttctt agtccgttat gtaggtagga atctgatgta atggttgttg gtattttgtc    5220
accattcatt tttatctggt tgttctcaag ttcggttacg agatccattt gtctatctag    5280
ttcaacttgg aaaatcaacg tatcagtcgg gcggcctcgc ttatcaacca ccaatttcat    5340
attgctgtaa gtgtttaaat ctttacttat tggtttcaaa acccattggt taagccttt    5400 aaactcatgg tagttatttt caagcattaa catgaactta aattcatcaa ggctaatctc    5460
tatatttgcc ttgtgagttt tcttttgtgt tagttctttt aataaccact cataaatcct    5520
```

-continued

| | |
|---|---|
| catagagtat ttgttttcaa aagacttaac atgttccaga ttatatttta tgaattttt | 5580 |
| taactgaaa agataaggca atatctcttc actaaaaact aattctaatt tttcgcttga | 5640 |
| gaacttggca tagtttgtcc actggaaaat ctcaaagcct ttaaccaaag gattcctgat | 5700 |
| ttccacagtt ctcgtcatca gctctctggt tgctttagct aatacaccat aagcattttc | 5760 |
| cctactgatg ttcatcatct gagcgtattg gttataagtg aacgataccg tccgttcttt | 5820 |
| ccttgtaggg ttttcaatcg tggggttgag tagtgccaca cagcataaaa ttagcttggt | 5880 |
| ttcatgctcc gttaagtcat agcgactaat cgctagttca tttgctttga aaacaactaa | 5940 |
| ttcagacata catctcaatt ggtctaggtg atttaat | 5978 |

<210> SEQ ID NO 79
<211> LENGTH: 3227
<212> TYPE: DNA
<213> ORGANISM: Artificial Sequence
<220> FEATURE:
<223> OTHER INFORMATION: Description of Artificial Sequence: Synthetic p100.38 plasmid polynucleotide

<400> SEQUENCE: 79

| | |
|---|---|
| gacgaaaggg cctcgtgata cgcctatttt tataggttaa tgtcatgata ataatggttt | 60 |
| cttagacgtc aggtggcact tttcggggaa atgtgcgcgg aaccccctatt tgtttatttt | 120 |
| tctaaataca ttcaaatatg tatccgctca tgagacaata accctgataa atgcttcaat | 180 |
| aatattgaaa aaggaagagt atgagtattc aacatttccg tgtcgccctt attccctttt | 240 |
| ttgcggcatt ttgccttcct gttttttgctc acccagaaac gctggtgaaa gtaaaagatg | 300 |
| ctgaagatca gttgggtgca cgagtgggtt acatcgaact ggatctcaac agcggtaaga | 360 |
| tccttgagag ttttcgcccc gaagaacgtt ttccaatgat gagcactttt aaagttctgc | 420 |
| tatgtggcgc ggtattatcc cgtattgacg ccgggcaaga gcaactcggt cgccgcatac | 480 |
| actattctca gaatgacttg gttgagtact caccagtcac agaaaagcat cttacggatg | 540 |
| gcatgacagt aagagaatta tgcagtgctg ccataaccat gagtgataac actgcggcca | 600 |
| acttacttct gacaacgatc ggaggaccga aggagctaac cgcttttttg cacaacatgg | 660 |
| gggatcatgt aactcgcctt gatcgttggg aaccggagct gaatgaagcc ataccaaacg | 720 |
| acgagcgtga caccacgatg cctgtagcaa tggcaacaac gttgcgcaaa ctattaactg | 780 |
| gcgaactact tactctagct tcccggcaac aattaataga ctggatggag gcggataaag | 840 |
| ttgcaggacc acttctgcgc tcggcccttc cggctggctg gtttattgct gataaatctg | 900 |
| gagccggtga gcgtgggtct cgcggtatca ttgcagcact ggggccagat ggtaagccct | 960 |
| cccgtatcgt agttatctac acgacgggga gtcaggcaac tatggatgaa cgaaatagac | 1020 |
| agatcgctga gataggtgcc tcactgatta agcattggta actgtcagac caagtttact | 1080 |
| catatatact ttagattgat ttaaaacttc atttttaatt tgtgcatccg aagatcagca | 1140 |
| gttcaacctg ttgatagtac gtactaagct ctcatgtttc acgtactaag ctctcatgtt | 1200 |
| taacgtacta agctctcatg tttaacgaac taaaccctca tggctaacgt actaagctct | 1260 |
| catggctaac gtactaagct ctcatgtttg aacaataaaa ttaatataaa tcagcaactt | 1320 |
| aaatagcctc taaggtttta agttttataa gaaaaaaaag aatatataag gcttttaaag | 1380 |
| ctagctttta aggtttcacc atgttctttc ctgcgttatc ccctgattct gtggataacc | 1440 |
| gtattaccgc ctttgagtga gctgataccg ctcgccgcag ccgaacgacc gagcgcagcg | 1500 |
| agtcagtgag cgaggaagcg gaagagcgcc caatacgcaa accgcctctc cccgcgcgtt | 1560 |
| ggccgattca ttaagacagc tgtctcttat acacatctca accctgaagc tcttgttggc | 1620 |

```
tagtgcgtag tcgttggcaa gctttccgct gtttctgcat tcttacgttt taggatgcat      1680
atggcggccg cataacttcg tatagcatac attatacgaa gttatctaga gttgcatgcc      1740
tgcaggtccg cttattatca cttattcagg cgtagcaacc aggcgtttaa gggcaccaat      1800
aactgcctta aaaaaattac gccccgccct gccactcatc gcagtactgt tgtaattcat      1860
taagcattct gccgacatgg aagccatcac aaacggcatg atgaacctga atcgccagcg      1920
gcatcagcac cttgtcgcct tgcgtataat atttgcccat ggtgaaaacg ggggcgaaga      1980
agttgtccat attggccacg tttaaatcaa aactggtgaa actcacccag ggattggctg      2040
agacgaaaaa catattctca ataaacccctt tagggaaata ggccaggttt tcaccgtaac      2100
acgccacatc ttgcgaatat atgtgtagaa actgccggaa atcgtcgtgg tattcactcc      2160
agagcgatga aaacgtttca gtttgctcat ggaaaacggt gtaacaaggg tgaacactat      2220
cccatatcac cagctcaccg tctttcattg ccatacggaa ttccggatga gcattcatca      2280
ggcgggcaag aatgtgaata aaggccggat aaaacttgtg cttatttttc tttacggtct      2340
ttaaaaaggc cgtaatatcc agctgaacgg tctggttata ggtacattga gcaactgact      2400
gaaatgcctc aaaatgttct ttacgatgcc attgggatat atcaacgtgg tatatccag      2460 tgatttttt ctccatttta gcttccttag ctcctgaaaa tctcgataac tcaaaaaata      2520
cgcccggtag tgatcttatt tcattatggt gaaagttgga acctcttacg tgccgatcaa      2580
cgtctcattt tcgccaaaag ttggcccagg gcttcccggt atcaacaggg acaccaggat      2640
ttatttattc tgcgaagtga tcttccgtca caggtattta ttcgactcta gataacttcg      2700
tatagcatac attatacgaa gttatggatc cagcttatcg ataccgtcaa acaaatcata      2760
aaaaatttat ttgctttcag gaaaattttt ctgtataata gattcaattg cgatgacgac      2820
gaacacgcat taaggaggtg aagagctcga attcgagcca atatgcgaga cacccgaga      2880 aaattcatcg atgatggttg agatgtgtat aagagacagc tgtcgtaata gcgaagaggc      2940
ccgcaccgat cgcccttccc aacagttgcg cagcctgaat ggcgaatggc gcctgatgcg      3000
gtattttctc cttacgcatc tgtgcggtat ttcacaccgc atatggtgca ctctcagtac      3060
aatctgctct gatgccgcat agttaagcca gccccgacac ccgccaacac ccgctgacgc      3120
gccctgacgg gcttgtctgc tcccggcatc cgcttacaga caagctgtga ccgtctccgg      3180
gagctgcatg tgtcagaggt tttcaccgtc atcaccgaaa cgcgcga                    3227
```

<210> SEQ ID NO 80
<211> LENGTH: 7877
<212> TYPE: DNA
<213> ORGANISM: Artificial Sequence
<220> FEATURE:
<223> OTHER INFORMATION: Description of Artificial Sequence: Synthetic
      pACYC-PTrc-sbm-ygfG plasmid266 - 1348:lacI 1577 -
      1769:PTrc1800 - 3944:sbm3967 - 4752:ygfG5208 - 6020:kanR6347
      - 7176:p15A ori polynucleotide

<400> SEQUENCE: 80

```
cgaggccggc cccgccaaca cccgctgacg cgccctgacg ggcttgtctg ctcccggcat       60
ccgcttacag acaagctgtg accgtctccg ggagctgcat gtgtcagagg ttttcaccgt      120
catcaccgaa acgcgcgagg cagcagatca attcgcgcgc gaaggcgaag cggcatgcat      180
ttacgttgac accatcgaat ggtgcaaaac ctttcgcggt atggcatgat agcgcccgga      240
agagagtcaa ttcagggtgg tgaatgtgaa accagtaacg ttatacgatg tcgcagagta      300
tgccggtgtc tcttatcaga ccgtttcccg cgtggtgaac caggccagcc acgtttctgc      360
```

| | |
|---|---|
| gaaaacgcgg gaaaaagtgg aagcggcgat ggcggagctg aattacattc ccaaccgcgt | 420 |
| ggcacaacaa ctggcgggca aacagtcgtt gctgattggc gttgccacct ccagtctggc | 480 |
| cctgcacgcg ccgtcgcaaa ttgtcgcggc gattaaatct cgcgccgatc aactgggtgc | 540 |
| cagcgtggtg gtgtcgatgg tagaacgaag cggcgtcgaa gcctgtaaag cggcggtgca | 600 |
| caatcttctc gcgcaacgcg tcagtgggct gatcattaac tatccgctgg atgaccagga | 660 |
| tgccattgct gtgaagctg cctgcactaa tgttccggcg ttatttcttg atgtctctga | 720 |
| ccagacaccc atcaacagta ttattttctc ccatgaagac ggtacgcgac tgggcgtgga | 780 |
| gcatctggtc gcattgggtc accagcaaat cgcgctgtta gcgggcccat taagttctgt | 840 |
| ctcggcgcgt ctgcgtctgg ctggctggca taaatatctc actcgcaatc aaattcagcc | 900 |
| gatagcggaa cggaaggcg actggagtgc catgtccggt tttcaacaaa ccatgcaaat | 960 |
| gctgaatgag ggcatcgttc ccactgcgat gctggttgcc aacgatcaga tggcgctggg | 1020 |
| cgcaatgcgc gccattaccg agtccgggct gcgcgttggt gcggatatct cggtagtggg | 1080 |
| atacgacgat accgaagaca gctcatgtta tcccgccg tcaaccacca tcaaacagga | 1140 |
| ttttcgcctg ctgggggcaaa ccagcgtgga ccgcttgctg caactctctc agggccaggc | 1200 |
| ggtgaagggc aatcagctgt tgcccgtctc actggtgaaa agaaaaacca ccctggcgcc | 1260 |
| caatacgcaa accgcctctc cccgcgcgtt ggccgattca ttaatgcagc tggcacgaca | 1320 |
| ggtttcccga ctggaaagcg ggcagtgagc gcaacgcaat taatgtgagt tagcgcgaat | 1380 |
| tgatctggtt tgacagctta tcatcgactg cacggtgcac caatgcttct ggcgtcaggc | 1440 |
| agccatcgga agctgtggta tggctgtgca ggtcgtaaat cactgcataa ttcgtgtcgc | 1500 |
| tcaaggcgca ctcccgttct ggataatgtt ttttgcgccg acatcataac ggttctggca | 1560 |
| aatattctga aatgagctgt tgacaattaa tcatccggct cgtataatgt gtggaattgt | 1620 |
| gagcggataa caatttcaca caggaaacag cgccgctgag aaaaagcgaa gcggcactgc | 1680 |
| tctttaacaa tttatcagac aatctgtgtg ggcactcgac cggaattatc gattaacttt | 1740 |
| attattaaaa attaaagagg tatatattaa tgtatcgatt aaataaggag gaataaacca | 1800 |
| tggctaacgt gcaggagtgg caacagcttg ccaacaagga attgagccgt cgggagaaaa | 1860 |
| ctgtcgactc gctggttcat caaaccgcgg aagggatcgc catcaagccg ctgtataccg | 1920 |
| aagccgatct cgataatctg gaggtgacag gtacccttcc tggtttgccg ccctacgttc | 1980 |
| gtggcccgcg tgccactatg tataccgccc aaccgtggac catccgtcag tatgctggtt | 2040 |
| tttcaacagc aaaagagtcc aacgcttttt atcgccgtaa cctggccgcc gggcaaaaag | 2100 |
| gtctttccgt tgcgtttgac cttgccaccc accgtggcta cgactccgat aacccgcgcg | 2160 |
| tggcgggcga cgtcggcaaa gcgggcgtcg ctatcgacac cgtggaagat atgaaagtcc | 2220 |
| tgttcgacca gatcccgctg gataaaatgt cggtttcgat gaccatgaat ggcgcagtgc | 2280 |
| taccagtact ggcgttttat atcgtcgccg cagaagagca aggtgttaca cctgataaac | 2340 |
| tgaccggcac cattcaaaac gatattctca agagtacct ctgccgcaac acctatattt | 2400 |
| acccaccaaa accgtcaatg cgcattatcg ccgacatcat cgcctggtgt tccggcaaca | 2460 |
| tgccgcgatt taataccatc agtatcagcg gttaccacat gggtgaagcg ggtgccaact | 2520 |
| gcgtgcagca ggtagcattt acgctcgctg atgggattga gtacatcaaa gcagcaatct | 2580 |
| ctgccggact gaaaattgat gacttcgctc ctcgcctgtc gttcttcttc ggcatcggca | 2640 |
| tggatctgtt tatgaacgtc gccatgttgc gtgcggcacg ttatttatgg agcgaagcgg | 2700 |
| tcagtggatt tggcgcacag gacccgaaat cactggcgct gcgtacccac tgccagacct | 2760 |

```
caggctggag cctgactgaa caggatccgt ataacaacgt tatccgcacc accattgaag    2820
cgctggctgc gacgctgggc ggtactcagt cactgcatac caacgccttt gacgaagcgc    2880
ttggtttgcc taccgatttc tcagcacgca ttgcccgcaa cacccagatc atcatccagg    2940
aagaatcaga actctgccgc accgtcgatc cactggccgg atcctattac attgagtcgc    3000
tgaccgatca aatcgtcaaa caagccagag ctattatcca acagatcgac gaagccggtg    3060
gcatggcgaa agcgatcgaa gcaggtctgc caaaacgaat gatcgaagag gcctcagcgc    3120
gcgaacagtc gctgatcgac cagggcaagc gtgtcatcgt tggtgtcaac aagtacaaac    3180
tggatcacga agacgaaacc gatgtacttg agatcgacaa cgtgatggtg cgtaacgagc    3240
aaattgcttc gctggaacgc attcgcgcca cccgtgatga tgccgccgta accgccgcgt    3300
tgaacgccct gactcacgcc gcacagcata acgaaaacct gctggctgcc gctgttaatg    3360
ccgctcgcgt tcgcgccacc ctgggtgaaa tttccgatgc gctggaagtc gctttcgacc    3420
gttatctggt gccaagccag tgtgttaccg gcgtgattgc gcaaagctat catcagtctg    3480
agaaatcggc ctccgagttc gatgccattg ttgcgcaaac ggagcagttc cttgccgaca    3540
atggtcgtcg cccgcgcatt ctgatcgcta agatgggcca ggatggacac gatcgcggcg    3600
cgaaagtgat cgccagcgcc tattccgatc tcggtttcga cgtagattta agcccgatgt    3660
tctctacacc tgaagagatc gcccgcctgg ccgtagaaaa cgacgttcac gtagtgggcg    3720
catcctcact ggctgccggt cataaaacgc tgatcccgga actggtcgaa gcgctgaaaa    3780
aatggggacg cgaagatatc tgcgtggtcg cgggtggcgt cattccgccg caggattacg    3840
ccttcctgca agagcgcggc gtggcggcga tttatggtcc aggtacacct atgctcgaca    3900
gtgtgcgcga cgtactgaat ctgataagcc agcatcatga ttaattctag aaaggaggaa    3960
taaaccatgt cttatcagta tgttaacgtt gtcactatca acaaagtggc ggtcattgag    4020
tttaactatg gccgaaaact taatgcctta agtaaagtct ttattgatga tcttatgcag    4080
gcgttaagcg atctcaaccg gccggaaatt cgctgtatca ttttgcgcgc accgagtgga    4140
tccaaagtct tctccgcagg tcacgatatt cacgaactgc cgtctggcgg tcgcgatccg    4200
ctctcctatg atgatccatt gcgtcaaatc acccgcatga tccaaaaatt cccgaaaccg    4260
atcatttcga tggtggaagg tagtgttttgg ggtggcgcat ttgaaatgat catgagttcc    4320
gatctgatca tcgccgccag tacctcaacc ttctcaatga cgcctgtaaa cctcggcgtc    4380
ccgtataacc tggtcggcat tcacaacctg acccgcgacg cgggcttcca cattgtcaaa    4440
gagctgattt ttaccgcttc gccaatcacc gcccagcgcg cgctggctgt cggcatcctc    4500
aaccatgttg tggaagtgga agaactggaa gatttcaccc tacaaatggc gcaccacatc    4560
tctgagaaag cgccgttagc cattgccgtt atcaaagaag agctgcgtgt actgggcgaa    4620
gcacacacca tgaactccga tgaatttgaa cgtattcagg ggatgcgccg cgcggtgtat    4680
gacagcgaag attaccagga agggatgaac gctttcctcg aaaaacgtaa acctaatttc    4740
gttggtcatt aagaattcga agcttgggcc cgaacaaaaa ctcatctcag aagaggatct    4800
gaatagcgcc gtcgaccatc atcatcatca tcattgagtt taaacggtct ccagcttggc    4860
tgttttggcg gatgagagaa gattttcagc ctgatacaga ttaaatcaga acgcagaagc    4920
ggtctgataa aacagaattt gcctggcggc agtagcgcgg tggtcccacc tgaccccatg    4980
ccgaactcag aagtgaaacg ccgtagcgcc gatggtagtg tggggtctcc ccatgcgaga    5040
gtagggaact gccaggcatc aaataaaacg aaaggctcag tcgaaagact gggcctttcg    5100
ttttatctgt tgtttgtcgg tgaacgctct cctgattaat taagacgtcc cgtcaagtca    5160
```

```
gcgtaatgct ctgccagtgt tacaaccaat taaccaattc tgattagaaa aactcatcga    5220
gcatcaaatg aaaactgcaat ttattcatat caggattatc aataccatat ttttgaaaaa    5280
gccgtttctg taatgaagga gaaaactcac cgaggcagtt ccataggatg gcaagatcct    5340
ggtatcggtc tgcgattccg actcgtccaa catcaataca acctattaat ttcccctcgt    5400 caaaataag gttatcaagt gagaaatcac catgagtgac gactgaatcc ggtgagaatg    5460
gcaaaagctt atgcatttct ttccagactt gttcaacagg ccagccatta cgctcgtcat    5520
caaaatcact cgcatcaacc aaaccgttat tcattcgtga ttgcgcctga gcgagacgaa    5580
atacgcgatc gctgttaaaa ggacaattac aaacaggaat cgaatgcaac cggcgcagga    5640
acactgccag cgcatcaaca atattttcac ctgaatcagg atattcttct aatacctgga    5700
atgctgtttt cccgggggatc gcagtggtga gtaaccatgc atcatcagga gtacggataa    5760
aatgcttgat ggtcggaaga ggcataaatt ccgtcagcca gtttagtctg accatctcat    5820
ctgtaacatc attggcaacg ctaccttgc catgtttcag aaacaactct ggcgcatcgg    5880
gcttcccata caatcgatag attgtcgcac ctgattgccc gacattatcg cgagcccatt    5940
tatacccata taaatcagca tccatgttgg aatttaatcg cggcctcgag caagacgttt    6000
cccgttgaat atggctcata caccccttg tattactgtt tatgtaagca gacagttta    6060 ttgttcatga tgatatattt ttatcttgtg caatgtaaca tcagagattt tgagacacaa    6120
cgtggctttg ttgaataaat cgaacttttg ctgagttgaa ggatcagatc acgcatcttc    6180
ccgacaacgc agaccgttcc gtggcaaagc aaaagttcaa aatcaccaac tggtccacct    6240
acaacaaagc tctcatcaac cgtggctccc tcactttctg gctggatgat ggggcgattc    6300
aggcctggta tgagtcagca acaccttctt cacgaggcag acctcagcgc tagcggagtg    6360
tatactggct tactatgttg gcactgatga gggtgtcagt gaagtgcttc atgtggcagg    6420 agaaaaagg ctgcaccggt gcgtcagcag aatatgtgat acaggatata ttccgcttcc    6480
tcgctcactg actcgctacg ctcggtcgtt cgactgcggc gagcggaaat ggcttacgaa    6540
cggggcggag atttcctgga agatgccagg aagatactta acaggaagt gagagggccg    6600 cggcaaagcc gttttccat aggctccgcc cccctgacaa gcatcacgaa atctgacgct    6660
caaatcagtg gtggcgaaac ccgacaggac tataaagata ccaggcgttt ccccctggcg    6720
gctccctcgt gcgctctcct gttcctgcct ttcggtttac cggtgtcatt ccgctgttat    6780
ggccgcgttt gtctcattcc acgcctgaca ctcagttccg ggtaggcagt tcgctccaag    6840
ctggactgta tgcacgaacc ccccgttcag tccgaccgct cgccttatc cggtaactat    6900 cgtcttgagt ccaacccgga agacatgca aaagcaccac tggcagcagc cactggtaat    6960
tgatttagag gagttagtct tgaagtcatg cgccggttaa ggctaaactg aaaggacaag    7020
ttttggtgac tgcgctcctc caagccagtt acctcggttc aaagagttgg tagctcagag    7080
aaccttcgaa aaaccgccct gcaaggcggt ttttcgttt tcagagcaag agattacgcg    7140
cagaccaaaa cgatctcaag aagatcatct tattaagggg tctgacgctc agtggaacga    7200
aaactcacgt taagggattt tggtcatgag attatcaaaa aggatcttca cctagatcct    7260
tttaaattaa aaatgaagtt ttaaatcaat ctaaagtata tatgagtaaa cttggtctga    7320
cagttaccaa tgcttaatca gtgaggcacc tatctcagcg atctgtctat ttcgttcatc    7380
catagttgcc tgactccccg tcgtgtagat aactacgata cgggagggct taccatctgg    7440
ccccagtgct gcaatgatac cgcgagaccc acgctcaccg gctccagatt tatcagcaat    7500
aaaccagcca gccggaaggg ccgagcgcag aagtggtcct gcaactttat ccgcctccat    7560
```

-continued

```
ccagtctatt aattgttgcc gggaagctag agtaagtagt tcgccagtta atagtttgcg    7620
caacgttgtt gccattgctg caggcatcgt ggtgtcacgc tcgtcgtttg gtatggcttc    7680
attcagctcc ggttcccaac gatcaaggcg agttacatga tcccccatgt tgtgcaaaaa    7740
agcggttagc tccttcggtc ctccgatcgt tgtcagaagt aagttggccg cagtgttatc    7800
actcatggtt atggcagcac tgcataattc tcttactgtc atgccatccg taagatgctt    7860
ttctgtgact ggtgagt                                                   7877
```

<210> SEQ ID NO 81
<211> LENGTH: 15179
<212> TYPE: DNA
<213> ORGANISM: Artificial Sequence
<220> FEATURE:
<223> OTHER INFORMATION: Description of Artificial Sequence: Synthetic Tn7tes plasmid polynucleotide

<400> SEQUENCE: 81

```
ggccacgatg cgtccggcgt agaggatctg ctcatgtttg acagcttatc atcgatgcat      60
aatgtgcctg tcaaatggac gaagcaggga ttctgcaaac cctatgctac tccgtcaagc     120
cgtcaattgt ctgattcgtt accaattatg acaacttgac ggctacatca ttcacttttt     180
cttcacaacc ggcacggaac tcgctcgggc tggccccggt gcattttta aatacccgcg      240 agaaatagag ttgatcgtca aaaccaacat tgcgaccgac ggtggcgata ggcatccggg     300
tggtgctcaa aagcagcttc gcctggctga tacgttggtc ctcgcgccag cttaagacgc     360
taatccctaa ctgctggcgg aaaagatgtg acagacgcga cggcgacaag caaacatgct     420
gtgcgacgct ggcgatatca aaattgctgt ctgccaggtg atcgctgatg tactgacaag     480
cctcgcgtac ccgattatcc atcggtggat ggagcgactc gttaatcgct tccatgcgcc     540
gcagtaacaa ttgctcaagc agatttatcg ccagcagctc cgaatagcgc ccttcccctt     600
gcccggcgtt aatgatttgc ccaaacaggt cgctgaaatg cggctggtgc gcttcatccg     660
ggcgaaagaa ccccgtattg gcaaatattg acggccagtt aagccattca tgccagtagg     720
cgcgcggacg aaagtaaacc cactggtgat accattcgcg agcctccgga tgacgaccgt     780
agtgatgaat ctctcctggc gggaacagca aaatatcacc cggtcggcaa acaaattctc     840
gtccctgatt tttcaccacc ccctgaccgc gaatggtgag attgagaata taacctttca     900
ttcccagcgg tcggtcgata aaaaaatcga gataaccgtt ggcctcaatc ggcgttaaac     960
ccgccaccag atgggcatta aacgagtatc ccggcagcag gggatcattt gcgcttcag    1020 ccatactttt catactcccg ccattcagag aagaaaccaa ttgtccatat tgcatcagac    1080
attgccgtca ctgcgtcttt tactggctct tctcgctaac caaaccggta acccgctta    1140 ttaaaagcat tctgtaacaa agcgggacca aagccatgac aaaaacgcgt aacaaaagtg    1200
tctataatca cggcagaaaa gtccacattg attatttgca cggcgtcaca ctttgctatg    1260
ccatagcatt tttatccata agattagcgg atcctacctg acgctttta tcgcaactct    1320 ctactgtttc tccatacccg ttttttggg ctagcgaatt cgagctcggt acccaagtct    1380
taaactagac agaatagttg taaactgaaa tcagtccagt tatgctgtga aaaagcatac    1440
tggacttttg ttatggctaa agcaaactct tcattttctg aagtgcaaat tgcccgtcgt    1500
attaaagagg ggcgtggcca agggcatggt aaagactata ttccatggct aacagtacaa    1560
gaagttcctt cttcaggtcg ttcccaccgt atttattctc ataagacggg acgagtccat    1620
catttgctat ctgacttaga gcttgctgtt tttctcagtc ttgagtggga gagcagcgtg    1680
ctagatatac gcgagcagtt ccccttatta cctagtgata ccaggcagat tgcaatagat    1740
```

```
agtggtatta agcatcctgt tattcgtggt gtagatcagg ttatgtctac tgattttta    1800 gtggactgca aagatggtcc ttttgagcag tttgctattc aagtcaaacc tgcagcagcc    1860
ttacaagacg agcgtacctt agaaaaacta gaactagagc gtcgctattg gcagcaaaag    1920
caaattcctt ggttcatttt tactgataaa gaaataaatc ccgtagtaaa agaaaatatt    1980
gaatggcttt attcagtgaa aacagaagaa gtttctgcgg agcttttagc acaactatcc    2040
ccattggccc atatcctgca agaaaaagga gatgaaaaca ttatcaatgt ctgtaagcag    2100
gttgatattg cttatgattt ggagttaggc aaaacattga gtgagatacg agccttaacc    2160
gcaaatggtt ttattaagtt caatatttat aagtctttca gggcaaataa gtgtgcagat    2220
ctctgtatta gccaagtagt gaatatgagt gagttgcgct atgtggcaaa ttaatgaggt    2280
tgtgctattt gataatgatc cgtatcgcat tttggctata gaggatggcc aagttgtctg    2340
gatgcaaata agcgctgata aaggagttcc acaagctagg gctgagttgt tgctaatgca    2400
gtatttagat gaaggccgct tagttagaac tgatgaccct tatgtacatc ttgatttaga    2460
agagccgtct gtagattctg tcagcttcca gaagcgcgag gaggattatc gaaaaattct    2520
tcctattatt aatagtaagg atcgtttcga ccctaaagtc agaagcgaac tcgttgagca    2580
tgtggtccaa gaacataagg ttactaaggc tacagtttat aagttgttac gccgttactg    2640
gcagcgtggt caaacgccta atgcattaat tcctgactac aaaaacagcg gtgcaccagg    2700
ggaaagacgt tcagcgacag gaacagcaaa gattggccga gccagagaat atggtaaggg    2760
tgaaggaacc aagtaacgc ccgagattga acgcctttt aggttgacca tagaaaagca    2820
cctgttaaat caaaaggta caaagaccac cgttgcctat agacgatttg tggacttgtt    2880
tgctcagtat tttcctcgca ttccccaaga ggattaccca acactacgtc agtttcgtta    2940
tttttatgat cgagaatacc ctaaagctca gcgcttaaag tctagagtta aagcaggggt    3000
atataaaaaa gacgtacgac ccttaagtag tacagccact tctcaggcgt taggccctgg    3060
gagtcgttat gagattgatg ccacgattgc tgatatttat ttagtggatc atcatgatcg    3120
ccaaaaaatc ataggaagac caacgcttta cattgtgatt gatgtgttta gtcggatgat    3180
cacgggcttt tatatcggct ttgaaaatcc gtcttatgtg gtggcgatgc aggcttttgt    3240
aaatgcttgc tctgacaaaa cggccatttg tgcccagcat gatattgaga ttagtagctc    3300
agactggccg tgtgtaggtt tgccagatgt gttgctagcg gaccgtggcg aattaatgag    3360
tcatcaggtc gaagccttag tttctagttt taatgtgcga gtggaaagtg ctccacctag    3420
acgtggcgat gctaaaggca tagtggaaag cacttttaga acactacaag ccgagtttaa    3480
gtcctttgca cctggcattg tagagggcag tcggatcaaa agccatggtg aaacagacta    3540
taggttagat gcatctctgt cggtatttga gttcacacaa attattttgc gtacgatctt    3600
attcagaaat aaccatctgg tgatggataa atacgatcga gatgctgatt ttcctacaga    3660
tttaccgtct attcctgtcc agctatggca atggggtatg cagcatcgta caggtagttt    3720
aagggctgtg gagcaagagc agttgcgagt agcgttactg cctcgccgaa aggtctctat    3780
ttcttcattt ggcgttaatt tgtggggttt gtattactcg gggtcagaga ttctgcgtga    3840
gggttggttg cagcggagca ctgatatagc tagacctcaa catttagaag cggcttatga    3900
cccagtgctg gttgatacga tttatttgtt tccgcaagtt ggcagccgtg tattttggcg    3960
ctgtaatctg acggaacgta gtcggcagtt taaggtctc tcattttggg aggtttggga    4020
tatacaagca caagaaaaac acaataaagc caatgcgaag caggatgagt taactaaacg    4080
cagggagctt gaggcgttta ttcagcaaac cattcagaaa gcgaataagt taacgcccag    4140
```

```
tactactgag cccaaatcaa cacgcattaa gcagattaaa actaataaaa aagaagccgt   4200
gacctcggag cgtaaaaaac gtgcggagca tttgaagcca agctcttcag gtgatgaggc   4260
taaagttatt cctttcaacg cagtggaagc ggatgatcaa gaagattaca gcctacccac   4320
atacgtgcct gaattatttc aggatccacc agaaaaggat gagtcatgag tgctacccgg   4380
attcaagcag tttatcgtga tacgggggta gaggcttatc gtgataatcc ttttatcgag   4440
gccttaccac cattacaaga gtcagtgaat agtgctgcat cactgaaatc ctctttacag   4500
cttacttcct ctgacttgca aaagtcccgt gttatcagag ctcataccat ttgtcgtatt   4560
ccagatgact attttcagcc attaggtacg catttgctac taagtgagcg tatttcggtc   4620
atgattcgag gtggctacgt aggcagaaat cctaaaacag gagatttaca aaagcattta   4680
caaaatggtt atgagcgtgt tcaaacggga gagttggaga catttcgctt tgaggaggca   4740
cgatctacgg cacaaagctt attgttaatt ggttgttctg gtagtgggaa gacgacctct   4800
cttcatcgta ttctagccac gtatcctcag gtgatttacc atcgtgaact caatgtagag   4860
caggtggtgt atttgaaaat agactgctcg cataatggtt cgctaaaaga aatctgcttg   4920
aatttttcca gagcgttgga tcgagccttg ggctcgaact atgagcgtcg ttatggctta   4980
aaacgtcatg gtatagaaac catgttggct ttgatgtcgc aaatagccaa tgcacatgct   5040
ttagggttgt tggttattga tgaaattcag catttaagcc gctctcgttc gggtggatct   5100
caagagatgc tgaactttt tgtgacgatg gtgaatatta ttggcgtacc agtgatgttg   5160
attggtaccc ctaaagcacg agagattttt gaggctgatt gcggtctgc acgtagaggg   5220 gcagggtttg gagctatatt ctgggatcct atacaacaaa cgcaacgtgg aaagcccaat   5280
caagagtgga tcgcttttac ggataatctt tggcaattac agcttttaca acgcaaagat   5340
gcgctgttat cggatgaggt ccgtgatgtg tggtatgagc taagccaagg agtgatggac   5400
attgtagtaa aacttttttgt actcgctcag ctccgtgcgc tagctttagg caatgagcgt   5460
attaccgctg gtttattgcg gcaagtgtat caagatgagt taaagcctgt gcaccccatg   5520
ctagaggcat tacgctcggg tatcccagaa cgcattgctc gttattctga tctagtcgtt   5580
cccgagattg ataaacggtt aatccaactt cagctagata tcgcagcgat acaagaacaa   5640
acaccagaag aaaaagccct tcaagagtta gataccgaag atcagcgtca tttatatctg   5700
atgctgaaag aggattacga ttcaagcctg ttaattccca ctattaaaaa agcgtttagc   5760
cagaatccaa cgatgacaag acaaaagtta ctgcctcttg ttttgcagtg gttgatggaa   5820
ggcgaaacgg tagtgtcaga actagaaaag ccctccaaga gtaaaaaggt tcggctata   5880 aaggtagtca gcccagcga ctgggatagc ttgcctgata cggatttacg ttatatctat   5940
tcacaacgcc aacctgaaaa aaccatgcat gaacggttaa aagggaaagg ggtaatagtg   6000
gatatggcga gcttatttaa acaagcaggt tagccatgag aaactttcct gttccgtact   6060
cgaatgagct gatttatagc actattgcac gggcaggcgt ttatcaaggg attgttagtc   6120
ctaagcagct gttggatgag gtgtatggca accgcaaggt ggtcgctacc ttaggtctgc   6180
cctcgcattt aggtgtgata gcaagacatc tacatcaaac aggacgttac gctgttcagc   6240
agcttattta tgagcatacc ttattccctt tatatgctcc gtttgtaggc aaggagcgcc   6300
gagacgaagc tattcggtta atggagtacc aagcgcaagg tgcggtgcat ttaatgctag   6360
gagtcgctgc ttctagagtt aagagcgata accgctttag atactgccct gattgcgttg   6420
ctcttcagct aaataggtat ggggaagcct tttggcaacg agattggtat ttgcccgctt   6480
tgccatattg tccaaaacac ggtgctttag tcttctttga tagagctgta gatgatcacc   6540
```

```
gacatcaatt tgggctttg ggtcatactg agctgctttc agactacccc aaagactccc   6600
tatctcaatt aacagcacta gctgcttata tagcccctct gttagatgct ccacgagcgc   6660
aagagctttc cccaagcctt gagcagtgga cgctgtttta tcagcgctta gcgcaggatc   6720
tagggctaac caaaagcaag cacattcgtc atgacttggt ggcggagaga gtgaggcaga   6780
cttttagtga tgaggcacta gagaaactgg atttaaagtt ggcagagaac aaggacacgt   6840
gttggctgaa aagtatattc cgtaagcata gaaaagcctt tagttattta cagcatagta   6900
ttgtgtggca agccttattg ccaaaactaa cggttataga agcgctacag caggcaagtg   6960
ctcttactga gcactctata acgacaagac ctgttagcca gtctgtgcaa cctaactctg   7020
aagatttatc tgttaagcat aaagactggc agcaactagt gcataaatac caaggaatta   7080
aggcggcaag acagtcttta gagggtgggg tgctatacgc ttggctttac cgacatgaca   7140
gggattggct agttcactgg aatcaacagc atcaacaaga gcgtctggca cccgccccta   7200
gagttgattg gaaccaaaga gatcgaattg ctgtacgaca actattaaga atcataaagc   7260
gtctagatag tagccttgat cacccaagag cgacatcgag ctggctgtta aagcaaactc   7320
ctaacggaac ctctcttgca aaaatctac agaaactgcc tttggtagcg ctttgcttaa    7380
agcgttactc agagagtgtg gaagattatc aaattagacg gattagccaa gcttttatta   7440
agcttaaaca ggaagatgtt gagcttaggc gctggcgatt attaagaagt gcaacgttat   7500
ctaaagagcg gataactgag gaagcacaaa gattcttgga aatggtttat ggggaagagt   7560
gagtggttag gctagctaca tttaatgaca atgtgcaggt tgtacatatt ggtcatttat   7620
tccgtaactc gggtcataag gagtggcgta ttttgtttg gtttaatcca atgcaagaac    7680
ggaaatggac tcgatttact catttgcctt tattaagtcg agctaaggtg gttaacagta   7740
caacaaagca aataaataag gcggatcgtg tgattgagtt tgaagcatcg gatcttcaac   7800
gagccaaaat aatcgatttt cctaatctct cgtcctttgc ttccgtacgc aacaaggatg   7860
gagcgcagag ttcatttatt tacgaagctg aaacaccata tagcaagact cgttatcaca   7920
tcccacagtt agagctagct cggtcattat ttttagggga tcctctagag tcgacctgca   7980
ggcatgcaag cttggctgtt ttggcggatg agagaagatt ttcagcctga tacagattaa   8040
atcagaacgc agaagcggtc tgataaaaca gaatttgcct ggcggcagta gcgcggtggt   8100
cccacctgac cccatgccga actcagaagt gaaacgccgt agcgccgatg gtagtgtggg   8160
gtctccccat gcgagagtag ggaactgcca ggcatcaaat aaaacgaaag gctcagtcga   8220
aagactgggc ctttcgtttt atctgttgtt tgtcggtgaa cgctctcctg agtaggacaa   8280
atccgccggg agcggatttg aacgttgcga agcaacggcc cggagggtgg cgggcaggac   8340
gcccgccata aactgccagg catcaaatta agcagaaggc catcctgacg gatggccttt   8400
ttgcgtttct acaaactctt tgtttatttt tctaaatac attcaaatat gtatccgctc    8460
atgagacaat aaccctgata aatgcttcaa taatattgaa aaaggaagag tatgagtatt   8520
caacatttcc gtgtcgccct tattcccttt tttgcggcat tttgccttcc tgttttgct    8580
cacccagaaa cgctggtgaa agtaaaagat gctgaagatc agttgggtgc acgagtgggt   8640
tacatcgaac tggatctcaa cagcggtaag atccttgaga gttttcgccc cgaagaacgt   8700
tttccaatga tgagcacttt taaagttctg ctatgtggcg cggtattatc ccgtgttgac   8760
gccgggcaag agcaactcgg tcgccgcata cactattctc agaatgactt ggttgagtac   8820
tcaccagtca cagaaaagca tcttacggat ggcatgacag taagagaatt atgcagtgct   8880
gccataacca tgagtgataa cactgcggcc aacttacttc tgacaacgat cggaggaccg   8940
```

```
aaggagctaa ccgctttttt gcacaacatg ggggatcatg taactcgcct tgatcgttgg    9000
gaaccggagc tgaatgaagc cataccaaac gacgagcgtg acaccacgat gcctgcagca    9060
atggcaacaa cgttgcgcaa actattaact ggcgaactac ttactctagc ttcccggcaa    9120
caattaatag actggatgga ggcggataaa gttgcaggac cacttctgcg ctcggccctt    9180
ccggctggct ggtttattgc tgataaatct ggagccggtg agcgtgggtc tcgcggtatc    9240
attgcagcac tggggccaga tggtaagccc tcccgtatcg tagttatcta cacgacgggg    9300
agtcaggcaa ctatggatga acgaaataga cagatcgctg agataggtgc ctcactgatt    9360
aagcattggt aactgtcaga ccaagtttac tcatatatac tttagattga tttacgcgcc    9420
ctgtagcggc gcattaagcg cggcgggtgt ggtggttacg cgcagcgtga ccgctacact    9480
tgccagcgcc ctagcgcccg ctcctttcgc tttcttccct ccctttctcg ccacgttcgc    9540
cgccggccag cctcgcagag caggattccc gttgagcacc gccaggtgcg aataagggac    9600
agtgaagaag gaacacccgc tcgcgggtgg gcctacttca cctatcctgc ccggcggcat    9660
caccggcgcc acaggtgcgg ttgctggcgc ctatatcgcc gacatcaccg atggggaaga    9720
tcgggctcgc cacttcgggc tcatgagcgc ttgtttcggc gtgggtatgg tggcaggccc    9780
cgtggccggg ggactgttgg gcgccatctc cttgcatgca ccattccttg cggcggcggt    9840
gctcaacggc ctcaacctac tactgggctg cttcctaatg caggagtcgc ataagggaga    9900
gcgtcgatcc ccgacagtaa gacgggtaag cctgttgatg ataccgctgc cttactgggt    9960
gcattagcca gtctgaatga cctgtcacgg gataatccga agtggtcaga ctggaaaatc   10020
agagggcagg aactgctgaa cagcaaaaag tcagatagca ccacatagca gacccgccat   10080
aaaacgccct gagaagcccg tgacgggctt ttcttgtatt atgggtagtt tccttgcatg   10140
aatccataaa aggcgcctgt agtgccattt accccattc actgccagag ccgtgagcgc   10200
agcgaactga atgtcacgaa aaagacagcg actcaggtgc ctgatggtcg agacaaaag   10260 gaatattcag cgatttgccc gagcttgcga gggtgctact taagccttta gggttttaag   10320
gtctgttttg tagaggagca acagcgtttt gcgacatcct tttgtaatac tgcggaactg   10380
actaaagtag tgagttatac acagggctgg gatctattct ttttatcttt ttttattctt   10440
tctttattct ataaattata accacttgaa tataaacaaa aaaaacacac aaaggtctag   10500
cggaatttac agagggtcta gcagaattta caagttttcc agcaaaggtc tagcagaatt   10560
tacagatacc cacaactcaa aggaaaagga ctagtaatta tcattgacta gcccatctca   10620
attggtatag tgattaaaat cacctagacc aattgagatg tatgtctgaa ttagttgttt   10680
tcaaagcaaa tgaactagcg attagtcgct atgacttaac ggagcatgaa accaagctaa   10740
ttttatgctg tgtggcacta ctcaaccca cgattgaaaa ccctacaagg aaagaacgga   10800
cggtatcgtt cacttataac caatacgttc agatgatgaa catcagtagg gaaaatgctt   10860
atggtgtatt agctaaagca accagagagc tgatgacgag aactgtggaa atcaggaatc   10920
ctttggttaa aggctttgag attttccagt ggacaaacta tgccaagttc tcaagcgaaa   10980
aattagaatt agttttagt gaagagatat tgccttatct tttccagtta aaaaaattca   11040
taaaatataa tctggaacat gttaagtctt ttgaaaacaa atactctatg aggatttatg   11100
agtggttatt aaaagaacta acacaaaaga aaactcacaa ggcaaatata gagattagcc   11160
ttgatgaatt taagttcatg ttaatgcttg aaaataacta ccatgagttt aaaaggctta   11220
accaatgggt tttgaaacca ataagtaaag atttaaacac ttcagcaat atgaaattgg   11280 tggttgataa gcgaggccgc ccgactgata cgttgatttt ccaagttgaa ctagatagac   11340
```

```
aaatggatct cgtaaccgaa cttgagaaca accagataaa aatgaatggt gacaaaatac   11400
caacaaccat tacatcagat tcctacctac ataacggact aagaaaaaca ctacacgatg   11460
ctttaactgc aaaaattcag ctcaccagtt ttgaggcaaa attttgagt gacatgcaaa    11520 gtaagtatga tctcaatggt tcgttctcat ggctcacgca aaaacaacga accacactag   11580
agaacatact ggctaaatac ggaaggatct gaggttctta tggctcttgt atctatcagt   11640
gaagcatcaa gactaacaaa caaaagtaga acaactgttc accgttacat atcaaaggga   11700
aaactgtcca tatgcacaga tgaaaacggt gtaaaaaaga tagatacatc agagcttta    11760 cgagttttg gtgcatttaa agctgttcac catgaacaga tcgacaatgt aacagatgaa    11820
cagcatgtaa cacctaatag aacaggtgaa accagtaaaa caaagcaact agaacatgaa   11880
attgaacacc tgagacaact tgttacagct caacagtcac acatagacag cctgaaacag   11940
gcgatgctgc ttatcgaatc aaagctgccg acaacacggg agccagtgac gcctcccgtg   12000
gggaaaaaat catggcaatt ctggaagaaa tagcgctttc agcctgtggg cggacaaaat   12060
agttgggaac tgggaggggt ggaaatggag tttttaagga ttatttaggg aagagtgaca   12120
aaatagatgg gaactgggtg tagcgtcgta agctaatacg aaaattaaaa atgacaaaat   12180
agtttggaac tagatttcac ttatctggtt ggtcgacact agtattaccc tgttatccct   12240
agatttaaat gatatcggat cctagtaagc cacgttttaa ttaatcagat gggtcaatag   12300
cggccgccaa ttcgcgcgcg aaggcgaagc ggcatgcatt tacgttgaca ccatcgaatg   12360
gtgcaaaacc tttcgcggta tggcatgata gcgcccggaa gagagtcaat tcagggtggt   12420
gaatgtgaaa ccagtaacgt tatacgatgt cgcagagtat gccggtgtct cttatcagac   12480
cgtttcccgc gtggtgaacc aggccagcca cgtttctgcg aaaacgcggg aaaaagtgga   12540
agcggcgatg gcggagctga attacattcc caaccgcgtg gcacaacaac tggcgggcaa   12600
acagtcgttg ctgattggcg ttgccacctc cagtctggcc ctgcacgcgc cgtcgcaaat   12660
tgtcgcggcg attaaatctc gcgccgatca actgggtgcc agcgtggtgg tgtcgatggt   12720
agaacgaagc ggcgtcgaag cctgtaaagc ggcggtgcac aatcttctcg cgcaacgcgt   12780
cagtgggctg atcattaact atccgctgga tgaccaggat gccattgctg tggaagctgc   12840
ctgcactaat gttccggcgt tatttcttga tgtctctgac cagacaccca tcaacagtat   12900
tattttctcc catgaagacg gtacgcgact gggcgtggag catctggtcg cattgggtca   12960
ccagcaaatc gcgctgttag cgggcccatt aagttctgtc tcggcgcgtc tgcgtctggc   13020
tggctggcat aaatatctca ctcgcaatca aattcagccg atagcggaac gggaaggcga   13080
ctggagtgcc atgtccggtt ttcaacaaac catgcaaatg ctgaatgagg gcatcgttcc   13140
cactgcgatg ctggttgcca acgatcagat ggcgctgggc gcaatgcgcg ccattaccga   13200
gtccgggctg cgcgttggtg cggatatctc ggtagtggga tacgacgata ccgaagacag   13260
ctcatgttat atcccgccgt caaccaccat caaacaggat tttcgcctgc tggggcaaac   13320
cagcgtggac cgcttgctgc aactctctca gggccaggcg gtgaagggca atcagctgtt   13380
gcccgtctca ctggtgaaaa gaaaaccac cctggcgccc aatacgcaaa ccgcctctcc    13440
ccgcgcgttg gccgattcat taatgcagct ggcacgacag gtttcccgac tggaaagcgg   13500
gcagtgagcg caacgcaatt aatgtgagtt agcgcgaatt gatctggttt gacagcttat   13560
catcgactgc acggtgcacc aatgcttctg cgtcaggca gccatcggaa gctgtggtat    13620
ggctgtgcag tcgtaaatc actgcataat tcgtgtcgct caaggcgcac tcccgttctg    13680
gataatgttt tttgcgccga catcataacg gttctggcaa atattctgaa atgagctgtt   13740
```

```
gacaattaat catccggctc gtataatgtg tggaattgtg agcggataac aatttcacac    13800
aggaaacagc gccgctgaga aaaagcgaag cggcactgct ctttaacaat ttatcagaca    13860
atctgtgtgg gcactcgacc ggaattatcg attaacttta ttattaaaaa ttaaagaggt    13920
atatattaat gtatcgatta aataaggagg aataaaccat ggcggacacg ttattgattc    13980
tgggtgatag cctgagcgcc gggtatcgaa tgtctgccag cgcggcctgg cctgccttgt    14040
tgaatgataa gtggcagagt aaaacgtcgg tagttaatgc cagcatcagc ggcgacacct    14100
cgcaacaagg actggcgcgc cttccggctc tgctgaaaca gcatcagccg cgttgggtgc    14160
tggttgaact gggcggcaat gacggtttgc gtggttttca gccacagcaa accgagcaaa    14220
cgctgcgcca gattttgcag gatgtcaaag ccgccaacgc tgaaccattg ttaatgcaaa    14280
tacgtctgcc tgcaaactat ggtcgccgtt ataatgaagc ctttagcgcc atttacccca    14340
aactcgccaa agagtttgat gttccgctgc tgcccttttt tatggaagag gtctacctca    14400
agccacaatg gatgcaggat gacggtattc atcccaaccg cgacgcccag ccgtttattg    14460
ccgactggat ggcgaagcag ttgcagcctt tagtaaatca tgactcataa tgactctaga    14520
aataatttaa atggaattcg aagcttgggc ccgaacaaaa actcatctca gaagaggatc    14580
tgaatagcgc cgtcgaccat catcatcatc atcattgagt ttaaacggtc tccagcttgg    14640
ctgttttggc ggatgagaga agattttcag cctgatacag attaaatcag aacgcagaag    14700
cggtctgata aaacagaatt tgcctggcgg cagtagcgcg gtggtcccac ctgaccccat    14760
gccgaactca gaagtgaaac gccgtagcgc cgatggtagt gtggggtctc cccatgcgag    14820
agtagggaac tgccaggcat caaataaaac gaaaggctca gtcgaaagac tgggcctttc    14880
gttttatctg ttgtttgtcg gtgaacgctc tcctgattaa ttaagacgtc ccgtcaagtc    14940
agcgtaatgc cctaggaggc gcgccacggc cgcgtcgacc ccacgcccct ctttaatacg    15000
acgggcaatt tgcacttcag aaaatgaaga gtttgctttta gccataacaa aagtccagta    15060
tgctttttca cagcataact ggactgattt cagtttacaa ctattctgtc tagtttaaga    15120
ctttattgtc atagtttaga tctattttgt tcagtttaag actttattgt ccgcccaca     15179
```

<210> SEQ ID NO 82
<211> LENGTH: 70
<212> TYPE: DNA
<213> ORGANISM: Artificial Sequence
<220> FEATURE:
<223> OTHER INFORMATION: Description of Artificial Sequence: Synthetic
      Del-fadE-F primer <400> SEQUENCE: 82

```
aaaaacagca acaatgtgag ctttgttgta attatattgt aaacatattg attccgggga    60
tccgtcgacc                                                          70
```

<210> SEQ ID NO 83
<211> LENGTH: 68
<212> TYPE: DNA
<213> ORGANISM: Artificial Sequence
<220> FEATURE:
<223> OTHER INFORMATION: Description of Artificial Sequence: Synthetic
      Del-fadE-R primer <400> SEQUENCE: 83

```
aaacggagcc tttcggctcc gttattcatt tacgcggctt caactttcct gtaggctgga    60
gctgcttc                                                            68
```

```
<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      fadE-L2 primer

<400> SEQUENCE: 84
cgggcaggtg ctatgaccag gac                                             23

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      fadE-R1 primer

<400> SEQUENCE: 85
cgcggcgttg accggcagcc tgg                                             23

<210> SEQ ID NO 86
<211> LENGTH: 70
<212> TYPE: DNA
<213> ORGANISM: Artificial Sequence
<220> FEATURE:
<223> OTHER INFORMATION: Description of Artificial Sequence: Synthetic
      Del-tonA-F primer

<400> SEQUENCE: 86
atcattctcg tttacgttat cattcacttt acatcagaga tataccaatg attccgggga    60
tccgtcgacc                                                            70

<210> SEQ ID NO 87
<211> LENGTH: 69
<212> TYPE: DNA
<213> ORGANISM: Artificial Sequence
<220> FEATURE:
<223> OTHER INFORMATION: Description of Artificial Sequence: Synthetic
      Del-tonA-R primer

<400> SEQUENCE: 87
gcacggaaat ccgtgcccca aaagagaaat tagaaacgga aggttgcggt tgtaggctgg    60
agctgcttc                                                             69

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      tonA-verF primer

<400> SEQUENCE: 88
caacagcaac ctgctcagca a                                               21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      tonA-verR primer

<400> SEQUENCE: 89
aagctggagc agcaaagcgt t                                               21
```

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Synthetic
    lacI-forward primer

<400> SEQUENCE: 90
ggctggctgg cataaatatc tc                                            22

<210> SEQ ID NO 91
<211> LENGTH: 79
<212> TYPE: DNA
<213> ORGANISM: Artificial Sequence
<220> FEATURE:
<223> OTHER INFORMATION: Description of Artificial Sequence: Synthetic
    lacZ-reverse primer

<400> SEQUENCE: 91
gcgttaaagt tgttctgctt catcagcagg atatcctgca ccatcgtctg gattttgaac    60
ttttgctttg ccacggaac                                                79

<210> SEQ ID NO 92
<211> LENGTH: 36
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 92
tgaattccat ggcgcaactc actcttcttt tagtcg                             36

<210> SEQ ID NO 93
<211> LENGTH: 39
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 93
cagtacctcg agtcttcgta tacatatgcg ctcagtcac                          39

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 94
ccttggggca tatgaaagct g                                             21

<210> SEQ ID NO 95
<211> LENGTH: 29
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 95
tttagtcatc tcgagtgcac ctcaccttt                                     29

<210> SEQ ID NO 96
<211> LENGTH: 35
<212> TYPE: DNA
<213> ORGANISM: Artificial Sequence
<220> FEATURE:
<223> OTHER INFORMATION: Description of Artificial Sequence: Synthetic
      pTrc_F primer

<400> SEQUENCE: 96
tttcgcgagg ccggccccgc caacacccgc tgacg                          35

<210> SEQ ID NO 97
<211> LENGTH: 39
<212> TYPE: DNA
<213> ORGANISM: Artificial Sequence
<220> FEATURE:
<223> OTHER INFORMATION: Description of Artificial Sequence: Synthetic
      pTrc_R primer

<400> SEQUENCE: 97
aaggacgtct taattaatca ggagagcgtt caccgacaa                      39

<210> SEQ ID NO 98
<211> LENGTH: 28
<212> TYPE: DNA
<213> ORGANISM: Artificial Sequence
<220> FEATURE:
<223> OTHER INFORMATION: Description of Artificial Sequence: Synthetic
      LF302 primer

<400> SEQUENCE: 98
atatgacgtc ggcatccgct tacagaca                                  28

<210> SEQ ID NO 99
<211> LENGTH: 32
<212> TYPE: DNA
<213> ORGANISM: Artificial Sequence
<220> FEATURE:
<223> OTHER INFORMATION: Description of Artificial Sequence: Synthetic
      LF303 primer

<400> SEQUENCE: 99
aattcttaag tcaggagagc gttcaccgac aa                             32

<210> SEQ ID NO 100
<211> LENGTH: 37
<212> TYPE: DNA
<213> ORGANISM: Artificial Sequence
<220> FEATURE:
<223> OTHER INFORMATION: Description of Artificial Sequence: Synthetic
      TREE044 primer

<400> SEQUENCE: 100
gaggaataaa ccatgaacgc aggaatttta ggagtag                        37

<210> SEQ ID NO 101
<211> LENGTH: 41
<212> TYPE: DNA
<213> ORGANISM: Artificial Sequence
<220> FEATURE:
<223> OTHER INFORMATION: Description of Artificial Sequence: Synthetic
      primer61

<400> SEQUENCE: 101
cccaagcttc gaattcttac ttaccccaac gaatgattag g                   41

```
<210> SEQ ID NO 102
<211> LENGTH: 71
<212> TYPE: DNA
<213> ORGANISM: Artificial Sequence
<220> FEATURE:
<223> OTHER INFORMATION: Description of Artificial Sequence: Synthetic
      TREE025 primer

<400> SEQUENCE: 102
cctgacagtg cgggcttttt ttttcgacca aaggtaacga ggtaacaacc gtgtaggctg      60
gagctgcttc g                                                          71

<210> SEQ ID NO 103
<211> LENGTH: 62
<212> TYPE: DNA
<213> ORGANISM: Artificial Sequence
<220> FEATURE:
<223> OTHER INFORMATION: Description of Artificial Sequence: Synthetic
      TREE026 primer

<400> SEQUENCE: 103
gtatatatta atgtatcgat taaataagga ggaataaacc atgcgagtgt tgaagttcgg      60
cg                                                                    62

<210> SEQ ID NO 104
<211> LENGTH: 59
<212> TYPE: DNA
<213> ORGANISM: Artificial Sequence
<220> FEATURE:
<223> OTHER INFORMATION: Description of Artificial Sequence: Synthetic
      TREE027 primer

<400> SEQUENCE: 104
ctgatgtacc gccgaacttc aacactcgca tggtttattc ctccttattt aatcgatac      59

<210> SEQ ID NO 105
<211> LENGTH: 28
<212> TYPE: DNA
<213> ORGANISM: Artificial Sequence
<220> FEATURE:
<223> OTHER INFORMATION: Description of Artificial Sequence: Synthetic
      TREE028 primer

<400> SEQUENCE: 105
gcgcccgtat ttcgtggtg ctgattac                                         28

<210> SEQ ID NO 106
<211> LENGTH: 28
<212> TYPE: DNA
<213> ORGANISM: Artificial Sequence
<220> FEATURE:
<223> OTHER INFORMATION: Description of Artificial Sequence: Synthetic
      TREE029 primer

<400> SEQUENCE: 106
gtaatcagca ccacgtaaat acgggcgc                                        28

<210> SEQ ID NO 107
<211> LENGTH: 25
<212> TYPE: DNA
<213> ORGANISM: Artificial Sequence
<220> FEATURE:
<223> OTHER INFORMATION: Description of Artificial Sequence: Synthetic
      TREE030 primer

<400> SEQUENCE: 107
tcagactcct aacttccatg agagg                                           25
```

```
<210> SEQ ID NO 108
<211> LENGTH: 50
<212> TYPE: DNA
<213> ORGANISM: Artificial Sequence
<220> FEATURE:
<223> OTHER INFORMATION: Description of Artificial Sequence: Synthetic
      Km_trc_overR primer

<400> SEQUENCE: 108
aatatttgcc agaaccgtta tgatgtcggc attccgggga tccgtcgacc                50

<210> SEQ ID NO 109
<211> LENGTH: 55
<212> TYPE: DNA
<213> ORGANISM: Artificial Sequence
<220> FEATURE:
<223> OTHER INFORMATION: Description of Artificial Sequence: Synthetic
      Km_trc_overF primer

<400> SEQUENCE: 109
cttcgaactg caggtcgacg gatccccgga atgccgacat cataacggtt ctggc          55

<210> SEQ ID NO 110
<211> LENGTH: 29
<212> TYPE: DNA
<213> ORGANISM: Artificial Sequence
<220> FEATURE:
<223> OTHER INFORMATION: Description of Artificial Sequence: Synthetic
      EG238 primer

<400> SEQUENCE: 110
gctgatcatt aactatccgc tggatgacc                                       29

<210> SEQ ID NO 111
<211> LENGTH: 40
<212> TYPE: DNA
<213> ORGANISM: Artificial Sequence
<220> FEATURE:
<223> OTHER INFORMATION: Description of Artificial Sequence: Synthetic
      TREE017 primer

<400> SEQUENCE: 111
actggaaagc gggcagtgag cgcaacgcaa ttaatgtaag                           40

<210> SEQ ID NO 112
<211> LENGTH: 16
<212> TYPE: DNA
<213> ORGANISM: Artificial Sequence
<220> FEATURE:
<223> OTHER INFORMATION: Description of Artificial Sequence: Synthetic
      TREE018 primer

<400> SEQUENCE: 112
tcactgcccg ctttcc                                                     16

<210> SEQ ID NO 113
<211> LENGTH: 55
<212> TYPE: DNA
<213> ORGANISM: Artificial Sequence
<220> FEATURE:
<223> OTHER INFORMATION: Description of Artificial Sequence: Synthetic
      TREE019 primer

<400> SEQUENCE: 113
accggcagat cgtatgtaat atgcatggtt tattcctcct tatttaatcg ataca          55
```

<210> SEQ ID NO 114
<211> LENGTH: 23
<212> TYPE: DNA
<213> ORGANISM: Artificial Sequence
<220> FEATURE:
<223> OTHER INFORMATION: Description of Artificial Sequence: Synthetic
      TREE020 primer

<400> SEQUENCE: 114
atgcatatta catacgatct gcc                                              23

<210> SEQ ID NO 115
<211> LENGTH: 38
<212> TYPE: DNA
<213> ORGANISM: Artificial Sequence
<220> FEATURE:
<223> OTHER INFORMATION: Description of Artificial Sequence: Synthetic
      TREE021 primer

<400> SEQUENCE: 115
ggtcgacgga tccccggaat taagcgtcaa cgaaaccg                              38

<210> SEQ ID NO 116
<211> LENGTH: 38
<212> TYPE: DNA
<213> ORGANISM: Artificial Sequence
<220> FEATURE:
<223> OTHER INFORMATION: Description of Artificial Sequence: Synthetic
      TREE022 primer

<400> SEQUENCE: 116
gaagcagctc cagcctacac cagacgatgg tgcaggat                              38

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      TREE023 primer

<400> SEQUENCE: 117
gcaaagacca gaccgttcat a                                                21

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      Kan/Chlor1 primer

<400> SEQUENCE: 118
attccgggga tccgtcgacc                                                  20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      Kan/Chlor4 primer

<400> SEQUENCE: 119
tgtaggctgg agctgcttcg                                                  20

<210> SEQ ID NO 120
<211> LENGTH: 74

```
<212> TYPE: DNA
<213> ORGANISM: Artificial Sequence
<220> FEATURE:
<223> OTHER INFORMATION: Description of Artificial Sequence: Synthetic
      TREE133 primer

<400> SEQUENCE: 120
aaaaacagca acaatgtgag ctttgttgta attatattgt aaacatattg tccgctgttt      60
ctgcattctt acgt                                                        74

<210> SEQ ID NO 121
<211> LENGTH: 72
<212> TYPE: DNA
<213> ORGANISM: Artificial Sequence
<220> FEATURE:
<223> OTHER INFORMATION: Description of Artificial Sequence: Synthetic
      TREE134 primer

<400> SEQUENCE: 121
gatgacgacg aacacgcatt aaggaggtga ataaggagga ataacatatg aaagctggca      60
ttcttggtgt tg                                                          72

<210> SEQ ID NO 122
<211> LENGTH: 72
<212> TYPE: DNA
<213> ORGANISM: Artificial Sequence
<220> FEATURE:
<223> OTHER INFORMATION: Description of Artificial Sequence: Synthetic
      TREE135 primer

<400> SEQUENCE: 122
gtaacgtcca acaccaagaa tgccagcttt catatgttat tcctccttat tcacctcctt      60
aatgcgtgtt cg                                                          72

<210> SEQ ID NO 123
<211> LENGTH: 70
<212> TYPE: DNA
<213> ORGANISM: Artificial Sequence
<220> FEATURE:
<223> OTHER INFORMATION: Description of Artificial Sequence: Synthetic
      TREE136 primer

<400> SEQUENCE: 123
aaacggagcc tttcggctcc gttattcatt tacgcggctt caactttccg ttatcggccc      60
cagcggattg                                                             70

<210> SEQ ID NO 124
<211> LENGTH: 70
<212> TYPE: DNA
<213> ORGANISM: Artificial Sequence
<220> FEATURE:
<223> OTHER INFORMATION: Description of Artificial Sequence: Synthetic
      TREE137 primer

<400> SEQUENCE: 124
cgcagtttgc aagtgacggt atataaccga aaagtgactg agcgtacatg attccgggga      60
tccgtcgacc                                                             70

<210> SEQ ID NO 125
<211> LENGTH: 70
<212> TYPE: DNA
<213> ORGANISM: Artificial Sequence
<220> FEATURE:
<223> OTHER INFORMATION: Description of Artificial Sequence: Synthetic
      TREE138 primer
```

```
<400> SEQUENCE: 125
gcaaattgcg tcatgtttta atccttatcc tagaaacgaa ccagcgcgga tgtaggctgg     60
agctgcttcg                                                           70

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      TREE139 primer

<400> SEQUENCE: 126
gcagcgacaa gttcctcagc                                                20

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      TREE140 primer

<400> SEQUENCE: 127
ccgcagaagc ttcagcaaac g                                              21

<210> SEQ ID NO 128
<211> LENGTH: 23
<212> TYPE: DNA
<213> ORGANISM: Artificial Sequence
<220> FEATURE:
<223> OTHER INFORMATION: Description of Artificial Sequence: Synthetic
      fadE-L2 primer

<400> SEQUENCE: 128
cgggcaggtg ctatgaccag gac                                            23

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      fadE-R2 primer

<400> SEQUENCE: 129
gggcaggata agctcgggag g                                              21

<210> SEQ ID NO 130
<211> LENGTH: 55
<212> TYPE: DNA
<213> ORGANISM: Artificial Sequence
<220> FEATURE:
<223> OTHER INFORMATION: Description of Artificial Sequence: Synthetic
      Km_trc_overF primer

<400> SEQUENCE: 130
cttcgaactg caggtcgacg gatccccgga atgccgacat cataacggtt ctggc         55

<210> SEQ ID NO 131
<211> LENGTH: 50
<212> TYPE: DNA
<213> ORGANISM: Artificial Sequence
<220> FEATURE:
<223> OTHER INFORMATION: Description of Artificial Sequence: Synthetic
      Km_trc_overR primer
```

<400> SEQUENCE: 131
aatatttgcc agaaccgtta tgatgtcggc attccgggga tccgtcgacc          50

<210> SEQ ID NO 132
<211> LENGTH: 68
<212> TYPE: DNA
<213> ORGANISM: Artificial Sequence
<220> FEATURE:
<223> OTHER INFORMATION: Description of Artificial Sequence: Synthetic
      TREE032 primer

<400> SEQUENCE: 132
gtatatatta atgtatcgat taaataagga ggaataaacc atgatggtaa ggatatttga    60
tacaacac                                                             68

<210> SEQ ID NO 133
<211> LENGTH: 60
<212> TYPE: DNA
<213> ORGANISM: Artificial Sequence
<220> FEATURE:
<223> OTHER INFORMATION: Description of Artificial Sequence: Synthetic
      TREE033 primer

<400> SEQUENCE: 133
ctaagtgttg tatcaaatat ccttaccatc atggtttatt cctccttatt taatcgatac    60

<210> SEQ ID NO 134
<211> LENGTH: 66
<212> TYPE: DNA
<213> ORGANISM: Artificial Sequence
<220> FEATURE:
<223> OTHER INFORMATION: Description of Artificial Sequence: Synthetic
      TREE034 primer

<400> SEQUENCE: 134
gatttgttgg ctatagttag agaagttact ggaaaattgt aacaaggaaa ccgtgtgatg    60
tcgaag                                                               66

<210> SEQ ID NO 135
<211> LENGTH: 62
<212> TYPE: DNA
<213> ORGANISM: Artificial Sequence
<220> FEATURE:
<223> OTHER INFORMATION: Description of Artificial Sequence: Synthetic
      TREE035 primer

<400> SEQUENCE: 135
gtaattcttc gacatcacac ggtttccttg ttacaatttt ccagtaactt ctctaactat    60
ag                                                                   62

<210> SEQ ID NO 136
<211> LENGTH: 22
<212> TYPE: DNA
<213> ORGANISM: Artificial Sequence
<220> FEATURE:
<223> OTHER INFORMATION: Description of Artificial Sequence: Synthetic
      TREE104 primer

<400> SEQUENCE: 136
ggtagcgaag gttttgcccg gc                                             22

<210> SEQ ID NO 137
<211> LENGTH: 22
<212> TYPE: DNA

```
<213> ORGANISM: Artificial Sequence
<220> FEATURE:
<223> OTHER INFORMATION: Description of Artificial Sequence: Synthetic
      TREE106 primer

<400> SEQUENCE: 137
gattggtgcc ccaggtgacc tg                                             22

<210> SEQ ID NO 138
<211> LENGTH: 72
<212> TYPE: DNA
<213> ORGANISM: Artificial Sequence
<220> FEATURE:
<223> OTHER INFORMATION: Description of Artificial Sequence: Synthetic
      TREE146 primer

<400> SEQUENCE: 138
gagttgcaac gcaaagctca acacaacgaa acaacaagg aaaccgtgtg agtgtaggct     60
ggagctgctt cg                                                        72

<210> SEQ ID NO 139
<211> LENGTH: 19
<212> TYPE: DNA
<213> ORGANISM: Artificial Sequence
<220> FEATURE:
<223> OTHER INFORMATION: Description of Artificial Sequence: Synthetic
      TREE151 primer

<400> SEQUENCE: 139
cttccacggc gtcggcctg                                                 19

<210> SEQ ID NO 140
<211> LENGTH: 36
<212> TYPE: DNA
<213> ORGANISM: Artificial Sequence
<220> FEATURE:
<223> OTHER INFORMATION: Description of Artificial Sequence: Synthetic
      IFF primer

<400> SEQUENCE: 140
gggtcaatag cggccgccaa ttcgcgcgcg aaggcg                              36

<210> SEQ ID NO 141
<211> LENGTH: 37
<212> TYPE: DNA
<213> ORGANISM: Artificial Sequence
<220> FEATURE:
<223> OTHER INFORMATION: Description of Artificial Sequence: Synthetic
      IFR primer

<400> SEQUENCE: 141
tggcgcgcct cctagggcat tacgctgact tgacggg                             37

<210> SEQ ID NO 142
<211> LENGTH: 70
<212> TYPE: DNA
<213> ORGANISM: Artificial Sequence
<220> FEATURE:
<223> OTHER INFORMATION: Description of Artificial Sequence: Synthetic
      ScpBC-KOfwd primer

<400> SEQUENCE: 142
gctcagtgaa tttatccaga cgcaatattt tgattaaagg aatttttatg attccgggga   60
tccgtcgacc                                                           70

<210> SEQ ID NO 143
```

```
<211> LENGTH: 69
<212> TYPE: DNA
<213> ORGANISM: Artificial Sequence
<220> FEATURE:
<223> OTHER INFORMATION: Description of Artificial Sequence: Synthetic
      ScpBC-KOrc primer

<400> SEQUENCE: 143
attgctgaag atcgtgacgg gacgagtcat taacccagca tcgagccggt tgtaggctgg      60
agctgcttc                                                              69

<210> SEQ ID NO 144
<211> LENGTH: 19
<212> TYPE: DNA
<213> ORGANISM: Artificial Sequence
<220> FEATURE:
<223> OTHER INFORMATION: Description of Artificial Sequence: Synthetic
      ScpBC check -60 fwd primer

<400> SEQUENCE: 144
cgggttctga cttgtagcg                                                   19

<210> SEQ ID NO 145
<211> LENGTH: 24
<212> TYPE: DNA
<213> ORGANISM: Artificial Sequence
<220> FEATURE:
<223> OTHER INFORMATION: Description of Artificial Sequence: Synthetic
      ScpBC check +60 rc primer

<400> SEQUENCE: 145
ccaacttcga agcaatgatt gatg                                             24
```